(12) United States Patent
Mulder et al.

(10) Patent No.: US 11,419,902 B2
(45) Date of Patent: *Aug. 23, 2022

(54) COMPOSITIONS COMPRISING BACTERIAL STRAINS

(71) Applicant: 4D Pharma Research Limited, Aberdeen (GB)

(72) Inventors: Imke Elisabeth Mulder, Aberdeen (GB); Parthena Fotiadou, Aberdeen (GB); Amy Beth Holt, Aberdeen (GB); Suaad Ahmed, Aberdeen (GB); Anna Ettorre, Aberdeen (GB); Samantha Yuille, Aberdeen (GB); Ted Dinan, Cobh (IE); John Cryan, Cork (IE)

(73) Assignee: 4D Pharma Research Limited, Aberdeen (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/013,026

(22) Filed: Sep. 4, 2020

(65) Prior Publication Data

US 2021/0052671 A1    Feb. 25, 2021

Related U.S. Application Data

(63) Continuation of application No. PCT/EP2019/062238, filed on May 13, 2019.

(30) Foreign Application Priority Data

May 11, 2018  (EP) .................................... 18171893
Jun. 15, 2018  (EP) .................................... 18178136
Jun. 25, 2018  (GB) .................................... 1810386
Aug. 17, 2018  (GB) .................................... 1813460
Oct. 29, 2018  (GB) .................................... 1817642
Dec. 12, 2018  (GB) .................................... 1820256
Dec. 12, 2018  (GB) .................................... 1820264

(51) Int. Cl.
| | |
|---|---|
| A61K 35/74 | (2015.01) |
| A61K 9/19 | (2006.01) |
| A61K 35/17 | (2015.01) |
| A61K 35/28 | (2015.01) |
| A23L 33/135 | (2016.01) |
| A23L 33/00 | (2016.01) |
| A61P 37/06 | (2006.01) |
| A61P 29/00 | (2006.01) |
| A61P 35/00 | (2006.01) |
| A61K 45/06 | (2006.01) |
| A61K 9/00 | (2006.01) |
| A61K 35/741 | (2015.01) |

(52) U.S. Cl.
CPC ............ *A61K 35/74* (2013.01); *A23L 33/135* (2016.08); *A23L 33/40* (2016.08); *A61K 9/0053* (2013.01); *A61K 9/19* (2013.01); *A61K 35/17* (2013.01); *A61K 35/28* (2013.01); *A61K 35/741* (2013.01); *A61P 29/00* (2018.01); *A61P 35/00* (2018.01); *A61P 37/06* (2018.01); *A23V 2002/00* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 11,007,233 B2 | 5/2021 | Mulder et al. | |
| 2004/0005304 A1 | 1/2004 | Brudnak | |
| 2004/0120963 A1 | 6/2004 | Ushida et al. | |
| 2016/0199424 A1 | 7/2016 | Berry et al. | |
| 2016/0223553 A1 | 8/2016 | Sears et al. | |
| 2017/0354697 A1 | 12/2017 | Schneider et al. | |
| 2018/0122511 A1 | 5/2018 | Apte et al. | |
| 2021/0275605 A1 | 9/2021 | Mulder et al. | |
| 2021/0315943 A1 | 10/2021 | Mulder et al. | |
| 2021/0361722 A1 | 11/2021 | Mulder et al. | |

FOREIGN PATENT DOCUMENTS

| | | |
|---|---|---|
| CN | 104415060 A | 3/2015 |
| CN | 105979952 A | 9/2016 |
| CN | 107028985 A | 8/2017 |
| EP | 1389464 A1 | 2/2004 |
| JP | S5557520 A | 4/1980 |
| WO | WO-03046580 A1 | 6/2003 |
| WO | WO-2004085628 A1 | 10/2004 |
| WO | WO-2005023179 A2 | 3/2005 |
| WO | WO-2013008039 A2 | 1/2013 |
| WO | WO-2013050792 A1 | 4/2013 |
| WO | WO-2014082050 A1 | 5/2014 |
| WO | WO-2014121304 A1 | 8/2014 |
| WO | WO-2014167338 A1 | 10/2014 |
| WO | WO-2015038731 A1 | 3/2015 |
| WO | WO-2016149449 A1 | 9/2016 |
| WO | WO-2016203220 A1 | 12/2016 |
| WO | WO-2017091783 A2 | 6/2017 |

(Continued)

OTHER PUBLICATIONS

Heinkoff et al. PNAS vol. 89, pp. 10915-10919, Nov. 1992.*

(Continued)

*Primary Examiner* — Oluwatosin A Ogunbiyi

(74) *Attorney, Agent, or Firm* — Wilson Sonsini Goodrich & Rosati

(57) ABSTRACT

The invention provides a composition comprising a bacterial strain of the genus *Megasphaera*, for use in stimulating the immune system in subject.

14 Claims, 72 Drawing Sheets

Specification includes a Sequence Listing.

(56) References Cited

FOREIGN PATENT DOCUMENTS

| WO | WO-2017091783 A3 | 7/2017 |
|----|------------------|--------|
| WO | WO-2017122197 A1 | 7/2017 |
| WO | WO-2018094190 A2 | 5/2018 |
| WO | WO-2018112363 A1 | 6/2018 |
| WO | WO-2018112365 A2 | 6/2018 |
| WO | WO-2018229189 A1 | 12/2018 |
| WO | WO-2018229216 A1 | 12/2018 |
| WO | WO-2018229236 A2 | 12/2018 |

OTHER PUBLICATIONS

Chatterjee et al. Cancer Immunol Immunother 1994 38:75-82.*
Yaghoubi et al. BBA Reviews on Cancer. 1874 (2020) 188388 pp. 1-17.*
Charkraborty et al. ecancer 2012, 6:ed16 DOI:10.3332/ecancer.2012.ed16.*
Corcos et al. Cancer Medicine 2013; 2(4):421-426.*
Ferreira, Daniela & Adega, Filomena & Chaves, Raquel. (2013). The Importance of Cancer Cell Lines as in vitro Models in Cancer Methylome Analysis and Anticancer Drugs Testing. 10.5772/1745.*
Smalley et al Cancer Discov Feb. 1, 2018 (8) (2) 140-142; DOI: 10.1158/2159-8290.CD-17-1355.*
Dhillion et al. Oncogene (2007) 26, 3279-3290.*
Clarridge, J. Impact of 16S rRNA Gene Sequence Analysis for Identification of Bacteria on Clinical Microbiology and Infectious Disease, Clin. Microbiol. Rev; 17(4):840-862 (2004).*
Eckschalager et al. Int. J. Mol. Sci. 2017, 18, 1414, 25 pages.*
Liu et al. Cell Physiol Biochem 2018; 46:1525-1535.*
Abbas, Ata, and Sanjay Gupta. "The role of histone deacetylases in prostate cancer." Epigenetics vol. 3,6 (2008): 300-9. doi:10.4161/epi.3.6.7273.
Abel and Zukin, "Epigenetic targets of HDAC inhibition in neurodegenerative and psychiatric disorders", 2008, Current Opinion Pharmacology, 2008. 8(1): 57-64, Feb. 2008.
Alenghat, Theresa et al., "Histone deacetylase 3 coordinates commensal-bacteria-dependent intestinal homeostasis",2013, Nature, 504: 153-157, Published: Nov. 3, 2013.
Allen, Irving C. et al., The NLRP3 inflammasome functions as a negative regulator of tumorigenesis during colitis-associated cancer, 2010, J Exp Aled.;207(5):1045-56.
Andreeff MD, PhD, Michael et al., Cell Proliferation and Differentiation, 2003,Holland-Frei Cancer Medicine. 6th edition, Chapter 3, 21 pages.
Angiolilli, Chiara et al., "Hisone deacetylase 3 regulates the inflammatory gene expression programme of rheumatoid arthritis fibroblast-like synoviocytes", Ann Rheum Dis, 2017, 76: 277-285, Epub Jul. 25, 2016.
Arenberg, et al., Interferon-y-inducible Protein10 (IP-10) Is an Angiostatic Factor That Inhibits Human Non-small Cell Lung Cancer (NSCLC) Tumorigenesis and Spontaneous Metastases. 1996. J. Exp.Med.184:981-92. Sep. 1, 1996.
Arvigo, M et al., Somatostatin and dopamine receptor interaction in prostate and lung cancer cell lines, 2010, J Endocrinol. ;207(3):309-17.
Ascierto, Paolo A et al., The role of BRAF V600 mutation in melanoma, 2012, Journal of Translational Medicine, 10,85, 9 pages.
Azad, M.B. et al., Probiotic supplementation during pregnancy or infancy for the prevention of asthma and wheeze: systematic review and meta-analysis BMJ 2013; 347 :f6471, Dec. 4, 2013.
Bae S, et al., α-Enolase expressed on the surfaces of monocytes and macrophages induces robust synovial inflammation in rheumatoid arthritis. J Immunol. Jul. 1, 2012;189(1):365-72. doi:10.4049/jimmunol.1102073. Epub May 23, 2012. PMID: 22623332.
Barnes, P.J. et al., Histone acetylation and deacetylation: importance in inflammatory lung diseases, Eur Resp, 2005, 25:552-563.
Bektas, Arsun et al. "Human T cell immunosenescence and inflammation in aging." Journal of leukocyte biology vol. 102,4 (2017): 977-988. doi:10.1189/jlb.3RI0716-335R.
Bell, Ryan A V, and Lynn A Megeney. "Evolution of caspase-mediated cell death and differentiation: twins separated at birth." Cell death and differentiation vol. 24,8 (2017): 1359-1368. doi:10.1038/cdd.2017.37.
Berthoud et al., "MIG (CXCL9) is a more sensitive measure than IFN-γ of vaccine induced T-cell responses in volunteers receiving investigated malaria vaccines" (2009) J Immunol Methods 340(1)33-41.
Bettelli E, Carrier Y, Gao W, Korn T, Strom TB, Oukka M, Weiner HL, Kuchroo VK. Reciprocal developmental pathways for the generation of pathogenic effector TH17 and regulatory T cells. Nature. May 11, 2006;441(7090):235-8. doi: 10.1038/nature04753. Epub Apr. 30, 2006. PMID: 16648838.
Bhat, Kumar M. R. et al., Transcriptional regulation of human MAP2 gene in melanoma: role of neuronal bHLH factors and Notch1signaling, 2006, Nucleic Acids Res.;34(13):3819-32.
Bloch F, et al., "Production of TNF-alpha ex vivo is predictive of an immune response to flu vaccination in a frail elderly population", Eur Cytokine Netw. Sep. 1, 2016;27(3):63-67. English. doi: 10.1684/ecn.2016.0378. PMID: 27910810.
Bonner et al., Significance of Neuron-specific Enolase Levels before and during Therapy for Small Cell LungCancer1 (2000) Clinical Cancer Research 6:597-601.
Bovenschen, H. Jorn et al., Foxp3 +Regulatory T Cells of Psoriasis Patients Easily Differentiate intoIL-17A-Producing Cells and Are Found in Lesional Skin, J Invest Dermatol, vol. 131, 2011, pp. 1853-1860.
Butler, Lisa M. et al., Suberoylanilide Hydroxamic Acid, an Inhibitor of Histone Deacetylase, Suppresses the Growth of Prostate Cancer Cells in Vitro and in Vivo, 2000,Cancer Res. 60:5165-5170.
Chai,Yuan-yuan et al. (2012), Antioxidant Activities of Stilbenoids from Rheum emodi Wall, Evidence-Based Complementary and Alternative Medicine, Article ID 603678, 7 pages, doi:10.1155/2012/603678.
Chan, Jason R et al. "IL-23 stimulates epidermal hyperplasia via TNF and IL-20R2-dependent mechanisms with implications for psoriasis pathogenesis." The Journal of experimental medicine vol. 203,12 (2006): 2577-87. doi:10.1084/jem.20060244.
Chen, Ming-Huang et al., Gene Expression-Based Chemical Genomics Identifies Potential Therapeutic Drugs in Hepatocellular Carcinoma, 2011,PLoS One.;6(11):e27186.
Cheng,H-W et al., Identification of thioridazine, an antipsychotic drug, as an antiglioblastoma and anticancer stem cell agent using public gene expression data, 2015, Cell Death Dis.;6:e1753.
Christensen, Dan P et al., Histone Deacetylase (HDAC) Inhibition as a Novel Treatment for Diabetes Mellitus (2011), Mol Med, 17 (5-6), 370-390.
Chun, Pusoon, Histone deacetylase inhibitors in hematological malignancies and solid tumors, 2015, Arch Pharm Res. 38(6):933-49.
Coffman, Robert L et al. "Vaccine adjuvants: putting innate immunity to work." Immunity vol. 33,4 (2010): 492-503. doi:10.1016/j.immuni.2010.10.002.
Corsini, Emanuela et al., High interleukin-10 production is associated with low antibody response to influenza vaccination in the elderly, J Leukocyte Biol 2006 80, 376-382.
Darrah, Patricia A. et al., IL-10 production differentially influences the magnitude, quality, and protective capacity of Th1 responses depending on the vaccine platform, J Exp Med, 2010 207(7), 1421-1433.
De Baere, Siegrid et al., Development of a HPLC-UV method for the quantitative determination of four short-chain fatty acids and lactic acid produced by intestinal bacteria during in vitro fermentation, (2013) J Pharm Biomed Anal, 80: 107-115.
Devarajan,Eswaran et al, Down-regulation of caspase 3 in breast cancer: a possible mechanism for chemoresistance, 2002, Oncogene. 12;21(57):8843-51.
Didierlaurent AM, et al., Enhancement of adaptive immunity by the human vaccine adjuvant AS01 depends on activated dendritic cells. J Immunol. Aug. 15, 2014;193(4):1920-30. doi: 10.4049/jimmunol.1400948. Epub Jul. 14, 2014. PMID: 25024381.
Eckburg, PB. et al., Diversity of the human intestinal microbial flora.Science. Jun. 10, 2005;308(5728):1635-8. Epub Apr. 14, 2005.

(56) References Cited

OTHER PUBLICATIONS

Fahy, J.V. Eosinophilic and neutrophilic inflammation in asthma: insights from clinical studies. Proc Am Thorac Soc. May 1, 2009;6(3):256-9. doi: 10.1513/pats.200808-087RM.
Felice C. et al. "Review article: selective histone deacetylase isoforms as potential therapeutic targets in inflammatory bowel diseases", 2015, Ailmentary Pharmacology and Therapeutics, 41: 26-38, Epub Nov. 4, 2014.
Fernández-Ruiz M, et al. "Baseline serum interleukin-6 to interleukin-2 ratio is associated with the response to seasonal trivalent influenza vaccine in solid organ transplant recipients", Vaccine.Dec. 16, 2015;33(51):7176-7182. doi: 10.1016/j.vaccine.2015.10.134. Epub Nov. 10, 2015. PMID: 26555352.
Fülöp T, Dupuis G, Witkowski JM, Larbi A. The Role of Immunosenescence in the Development of Age-Related Diseases. Rev Invest Clin. Mar.-Apr. 2016;68(2):84-91. PMID: 27103044.
Fraietta, Joseph A et al. "Determinants of response and resistance to CD19 chimeric antigen receptor (CAR) T cell therapy of chronic lymphocytic leukemia." Nature medicine vol. 24,5 (2018): 563-571. doi:10.1038/s41591-018-0010-1.
Frank, D. et al., Molecular-phylogenetic characterization of microbial community imbalances in human inflammatory bowel diseases. 2007. PNAS. 104(34):13780-5.online Aug. 15, 2007.
Fulop, Tamas et al., "Immunosenescence and Cancer" (2013) Critical Reviews in Oncogenesis 2013;18(6):489-513.
Fulop, Tamas et al. "Immunosenescence and Inflamm-Aging As Two Sides of the Same Coin: Friends or Foes?." Frontiers in immunology vol. 8 1960. Jan. 10, 2018, doi: 10.3389/fimmu.2017.01960.
Gagnon, Melanie et al "Comparison of the Caco-2, HT-29 and the mucus-secreting HT29-MTX intestinal cell models to investigate *Salmonella* adhesion and invasion", 2013, Journal of Microbiological Methods. 94: 274-279, Epub Jul. 5, 2013.
Gasche, Christoph et al. (2000) A Simple Classification of Crohn's Disease: Report of the Working Party for the World Congresses of Gastroenterology, Vienna 1998, Inflammatory Bowel Diseases 6: 8-15.
Gaur and Aggarwal, Regulation of proliferation, survival and apoptosis by members of the TNF superfamily* (2003).Biochem Pharmacol. ;66(8):1403-8.
Genbank NCBIReference Sequence: JX424772.1, Megasphaera massiliensis strain NP3 16Sribosomal RNA gene, partial sequence., retrieved from EBI accession No. EM STD:JX424772, accessed Dec. 2, 2020.
Genbank NCBIReference Sequence: LN998020.1, *Megasphaera* sp. MTCC 12521 partial 16S rRNAgene, strain MTCC 12521, isolate DISK18, retrieved from EBI accession No. EM STD:LN998020, accessed Dec. 2, 2020.
Gerland Vaux, Apoptosis in the development and treatment of cancer, 2005, Carcinogenesis.Feb. 2005;26(2):263-70.
Glauben, Rainer et al., "Histone Hyperacetylation Is Associated with Amelioration of Experimental Colitis in Mice", Journal of Immunology, 2006, 176: 5015-5022.
Glenn, Justin D, and Katharine A Whartenby. "Mesenchymal stem cells: Emerging mechanisms of immunomodulation and therapy." World journal of stem cells vol. 6,5 (2014): 526-39. doi:10.4252/wjsc.v6.i5.526.
Glenn, Justin D and Whartenby, Katharine, Mesenchymal stem cells: Emerging mechanisms of immunomodulation and therapy, World J Stem Cells Nov. 26, 2014; 6(5): 526-539, ISSN 1948-0210.
Goldin, B. R. and Gorbach, S. L., Clinical Indications for Probiotics: An Overview, Clin Infect Dis., 2008, vol. 46, No. 2, pp. 96-100.
Goldin, B.R. et al., Clinical indications for probiotics: an overview. Clin Infect Dis. Feb. 1, 2008;46 Suppl 2:S96-100; discussion S144-51. doi: 10.1086/523333.
Gonneaud Alexis, et al., "The histone deacetylase Hdac1 regulates inflammatory signalling in intestinal epithelial cells", 2014, Journal of Inflammation, 11: 43, doi: 10.1186/s12950-014-0043-2. Dec. 20, 2014.
Grabiec, Aleksander M et al., Targeting histone deacetylase activity in rheumatoid arthritis and asthma as prototypes of inflammatory disease: should we keep our HATs on?, 2008, Arthritis Res Ther. 10:226.
Gray SG. and Dangond F. "Rationale for the use of histone deacetylase inhibitors as a dual therapeutic modality in multiple sclerosis.", Epigenetics. Apr.-Jun. 2006;1(2):67-75. Epub Mar. 5, 2006.
Haabeth et al. A model for cancer-suppressive inflammation. (2012) OncoImmunology 1(1):1146-1152.
Haumaitre, Cécile et al. "Histone deacetylase inhibitors modify pancreatic cell fate determination and amplify endocrine progenitors." Molecular and cellular biology vol. 28,20 (2008): 6373-83. doi:10.1128/MCB.00413-08.
Heng, Boon Chin et al., Strategies for directing the differentiation of stem cells into the cardiomyogenic lineage in vitro (2004) Cardiovasc Res. Apr. 1, 2004;62(1):34-42.
Hommes, D W et al., Mitogen activated protein (MAP) kinase signal transduction pathways and novel anti-inflammatory targets, Gut Jan. 2003;52(1):144-51. doi: 10.1136/gut.52.1.144.
Hoover, David M. et al., The Structure of Human Macrophage Inflammatory Protein-3x/CCL20,2002, J Biol Chem. 277(40):37647-54.
Huang, Yunda et al., Cell-Mediated Immune Predictors of Vaccine Effect on Viral Load and CD4 Count in a Phase 2Therapeutic HIV-1 Vaccine Clinical Trial, EBio Medicine (Cell) 2017, 24,195-204.
International Search Report dated Oct. 4, 2019 for International Application Serial No. PCT/EP2019/062238,(7 pages).
Jandaghi, Pouria et al., Expression of DRD2 Is Increased in Human Pancreatic Ductal Adenocarcinoma and Inhibitors Slow Tumor Growth in Mice, 2016, Gastroenterology;151(6):1218-1231.
Johnsen, LG et al,, Gas chromatography—mass spectrometry data processing made easy., 2017, J Chromatogr A, 1503, 57-64.
Jones, Jeremy C. et al., Non-V600BRAF Mutations Define a Clinically Distinct Molecular Subtype of Metastatic Colorectal Cancer, 2017, J Clin Oncol. Aug. 10, 2017;35(23): 2624-2630.
Jung et al ,HDAC2 overexpression confers oncogenic potential to human lung cancer cells by deregulating expression of apoptosis and cell cycle proteins (2012) J Cell Biochem113: 2167-2177.
Kailasapathy, K. Microencapsulation of Probiotic Bacteria: Technology and Potential Applications. Curr. Issues Intest. Microbiol. (2002) 3: 39-48.
Kang, S. et al. (2010) "Dysbiosis of fecal microbiota in Crohn's disease patients as revealed by a custom phylogenetic microarray," Inflammatory Bowel Diseases. Dec. 2010;16(12):2034-2042.doi: 10.1002/ibd.21319.
Kaser,Arthur et al., Increased Expression of CCL20 in Human Inflammatory Bowel Disease, 2004,J ClinImmunol.;24(1):74-85.
Knudsen, Niels Peter H et al. "Different human vaccine adjuvants promote distinct antigen-independent immunological signatures tailored to different pathogens." Scientific reports vol. 6 19570. Jan. 21, 2016, doi:10.1038/srep19570.
Kondelkova, Kateřina et al., Regulatory T Cells (Treg) And Their Roles In Immune System With Respect To Immunopathological Disorders, 2010,ActaMedica (Hradec Kralove).;53(2):73-7.
Leal, I S et al. "Interleukin-6 regulates the phenotype of the immune response to a tuberculosis subunit vaccine." Immunology vol. 103,3 (2001): 375-81. doi:10.1046/j.1365-2567.2001.01244.x.
Lee, Sang Hoon et al, "Characterization of microbiome in bronchoalveolar lavage fluid of patients with lung cancer comparing with benign mass like lesions", Lung Cancer, Elsevier, Amsterdam, NL, vol. 102, Oct. 31, 2016 (Oct. 31, 2016), pp. 89-95, XP029848342, ISSN: 0169-5002, DOI:10.1016/J.LUNGCAN.2016.10.016.
Lefeber, Dirk J. et al., Th1-DirectingAdjuvants Increase the Immunogenicity of Oligosaccharide-Protein Conjugate Vaccines Related to *Streptococcus pneumoniae* Type 3, Infect Immun 71(12)6915-6920.
Lejeune et al. Efficiency of Recombinant Human TNF in Human Cancer Therapy. Cancer Immun. 6:6 (2006).
Leng, Corinna etal., Reduction of graft-versus-host disease by histone deacetylase inhibitor suberonylanilide hydroxamic acid is

(56) References Cited

OTHER PUBLICATIONS associated with modulation of inflammatory cytokine milieu and involves inhibition of STAT1 (2006), Experimental Hematology 34 (2006) 776-787.
Leoni, Flavio et al. "The histone deacetylase inhibitor ITF2357 reduces production of pro-inflammatory cytokines in vitro and systemic inflammation in vivo." Molecular medicine (Cambridge, Mass.) vol. 11,1-12 (2005): 1-15. doi:10.2119/2006-00005. Dinarello.
Leslie, et al., Trehalose and sucrose protect both membranes and proteins in intact bacteria during drying. (1995) Appl. Environ. Microbiol. 61, 3592-3597.
Li et al, "Aluminum Hydroxide Adjuvants Activate Caspase-1 and Induce IL-113 andIL-18 Release" (2007) J Immunol, 178(8),5271-5276.
Li, Hanfen et al., AluminumHydroxide Adjuvants Activate Caspase-1 and Induce IL-1β and IL-18 Release, J Immunol Apr. 15, 2007, 178 (8) 5271-5276; DOI:https://doi.org/10.4049/jimmunol.178.8.5271.
Li, Jie et al., Genome-wide shRNA screen revealed integrated mitogenic signaling between dopamine receptor D2 (DRD2) and epidermal growth factor receptor (EGFR) in glioblastoma, 2014,Oncotarget.;5(4):882-93.
Li, Wei et al., "Structural changes of gut microbiota in Parkinson's disease and its correlation with clinical features", Science China Life Sciences, 2017, vol. 60, No. 11:1223-1233.
Lim, Jae Sung et al., Flagellin-dependentTLR5/caveolin-1 as a promising immune activator in immunosenescence, Aging Cell, 2015, 14, pp. 907-915.
Liu, Feifei et al., Targeting ERK, an Achilles' Heel of the MAPK pathway, in cancer therapy, 2018, Acta Pharmaceutica Sinica B; 8, 4; 552-562.
Livak KJ, Schmittgen TD., Analysis of relative gene expression data using real-time quantitative PCR and the 2(-Delta Delta C(T)) Method. Methods. Dec. 2001;25(4):402-8. doi: 10.1006/meth.2001.1262. PMID: 11846609.
Luo, Jie et al., Vascular endothelial growth factor promotes the activation of hepatic stellate cells in chronic schistosomiasis, Immunology and Cell Biology, 2016, pp. 1-9.
Machiels, K., A decrease of the butyrate-producing species *Roseburia hominis* and *Faecalibacterium prausnitzii* defines dysbiosis in patients with ulcerative colitis. Gut. Aug. 2014;63(8):1275-83. doi: 10.1136/gutjnl-2013-304833. Epub Sep. 10, 2013.
Macpherson, AJ. et al., IgA responses in the intestinal mucosa against pathogenic and non-pathogenic microorganisms. Oct. 2001. 3(12). 1021-1035.
Macpherson, AJ., et al., The functions of mucosal T cells in containing the indigenous commensal flora of the intestine.Cell Mol Life Sci. Dec. 2002;59(12):2088-96.
Maddodi, Nityanand et al., OncogenicBRAFV600E Induces Expression of Neuronal Differentiation Marker MAP2 in Melanoma Cells by Promoter Demethylation and Down-regulation of Transcription Repressor HES1, Jan. 1, 2010, The Journal Of Biological Chemistry vol. 285,No. 1, pp. 242-254.
Mao, Min etal., Dopamine D2 receptor blocker thioridazine induces cell death in human uterine cervical carcinoma cell line SiHa, 2015,J Obstet Gynaecol Res.;41(8):1240-5.
Martinon, Fabio et al., The Inflammasome: A Molecular Platform Triggering Activation of Inflammatory Caspases and Processing of proIL-β, (2002) Mol Cell .;10(2):417-26.
Martinon, Fabio et al., The Inflammasome: A Molecular Platform Triggering Activation of Inflammatory Caspases and Processing of proIL-B, 2002, MolCell;10(2):417-26.
Masco, L., et al., Identification of Bifidobacterium Species Using rep-PCR Fingerprinting. Systematic and Applied Microbiology 26(4):557-63 • Nov. 2003.
Mazmanian, SK., An immunomodulatory molecule of symbiotic bacteria directs maturation of the host immune system. Cell. Jul. 15, 2005;122(1):107-18.

Menezes, Joao R. L. and Luskin, Marla B., Expression of Neuron-Specific Tubulin Defines a Novel Population in the Proliferative Layers of the Developing Telencephalon,1994, Journal of Neuroscience, 14 (9) 5399-5416.
Minamiya Y, et al., Expression of histone deacetylase 1 correlates with a poor prognosisin patients with adenocarcinoma of the lung. Lung Cancer. Nov. 2011;74(2):300-4.doi: 10.1016/j.lungcan.2011.02.019. Epub Apr. 5, 2011. PMID: 21466904.
Mitropoulou, G. et al. Immobilization Technologies in Probiotic Food Production. (2013) Journal Nutr Metab. (2013) 716861.
Miyamoto-Shinohara et al. Survival of freeze-dried bacteria. J Gen Appl Microbiol 54(1):9-24 (2008).
Mohanty, Subhasis et al. "Prolonged proinflammatory cytokine production in monocytes modulated by interleukin 10 after influenza vaccination in older adults." The Journal of infectious diseases vol. 211,7 (2015): 1174-84. doi: 10.1093/infdis/jiu573.
Molsey, Amber et al., Glucose Regulates Insulin Gene Transcription by Hyperacetylation of Histone H4*, 2003, The Journal Of Biological Chemistry, 278, 19660-6.
Monneret C., Histone deacetylase inhibitors for epigenetic therapy of cancer. Anticancer Drugs. Apr. 2007;18(4):363-70. doi: 10.1097/CAD.0b013e328012a5db. Erratum in: Anticancer Drugs. Jun. 2007;18(5):219. PMID: 17351388.
Morel S, et al. "Adjuvant System AS03 containing α-tocopherol modulates innate immune response and leads to improved adaptive immunity", Vaccine. Mar. 16, 2011;29(13):2461-73. doi: 10.1016/j.vaccine.2011.01.011. Epub Jan. 20, 2011. PMID:21256188.
Mu, Jiasheng et al., Thioridazine, an antipsychotic drug, elicits potent antitumor effects in gastric cancer, ONCOLREP., vol. 31, No. 5, 2014, pp. 2107-2114.
Mu, Zhanglei et al., "Molecular Biology of Atopic Dermatitis", Clinic Rev Allerg Immunol, 2014, 26 pages.
Murphy, Craig A et al. "Divergent pro- and anti inflammatory roles for IL-23 and IL-12 in joint autoimmune inflammation." The Journal of experimental medicine vol. 198,12 (2003): 1951-7. doi:10.1084/jem.20030896.
Mwakwari, Sandra et al., Macrocyclic Histone Deacetylase Inhibitors, 2010, Curr Top Med Chem. 10 (14): 1423-40.
Nallabelli, Nayudu et al., "Biochemical and genome sequence analyses of *Megasphaera* sp. strain DISK18from dental plaque of a healthy individual reveals commensal lifestyle", Scientific Reports, vol. 6, No. 1, Sep. 21, 2016(Sep. 21, 2016), XP055504215, DOI: 10.1038/srep33665.
Nocito, Antonio et al, Serotonin Regulates Macrophage-Mediated Angiogenesis in a Mouse Model of Colon Cancer Allografts, 2008, Cancer Res., 68(13):5152-8.
Nowak, Elizabeth C. et al., Tryptophanhydroxylase-1 regulates immune tolerance and inflammation, 2012, JEM,209(11):2127.
Olafsdottir, Thorunn et al., "Molecular signatures of vaccine adjuvants", Vaccine 33(40)5302-5307.
Pace et al. Macrophage activation: Priming activity from a T-cell hybridoma is attributable to interferon. (1983) PNAS. 80:3782-6.
Padmanabhan, Roshan et al, "Non-contiguous finished genome sequence and description of *Megasphaera massiliensis* sp. nov.", Standards In Genomic Sciences, vol. 8,No. 3, Aug. 7, 2013 (Aug. 7, 2013), p. 525-538, XP055504182, DOI:10.4056/sigs.4077819.
Park, Matthew K et al., The CXC Chemokine Murine Monokine Induced by IFN-γ (CXC Chemokine Ligand 9) Is Made by APCs, Targets Lymphocytes Including Activated B Cells, and Supports Antibody Responses to a Bacterial Pathogen In Vivo, J Immunol Aug. 1, 2002, 169 (3)1433-1443; DOI: https://doi.org/10.4049/jimmunol.169.3.1433.
Park, Mi Sun et al., Thioridazine inhibits angiogenesis and tumor growth by targeting the VEGFR-2/PI3K/mTOR pathway in ovarian cancer xenografts,2014, Oncotarget.;5(13):4929-34.
Pornour, Majid et al. New Perspective Therapy of Breast Cancer Based on Selective Dopamine Receptor D2 Agonist and Antagonist Effects on MCF-7 Cell Line, 2015, Recent Pat Anticancer Drug Discov.;10(2):214-23.
Prabhu, Varun Vijay et al., DDIS-08.The Small Molecule Imipridone ONC201 Is Active In Glioblastoma With Drd2pathwayDysregulation, Nov. 1, 2017,Neuro-Oncology, vol. 19, issue suppl 6, p. vi60, abstract.

(56) References Cited

OTHER PUBLICATIONS

Quint, Karl et al., Clinical significance of histone deacetylases 1, 2, 3, and 7: HDAC2 is an independent predictor of survival in HCC (2011), Virchows Arch 459:129-139, DOI10.1007/s00428-011-1103-0.

Reddy, Pavan et al., Histone deacetylase inhibition modulates indoleamine 2,3-dioxygenase-dependent DC functions and regulates experimental graft-versus-host disease in mice, J Clin Invest, vol. 118, 2008, pp. 2562-2573.

Reilly, Christopher M et al. "HDAC inhibition in lupus models." Molecular medicine (Cambridge, Mass.) vol. 17,5-6 (2011):417-25. doi: 10.2119/molmed.2011.00055.

Ren, Ke and Torres, Richard, Role of interleukin-1 during pain and inflammation, 2009, Brain Res Rev.;60(1):57-64.

Ren, Yuan et al., Therapeutic effects of histone deacetylase inhibitors in a murine asthma model, Inflamm. Res., 2016, 65:995-1008, DOI 10.1007/s00011-016-0984-4.

Ruan, Y. et al., Interleukin 8 enhances the immune response of ducks to avian influenza vaccine, 2014, Acta Virol. 58(4):356-8.

Sachlos, Eleftherios et al., Identification of Drugs Including a Dopamine Receptor Antagonist that Selectively Target Cancer Stem Cells, 2012, Cell.;149(6):1284-97.

Saito, Akiko et al., A synthetic inhibitor of histone deacetylase, MS-27-275, with marked in vivo antitumor activity against human tumors, 1999,ProcNatl Acad Sci USA. 96:4592-4597.

Sasaki-Imamura, Takako et al. "Production of indole from L-tryptophan and effects of these compounds on biofilm formation by Fusobacterium nucleatum ATCC 25586." Applied and environmental microbiology vol. 76,13 (2010): 4260-8. doi:10.1128/AEM.00166-10.

Scanlan PD., et al., Culture-independent analyses of temporal variation of the dominant fecal microbiota and targeted bacterial subgroups in Crohn's disease. J Clin Microbiol. Nov. 2006;44(11):3980-8. Epub Sep. 20, 2006.

Selvan, Senthamil et al., Expression of neuron specific enolase (NSE) in metastatic melanoma: Implications for progression of disease (2008), Cancer Research, AACR Annual Meeting Apr. 12-16, 2008.

Sgadari, C. et al., Interferon-inducible protein-10 identified as a mediator of tumor necrosis in vivo. (1996) PNAS. 93:13791-6.

Sgadari et al. Mig, the Monokine Induced By Interferon-g, Promotes Tumor Necrosis In Vivo. (1997) Blood. 89:2635-43.Nov. 26, 1996.

Shin, Ji Hyun et al., Sertindole, a Potent Antagonist at Dopamine D2 Receptors, Induces Autophagy by Increasing Reactive Oxygen Species in SH-SY5Y Neuroblastoma Cells, 2012, Biol Pharm Bull. ;35(7):1069-75.

Singh, Nagendra et al. "Activation of Gpr109a, receptor for niacin and the commensal metabolite butyrate, suppresses colonic inflammation and carcinogenesis." Immunity vol. 40,1 (2014): 128-39. doi:10.1016/j.immuni.2013.12.007.

Smart, Kathleen F. et al., "Analytical platform for metabolome analysis of microbial cells using methyl chloroformate derivatization followed by gas chromatography-mass spectrometry", 2010, Nature Protocols. 10:1709-29, Epub Sep. 30, 2010.

Smith and Waterman, "Comparison of biosequences", Advances in Applied Mathematics, vol. 2, Issue 4, Dec. 1981, pp. 482-489.

Soltani, Mohammad H et al, Microtubule-Associated Protein 2, a Marker of Neuronal Differentiation, Induces Mitotic Defects, Inhibits Growth of Melanoma Cells, and Predicts Metastatic Potential of Cutaneous Melanoma, 2005, Am J Pathol;166:1841-50.

Song CK, et al., Chemotherapy enhances CD8(+) T cell-mediated antitumor immunity induced by vaccination with vaccinia virus. Mol Ther. Aug. 2007;15(8):1558-63. doi: 10.1038/sj.mt.6300221. Epub Jun. 5, 2007. PMID: 17551502.

Song, Jaehwi et al, Increased expression of histone deacetylase 2 is found in human gastric cancer, 2005, APMIS 113: 264-268.

Spengler, Gabriella et al., Thioridazine Induces Apoptosis of Multidrug-resistant Mouse Lymphoma Cells Transfected with the Human ABCB1 and Inhibits the Expression ofP-Glycoprotein, 2011, AnticancerRes. ;31(12):4201-5.

Spor, A. et al., Unravelling the effects of the environment and host genotype on the gut microbiome. Nat Rev Microbiol. Apr. 2011;9(4):279-90. doi: 10.1038/nrmicro2540.

Srutkova, D. et al., Efficiency of PCR-based methods in discriminating *Bifidobacterium longum* ssp. *longum* and *Bifidobacterium longum* ssp. infantis strains of human origin.J Microbiol Methods. Oct. 2011;87(1):10-6. doi: 10.1016/j.mimet.2011.06.014. Epub Jul. 2, 2011.

Strobel, H.J. Basic laboratory culture methods for anaerobic bacteria. Methods Mol Biol. 2009;581:247-61. doi: 10.1007/978-1-60761-214-8_16.

Su, Baowei et al., The effects of IL-6 and TNF-alpha as molecular adjuvants on immune responses to FMDV and maturation of dendritic cells by DNA vaccination. (2008)Vaccine. 26. 5111-22. 10.1016/j.vaccine.2008.03.089.

Tanaka and Sakaguchi, Regulatory T cells in cancer immunotherapy, 2017, Cell Res.;27(1):109-118.

Tanaka, Toshio et al. "IL-6 in inflammation, immunity, and disease." Cold Spring Harbor perspectives in biology vol. 6,10 a016295. Sep. 4, 2014, doi:10.1101/cshperspect.a016295.

Tao, R., de Zoeten, E.,Özkaynak, E. et al., Deacetylase inhibition promotes the generation and function of regulatory T cells. (2007) Nat Med 13, 1299-1307, https://doi.org/10.1038/nm1652.

Terry, Natalie, and Kara Gross Margolis. "Serotonergic Mechanisms Regulating the GI Tract: Experimental Evidence and Therapeutic Relevance." Handbook of experimental pharmacology vol. 239 (2017): 319-342. doi:10.1007/164_2016_103.

Thangaraju, Muthusamy et al., GPR109A Is a G-protein-Coupled Receptor for the Bacterial Fermentation Product Butyrate and Functions as a Tumor Suppressor in Colon (2009). Cancer Res. 67, 9: 2826-2832, Published Online First Mar. 10, 2009; DOI:10.1158/0008-5472.CAN-08-4466.

Toshkov, Ilia A et al. "Mitigation of Radiation-Induced Epithelial Damage by the TLR5 Agonist Entolimod in a Mouse Model of Fractionated Head and Neck Irradiation." Radiation research vol. 187,5 (2017): 570-580. doi:10.1667/RR14514.1.

Tovar-Castillo, LE, et al., Under-expression of VHL and over-expression of HDAC-1, HIF-1alpha, LL-37, and IAP-2 in affected skin biopsies of patients with psoriasis. Int J Dermatol. Mar. 2007;46(3):239-46.doi: 10.1111/j.1365-4632.2006.02962.x. PMID: 17343577.

UniProtKB—P15056 (BRAF_HUMAN), https://www.uniprot.org/uniprot/P15056,accessed Dec. 18, 2020.

Visnyei, Koppany et al., A Molecular Screening Approach to Identify and Characterize Inhibitors of Glioblastoma Stem Cells, 2011,Mol Cancer Ther.;10(10):1818-28.

Vizin, Tjasa, and Janko Kos. "Gamma-enolase: a well-known tumour marker, with a less-known role in cancer." Radiology and oncology vol. 49,3 217-26. Aug. 21, 2015, doi:10.1515/raon-2015-0035.

Walmsley, R S et al. "A simple clinical colitis activity index." Gut vol. 43,1 (1998): 29-32. doi:10.1136/gut.43.1.29.

Wang, Xia, and Yong Lin. "Tumor necrosis factor and cancer, buddies or foes?." Acta pharmacologica Sinica vol. 29,11 (2008): 1275-88. doi: 10.1111/j.1745-7254.2008.00889.x.

Weinberger, Birgit, Adjuvant strategies to improve vaccination of the elderly population, Current Opinion in Pharmacology 2018, 41:34-41.

West and Johnstone, "New and emerging HDAC inhibitors for cancer treatment", The Journal of Clinical Investigation, 2014, 124, 30-39, Epub Jan. 2, 2014.

Written Opinion of the International Searching Authority dated Oct. 4, 2019 for International Application Serial No. PCT/EP2019/062238, (11 pages).

Xie, Songbo et al., Microtubule-Binding Proteins as Promising Biomarkers of Paclitaxel Sensitivity in Cancer Chemotherapy, 2016; Med Res Rev; 36,2: 300-312.

(56) References Cited

OTHER PUBLICATIONS

Yuille Samantha et al., "Human gut bacteria as potent class I histone deacetylase inhibitors in vitro through production of butyric acid and valeric acid", Plos One, vol. 13, No. 7, Jul. 27, 2018(Jul. 27, 2018), XP009508155.

Zhang, Mingming et al., Butyrate inhibits interleukin-17 and generates Tregs to ameliorate colorectal colitis in rats, 2016, BMC Gastroenterol.; 16: 84.

Zhang, Zhenhuan et al., Quantitation of HDAC1 mRNA expression in invasive carcinoma of the breast,(2005), Breast Cancer Research and Treatment, 94: 11-16, DOI10.1007/s10549-005-6001-1.

Zhi, Qiongjie et al. "Predictive and prognostic value of preoperative serum tumor markers in resectable adenosqamous lung carcinoma." Oncotarget vol. 7,40 (2016): 64798-64809. doi:10.18632/oncotarget. 11703.

Zhou, Qing et al. "Program death-1 signaling and regulatory T cells collaborate to resist the function of adoptively transferred cytotoxic T lymphocytes in advanced acute myeloid leukemia." Blood vol. 116,14 (2010): 2484-93. doi:10.1182/blood-2010-03-275446.

Zimmerman Stephan et al, Reduced Body Size and Decreased Intestinal Tumor Rates in HDAC2-Mutant Mice, 2007, Cancer Res 67: 9047-54.

Ahmed, Suaad, "In vitro Characterization of Gut Microbiota-Derived Bacterial Strains With Neurorotective Properties", Frontiers in Cellular Neuroscience, 2019, vol. 13, article 402, pp. 1-17.

Narushima, et al., Characterization of the 17 strains of regulatory T cell-inducing human-derived Clostridia. Gut Microbes Mar. 18, 2014; 5:3, 333-339.

Qin, Meng-Bin et al, Inhibition of SPHK1 Suppresses Phorbol 12-Myristate 13-Acetate-Induced Metastatic Phenotype in Colorectal Cancer HT-29 Cells, Oncology Research Featuring Preclinical and Clinical Cancer Therapeutics, 2011, vol. 19, No. 12, pp. 573-582(10).

Jeon, B., Choi, O., Um, Y. et al. Production of medium-chain carboxylic acids by *Megasphaera* sp. MH with supplemental electron acceptors. Biotechnol Biofuels 9, 129 (2016). https://doi.org/10.1186/S13068-016-0549-3.

Yoshikawa, Shota et al., "Valerate productions by Megasphaera elsdenii isolated from pig feces", Journal of Bioscience and Bioengineering, 2018, vol. 125. No. 5, pp. 519-524.

Hull et al.: HDAC Inhibitors as Epigenetic Regulators of the Immune System: Impacts on Cancer Therapy and Inflammatory Diseases. Biomed Res Int. 2016(8797206):1-16 doi:10.1155/2016/8797206 (2016).

U.S. Appl. No. 17/095,427 Non-Final Office Action dated Mar. 17, 2022.

Zhaoji et al.: Research progress of histone deacetylase inhibitors. J Int Pharm Res. 44(12):1098-1124 (Title and Abstract English) (2017).

* cited by examiner

Level of β3 Tubulin expression
Figure 1A: Immunolabelling and cell imaging
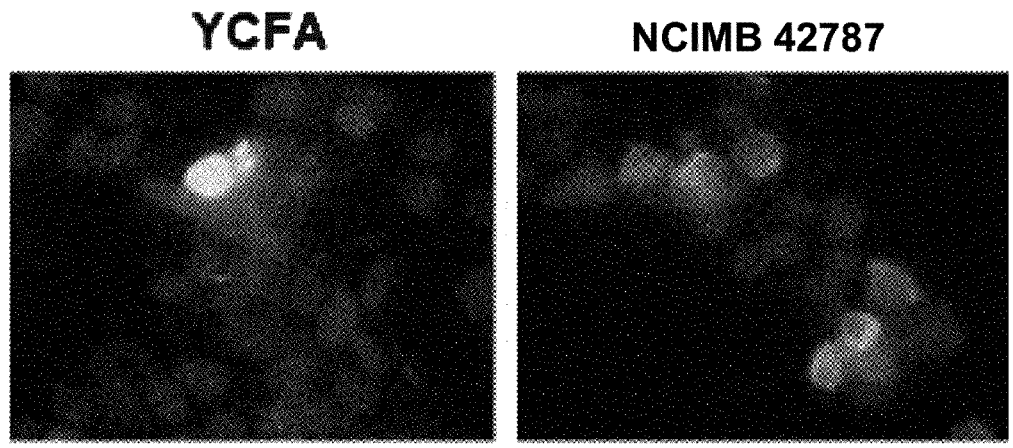
Figure 1B: Immunoblotting
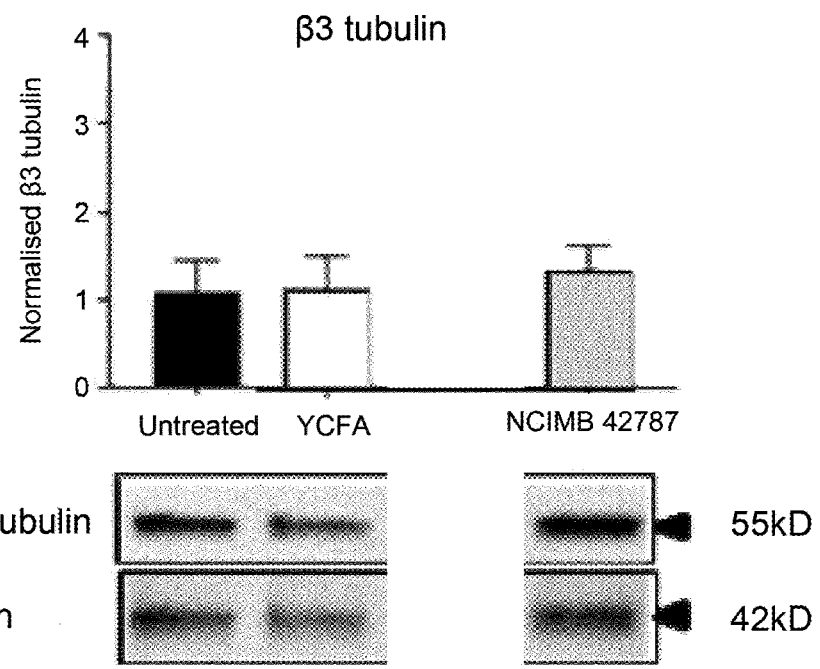

Level of MAP2 expression
Figure 2A: Immunolabelling and cell imaging
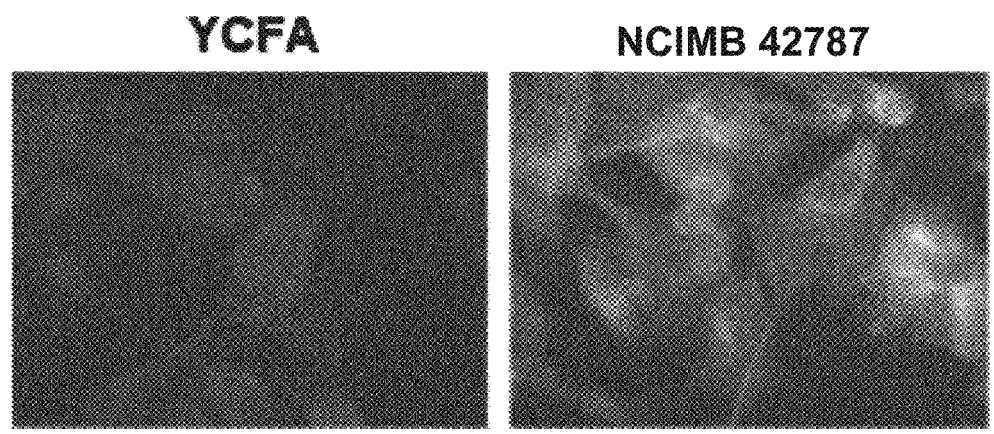
Figure 2B: Immunoblotting
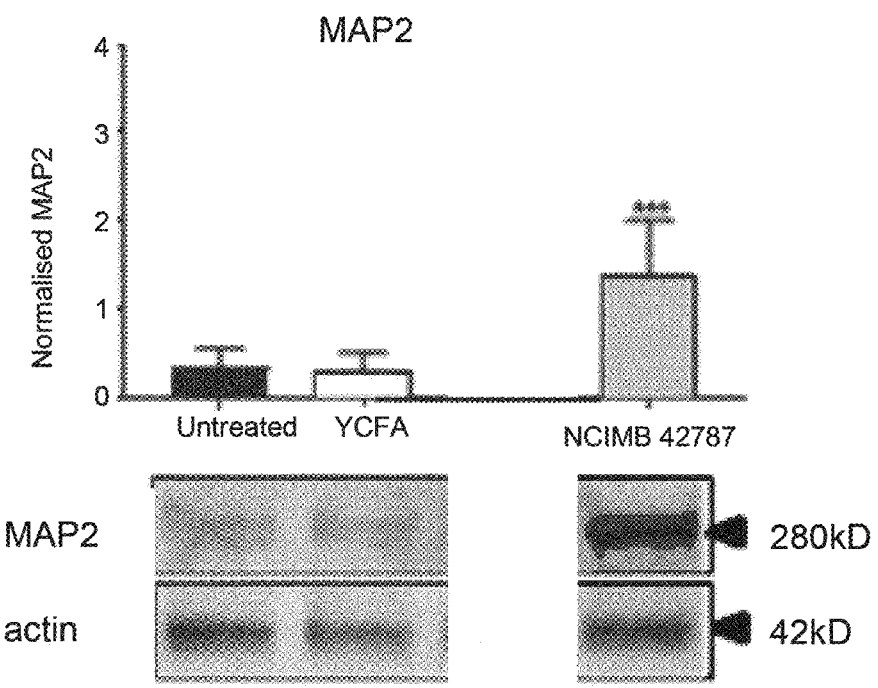

Figure 2C: Fold change in expression
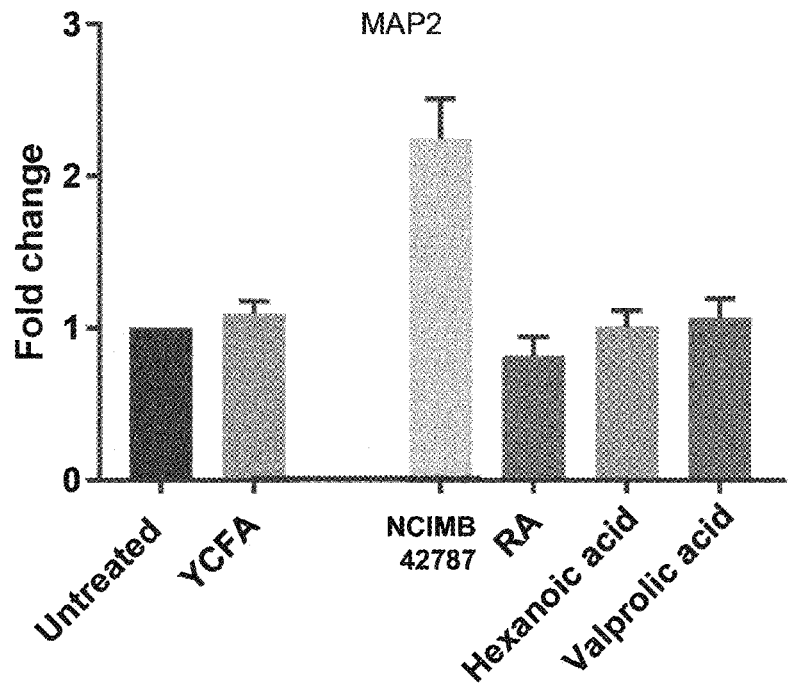
Figure 3: Change in DRD2 expression
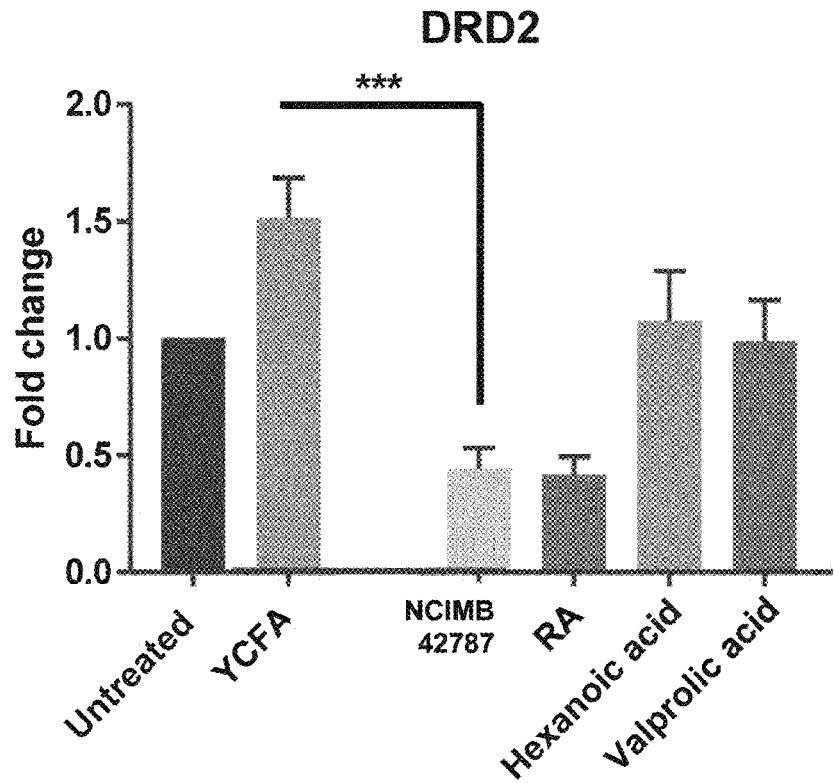

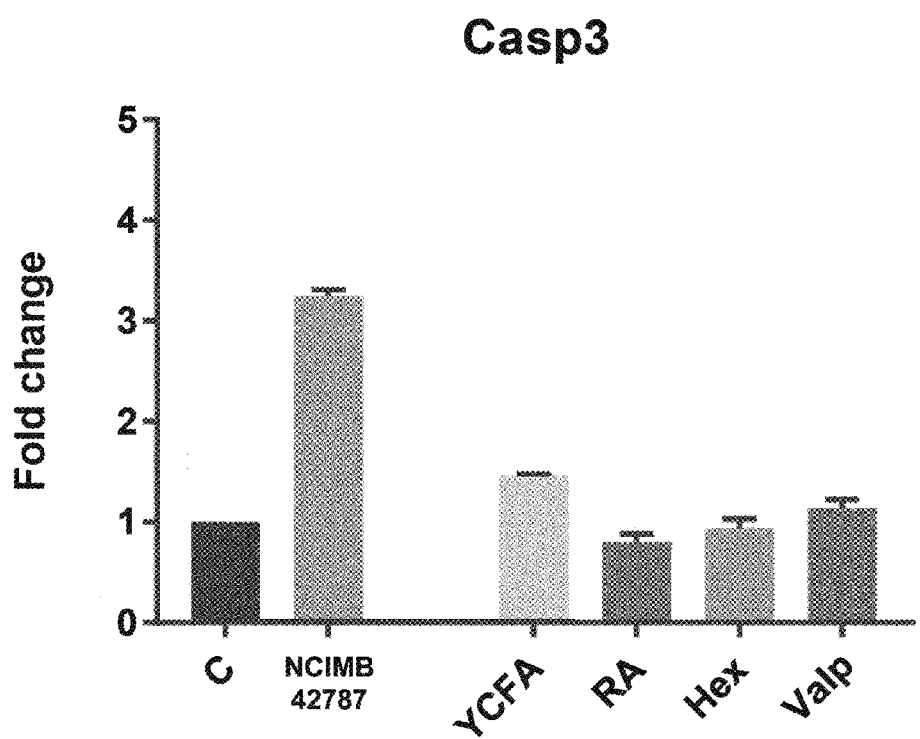
Figure 4: Change in Casp3 expression

Figure 5: Change in cell viability
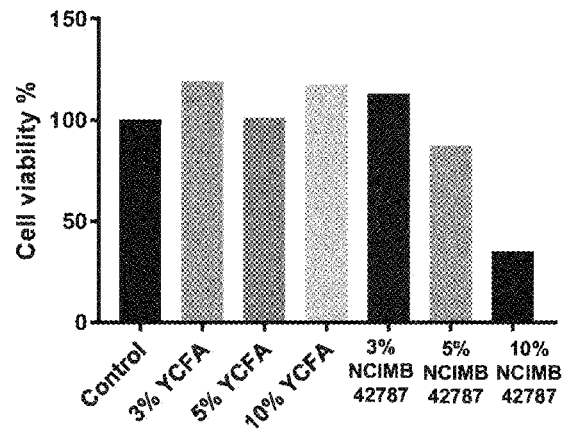
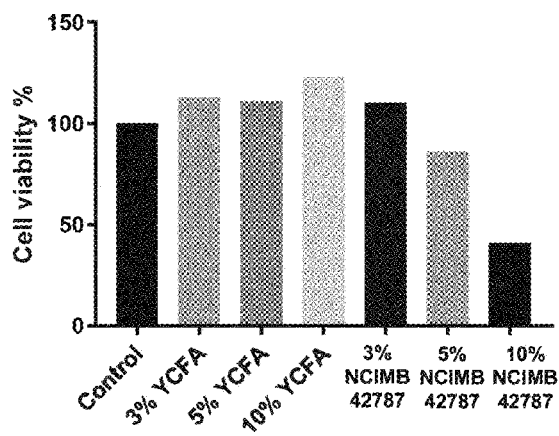
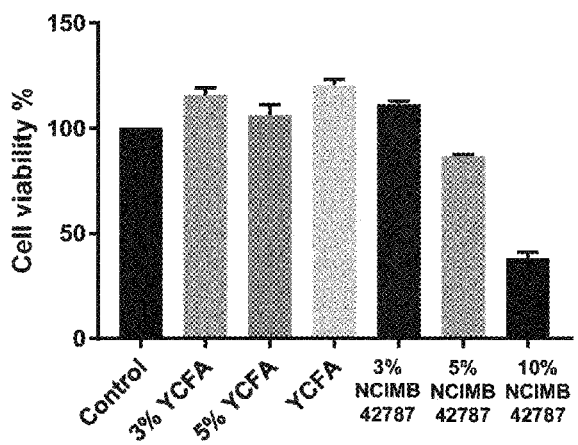

Cell phenotyping

Cell phenotyping

Cell phenotyping

Cytokine analysis

IL-1Beta

TNF-a

IL-23

Cytokine analysis

Cytokine analysis

Flow cytometry analysis

Flow cytometry analysis

Flow cytometry analysis

Figure 9: Secretion of IL-8 from U373
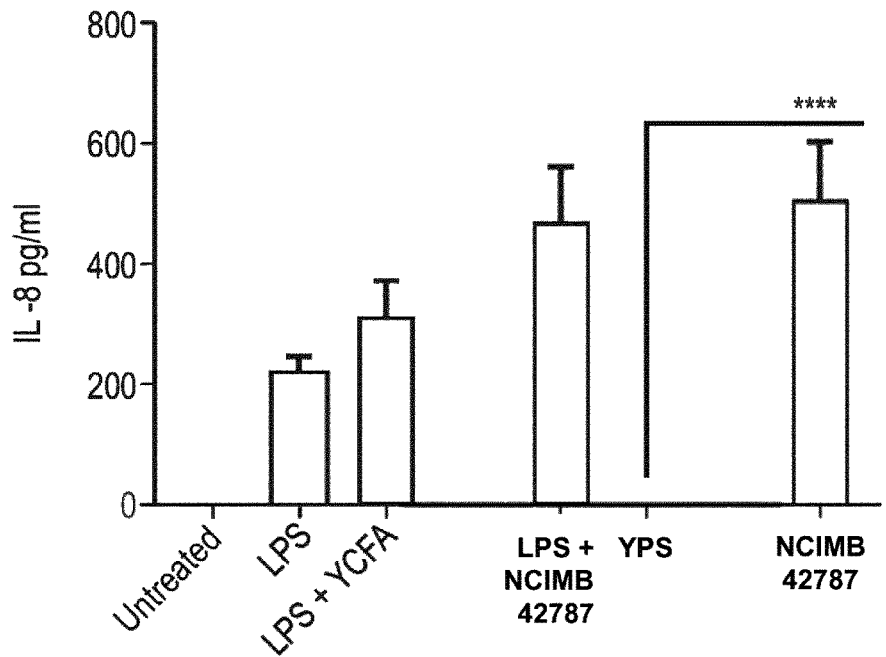
Figure 10: HDAC activity assay
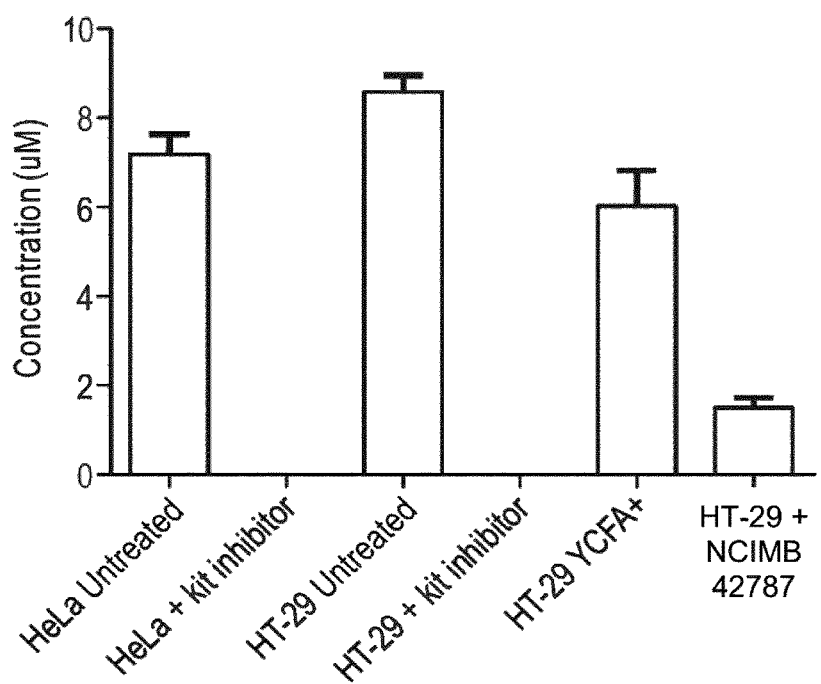

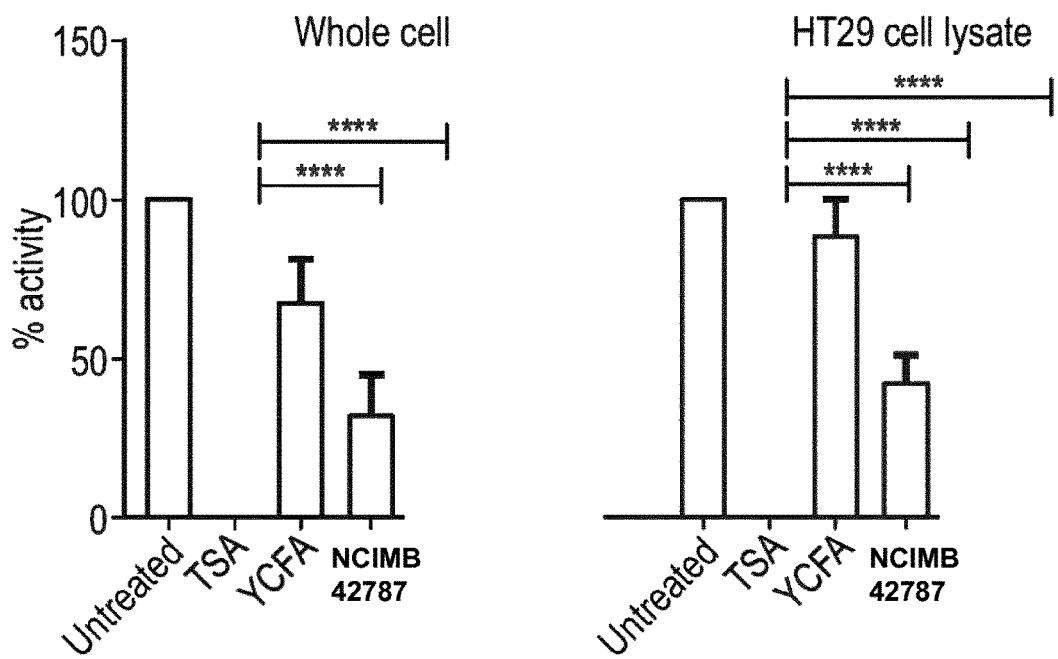
Figure 11A: Strain-induced changes in whole cell and cell lysate HDAC activity
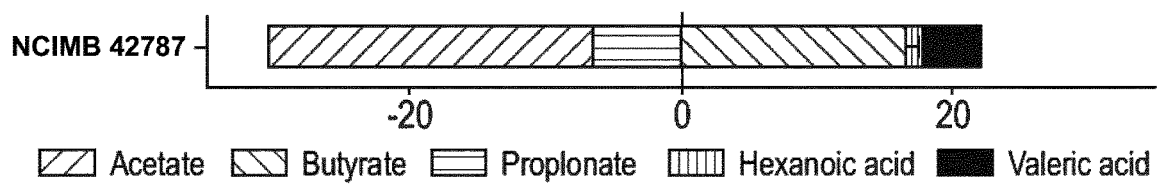
Figure 11B: Metabolite production by strains

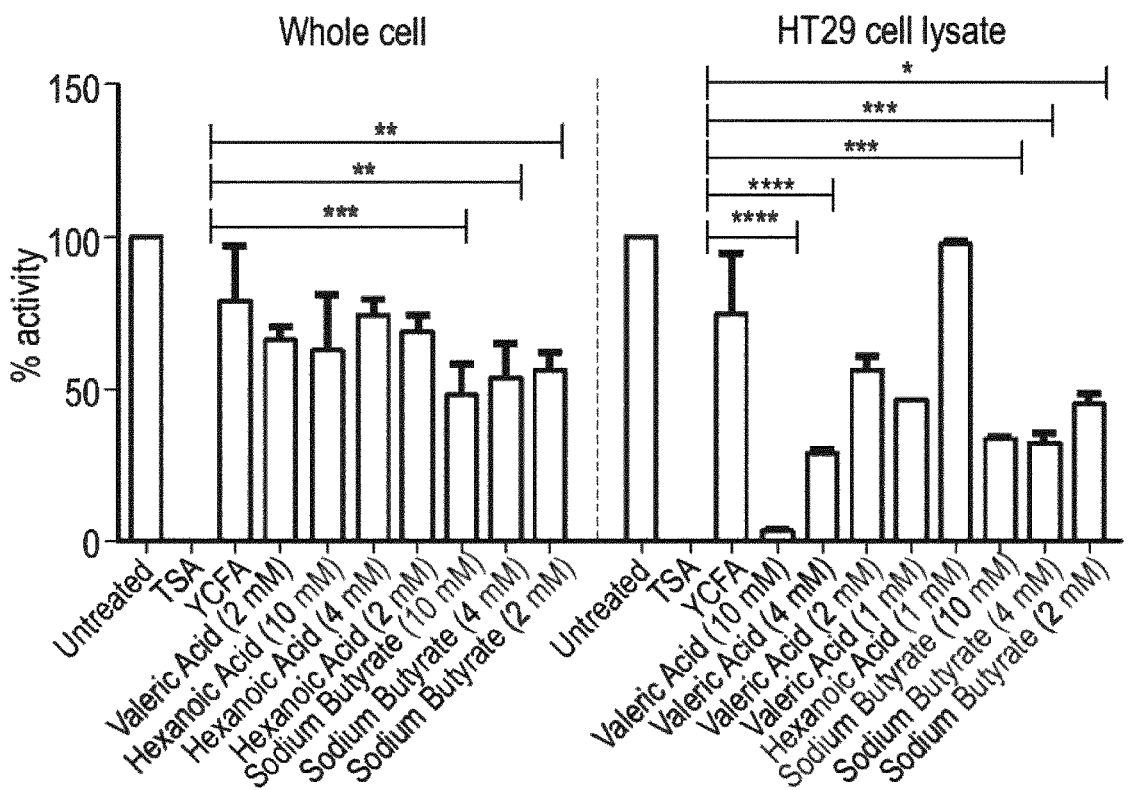
Figure 11C: Acid-induced changes in histone deacetylase activity

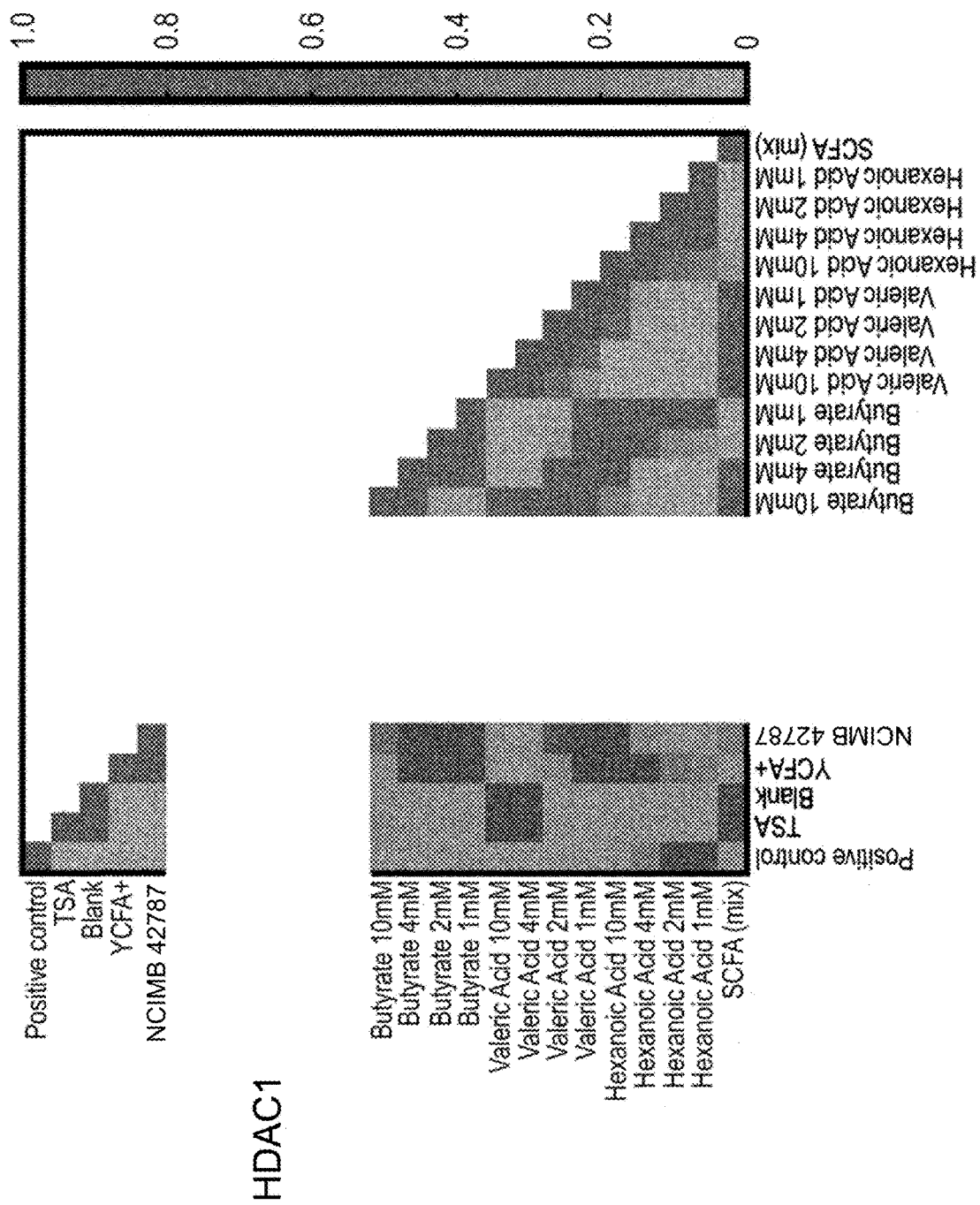
Figure 12A: HDAC1 inhibition

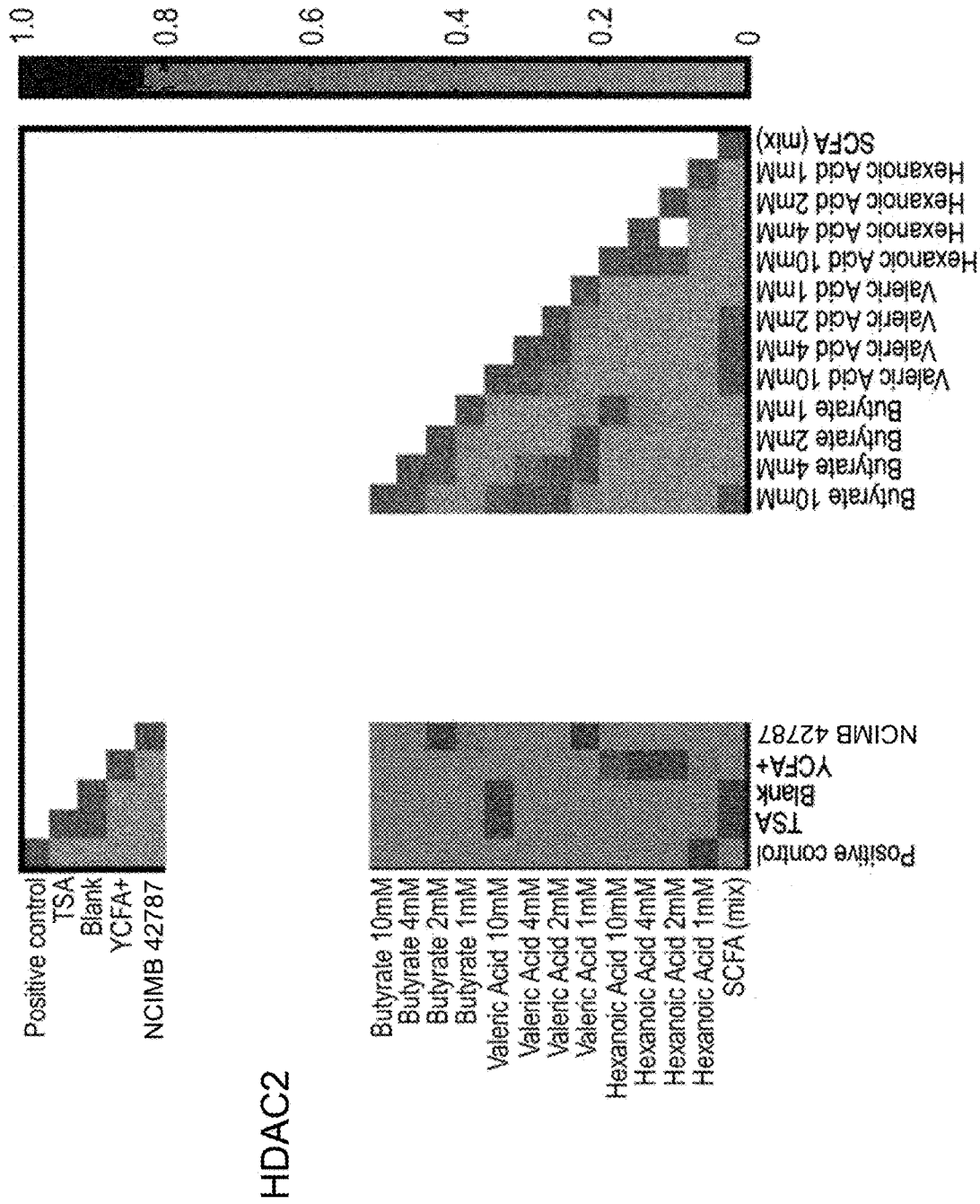
Figure 12B: HDAC2 inhibition

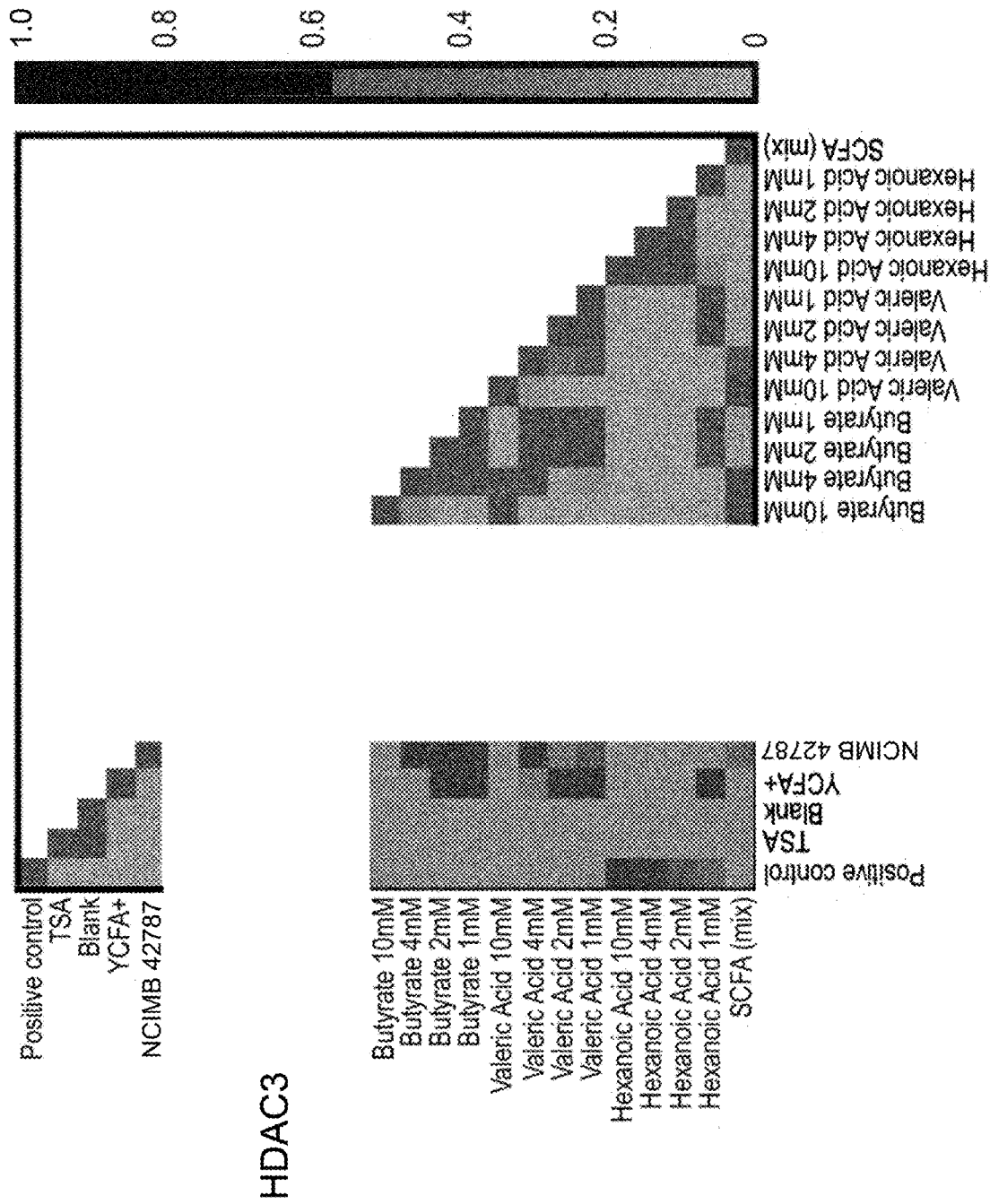
Figure 12C: HDAC3 inhibition

Figure 13A: Inhibition of Class I HDACs
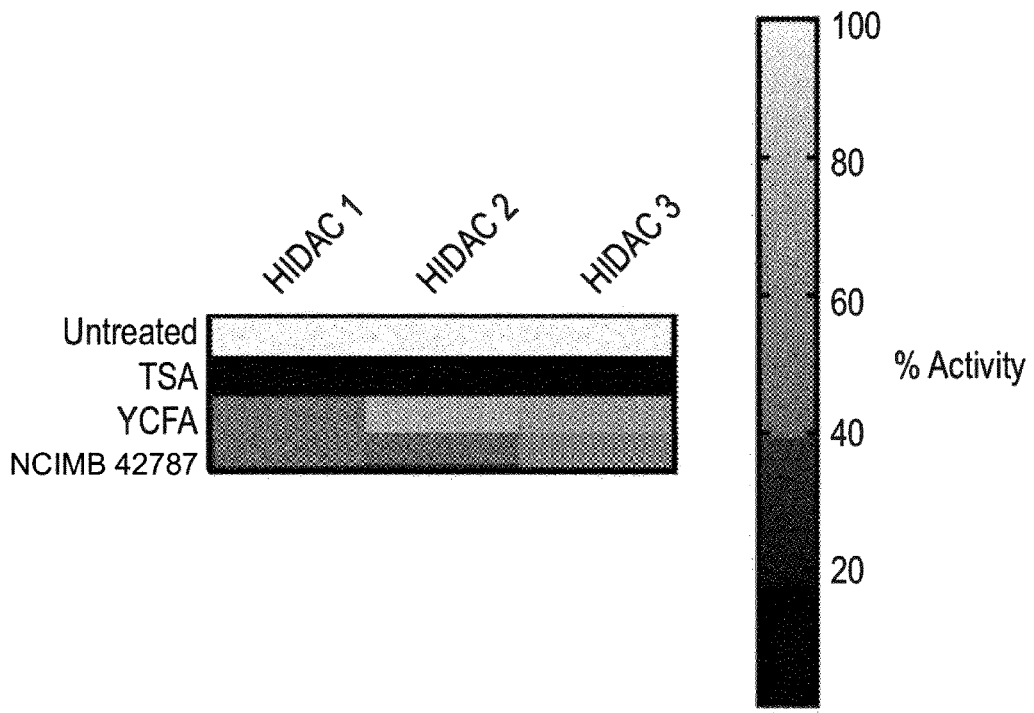
Figure 13B: HDAC1 inhibition
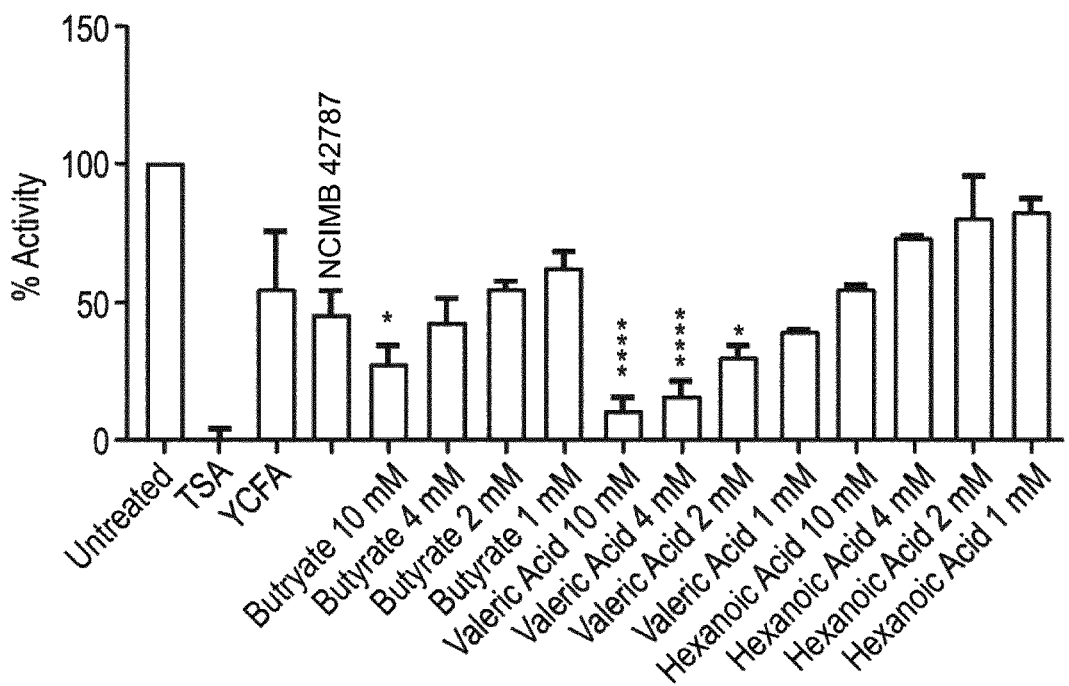

Figure 13C: HDAC2 inhibition
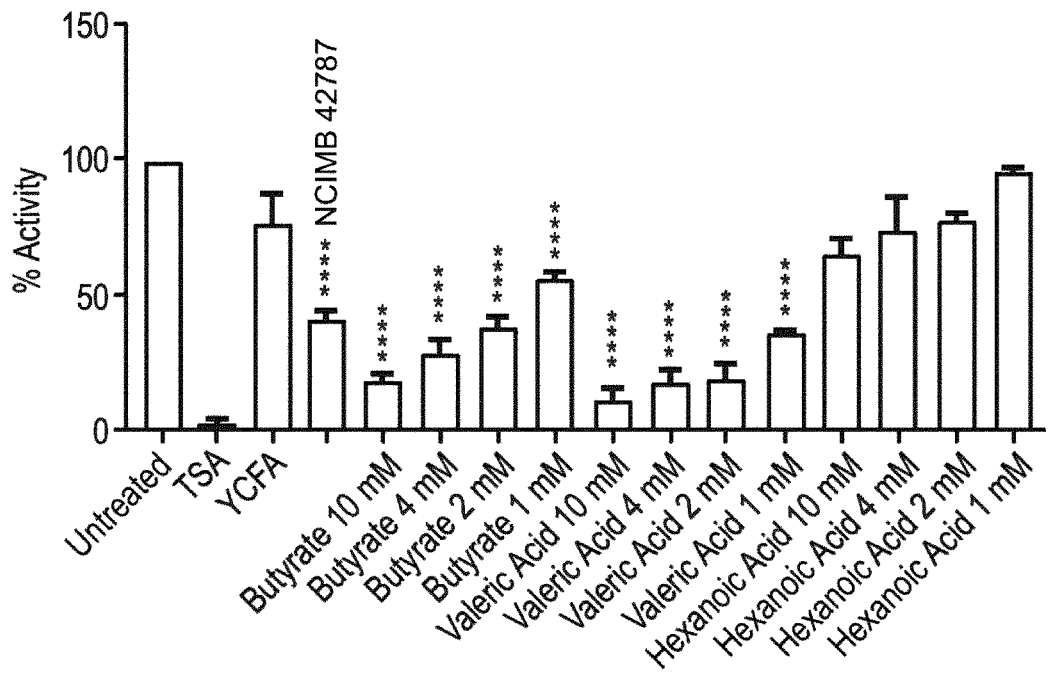
Figure 13D: HDAC3 inhibition
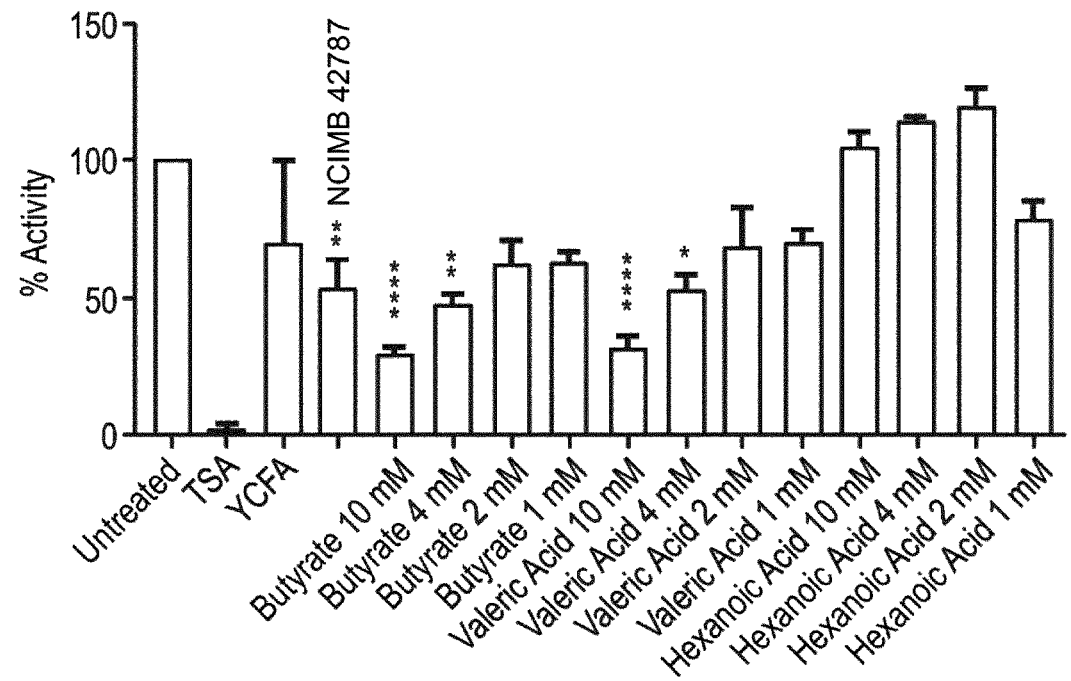

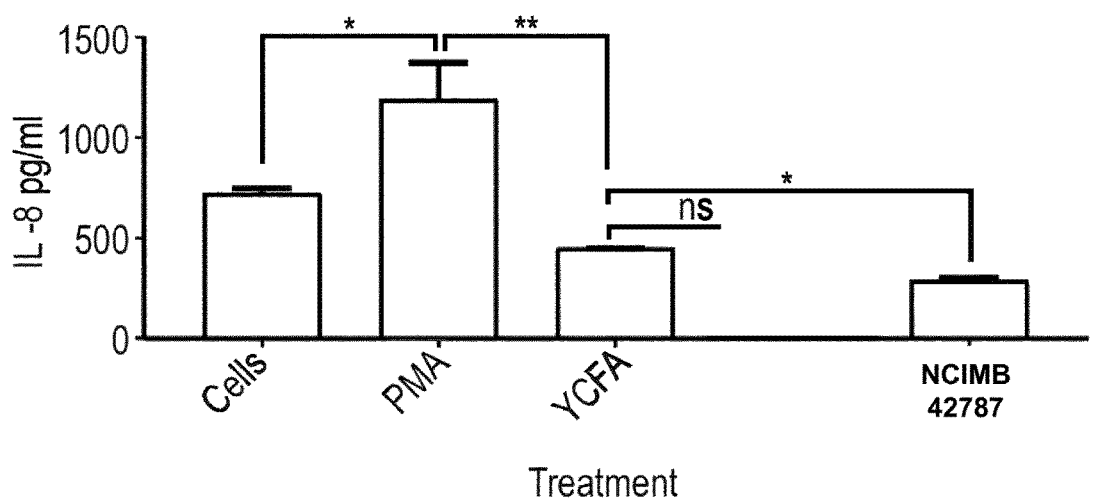
Figure 14A: IL-8 secretion

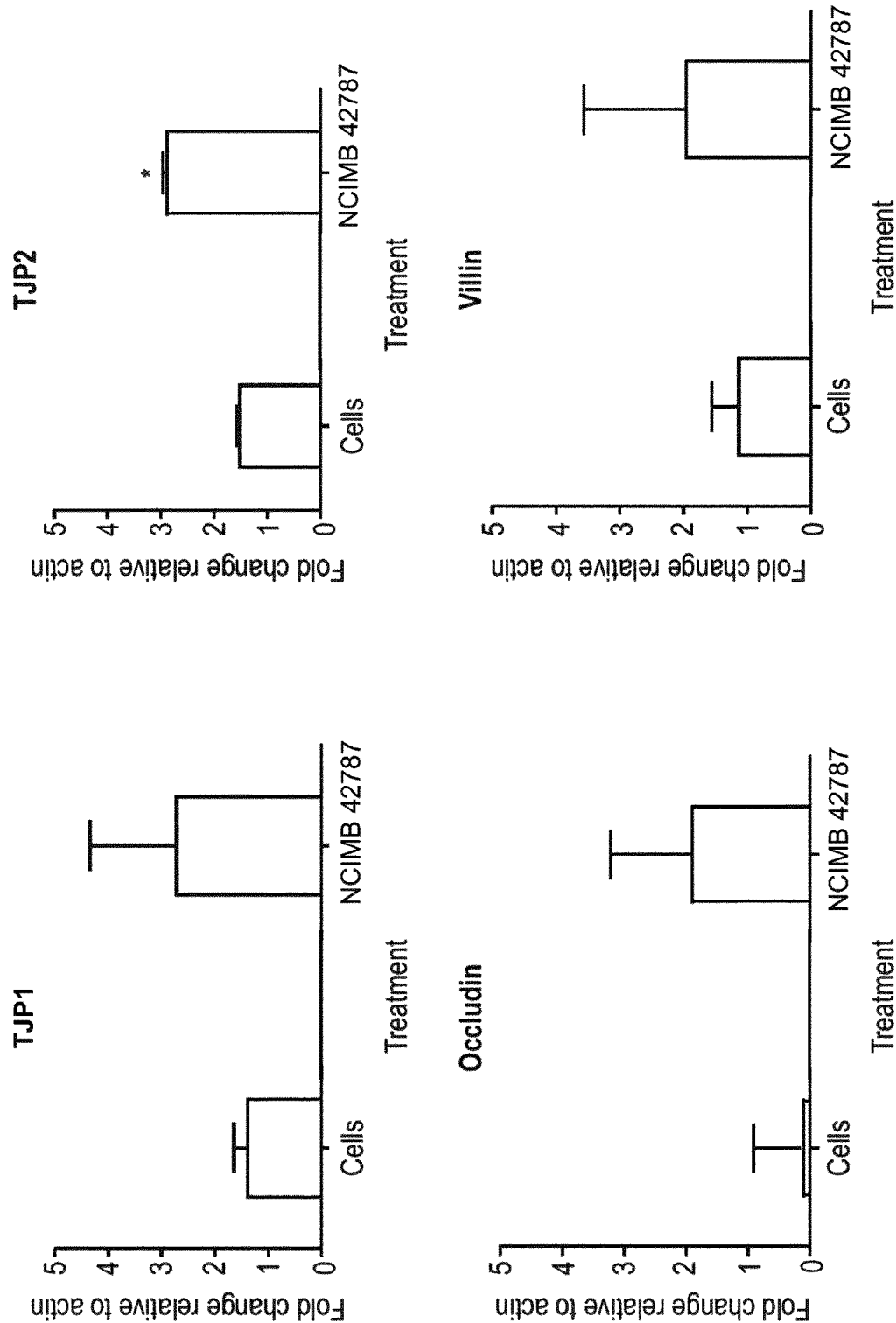
Figure 14B: Occludin, Villin, TJP1 and TJP2 mRNA expression

Figure 14C: TJP1 mRNA expression
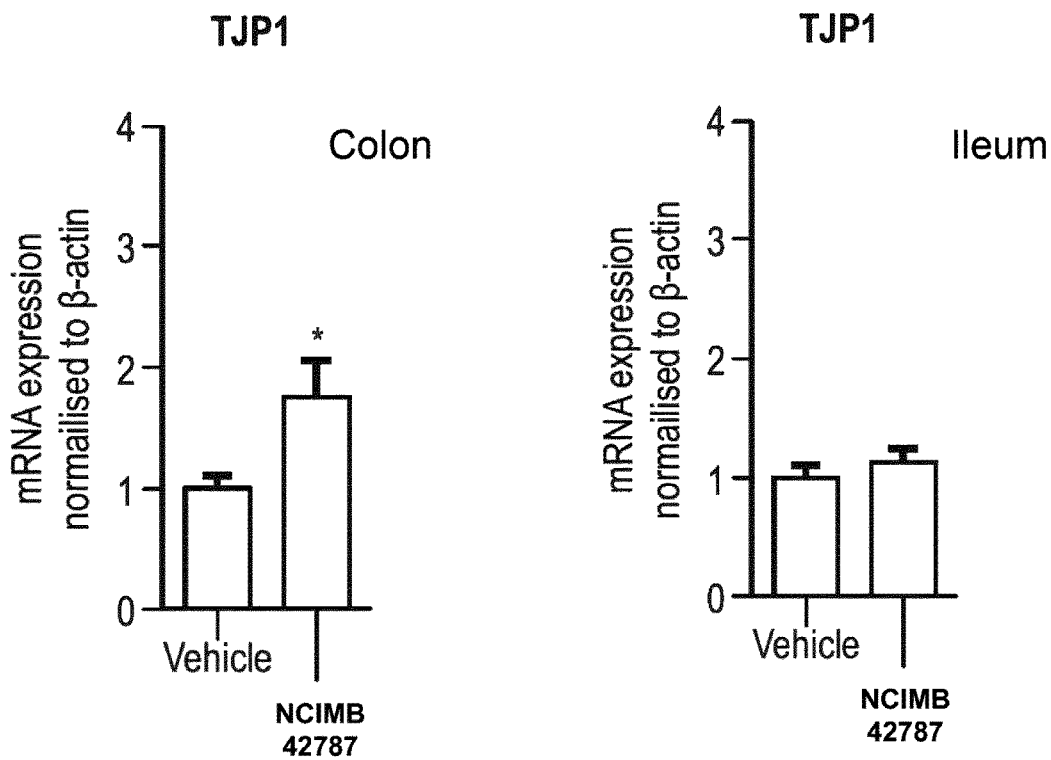
Figure 14D: Occludin mRNA expression
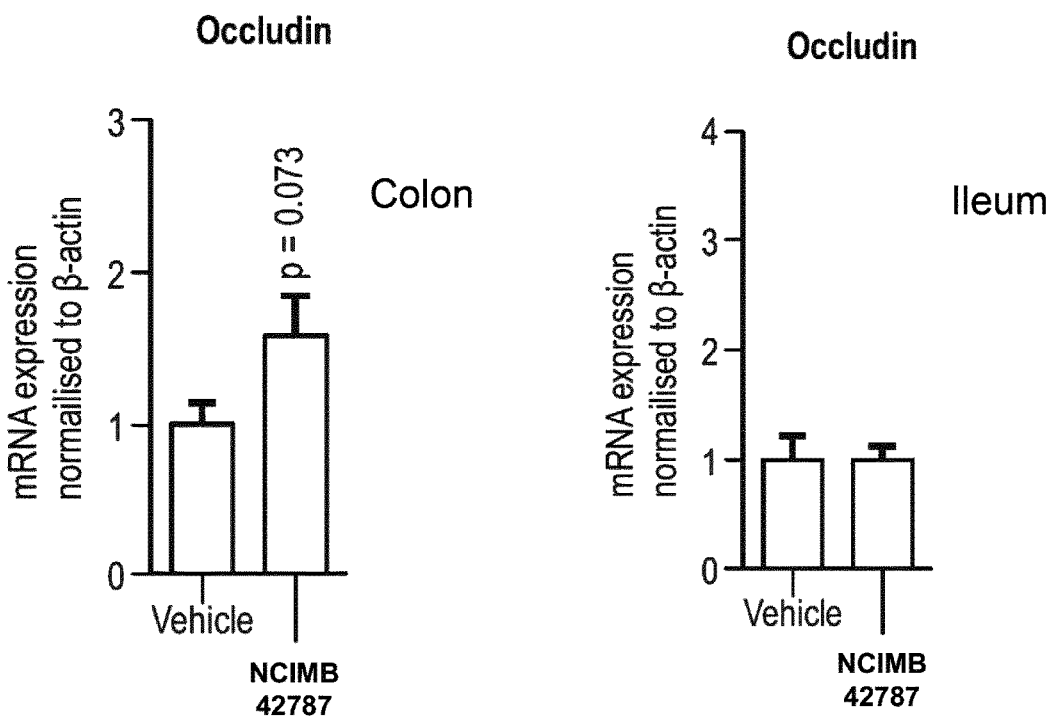

Figure 14E: Permeability in the Ileum
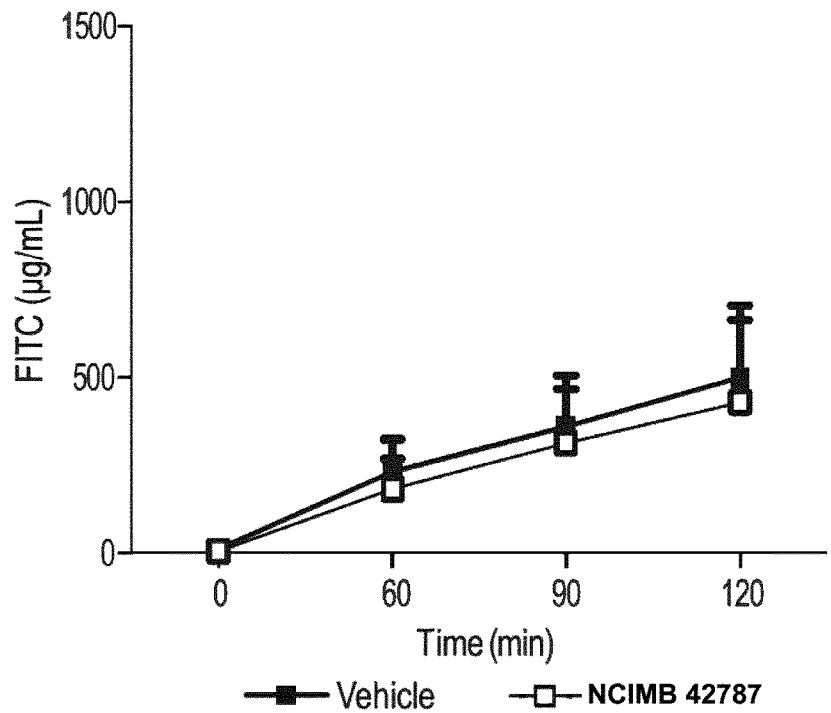
Figure 14F: Permeability in the Colon
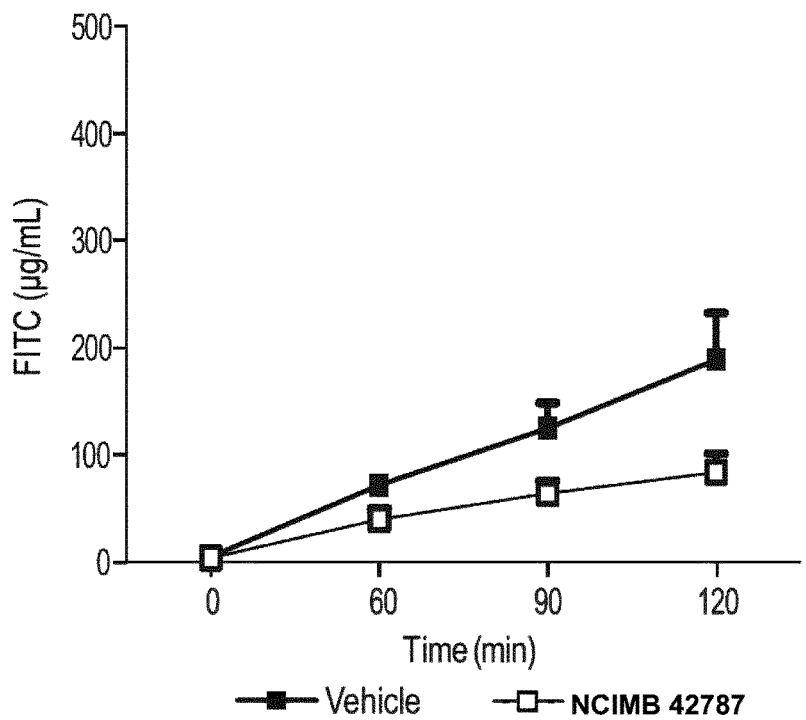

Figure 15: Changes in Hippocampal Expression of TLR-4
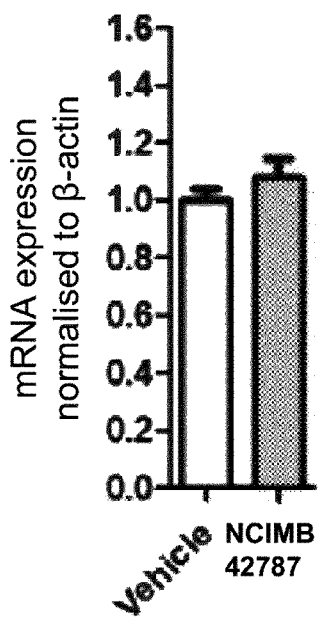
Figure 16: Changes in Hippocampal Expression of TNF-α
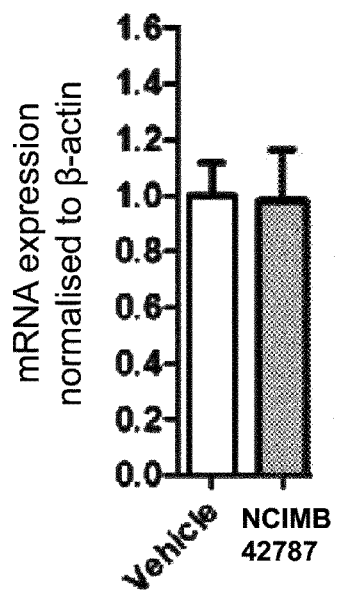
Figure 17: Changes in Hippocampal Expression of IL-1β
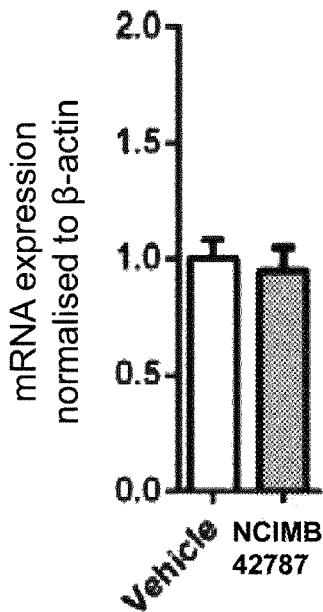
Figure 18: Changes in Hippocampal Expression of IL-6
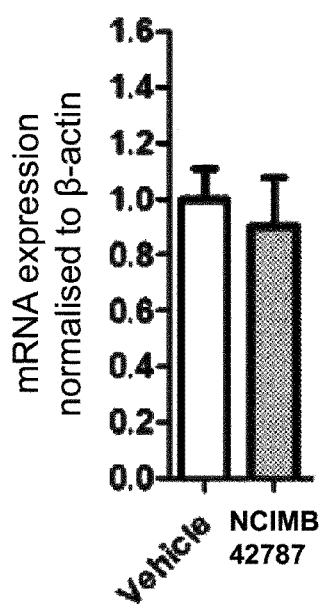

Figure 19: Changes in Hippocampal Expression of CD11b
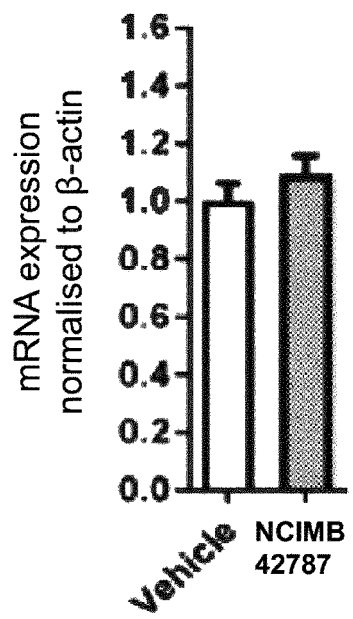
Figure 20: Changes in Amygdala Expression of TLR-4
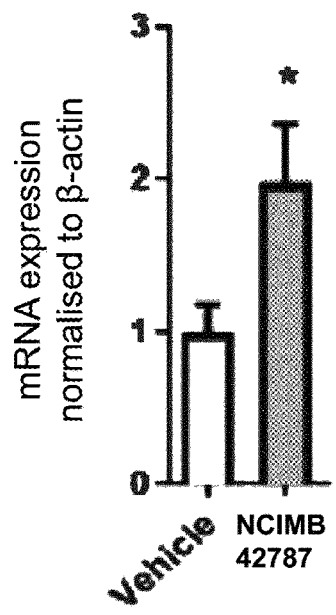
Figure 21: Changes in Amygdala Expression of CD11b
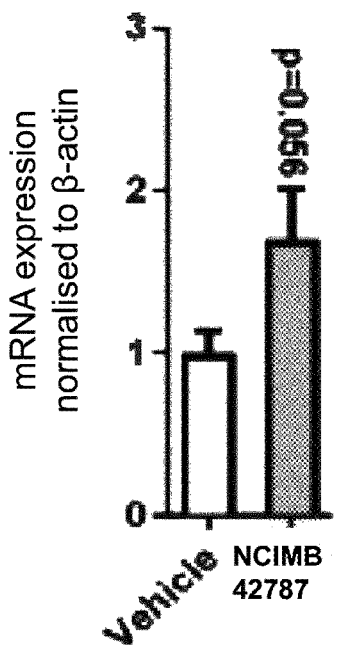
Figure 22: Changes in Amygdala Expression of IL-6
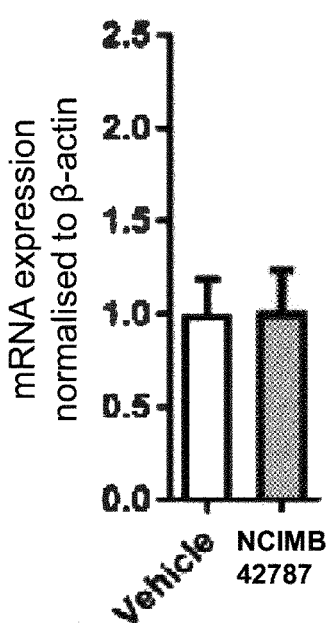

Figure 23: Changes in Prefrontal Cortex expression of TLR-4
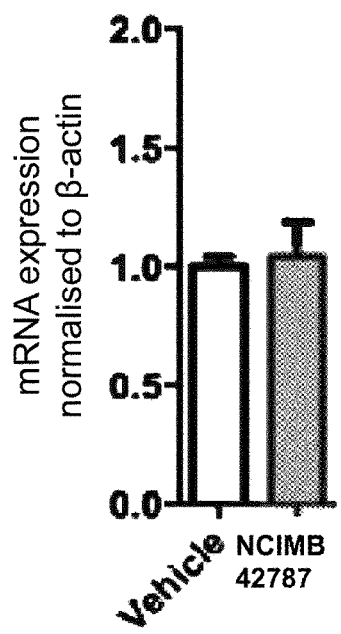
Figure 24: Changes in Prefrontal Cortex expression of CD11b
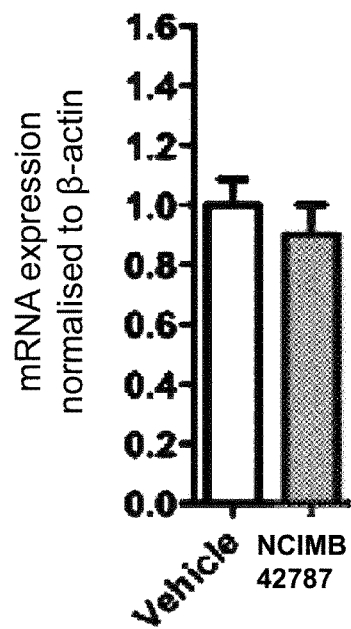
Figure 25: Changes in Prefrontal Cortex expression of IL-6
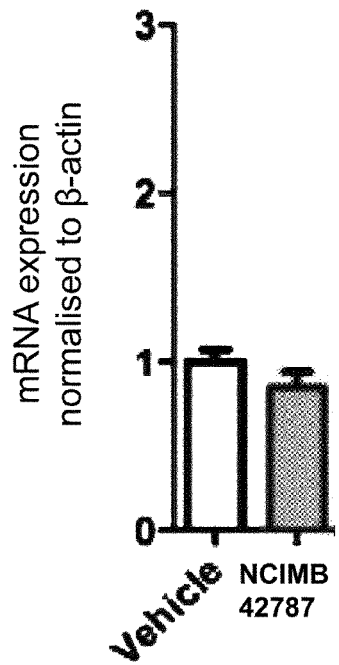

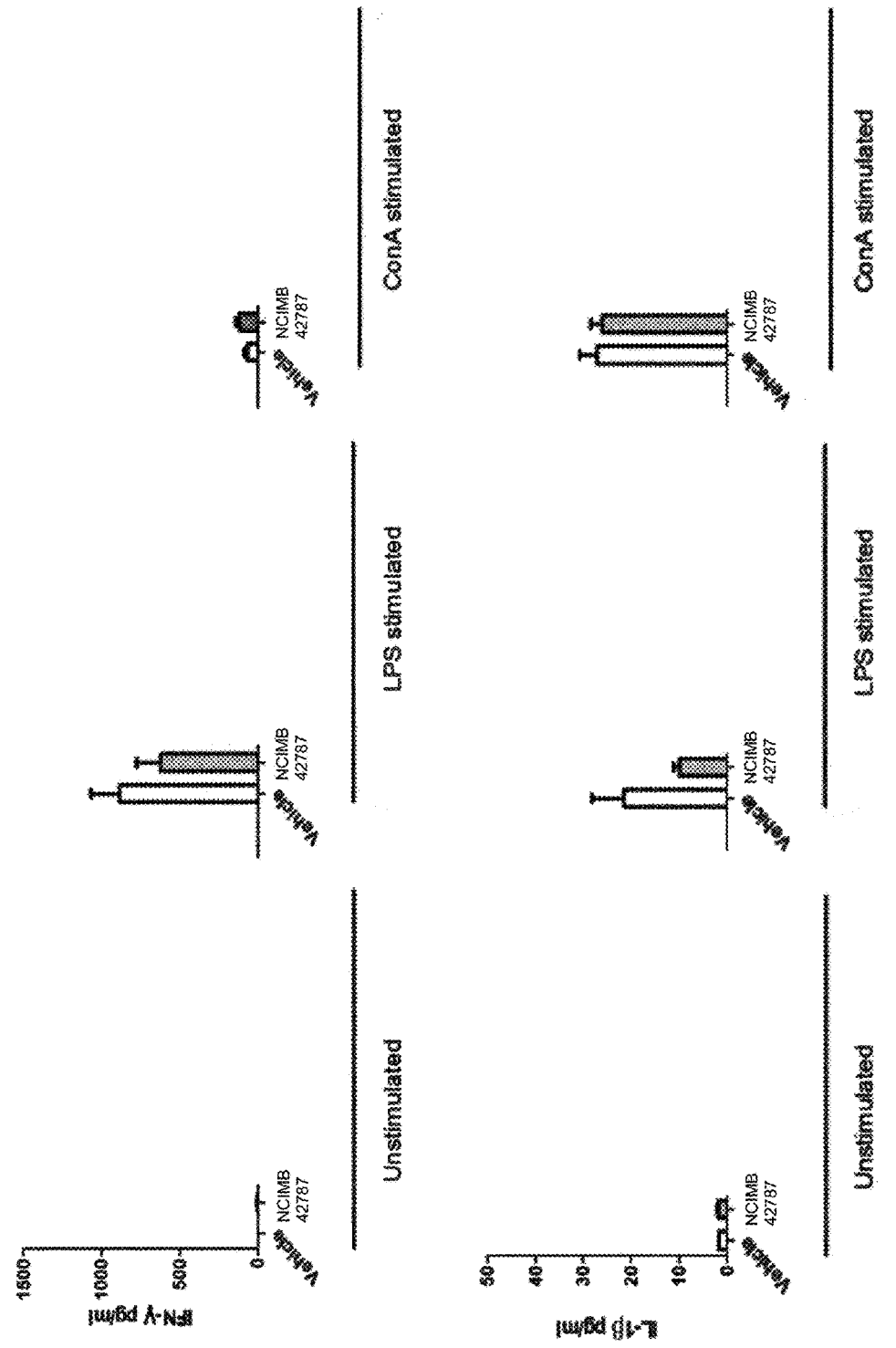
Figure 26: Effect on Interferon-γ production from Splenocytes
Figure 27: Effect on IL-1β production from Splenocytes

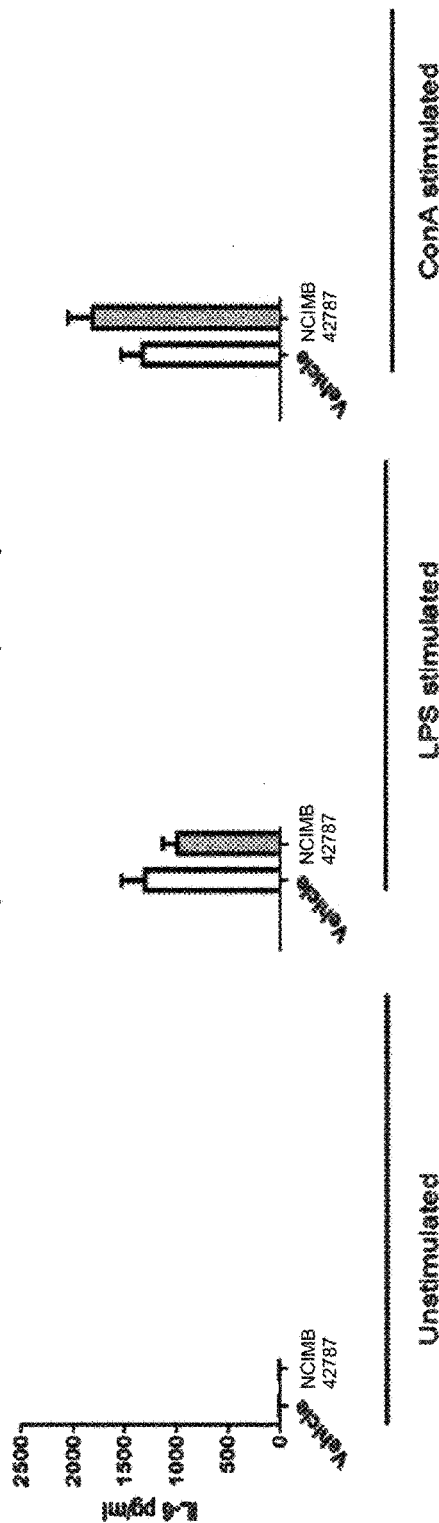
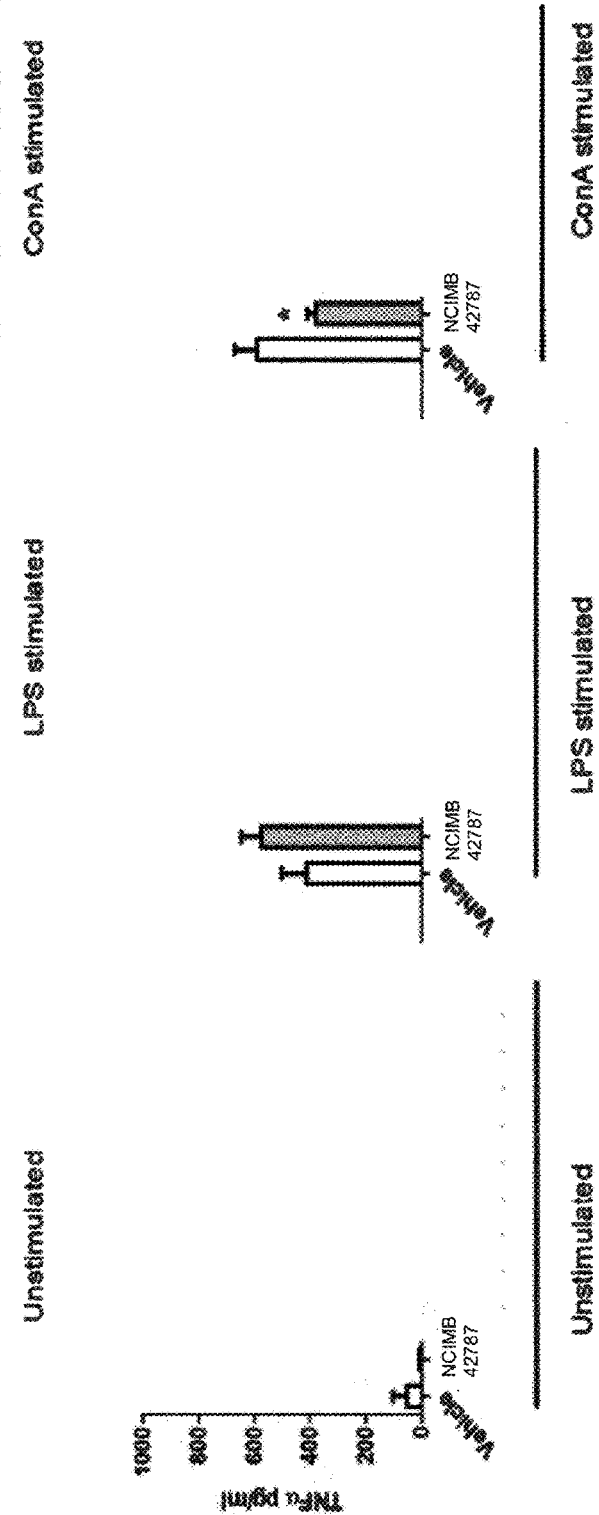

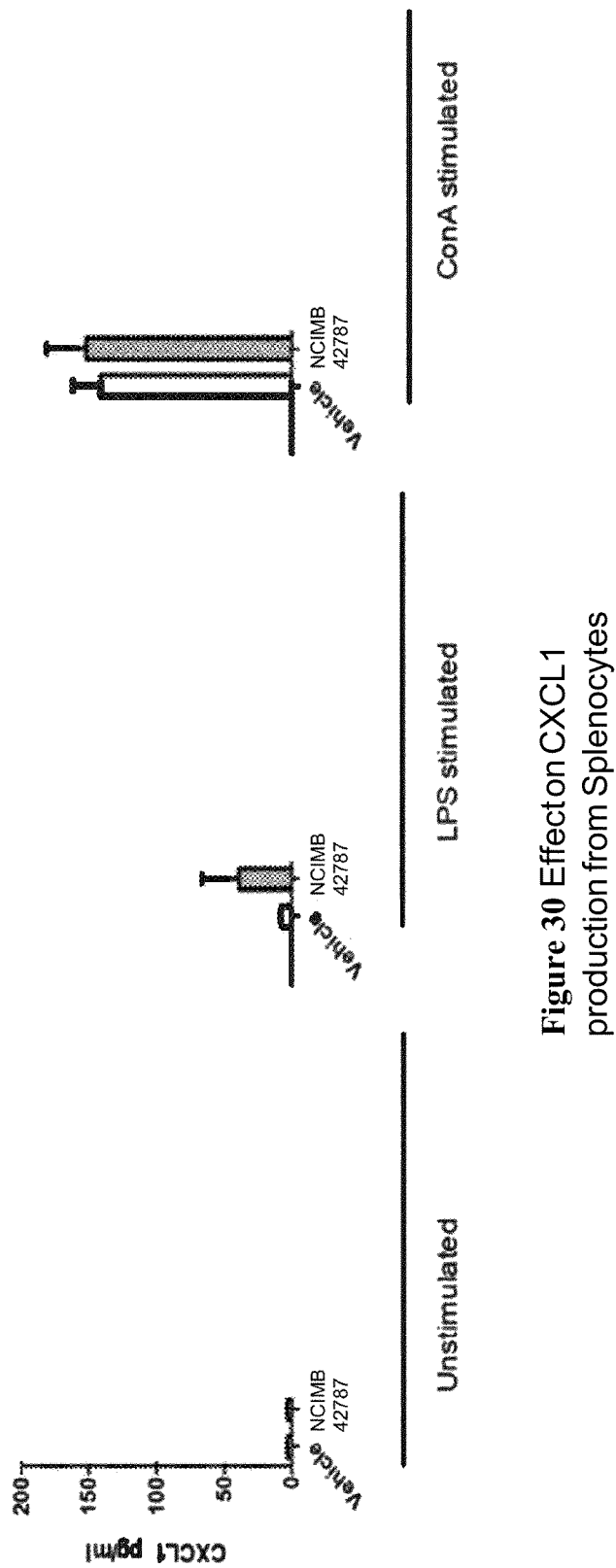
Figure 30 Effect on CXCL1 production from Splenocytes

SKMEL2 cell line - MAP2 gene expression

SKMEL2 cell line – clonogenic survival

SKMEL2 cell line – soft agar growth

SKMEL2 cell line – ERK signalling

SKMEL28 cell line – MAP2 gene expression

SKMEL28 cell line – clonogenic survival

SKMEL28 cell line – soft agar growth

SKMEL28 cell line – ERK signalling

SKMEL31 cell line – MAP2 gene expression

SKMEL31 cell line – clonogenic survival

SKMEL31 cell line – soft agar growth

SKMEL31 cell line – ERK signalling

451Lu cell line – MAP2 gene expression

451Lu cell line – clonogenic survival

451Lu cell line – soft agar growth

451Lu cell line – ERK signalling

HT-29 cell line -- MAP2 gene expression

HT-29 cell line – clonogenic survival

HT-29 cell line – soft agar growth

HT-29 cell line – soft agar growth (colonies after treatments)

HT-29 cell line – ERK signalling

Caco2 cells – GPR109a expression

HMC3 cells

HEK-TLR4 cells

U373 cells

U373 cells

Figure 65
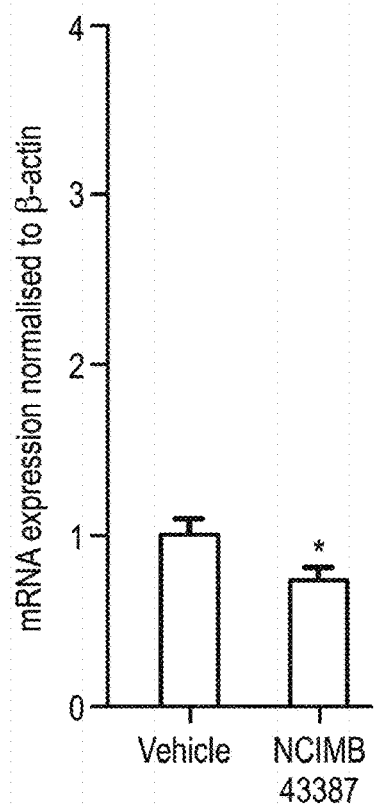
Figure 66
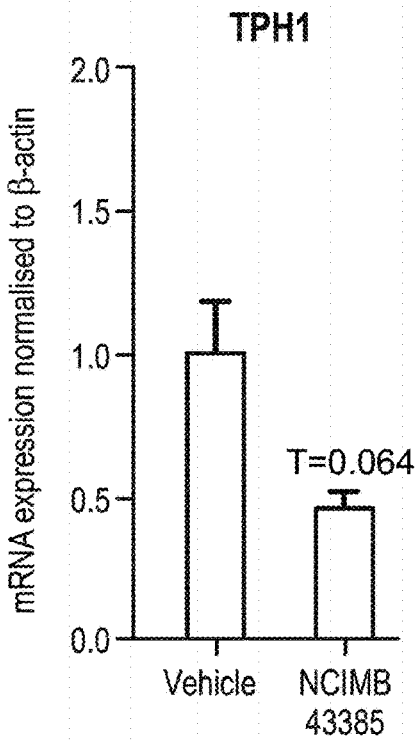 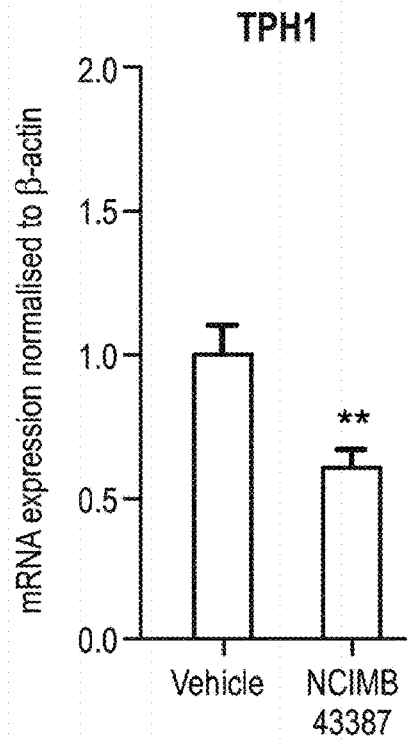

Interferon-γ

Interleukin-6

SEQUENCE LISTING

<160> NUMBER OF SEQ ID NOS: 15

<210> SEQ ID NO 1
<211> LENGTH: 1398
<212> TYPE: DNA
<213> ORGANISM: Megasphaera massiliensis
<220> FEATURE:
<223> OTHER INFORMATION: consensus 16S rRNA sequence for Megasphaera massiliensis strain MRx0029

<400> SEQUENCE: 1

```
tgagaagctt gcttcttatc gattctagtg gcaaacgggt gagtaacgcg taagcaacct      60
gcccttcaga tggggacaac agctggaaac ggctgctaat accgaatacg ttctttccgc     120
cgcatgacgg gaagaagaaa gggaggcctt cgggctttcg ctggaggagg ggcttgcgtc     180
tgattagcta gttggagggg taacggccca ccaaggcgac gatcagtagc cggtctgaga     240
ggatgaacgg ccacattggg actgagacac ggcccagact cctacgggag gcagcagtgg     300
ggaatcttcc gcaatggacg aaagtctgac ggagcaacgc cgcgtgaacg atgacggcct     360
tcgggttgta aagttctgtt atatgggacg aacaggacat cggttaatac ccggtgtctt     420
tgacggtacc gtaagagaaa gccacggcta actacgtgcc agcagccgcg gtaatacgta     480
ggtggcaagc gttgtccgga attattgggc gtaaagggcg cgcaggcggc atcgcaagtc     540
ggtcttaaaa gtgcgggct taaccccgtg aggggaccga aactgtgaag ctcgagtgtc      600
ggagaggaaa gcggaattcc tagtgtagcg gtgaaatgcg tagatattag gaggaacacc     660
agtggcgaaa gcggctttct ggacgacaac tgacgctgag gcgcgaaagc caggggagca     720
aacgggatta gataccccgg tagtcctggc cgtaaacgat ggatactagg tgtaggaggt     780
atcgactcct tctgtgccgg agttaacgca ataagtatcc cgcctgggga gtacggccgc     840
aaggctgaaa ctcaaaggaa ttgacggggg cccgcacaag cggtggagta tgtggtttaa     900
ttcgacgcaa cgcgaagaac cttaccaagc cttgacattg attgctacgg aaagagattt     960
ccggttcttc ttcggaagac aagaaaacag gtggtgcacg gctgtcgtca gctcgtgtcg    1020
tgagatgttg ggttaagtcc cgcaacgagc gcaaccccta tcttctgttg ccagcacctc    1080
gggtggggac tcagaagaga ctgccgcaga caatgcggag gaaggcgggg atgacgtcaa    1140
gtcatcatgc cccttatggc ttgggctaca cacgtactac aatggctctt aatagaggga    1200
agcgaaggag cgatccggag caaacccaa aaacagagtc ccagttcgga ttgcaggctg     1260
caactcgcct gcatgaagca ggaatcgcta gtaatcgcag gtcagcatac tgcggtgaat    1320
acgttcccgg gccttgtaca caccgcccgt cacaccacga aagtcattca cacccgaagc    1380
cggtgaggca accgcaag                                                  1398
```

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      GAPDH forward primer

<400> SEQUENCE: 2

```
ggtatcgtgg aaggactcat g                                                21
```

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      GAPDH reverse primer

<400> SEQUENCE: 3

```
atgccagtga gcttcccgtt c                                                21
```

-continued

```
<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      MAP2 forward primer

<400> SEQUENCE: 4
ctcagcaccg ctaacagagg                                                   20

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      MAP2 reverse primer

<400> SEQUENCE: 5
cattggcgct tctctcctc                                                    19

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      GPR109a forward primer

<400> SEQUENCE: 6
atgttggcta tgaaccgcca g                                                 21

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      GPR109a reverse primer

<400> SEQUENCE: 7
gctgctgtcc gattggaga                                                    19

<210> SEQ ID NO 8
<211> LENGTH: 1409
<212> TYPE: DNA
<213> ORGANISM: Megasphaera sp.
<220> FEATURE:
<223> OTHER INFORMATION: consensus 16S rRNA sequence for the Megasphaera
      strain deposited under accession number NCIMB 43385

<400> SEQUENCE: 8
ggctggttcc ttgcggttgc ctcaccggct tcgggtgtga atgactttcg tggtgtgacg      60
ggcggtgtgt acaaggcccg ggaacgtatt caccgcagta tgctgacctg cgattactag    120
cgattcctgc ttcatgcagg cgagttgcag cctgcaatcc gaactgggac tctgttttg     180 gggtttgctc cggatcgctc cttcgcttcc ctctattaag agccattgta gtacgtgtgt    240
agcccaagcc ataaggggca tgatgacttg acgtcatccc cgccttcctc cgcattgtct    300
gcggcagtct cttctgagtc cccacccctta gtgctggcaa cagaagatag gggttgcgct    360
cgttgcggga cttaacccaa catctcacga cacgagctga cgacagccgt gcaccacctg    420
ttttcttgtc ttccgaagaa gaaccggaaa tctctttccg tagcaatcaa tgtcaaggct    480
tggtaaggtt cttcgcgttg cgtcgaatta aaccacatac tccaccgctt gtgcgggccc    540
```

```
ccgtcaattc ctttgagttt cagccttgcg gccgtactcc ccaggcggga tacttattgc    600
gttaactccg gcacagaagg agtcgatacc tcctacacct agtatccatc gtttacggcc    660
aggactaccg gggtatctaa tcccgtttgc tccctggct ttcgcgcctc agcgtcagtt     720
gtcgtccaga aagccgcttt cgccactggt gttcctccta atatctacgc atttcaccgc    780
tacactagga attccgcttt cctctccgac actcgagctt cacagtttcg gtcccctcac    840
ggggttaagc cccgcacttt taagaccgac ttgcgatgcc gctgcgcgc ctttacgcc      900 caataattcc ggacaacgct tgccacctac gtattaccgc ggctgctggc acgtagttag    960
ccgtggcttt ctcttacggt accgtcaggg ataacgggta ttgaccgcta tcctgttcgt    1020
cccatataac agaactttac aacccgaagg ccgtcatcgt tcacgcggcg ttgctccgtc    1080
agactttcgt ccattgcgga agattcccca ctgctgcctc ccgtaggagt ctgggccgtg    1140
tctcagtccc aatgtggccg ttcatcctct cagaccggct actgatcgtc gccttggtgg    1200
gccgttaccc ctccaactag ctaatcagac gcaagcccct cctccagcga aagcccgaag    1260
gcctcccttt cttcatcccg tcatgcggcg gaaagaacgt attcggtatt agcagccgtt    1320
tccagctgtt gtccccatct gaagggcagg ttgcttacgc gttactcacc cgtttgccac    1380
tcgaattgat aagaagcaag cttctcatc                                     1409

<210> SEQ ID NO 9
<211> LENGTH: 1415
<212> TYPE: DNA
<213> ORGANISM: Megasphaera massilliensis
<220> FEATURE:
<223> OTHER INFORMATION: consensus 16S rRNA sequence for the Megasphaera
      massilliensis strain deposited under accession number NCIMB 43388

<400> SEQUENCE: 9
ggctggttcc ttgcggttgc ctcaccggct tcgggtgtga atgactttcg tggtgtgacg    60
ggcggtgtgt acaaggcccg ggaacgtatt caccgcagta tgctgacctg cgattactag    120
cgattcctgc ttcatgcagg cgagttgcag cctgcaatcc gaactgggac tctgttttg    180 gggtttgctc cggatcgctc cttcgcttcc ctctattaag agccattgta gtacgtgtgt    240
agcccaagcc ataaggggca tgatgacttg acgtcatccc cgccttcctc cgcattgtct    300
gcggcagtct cttctgagtc cccaccgag gtgctggcaa cagaagatag gggttgcgct    360
cgttgcggga cttaacccaa catctcacga cacgagctga cgacagccgt gcaccacctg    420
tttctttgtc ttccgaagaa gaaccggaaa tctctttccg tagcaatcaa tgtcaaggct    480
tggtaaggtt cttcgcgttg cgtcgaatta aaccacatac tccaccgctt gtgcgggccc    540
ccgtcaattc ctttgagttt cagccttgcg gccgtactcc ccaggcggga tacttattgc    600
gttaactccg gcacagaagg agtcgatacc tcctacacct agtatccatc gtttacggcc    660
aggactaccg gggtatctaa tcccgtttgc tccctggct ttcgcgcctc agcgtcagtt     720
gtcgtccaga aagccgcttt cgccactggt gttcctccta atatctacgc atttcaccgc    780
tacactagga attccgcttt cctctccgac actcgagctt cacagtttcg gtcccctcac    840
ggggttaagc cccgcacttt taagaccgac ttgcgatgcc gctgcgcgc ctttacgcc      900 caataattcc ggacaacgct tgccacctac gtattaccgc ggctgctggc acgtagttag    960
ccgtggcttt ctcttacggt accgtcaaag acaccgggta ttaaccgatg tcctgttcgt    1020
cccatataac agaactttac aacccgaagg ccgtcatcgt tcacgcggcg ttgctccgtc    1080
agactttcgt ccattgcgga agattcccca ctgctgcctc ccgtaggagt ctgggccgtg    1140
```

```
tctcagtccc aatgtggccg ttcatcctct cagaccggct actgatcgtc gccttggtgg    1200
gccgttaccc ctccaactag ctaatcagac gcaagcccct cctccagcga aagcccgaag    1260
gcctcccttt cttcttcccg tcatgcggcg gaaagaacgt attcggtatt agcagccgtt    1320
tccagctgtt gtcccatct gaagggcagg ttgcttacgc gttactcacc cgtttgccac     1380
tagaatcgat aagaagcaag cttctcatgt cttct                               1415
```

<210> SEQ ID NO 10
<211> LENGTH: 1433
<212> TYPE: DNA
<213> ORGANISM: Megasphaera massilliensis
<220> FEATURE:
<223> OTHER INFORMATION: consensus 16S rRNA sequence for the Megasphaera
      massilliensis strain deposited under accession number NCIMB 43389

<400> SEQUENCE: 10

```
cgacggctgg ttccttgcgg ttgcctcacc ggcttcgggt gtgaatgact ttcgtggtgt      60
gacgggcggt gtgtacaagg cccgggaacg tattcaccgc agtatgctga cctgcgatta    120
ctagcgattc ctgcttcatg caggcgagtt gcagcctgca atccgaactg ggactctgtt    180
tttgggtttt gctccggatc gctccttcgc ttccctctat taagagccat tgtagtacgt    240
gtgtagccca agccataagg ggcatgatga cttgacgtca tccccgcctt cctccgcatt    300
gtctgcggca gtctcttctg agtccccacc cgaggtgctg gcaacagaag ataggggttg    360
cgctcgttgc gggacttaac ccaacatctc acgacacgag ctgacgacag ccgtgcacca    420
cctgttttct tgtcttccga agaagaaccg gaaatctctt ccgtagcaa tcaatgtcaa     480 ggcttggtaa ggttcttcgc gttgcgtcga attaaaccac atactccacc gcttgtgcgg    540
gcccccgtca attcctttga gtttcagcct tgcggccgta ctcccaggc gggatactta     600 ttgcgttaac tccggcacag aaggagtcga tacctcctac acctagtatc catcgtttac    660
ggccaggact accggggtat ctaatcccgt ttgctcccct ggctttcgcg cctcagcgtc    720
agttgtcgtc cagaaagccg ctttcgccac tggtgttcct cctaatatct acgcatttca    780
ccgctacact aggaattccg cttttcctctc cgacactcga gcttcacagt ttcggtcccc    840
tcacggggtt aagccccgca cttttaagac cgacttgcga tgccgcctgc gcgcccttta    900
cgcccaataa ttccggacaa cgcttgccac ctacgtatta ccgcggctgc tggcacgtag    960
ttagccgtgg ctttctctta cggtaccgtc aaagacaccg ggtattaacc gatgccctgt    1020
tcgtcccata taacagaact ttacaaccccg aaggccgtca tcgttcacgc ggcgttgctc    1080
cgtcagactt tcgtccattg cggaagattc cccactgctg cctcccgtag gagtctgggc    1140
cgtgtctcag tcccaatgtg gccgttcatc ctctcagacc ggctactgat cgtcgccttg    1200
gtgggccgtt acccctccaa ccagctaatc agacgcaagc ccctcctcca gcgaaagccc    1260
gaaggcctcc ctttcttctt cccgtcatgc ggcggaaaga acgtattcgg tattagcagc    1320
cgtttccagc tgttgtcccc atctgaaggg caggttgctt acgcgttact cacccgtttg    1380
ccactagaat cgataagaag caagcttctc atgtcttctc gttcgacttg cat           1433
```

<210> SEQ ID NO 11
<211> LENGTH: 1431
<212> TYPE: DNA
<213> ORGANISM: Megasphaera sp.
<220> FEATURE:
<223> OTHER INFORMATION: consensus 16S rRNA sequence for the Megasphaera
      strain deposited under accession number NCIMB 43386

<400> SEQUENCE: 11

```
cgacggctgg ttccttgcgg ttgcctcacc ggcttcgggt gtgaatgact ttcgtggtgt    60
gacgggcggt gtgtacaagg cccgggaacg tattcaccgc agtatgctga cctgcgatta   120
ctagcgattc ctgcttcatg caggcgagtt gcagcctgca atccgaactg ggactctgtt   180
tttggggttt gctccggatc gctccttcgc ttccctctat taagagccat tgtagtacgt   240
gtgtagccca agccataagg ggcatgatga cttgacgtca tccccgcctt cctccgcatt   300
gtctgcggca gtctcttctg agtccccacc cttagtgctg gcaacagaag ataggggttg   360
cgctcgttgc gggacttaac ccaacatctc acgacacgag ctgacgacag ccgtgcacca   420
cctgttttct tgtcttccga agaagaaccg gaaatctctt tccgtagcaa tcaatgtcaa   480
ggcttggtaa ggttcttcgc gttgcgtcga attaaaccac atactccacc gcttgtgcgg   540
gccccgtca attcctttga gtttcagcct tgcggccgta ctccccaggc gggatactta    600
ttgcgttaac tccggcacag aaggagtcga tacctcctac acctagtatc catcgtttac   660
ggccaggact accggggtat ctaatcccgt ttgctcccct ggctttcgcg cctcagcgtc   720
agttgtcgtc cagaaagccg cttttcgcca ctggtgttcct cctaatatct acgcatttca   780
ccgctacact aggaattccg cttttcctctc cgacactcga gcttcacagt ttcggtcccc   840
tcacggggtt aagccccgca ctttttaagac cgacttgcga tgccgcctgc gcgcccttta   900
cgcccaataa ttccggacaa cgcttgccac ctacgtatta ccgcggctgc tggcacgtag   960
ttagccgtgg ctttctctta cggtaccgtc agggataacg ggtattgacc gctatcctgt  1020
tcgtcccata taacagaact ttacaacccg aaggccgtca tcgttcacgc ggcgttgctc  1080
cgtcagactt tcgtccattg cggaagattc cccactgctg cctcccgtag gagtctgggc  1140
cgtgtctcag tcccaatgtg gccgttcatc ctctcagacc ggctactgat cgtcgccttg  1200
gtgggccgtt accctccaa ctagctaatc agacgcaagc ccctcctcca gcgaaagccc   1260
gaaggcctcc ctttcttcat cccgtcatgc ggcggaaaga acgtattcgg tattagcagc  1320
cgtttccagc tgttgtcccc atctgaaggg caggttgctt acgcgttact cacccgtttg  1380
ccactcgaat tgataagaag caagcttctc atctcttctc gttcgactgc a           1431
```

<210> SEQ ID NO 12
<211> LENGTH: 1434
<212> TYPE: DNA
<213> ORGANISM: Megasphaera sp.
<220> FEATURE:
<223> OTHER INFORMATION: consensus 16S rRNA sequence for the Megasphaera
      strain deposited under accession number NCIMB 43387

<400> SEQUENCE: 12

```
tcgaacggct ggttccttgc ggttgcctca ccggcttcgg gtgtgaatga ctttcgtggt    60
gtgacgggcg gtgtgtacaa ggcccgggaa cgtattcacc gcagtatgct gacctgcgat   120
tactagcgat tcctgcttca tgcaggcgag ttgcagcctg caatccgaac tgggactctg   180
tttttggggt tgctccgga tcgctccttc gcttccctct attaagagcc attgtagtac   240
gtgtgtagcc caagccataa ggggcatgat gacttgacgt catccccgcc ttcctccgca   300
ttgtctgcgg cagtctcttc tgagtcccca cccttagtgc tggcaacaga ataggggt   360
tgcgctcgtt gcgggactta acccaacatc tcacgacacg agctgacgac agccgtgcac   420
cacctgtttt cttgtcttcc gaagaagaac cggaaatctc tttccgtagc aatcaatgtc   480
aaggcttggt aaggttcttc gcgttgcgtc gaattaaacc acatactcca ccgcttgtgc   540
```

```
gggcccccgt caattcctttt gagtttcagc cttgcggccg tactccccag gcgggatact    600
tattgcgtta actccggcac agaaggagtc gatacctcct acacctagta tccatcgttt    660
acggccagga ctaccggggt atctaatccc gtttgctccc ctggctttcg cgcctcagcg    720
tcagttgtcg tccagaaagc cgctttcgcc actggtgttc ctcctaatat ctacgcattt    780
caccgctaca ctaggaattc cgctttcctc tccgacactc gagcttcaca gtttcggtcc    840
cctcacgggg ttaagccccg cacttttaag accgacttgc gatgccgcct gcgcgccctt    900
tacgcccaat aattccggac aacgcttgcc acctacgtat taccgcggct gctggcacgt    960
agttagccgt ggctttctct tacggtaccg tcagggataa cgggtattga ccgctatcct   1020
gttcgtccca tataacagaa ctttacaacc cgaaggccgt catcgttcac gcggcgttgc   1080
tccgtcagac tttcgtccat tgcggaagat tccccactgc tgcctcccgt aggagtctgg   1140
gccgtgtctc agtcccaatg tggccgttca tcctctcaga ccggctactg atcgtcgcct   1200
tggtgggccg ttaccctcc aactagctaa tcagacgcaa gccctcctc cagcgaaagc    1260 ccgaaggcct cccttcttc atcccgtcat gcggcggaaa gaacgtattc ggtattagca   1320
gccgtttcca gctgttgtcc ccatctgaag ggcaggttgc ttacgcgtta ctcacccgtt   1380
tgccactcga attgataaga agcaagcttc tcatctcttc tcgttcgact tgca         1434
```

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      neuron specific enolase (NSE)/enolase 2 qPCR forward primer

<400> SEQUENCE: 13
ccctgtatcg taagaacggt                                                  20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      neuron specific enolase (NSE)/enolase 2 qPCR reverse primer

<400> SEQUENCE: 14
gccaccattg atcacgttga                                                  20

<210> SEQ ID NO 15
<211> LENGTH: 15
<212> TYPE: DNA
<213> ORGANISM: Artificial Sequence
<220> FEATURE:
<223> OTHER INFORMATION: Description of Artificial Sequence: Synthetic
      biotype identifying repetitive sequence

<400> SEQUENCE: 15
gtggtggtgg tggtg                                                       15

COMPOSITIONS COMPRISING BACTERIAL STRAINS

CROSS-REFERENCE

This application is a continuation of International Application No. PCT/EP2019/062238, filed May 13, 2019, which claims the benefit of Great Britain Application No. 1820256.4, filed Dec. 12, 2018, Great Britain Application No. 1820264.8, filed Dec. 12, 2018, Great Britain Application No. 1817642.0, filed Oct. 29, 2018, Great Britain Application No. 1813460.1, filed Aug. 17, 2018, Great Britain Application No. 1810386.1, filed Jun. 25, 2018, European Patent Application No. 18178136.0, filed Jun. 15, 2018 and European Application No. 18171893.3, filed May 11, 2018; all of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Oct. 5, 2020, is named 56708_738_301 SL.txt and is 15,238 bytes in size.

TECHNICAL FIELD

This invention is in the field of compositions comprising bacterial strains isolated from the mammalian digestive tract and the use of such compositions in the treatment of disease, in particular cancer, and in particular in stimulating the immune system in the treatment of disease.

BACKGROUND TO THE INVENTION

The human intestine is thought to be sterile in utero, but it is exposed to a large variety of maternal and environmental microbes immediately after birth. Thereafter, a dynamic period of microbial colonization and succession occurs, which is influenced by factors such as delivery mode, environment, diet and host genotype, all of which impact upon the composition of the gut microbiota, particularly during early life. Subsequently, the microbiota stabilizes and becomes adult-like [1]. The human gut microbiota contains more than 500-1000 different phylotypes belonging essentially to two major bacterial divisions, the Bacteroidetes and the Firmicutes [2]. The successful symbiotic relationships arising from bacterial colonization of the human gut have yielded a wide variety of metabolic, structural, protective and other beneficial functions. The enhanced metabolic activities of the colonized gut ensure that otherwise indigestible dietary components are degraded with release of by-products providing an important nutrient source for the host. Similarly, the immunological importance of the gut microbiota is well-recognized and is exemplified in germfree animals which have an impaired immune system that is functionally reconstituted following the introduction of commensal bacteria [3-5].

Dramatic changes in microbiota composition have been documented in gastrointestinal disorders such as inflammatory bowel disease (IBD). For example, the levels of *Clostridium* cluster XIVa bacteria are reduced in IBD patients whilst numbers of *E. coli* are increased, suggesting a shift in the balance of symbionts and pathobionts within the gut [6-9]. Interestingly, this microbial dysbiosis is also associated with imbalances in T effector cell populations.

In recognition of the potential positive effect that certain bacterial strains may have on the animal gut, various strains have been proposed for use in the treatment of various diseases (see, for example, [10-13]). Also, certain strains, including mostly *Lactobacillus* and *Bifidobacterium* strains, have been proposed for use in treating various inflammatory and autoimmune diseases that are not directly linked to the intestines (see [14] and [15] for reviews). However, the relationship between different diseases and different bacterial strains, and the precise effects of particular bacterial strains on the gut and at a systemic level and on any particular types of diseases, are poorly characterised.

WO2015038731 discusses a method of treating colon cancer by disruption of a colonic biofilm by administration of an antimicrobial agent or a probiotic agent. The application lists a large number of bacteria that may be used in a probiotic but provides no demonstration of the efficacy of any of the bacteria in the treatment of colon cancer. Instead, this application focuses on the diagnostic potential of biofilms in colorectal cancer.

EMBL database accession number XP002787383 provides a 16S rRNA gene sequence of a proposed *Megasphaera* sp, while EMBL database accession number XP002787384 provides a 16S rRNA gene of a *Megasphaera massiliensis* strain. These documents detail the genomic analysis of isolated strains and provide no guidance towards the therapeutic benefit of *Megasphaera*.

Ahmed et al (submitted to Frontiers Cellular Neuroscience) considers in vitro characterisation of gut microbiota-derived bacterial strains.

There is a requirement in the art for new methods of treating diseases. There is also a requirement for the potential effects of gut bacteria to be characterised so that new therapies using gut bacteria can be developed.

SUMMARY OF THE INVENTION

The inventors have developed new compositions comprising a bacterial strain of the genus *Megasphaera* that can be used in stimulating the immune system and treating and preventing disease, in particular cancer.

The invention therefore provides a composition comprising a bacterial strain of the genus *Megasphaera*, for use in stimulating the immune system in subject. Preferably, the bacterial strain is of the species *Megasphaera* massiliensis.

In further aspects, the invention provides a composition comprising a bacterial strain of the genus *Megasphaera*, for use in treating or preventing cancer, such as metastatic melanoma, breast cancer, ovarian cancer, cervical cancer, neuroblastoma, glioblastoma, carcinoma, lung cancer, chronic lymphocyte leukemia, prostate cancer, lymphoma and/or gastric cancer. In further aspects, the invention provides a composition comprising a bacterial strain of the genus *Megasphaera*, for use in treating or preventing cancer, such as colorectal cancer and/or haematological malignancies.

In further aspects, the invention provides a composition comprising a bacterial strain of the genus *Megasphaera*, for use in treating, preventing or delaying immunosenescence.

In further aspects, the invention provides a composition comprising a bacterial strain of the genus *Megasphaera*, for use as a vaccine adjuvant.

In further aspects, the invention provides a composition comprising a bacterial strain of the genus *Megasphaera*, for use in enhancing a cell therapy, such as CAR-T.

Preferably, the bacteria used in the invention is the strain deposited under accession number 42787 at NCIMB.

Further numbered embodiments of the invention are provided below:

1. A composition comprising a bacterial strain of the genus *Megasphaera*, for use in stimulating the immune system in subject.
2. The composition of embodiment 1, for use in treating or preventing cancer, such as metastatic melanoma, breast cancer, ovarian cancer, cervical cancer, neuroblastoma, glioblastoma, carcinoma, lung cancer, chronic lymphocyte leukemia, prostate cancer, lymphoma, gastric cancer, colorectal cancer and/or haematological malignancies.
3. The composition for use according to embodiment 2, wherein the composition has histone deacetylase inhibitory activity.
4. The composition for use according to embodiment 2 or embodiment 3, wherein the composition up-regulates pro-inflammatory cytokines.
5. The composition for use according to any one of embodiments 2-4, for use in reducing gut barrier permeability.
6. The composition of embodiment 1, for use in treating, preventing or delaying immunosenescence.
7. The composition of embodiment 1, for use as a vaccine adjuvant.
8. The composition of embodiment 1, for use in enhancing a cell therapy, such as CAR-T.
9. The composition of any preceding embodiment, for use in increasing the expression level and/or activity of Caspase 3, MAP2, IL-1β, IL-23 and/or TNF-α.
10. The composition of any preceding embodiment, for use in a method of selectively decreasing the number and/or percentage of Tregs in a cell population.
11. The composition of any preceding embodiment, wherein the bacterial strain has a 16S rRNA sequence that is at least 95%, 96%, 97%, 98%, 99%, 99.5% or 99.9% identical to the 16S rRNA sequence of a bacterial strain of the genus *Megasphaera*.
12. The composition of any preceding embodiment, wherein the bacterial strain has a 16s rRNA gene sequence that is at least 95%, 96%, 97%, 98%, 99%, 99.5% or 99.9% identical to any one of SEQ ID NOs:8, 9, 10, 11 or 12 or wherein the bacterial strain has a 16s rRNA gene sequence represented by any one of SEQ ID NOs:8, 9, 10, 11 or 12.
13. The composition of any preceding embodiment, wherein the bacterial strain is of *Megasphaera massiliensis*
14. The composition of any preceding embodiment, wherein the bacterial strain has a 16s rRNA gene sequence that is at least 95%, 96%, 97%, 98%, 99%, 99.5% or 99.9% identical to SEQ ID NO:1 or wherein the bacterial strain has a 16s rRNA gene sequence represented by SEQ ID NO:1.
15. The composition of any preceding embodiment, wherein the bacterial strain is the strain deposited under accession number 42787 at NCIMB.
16. The composition of any preceding embodiment, wherein the composition is for oral administration.
17. The composition of any preceding embodiment, wherein the composition comprises one or more pharmaceutically acceptable excipients or carriers.
18. The composition of any preceding embodiment, wherein the bacterial strain is lyophilised.
19. A food product comprising the composition of any preceding embodiment, for the use of any preceding claim.
20. A method of treating or preventing a disease or condition associated with reduced immunostimulation, comprising administering a composition comprising a bacterial strain of the genus *Megasphaera* to a patient in need thereof
21. A composition comprising a cell of the bacterial strain defined in any of embodiments 1 to 16, wherein the cell expresses one or more heterologous antigens.
22. The composition according to embodiment 21, wherein the cell presents the one or more heterologous antigens.
23. The composition according to embodiment 21 or embodiment 22, for use as a vaccine.
24. A cell of the bacterial strain defined in any of embodiments 1 to 18, wherein the cell expresses one or more heterologous antigens.
25. The cell according to embodiment 24, wherein the cell presents the one or more heterologous antigens.
26. The cell according to embodiment 24 or embodiment 25, for use as a vaccine.
27. A bacterial strain for use in therapy, wherein the bacterial strain has a 16S rRNA sequence that is at least 95%, 96%, 97%, 98%, 99%, 99.5% or 99.9% identical to any one of SEQ ID NOs:8, 9, 10, 11 or 12.
28. A bacterial strain having the 16S rRNA sequence represented by any one of SEQ ID NOs: 8, 9, 10, 11 or 12 for use in therapy.

BRIEF DESCRIPTION OF DRAWINGS

FIGS. 1A-1B: Levels of 133 Tubulin expression: immunostaining and cell imaging (FIG. 1A); immunoblotting (FIG. 1B)

FIGS. 2A-2C: Levels of MAP2 expression: immunostaining and cell imaging (FIG. 2A); immunoblotting (FIG. 2B); fold change in expression (FIG. 2C)

FIG. 3: Change in DRD2 expression

FIG. 4: Change in Casp3 expression

FIG. 5: Change in cell viability

FIG. 8A, FIG. 8B, FIG. 8C) by Flow Cytometry for the data presented in FIG. 6.

FIG. 9: Secretion of Interleukin-8 (IL-8)).

FIG. 10: Change in histone deacetylase (HDAC) activity

FIG. 11A: Strain-induced changes in whole cell and cell lysate histone deacetylase activity; FIG. 11B: metabolite production by strains; FIG. 11C: acid-induced changes in histone deacetylase activity.

FIG. 12A: HDAC1 inhibition; FIG. 12B: HDAC2 inhibition; FIG. 12C: HDAC3 inhibition.

FIG. 13A: Inhibition of Class I HDACs; FIG. 13B: inhibition of HDAC1; FIG. 13C: inhibition of HDAC2; FIG. 13D: inhibition of HDAC3.

FIGS. 14A-14F: Effects on intestinal barrier function. FIG. 14A: IL-8 secretion;

FIG. 14B: Occludin, Villin, TJP1 and TJP2 mRNA expression; FIG. 14C: TJP1 mRNA expression; FIG. 14D: Occludin mRNA expression; FIG. 14E: Permeability in the Ileum; FIG. 14F: Permeability in the Colon.

FIG. 15: Changes in Hippocampal expression of Toll-like Receptor 4 (TLR-4).

FIG. 16: Changes in Hippocampal expression of TNF-α.
FIG. 17: Changes in Hippocampal expression of Interleukin-1β (IL-1β).
FIG. 18: Changes in Hippocampal expression of Interleukin-6 (IL-6).
FIG. 19: Changes in Hippocampal expression of CD11b.
FIG. 20: Changes in Amygdala expression of TLR-4.
FIG. 21: Changes in Amygdala expression of CD11b.
FIG. 22: Changes in Amygdala expression of IL-6.
FIG. 23: Changes in Prefrontal Cortex expression of TLR-4.
FIG. 24: Changes in Prefrontal Cortex expression of CD11b.
FIG. 25: Changes in Prefrontal Cortex Expression of IL-6.
FIG. 26: Effect on Interferon-γ production from mouse splenocytes from mice administered MRx0029.
FIG. 27: Effect on IL-1β production from mouse splenocytes from mice administered MRx0029.
FIG. 28: Effect on IL-6 production from mouse splenocytes from mice administered MRx0029.
FIG. 29: Effect on TNF-α production from splenocytes from mice administered MRx0029.
FIG. 30: Effect on CXCL1 production from splenocytes from mice administered MRx0029.
FIG. 62A: SCFA and MCFA;
FIG. 62B: Succinic acid, 4-Hydroxy-Phenyl Acetic Acid;
FIG. 62C: SCFA standards vs NCIMB 42787.
FIG. 64A: IL-8;
FIG. 64B: IL-6.
FIG. 65: *Megasphaera* strain NCIMB 43387 affects colonic IDO-1 mRNA expression in BALB/c mice.
FIG. 66: *Megasphaera* strains NCIMB 43385 and NCIMB 43387 affect colonic Tph1 mRNA expression in BALB/c mice.
FIG. 67A: IFNγ;
FIG. 67B: IL-6.

DISCLOSURE OF THE INVENTION

Bacterial Strains

Figure 6A:
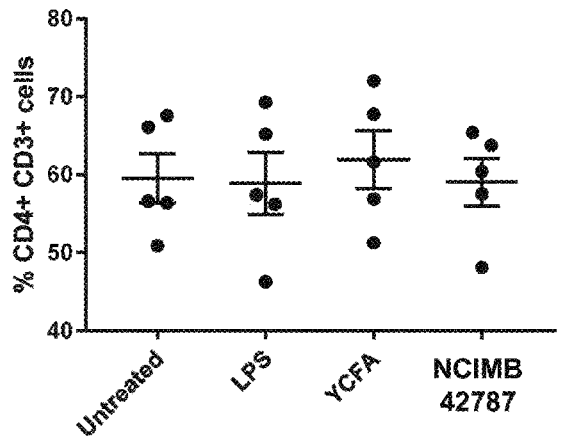
FIGS. 6A-6H: Cell phenotyping of CD4 T helper cells (FIG. 6A); CD4+ activated cells (FIG. 6B); Tregs cells (FIG. 6C); CD8 cytotoxic T cells (FIG. 6D); CD8+ activated cells (FIG. 6E); B cells (FIG. 6F); CD8/Treg ratio (FIG. 6G); Activated CD8/Treg ratio (FIG. 6H).
Figure 6B:
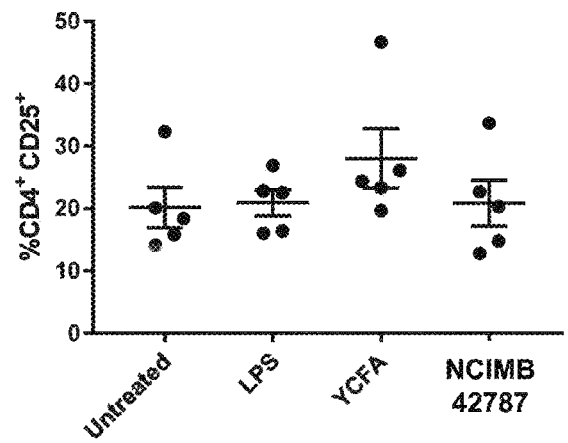

The compositions of the invention comprise a bacterial strain of the genus *Megasphaera*. The Examples demonstrate that bacteria of this genus are useful for stimulating the immune system and for treating disease, in particular cancer. The preferred bacterial strains are of the species *Megasphaera massiliensis*.

Examples of *Megasphaera* species for use in the invention include *Megasphaera elsdenii*, *Megasphaera cerevisiae*, *Megasphaera massiliensis*, *Megasphaera indica*, *Megasphaera paucivorans*, *Megasphaera sueciensis* and *Megasphaera micronuciformis*. A further example of a *Megasphaera* species for use in the invention is *Megasphaera hexanoica*. The *Megasphaera* are obligately anaerobic, lactate-fermenting, gastrointestinal microbe of ruminant and non-ruminant mammals, including humans.

The type strain of *M. massiliensis* is NP3 (=CSUR P245=DSM 26228) [16]. The GenBank accession number for the 16S rRNA gene sequences of *M. massiliensis* strain NP3 is JX424772.1.

All microorganism deposits were made under the terms of the Budapest Treaty and thus viability of the deposit is assured. Maintenance of a viable culture is assured for 30 years from the date of deposit. During the pendency of the application, access to the deposit will be afforded to one determined by the Commissioner of the United States Patent and Trademark Office to be entitled thereto. All restrictions on the availability to the public of the deposited microorganisms will be irrevocably removed upon the granting of a patent for this application. The deposit will be maintained for a term of at least thirty (30) years from the date of the deposit or for the enforceable life of the patent or for a period of at least five (5) years after the most recent request for the furnishing of a sample of the deposited material, whichever is longest. The deposit will be replaced should it become necessary due to inviability, contamination or loss of capability to function in the manner described in the specification.

The *Megasphaera massiliensis* bacterium tested in the Examples is referred to herein as strain MRx0029. A 16S rRNA sequence for the MRx0029 strain that was tested is provided in SEQ ID NO:1.

Strain MRx0029 was deposited with the international depositary authority NCIMB, Ltd. (Ferguson Building, Aberdeen, AB21 9YA, Scotland) by 4D Pharma Research Ltd. (Life Sciences Innovation Building, Cornhill Road, Aberdeen, AB25 2ZS, Scotland) on 13 Jul. 2017 as "*Megasphaera massiliensis* MRx0029" and was assigned accession number NCIMB 42787.

Bacterial strains closely related to the strain tested in the Examples are also expected to be effective for stimulating the immune system and for treating and preventing disease, in particular cancer. In certain embodiments, the bacterial strain for use in the invention has a 16S rRNA sequence that is at least 95%, 96%, 97%, 98%, 99%, 99.5% or 99.9% identical to SEQ ID NO:1. Preferably, the bacterial strain for use in the invention has the 16S rRNA sequence represented by SEQ ID NO:1.

Bacterial strains that are biotypes of strains MRx0029 are also expected to be effective for stimulating the immune system and for treating and preventing disease, in particular cancer. A biotype is a closely related strain that has the same or very similar physiological and biochemical characteristics.

Strains that are biotypes of strains MRx0029 and that are suitable for use in the invention may be identified by sequencing other nucleotide sequences for strains MRx0029. For example, substantially the whole genome may be sequenced and a biotype strain for use in the invention may have at least 95%, 96%, 97%, 98%, 99%, 99.5% or 99.9% sequence identity across at least 80% of its whole genome (e.g. across at least 85%, 90%, 95% or 99%, or across its whole genome). Other suitable sequences for use in identifying biotype strains may include hsp60 or repetitive sequences such as BOX, ERIC, $(GTG)_5$ (SEQ ID NO: 15), or REP or [17]. Biotype strains may have sequences with at least 95%, 96%, 97%, 98%, 99%, 99.5% or 99.9% sequence identity to the corresponding sequence of the strains MRx0029.

Alternatively, strains that are biotypes of strains MRx0029 and that are suitable for use in the invention may be identified by using strains MRx0029 and restriction fragment analysis and/or PCR analysis, for example by using fluorescent amplified fragment length polymorphism (FAFLP) and repetitive DNA element (rep)-PCR fingerprinting, or protein profiling, or partial 16S or 23S rDNA sequencing. In preferred embodiments, such techniques may be used to identify other *Megasphaera massiliensis* strains.

In certain embodiments, strains that are biotypes of strains MRx0029 and that are suitable for use in the invention are strains that provide the same pattern as strains MRx0029 when analysed by amplified ribosomal DNA restriction analysis (ARDRA), for example when using Sau3AI restriction enzyme (for exemplary methods and guidance see, for example, [18]). Alternatively, biotype strains are identified as strains that have the same carbohydrate fermentation patterns as strains MRx0029.

Other *Megasphaera* strains that are useful in the compositions and methods of the invention, such as biotypes of strains MRx0029, may be identified using any appropriate method or strategy, including the assays described in the Examples. For instance, strains for use in the invention may be identified by adding to cell lysate or whole cells and testing for MAP2 expression, DRD2 expression, cytokine levels or cell survival. In particular, bacterial strains that have similar growth patterns, metabolic type and/or surface antigens to strains MRx0029 may be useful in the invention. A useful strain will have comparable immune modulatory activity to strains MRx0029. In particular, a biotype strain will elicit comparable effects on MAP2 expression, DRD2 expression, cytokine levels or cell survival as shown in the Examples, which may be identified by using the culturing and administration protocols described in the Examples. A biotype strain may elicit comparable effects on histone deacetylase inhibitory activity as shown in the Examples, which may be identified by using the culturing and administration protocols described in the Examples.

In some embodiments, bacterial strains useful in the invention may be identified by routinely profiling the production and consumption of metabolites by a bacterial strain. The inventors have found that the bacterial strain used in the Examples produces butyrate, valeric acid and hexanoic acid and consumes acetate and propionate (see FIGS. 54-56). The *Megasphaera massiliensis* strains Ref 1, Ref 2 and Ref 3 were also found to consume and produce these metabolites (see FIGS. 54-56). Therefore, in some embodiments, the bacterial strain of the invention produces one or more of the metabolites butyrate, valeric acid and hexanoic acid. In some embodiments, the bacterial strain of the invention consumes one or both of acetate and propionate. In preferred embodiments, the bacterial strain of the invention produces butyrate, valeric acid and hexanoic acid and consumes acetate and propionate.

A particularly preferred strain of the invention is the *Megasphaera massiliensis* MRx0029 strain. This is the exemplary strain tested in the Examples and shown to be effective for treating disease. Therefore, the invention provides a cell, such as an isolated cell, of the *Megasphaera*

*massiliensis* strain MRx0029, or a derivative thereof. The invention also provides a composition comprising a cell of the *Megasphaera massiliensis* strain MRx0029, or a derivative thereof. The invention also provides a biologically pure culture of the *Megasphaera massiliensis* strain MRx0029. The invention also provides a cell of the *Megasphaera massiliensis* strain MRx0029, or a derivative thereof, for use in therapy, in particular for the diseases described herein.

A particularly preferred strain of the invention is the *Megasphaera massiliensis* strain deposited under accession number NCIMB 42787. This is the exemplary MRx0029 strain tested in the Examples and shown to be effective stimulating the immune system and for treating and preventing disease, in particular cancer. Therefore, the invention provides a cell, such as an isolated cell, of the *Megasphaera massiliensis* strain deposited under accession number NCIMB 42787, or a derivative thereof. The invention also provides a composition comprising a cell of the *Megasphaera massiliensis* strain deposited under accession number NCIMB 42787, or a derivative thereof. The invention also provides a biologically pure culture of the *Megasphaera massiliensis* strain deposited under accession number NCIMB 42787. The invention also provides a cell of the *Megasphaera massiliensis* strain deposited under accession number NCIMB 42787, or a derivative thereof, for use in therapy, in particular for the diseases described herein.

A derivative of the strain of the invention may be a daughter strain (progeny) or a strain cultured (subcloned) from the original. A derivative of a strain of the invention may be modified, for example at the genetic level, without ablating the biological activity. In particular, a derivative strain of the invention is therapeutically active. A derivative strain will have comparable therapeutic activity to the MRx0029 strain. In particular, a derivative strain will elicit comparable effects on MAP2 expression, DRD2 expression, cytokine levels or cell survival as shown in the Examples, which may be identified by using the culturing and administration protocols described in the Examples. A derivative strain may elicit comparable effects on histone deacetylase inhibitory activity as shown in the Examples, which may be identified by using the culturing and administration protocols described in the Examples. A derivative of the MRx0029 strain will generally be a biotype of the MRx0029 strain.

References to cells of the *Megasphaera massiliensis* MRx0029 strain encompass any cells that have the same safety and therapeutic efficacy characteristics as the strain MRx0029, and such cells are encompassed by the invention.

In preferred embodiments, the bacterial strains in the compositions of the invention are viable and capable of partially or totally colonising the intestine.

The inventors have found that *Megasphaera massiliensis* strains increase the activation of inflammatory cytokines such as IL-1β, TNF-α, MIP-3α, IL-23, IL-8 and/or IL-6.

The inventors have found that *Megasphaera massiliensis* strains increase the activation of immune cells and enhance secretion of cytokines such as IL-1β, TNF-α, MIP-3α, IL-23, IL-8 and/or IL-6.

In preferred embodiments, the invention provides a composition comprising the strain deposited at NCIMB under accession number NCIMB 42787, or a derivative or biotype thereof, preferably for use in stimulating the immune system and for treating and preventing disease, in particular cancer, most preferably brain cancer, such as neuroblastoma. In preferred embodiments, the invention provides a composition comprising the strain deposited at NCIMB under accession number NCIMB 42787, or a derivative or biotype thereof, preferably for use in treating or preventing metastatic melanoma, breast cancer, ovarian cancer, cervical cancer, glioblastoma, carcinoma, lung cancer, chronic lymphocyte leukemia, prostate cancer, lymphoma, gastric cancer, colorectal cancer and/or haematological malignancies.

In preferred embodiments, the bacterial strains in the compositions of the invention are viable and capable of partially or totally colonising the intestine.

In certain embodiments, the composition of the invention does not comprise a cell of the *Megasphaera massiliensis* strain 42787.

In some embodiments, the bacterial strain in the compositions of the invention is a bacterial strain of the genus *Megasphaera*, wherein the bacterial strain is not the strain deposited under accession number NCIMB 42787.

In some embodiments, the bacterial strain in the compositions of the invention is a bacterial strain of the species *Megasphaera massiliensis*, wherein the bacterial strain is not the strain deposited under accession number NCIMB 42787.

These bacterial strains were deposited with the international depositary authority NCIMB, Ltd. (Ferguson Building, Aberdeen, AB21 9YA, Scotland) by 4D Pharma Research Ltd. (Life Sciences Innovation Building, Cornhill Road, Aberdeen, AB25 2ZS, Scotland) on 6 May 2019 as *Megasphaera massiliensis* (under accession numbers NCIMB 43388 and NCIMB 43389) and *Megasphaera* spp. (accession numbers NCIMB 43385, NCIMB 43386 and NCIMB 43387). Accordingly, in an alternative embodiment, the compositions of the invention comprise one or more of these bacterial strains, or biotypes or derivatives thereof. For the avoidance of doubt, Ref 1 referred to above is the strain deposited under accession number NCIMB 43385, Ref 2 referred to above is the strain deposited under accession number NCIMB 43388, and Ref 3 referred to above is the strain deposited under accession number NCIMB 43389. All microorganism deposits were made under the terms of the Budapest Treaty and thus viability of the deposit is assured. Maintenance of a viable culture is assured for 30 years from the date of deposit. During the pendency of the application, access to the deposit will be afforded to one determined by the Commissioner of the United States Patent and Trademark Office to be entitled thereto. All restrictions on the availability to the public of the deposited microorganisms will be irrevocably removed upon the granting of a patent for this application. The deposit will be maintained for a term of at least thirty (30) years from the date of the deposit or for the enforceable life of the patent or for a period of at least five (5) years after the most recent request for the furnishing of a sample of the deposited material, whichever is longest. The deposit will be replaced should it become necessary due to inviability, contamination or loss of capability to function in the manner described in the specification.

Bacterial strains closely related to the strains tested in the Examples are also expected to be effective for stimulating the immune system and for treating and preventing disease, in particular cancer.

In certain embodiments, the bacterial strain for use in the invention is the *Megasphaera massiliensis* strain deposited under accession number NCIMB 43388. In certain embodiments, the invention provides a cell of the strain deposited under accession number NCIMB 43388, or a derivative thereof, for use in therapy. In certain embodiments, the invention provides a cell of the strain deposited under accession number NCIMB 43388, or derivative thereof for use in stimulating the immune system and for treating and preventing disease, in particular cancer. In certain embodiments, the invention provides a cell of the strain deposited under accession number NCIMB 43388, for use in any one of the diseases described herein.

In preferred embodiments, the invention provides a composition comprising the strain deposited at NCIMB under accession number NCIMB 43388, or a derivative or biotype thereof, preferably for use in stimulating the immune system and for treating and preventing disease, in particular cancer, most preferably brain cancer, such as neuroblastoma. In preferred embodiments, the invention provides a composition comprising the strain deposited at NCIMB under accession number NCIMB 43388, or a derivative or biotype thereof, preferably for use in treating or preventing metastatic melanoma, breast cancer, ovarian cancer, cervical cancer, glioblastoma, carcinoma, lung cancer, chronic lymphocyte leukemia, prostate cancer, lymphoma, gastric cancer, colorectal cancer and/or haematological malignancies.

In certain embodiments, the composition of the invention does not comprise a cell of the *Megasphaera massiliensis* strain deposited under accession number NCIMB 43388. In some embodiments, the bacterial strain in the compositions of the invention is a bacterial strain of the genus *Megasphaera*, wherein the bacterial strain is not the strain deposited under accession number NCIMB 43388. In some embodiments, the bacterial strain in the compositions of the invention is a bacterial strain of the species *Megasphaera massiliensis*, wherein the bacterial strain is not the strain deposited under accession number NCIMB 43388.

Accordingly, in certain embodiments, the bacterial strain for use in the invention is the *Megasphaera massiliensis* deposited under accession number NCIMB 43389. In certain embodiments, the invention provides a cell of the strain deposited under accession number NCIMB 43389, or a derivative thereof, for use in therapy. In certain embodiments, the invention provides a cell of the strain deposited under accession number NCIMB 43389, or derivative thereof for use in stimulating the immune system and for treating and preventing disease, in particular cancer. In certain embodiments, the invention provides a cell of the strain deposited under accession number NCIMB 43389, for use in any one of the diseases described herein.

In preferred embodiments, the invention provides a composition comprising the strain deposited at NCIMB under accession number NCIMB 43389, or a derivative or biotype thereof, preferably for use in stimulating the immune system and for treating and preventing disease, in particular cancer, most preferably brain cancer, such as neuroblastoma. In preferred embodiments, the invention provides a composition comprising the strain deposited at NCIMB under accession number NCIMB 43389, or a derivative or biotype thereof, preferably for use in treating or preventing metastatic melanoma, breast cancer, ovarian cancer, cervical cancer, glioblastoma, carcinoma, lung cancer, chronic lymphocyte leukemia, prostate cancer, lymphoma, gastric cancer, colorectal cancer and/or haematological malignancies.

In certain embodiments, the composition of the invention does not comprise a cell of the *Megasphaera massiliensis* strain deposited under accession number NCIMB 43389. In some embodiments, the bacterial strain in the compositions of the invention is a bacterial strain of the genus *Megasphaera*, wherein the bacterial strain is not the strain deposited under accession number NCIMB 43389. In some embodiments, the bacterial strain in the compositions of the invention is a bacterial strain of the species *Megasphaera massiliensis*, wherein the bacterial strain is not the strain deposited under accession number NCIMB 43389.

In certain embodiments, the bacterial strain for use in the invention has a 16S rRNA sequence that is at least 95%, 96%, 97%, 98%, 99%, 99.5% or 99.9% identical to SEQ ID NO:9. In certain embodiments, the bacterial strain for use in the invention has the 16S rRNA sequence represented by SEQ ID NO:9. In certain embodiments, the invention provides a bacterial strain having a 16S rRNA sequence that is at least 95%, 96%, 97%, 98%, 99%, 99.5% or 99.9% identical to SEQ ID NO:9 for use in therapy. In certain embodiments, the invention provides a bacterial strain having the 16S rRNA sequence represented by SEQ ID NO:9 for use in therapy.

In certain embodiments, the bacterial strain for use in the invention has a 16S rRNA sequence that is at least 95%, 96%, 97%, 98%, 99%, 99.5% or 99.9% identical to SEQ ID NO:10. In certain embodiments, the bacterial strain for use in the invention has the 16S rRNA sequence represented by SEQ ID NO:10. In certain embodiments, the invention provides a bacterial strain having a 16S rRNA sequence that is at least 95%, 96%, 97%, 98%, 99%, 99.5% or 99.9% identical to SEQ ID NO:10 for use in therapy. In certain embodiments, the invention provides a bacterial strain having the 16S rRNA sequence represented by SEQ ID NO:10 for use in therapy.

In certain embodiments, the bacterial strain for use in the invention has a 16S rRNA sequence that is at least 95%, 96%, 97%, 98%, 99%, 99.5% or 99.9% identical to the 16S rRNA sequence of a bacterial strain of the genus *Megasphaera*. In certain embodiments, the bacterial strain for use in the invention is of the genus *Megasphaera*.

In certain embodiments, the bacterial strain for use in the invention is the *Megasphaera* strain deposited under accession number NCIMB 43385. In certain embodiments, the invention provides a cell of the strain deposited under accession number NCIMB 43385, or a derivative thereof, for use in therapy. In certain embodiments, the invention provides a cell of the strain deposited under accession number NCIMB 43385, or derivative thereof for use in stimulating the immune system and for treating and preventing disease, in particular cancer. In certain embodiments, the invention provides a cell of the strain deposited under accession number NCIMB 43385, for use in any one of the diseases described herein.

In preferred embodiments, the invention provides a composition comprising the strain deposited at NCIMB under accession number NCIMB 43385, or a derivative or biotype thereof, preferably for use in stimulating the immune system and for treating and preventing disease, in particular cancer, most preferably brain cancer, such as neuroblastoma. In preferred embodiments, the invention provides a composition comprising the strain deposited at NCIMB under accession number NCIMB 43385, or a derivative or biotype thereof, preferably for use in treating or preventing metastatic melanoma, breast cancer, ovarian cancer, cervical cancer, glioblastoma, carcinoma, lung cancer, chronic lymphocyte leukemia, prostate cancer, lymphoma, gastric cancer, colorectal cancer and/or haematological malignancies.

In certain embodiments, the composition of the invention does not comprise a cell of the *Megasphaera massiliensis* strain deposited under accession number NCIMB 43385. In some embodiments, the bacterial strain in the compositions of the invention is a bacterial strain of the genus *Megasphaera*, wherein the bacterial strain is not the strain deposited under accession number NCIMB 43385. In some embodiments, the bacterial strain in the compositions of the invention is a bacterial strain of the species *Megasphaera*

*massiliensis*, wherein the bacterial strain is not the strain deposited under accession number NCIMB 43385.

In certain embodiments, the bacterial strain for use in the invention is the *Megasphaera* strain deposited under accession number NCIMB 43386. In certain embodiments, the invention provides a cell of the strain deposited under accession number NCIMB 43386, or a derivative thereof, for use in therapy. In certain embodiments, the invention provides a cell of the strain deposited under accession number NCIMB 43386, or derivative thereof for use in stimulating the immune system and for treating and preventing disease, in particular cancer. In certain embodiments, the invention provides a cell of the strain deposited under accession number NCIMB 43386, for use in any one of the diseases described herein.

In preferred embodiments, the invention provides a composition comprising the strain deposited at NCIMB under accession number NCIMB 43386, or a derivative or biotype thereof, preferably for use in stimulating the immune system and for treating and preventing disease, in particular cancer, most preferably brain cancer, such as neuroblastoma. In preferred embodiments, the invention provides a composition comprising the strain deposited at NCIMB under accession number NCIMB 43386, or a derivative or biotype thereof, preferably for use in treating or preventing metastatic melanoma, breast cancer, ovarian cancer, cervical cancer, glioblastoma, carcinoma, lung cancer, chronic lymphocyte leukemia, prostate cancer, lymphoma, gastric cancer, colorectal cancer and/or haematological malignancies.

In certain embodiments, the composition of the invention does not comprise a cell of the *Megasphaera massiliensis* strain deposited under accession number NCIMB 43386. In some embodiments, the bacterial strain in the compositions of the invention is a bacterial strain of the genus *Megasphaera*, wherein the bacterial strain is not the strain deposited under accession number NCIMB 43386. In some embodiments, the bacterial strain in the compositions of the invention is a bacterial strain of the species *Megasphaera massiliensis*, wherein the bacterial strain is not the strain deposited under accession number NCIMB 43386.

In certain embodiments, the bacterial strain for use in the invention is the *Megasphaera* strain deposited under accession number NCIMB 43387. In certain embodiments, the invention provides a cell of the strain deposited under accession number NCIMB 43387, or a derivative thereof, for use in therapy. In certain embodiments, the invention provides a cell of the strain deposited under accession number NCIMB 43387, or derivative thereof for use in stimulating the immune system and for treating and preventing disease, in particular cancer. In certain embodiments, the invention provides a cell of the strain deposited under accession number NCIMB 43387, for use in any one of the diseases described herein.

In preferred embodiments, the invention provides a composition comprising the strain deposited at NCIMB under accession number NCIMB 43387, or a derivative or biotype thereof, preferably for use in stimulating the immune system and for treating and preventing disease, in particular cancer, most preferably brain cancer, such as neuroblastoma. In preferred embodiments, the invention provides a composition comprising the strain deposited at NCIMB under accession number NCIMB 43387, or a derivative or biotype thereof, preferably for use in treating or preventing metastatic melanoma, breast cancer, ovarian cancer, cervical cancer, glioblastoma, carcinoma, lung cancer, chronic lymphocyte leukemia, prostate cancer, lymphoma, gastric cancer, colorectal cancer and/or haematological malignancies.

In certain embodiments, the composition of the invention does not comprise a cell of the *Megasphaera massiliensis* strain deposited under accession number NCIMB 43387. In some embodiments, the bacterial strain in the compositions of the invention is a bacterial strain of the genus *Megasphaera*, wherein the bacterial strain is not the strain deposited under accession number NCIMB 43387. In some embodiments, the bacterial strain in the compositions of the invention is a bacterial strain of the species *Megasphaera massiliensis*, wherein the bacterial strain is not the strain deposited under accession number NCIMB 43387.

In certain embodiments, the bacterial strain for use in the invention has a 16S rRNA sequence that is at least 95%, 96%, 97%, 98%, 99%, 99.5% or 99.9% identical to SEQ ID NO:8. In certain embodiments, the bacterial strain for use in the invention has a 16S rRNA sequence that is at least 95%, 96%, 97%, 98%, 99%, 99.5% or 99.9% identical to SEQ ID NO:11. In certain embodiments, the bacterial strain for use in the invention has a 16S rRNA sequence that is at least 95%, 96%, 97%, 98%, 99%, 99.5% or 99.9% identical to SEQ ID NO:12. In certain embodiments, the bacterial strain for use in the invention has a 16S rRNA sequence that is at least 95%, 96%, 97%, 98%, 99%, 99.5% or 99.9% identical to SEQ ID NOs:8, 11 or 12. In certain embodiments, the invention provides a bacterial strain having a 16S rRNA sequence that is at least 95%, 96%, 97%, 98%, 99%, 99.5% or 99.9% identical to SEQ ID NOs:8, 11 or 12 for use in therapy.

In certain embodiments, the bacterial strain for use in the invention has the 16S rRNA sequence represented by SEQ ID NO:8. In certain embodiments, the bacterial strain for use in the invention has the 16S rRNA sequence represented by SEQ ID NO:11. In certain embodiments, the bacterial strain for use in the invention has the 16S rRNA sequence represented by SEQ ID NO:12. In certain embodiments, the bacterial strain for use in the invention has the 16S rRNA sequence represented by SEQ ID NOs: 8, 11 or 12. In certain embodiments, the invention provides a bacterial strain having the 16S rRNA sequence represented by SEQ ID NOs: 8, 11 or 12 for use in therapy.

Bacterial strains that are biotypes of one or more of the strains deposited under accession numbers NCIMB 43385, NCIMB 43386, NCIMB 43387, NCIMB 43388 and/or NCIMB 43389 are also expected to be effective for stimulating the immune system and for treating and preventing disease, in particular cancer. A biotype is a closely related strain that has the same or very similar physiological and biochemical characteristics.

In certain embodiments, the invention provides the bacterial strains deposited under accession numbers NCIMB 43385, NCIMB 43386, NCIMB 43387, NCIMB 43388 and/or NCIMB 43389, or biotypes thereof, for use in therapy.

Strains that are biotypes of one or more of the strains deposited under accession numbers NCIMB 43385, NCIMB 43386, NCIMB 43387, NCIMB 43388 and/or NCIMB 43389 and that are suitable for use in the invention may be identified by sequencing other nucleotide sequences for one or more of the strains deposited under accession numbers NCIMB 43385, NCIMB 43386, NCIMB 43387, NCIMB 43388 and/or NCIMB 43389. For example, substantially the whole genome may be sequenced and a biotype strain for use in the invention may have at least 85%, 90%, 95%, 96%, 97%, 98%, 99%, 99.5% or 99.9% sequence identity across at least 80% of its whole genome (e.g. across at least 85%, 90%, 95% or 99%, or across its whole genome). Other suitable sequences for use in identifying biotype strains may include hsp60 or repetitive sequences such as BOX, ERIC, (GTG)$_5$ (SEQ ID NO: 15), or REP. Biotype strains may have sequences with at least 85%, 90%, 95%, 96%, 97%, 98%, 99%, 99.5% or 99.9% sequence identity to the corresponding sequence of one or more of the strains deposited under accession numbers NCIMB 43385, NCIMB 43386, NCIMB 43387, NCIMB 43388 and/or NCIMB 43389.

Alternatively, strains that are biotypes of one or more of the strains deposited under accession numbers NCIMB 43385, NCIMB 43386, NCIMB 43387, NCIMB 43388 and/or NCIMB 43389 and that are suitable for use in the invention may be identified by using one or more of the strains deposited under accession numbers NCIMB 43385, NCIMB 43386, NCIMB 43387, NCIMB 43388 and/or NCIMB 43389 and restriction fragment analysis and/or PCR analysis, for example by using fluorescent amplified fragment length polymorphism (FAFLP) and repetitive DNA element (rep)-PCR fingerprinting, or protein profiling, or partial 16S or 23S rDNA sequencing. In preferred embodiments, such techniques may be used to identify other *Megasphaera massihensis* strains.

In certain embodiments, strains that are biotypes of one or more of the strains deposited under accession numbers NCIMB 43385, NCIMB 43386, NCIMB 43387, NCIMB 43388 and/or NCIMB 43389 and that are suitable for use in the invention are strains that provide the same pattern as one or more of the strains deposited under accession numbers NCIMB 43385, NCIMB 43386, NCIMB 43387, NCIMB 43388 and/or NCIMB 43389 when analysed by amplified ribosomal DNA restriction analysis (ARDRA), for example when using Sau3AI restriction enzyme. Alternatively, biotype strains are identified as strains that have the same carbohydrate fermentation patterns as one or more of the strains deposited under accession numbers NCIMB 43385, NCIMB 43386, NCIMB 43387, NCIMB 43388 and/or NCIMB 43389.

Other strains that are useful in the compositions and methods of the invention, such as biotypes of one or more of the strains deposited under accession numbers NCIMB 43385, NCIMB 43386, NCIMB 43387, NCIMB 43388 and/or NCIMB 43389, may be identified using any appropriate method or strategy, including the assays described in the Examples. For instance, strains for use in the invention may be identified by adding to cell lysate or whole cells and testing for MAP2 expression, DRD2 expression, cytokine levels or cell survival. In particular, bacterial strains that have similar growth patterns, metabolic type and/or surface antigens to one or more of the strains deposited under accession numbers NCIMB 43385, NCIMB 43386, NCIMB 43387, NCIMB 43388 and/or NCIMB 43389 may be useful in the invention. A useful strain will have comparable immune modulatory activity to one or more of the strains deposited under accession numbers NCIMB 43385, NCIMB 43386, NCIMB 43387, NCIMB 43388 and/or NCIMB 43389. In particular, a biotype strain will elicit comparable effects on MAP2 expression, DRD2 expression, cytokine levels or cell survival as shown in the Examples, which may be identified by using the culturing and administration protocols described in the Examples. A biotype strain may elicit comparable effects on histone deacetylase inhibitory activity as shown in the Examples, which may be identified by using the culturing and administration protocols described in the Examples.

In certain embodiments, preferred strains of the invention are strains deposited under accession numbers NCIMB 43385, NCIMB 43386, NCIMB 43387, NCIMB 43388 and/or NCIMB 43389. These are exemplary strains tested in the Examples and shown to be effective for treating disease. Therefore, the invention provides a cell, such as an isolated cell, of one or more of the strains deposited under accession numbers NCIMB 43385, NCIMB 43386, NCIMB 43387, NCIMB 43388 and/or NCIMB 43389, or a derivative thereof. The invention also provides a composition comprising a cell of one of more of the strains deposited under accession numbers NCIMB 43385, NCIMB 43386, NCIMB 43387, NCIMB 43388 and/or NCIMB 43389, or a derivative thereof. The invention also provides a biologically pure culture of one or more of the strains deposited under accession numbers NCIMB 43385, NCIMB 43386, NCIMB 43387, NCIMB 43388 and/or NCIMB 43389. The invention also provides a cell of one or more of the strains deposited under accession numbers NCIMB 43385, NCIMB 43386, NCIMB 43387, NCIMB 43388 and/or NCIMB 43389, or a derivative thereof, for use in therapy, in particular for the diseases described herein.

A derivative of the strain of the invention may be a daughter strain (progeny) or a strain cultured (subcloned) from the original. A derivative of a strain of the invention may be modified, for example at the genetic level, without ablating the biological activity. In particular, a derivative strain of the invention is therapeutically active. A derivative strain will have comparable therapeutic activity to one or more of the strains deposited under accession numbers NCIMB 43385, NCIMB 43386, NCIMB 43387, NCIMB 43388 and/or NCIMB 43389. In particular, a derivative strain will elicit comparable effects on MAP2 expression, DRD2 expression, cytokine levels or cell survival as shown in the Examples, which may be identified by using the culturing and administration protocols described in the Examples. A derivative strain may elicit comparable effects on histone deacetylase inhibitory activity as shown in the Examples, which may be identified by using the culturing and administration protocols described in the Examples. A derivative of one or more of the strains deposited under accession numbers NCIMB 43385, NCIMB 43386, NCIMB 43387, NCIMB 43388 and/or NCIMB 43389 will generally be a biotype of one or more of the strains deposited under accession numbers NCIMB 43385, NCIMB 43386, NCIMB 43387, NCIMB 43388 and/or NCIMB 43389, respectively.

Figure 58:
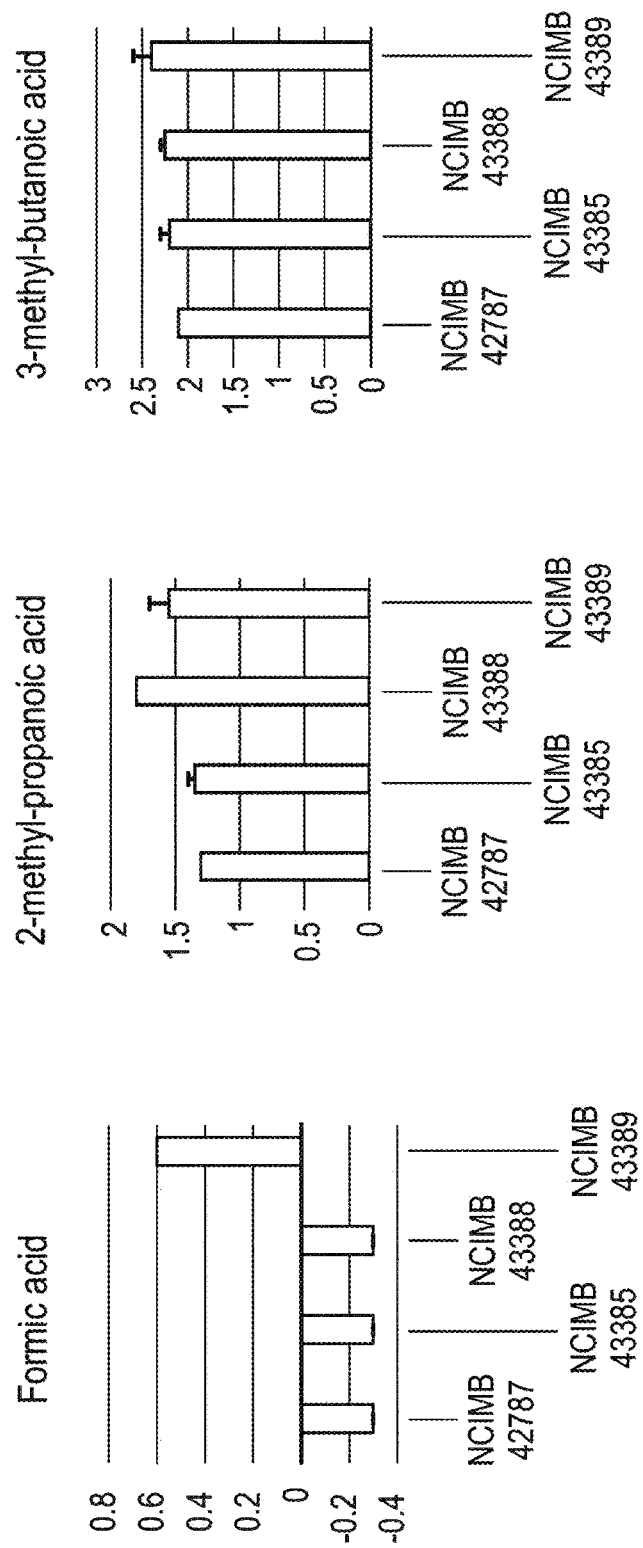
FIG. 58: Organic acid production and consumption by NCIMB 42787, NCIMB 43385, NCIMB 43388 and NCIMB 43389.

The inventors have found that the bacterial strain used in the Examples produces 2-methyl-propanoic acid and 3-methyl-butanoic acid and consumes formic acid (see FIG. 58). The strains deposited under accession numbers NCIMB 43385, NCIMB 43388 and NCIMB 43389 were also found to produce 2-methyl-propanoic acid and 3-methyl-butanoic acid. In addition, the strains deposited under accession numbers NCIMB 43385 and NCIMB 43388 were also found to consume formic acid. Therefore, in some embodiments, the bacterial strain of the invention produces one or more of the metabolites 2-methyl-propanoic acid and-3-methyl-butanoic acid. In some embodiments, the bacterial strain of the invention consumes formic acid. In some embodiments, the bacterial strain of the invention produces 2-methyl-propanoic acid and 3-methyl-butanoic acid and consumes formic acid. In preferred embodiments, the bacterial strain of the invention produces butyrate, valeric acid, hexanoic acid, 2-methyl-propanoic acid and-3-methyl-butanoic acid, and consumes acetate, propionate and formic acid.

In certain embodiments, the production of butyrate and/or valeric acid generates IL-8 secretion. Accordingly, in certain embodiments, the compositions of the invention may stimulate the immune system via the production of butyrate and/or valeric acid.

In certain embodiments, the compositions of the invention do not comprise *Megasphaera* elsdenii. In certain embodiments, the bacterial strain useful in the compositions and methods of the invention is not *Megasphaera* elsdenii.

Therapeutic Uses

Stimulating the Immune System

The Examples show that administration of the compositions of the invention can lead to immune stimulation in human peripheral blood mononuclear cells (PBMCs). Since administration of the compositions of the invention were shown to have an immunostimulatory effect on PBMCs, compositions of the invention may be useful in the treatment of disease, in particular diseases characterised by reduced immune activation and diseases treatable by an increased immune response. In certain embodiments, the compositions of the invention are for use in stimulating the immune system. In certain embodiments, the compositions of the invention are for use in treating disease by stimulating the immune system. In certain embodiments, the compositions of the invention are for use in promoting an immune response.

Figure 6C:
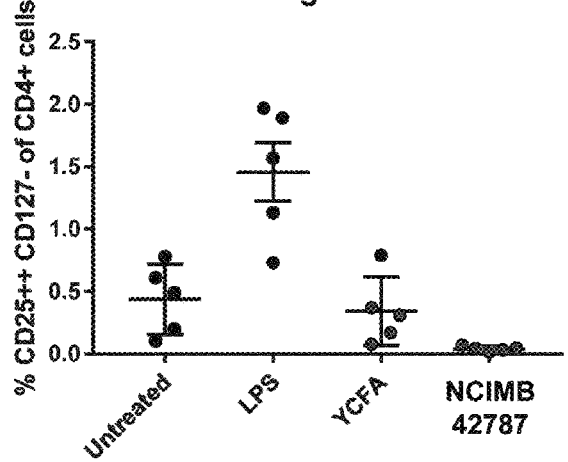

The Examples show that administration of the compositions of the invention can lead to a decrease in the percentage of Tregs in PBMCs (FIG. 6C). Tregs, also known as suppressor T cells, are a population of T cells which function to suppress the immune response. Tregs are characterised by the high expression of cell-surface marker CD25 and the low expression of CD127 [19]. Since administration of the compositions of the invention were shown to selectively reduce the population of Tregs (FIG. 6C), compositions of the invention may be useful in the treatment of diseases characterised by an increase in the percentage of Tregs in a cell population. In one embodiment, the compositions of the invention may be useful for treating or preventing diseases characterised by an increase in the percentage of Tregs in a cell population. In one embodiment, the compositions of the invention may be useful for treating or preventing diseases characterised by an increase in the percentage of CD4+ CD25+CD127− cells in a cell population. In one embodiment, the compositions of the invention are for use in treating or preventing diseases by decreasing the percentage of Tregs in cell populations. In one embodiment, compositions of the invention are for use in reducing suppression of the immune response by Tregs. In one embodiment, compositions of the invention are for use in stimulating the immune response by the selective reduction of Tregs. In one embodiment, compositions of the invention are for use in immunostimulation, wherein the compositions of the invention reduce the number or percentage of Tregs.

The Examples demonstrate that the compositions of the invention may be able to selectively target Tregs, without significantly affecting cells such as B cells, CD4 T cells or CD8 T cells. Therefore, compositions of the invention may selectively reduce Tregs in PBMCs, without significantly affecting the percentage of the other cell types tested. In one embodiment, compositions of the invention are for use in selectively reducing the number or percentage of Tregs, wherein the number or percentage of CD4 T cells does not significantly change. In one embodiment, compositions of the invention are for use in selectively reducing the number or percentage of Tregs, wherein the number or percentage of CD8 T cells does not significantly change. In one embodiment, compositions of the invention are for use in selectively reducing the number or percentage of Tregs, wherein the number or percentage of B cells does not significantly change. In a further embodiment, compositions of the invention are for use in selectively reducing the number or percentage of Tregs, wherein the number or percentage of B cells, CD4 T cells and/or CD8 T cells does not significantly change.

The decrease in the percentage of Tregs was particularly surprising because the *Megasphaera massiliensis* MRx0029 strain produces butyrate, and butyrate has been associated with increased Treg cell levels in the blood and increased Treg activity [20]. Therefore, it was unexpected that the compositions of the invention would lead to a decrease in the percentage of Tregs in PBMCs.

The Examples also show that administration of the compositions of the invention can lead to an increase in the ratio of CD8+ T cells to Treg cells. CD8+ T cells (CD8 cells) are cytotoxic T cells, and play key roles in the immune defence against intracellular pathogens. Since administration of the compositions of the invention were shown to increase the ratio of both CD8/Treg cells and activated CD8/Treg cells (FIG. 6G and FIG. 6H), compositions of the invention may be useful in the treatment of diseases characterised by a decrease in the ratio of CD8/Treg and/or activated CD8/Treg cells. In one embodiment, the compositions of the invention are for use in treating or preventing diseases characterised by decrease in the ratio of CD8/Treg cells. In one embodiment, the compositions of the invention are for use in treating or preventing diseases characterised by decrease in the ratio of activated CD8/Treg cells. In one embodiment, the compositions of the invention are for use in treating or preventing diseases by decreasing the percentage of Tregs in cell populations, thereby increasing the ratio of CD8/Treg cells. In one embodiment, the compositions of the invention are for use in treating or preventing diseases by decreasing the percentage of Tregs in cell populations, thereby increasing the ratio of CD8/Treg cells, wherein the increase in the ratio of CD8/Treg cells results in immunostimulation. In another embodiment, the compositions of the invention are for use in treating or preventing diseases by decreasing the percentage of Tregs in cell populations, thereby increasing the ratio of activated CD8/Treg cells. In one embodiment, the compositions of the invention are for use in treating or preventing diseases by decreasing the percentage of Tregs in cell populations, thereby increasing the ratio of CD8/Treg cells, wherein the increase in the ratio of activated CD8/Treg cells results in immune stimulation. In one embodiment, compositions of the invention are for use in stimulating the immune response by increasing the ratio of CD8/Treg cells. In one embodiment, compositions of the invention are for use in stimulating the immune response by increasing the ratio of activated CD8/Treg cells.

Figure 6D:
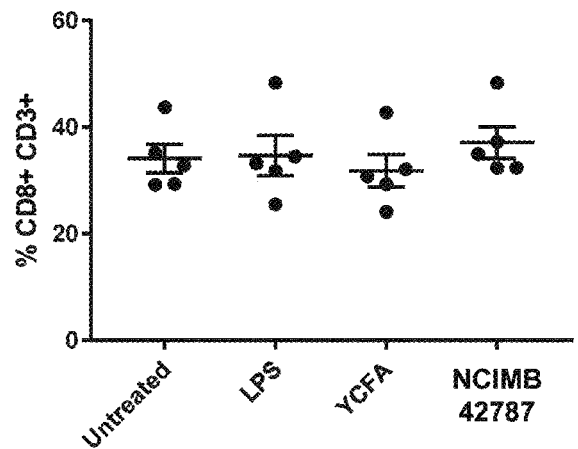
Figure 6E:
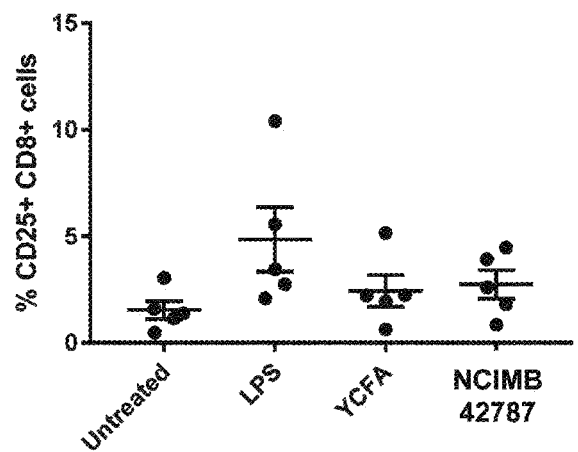
Figure 6F:
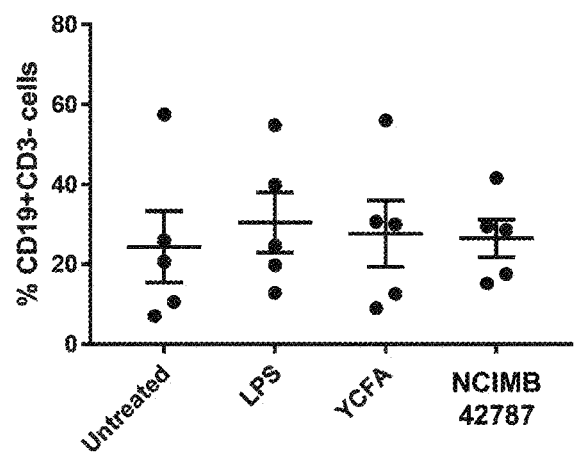

The Examples also show that administration of the compositions of the invention can lead to an increase in the percentage of CD19+CD3− cells in PBMCs (FIG. 6F). Therefore, administration of the compositions of the invention can lead to an increase in the percentage of B cells in a cell population. Since administration of the compositions of the invention were shown to increase the percentage of B cells, compositions of the invention may be useful in the treatment of diseases characterised by a decrease in the number or percentage of B cells. In one embodiment, the compositions of the invention are for use in treating or preventing diseases characterised by decrease in the number or percentage of B cells. In one embodiment, the compositions of the invention are for use in treating or preventing diseases characterised by decrease in the number or percentage of CD19+CD3− cells. In one embodiment, the compositions of the invention are for use in treating or preventing diseases by increasing the number or percentage of B cells in cell populations, wherein the increase in number or percentage of B cells results in immune stimulation. In one embodiment, compositions of the invention are for use in stimulating the immune response by increasing the number or percentage of B cells.

The Examples also show that administration of the compositions of the invention can lead to an increase in the percentage of CD8 T-cytotoxic cells (FIG. 6D) in PBMCs. Therefore, administration of the compositions of the invention can lead to an increase in the percentage of CD8 T cells in a cell population. Since administration of the compositions of the invention were shown to increase the percentage of CD8 T-cytotoxic cells, compositions of the invention may be useful in the treatment of diseases characterised by a decrease in the number or percentage of CD8 T-cytotoxic cells. In one embodiment, the compositions of the invention are for use in treating or preventing diseases characterised by decrease in the number or percentage of CD8 T-cytotoxic cells. In one embodiment, the compositions of the invention are for use in treating or preventing diseases by increasing the number or percentage of CD8 T-cytotoxic cells in cell populations, wherein the increase in number or percentage of CD8 T-cytotoxic cells results in immune stimulation. In one embodiment, compositions of the invention are for use in stimulating the immune response by increasing the number or percentage of CD8 T-cytotoxic cells.

The Examples also show that administration of the compositions of the invention can lead to an increase in the percentage of CD8+ activated cells (FIG. 6E) in PBMCs. Therefore, administration of the compositions of the invention can lead to an increase in the percentage of CD8+ activated cells in a cell population. Since administration of the compositions of the invention were shown to increase the percentage of CD8+ activated cells, compositions of the invention may be useful in the treatment of diseases characterised by a decrease in the number or percentage of CD8+ activated cells. In one embodiment, the compositions of the invention are for use in treating or preventing diseases characterised by decrease in the number or percentage of CD8+ activated cells. In one embodiment, the compositions of the invention are for use in treating or preventing diseases by increasing the number or percentage of CD8+ activated cells in cell populations, wherein the increase in number or percentage of CD8+ activated cells results in immune stimulation. In one embodiment, compositions of the invention are for use in stimulating the immune response by increasing the number or percentage of CD8+ activated cells.

The Examples show that administration of the compositions of the invention can lead to an increase in expression of pro-inflammatory molecules in PBMCs, such as pro-inflammatory cytokines (FIG. 7 and FIG. 9). Examples of immune-stimulatory (e.g. pro-inflammatory) molecules that showed an increase in expression levels upon administration of compositions of the invention include IL-23, TNF-α, IL-1β, MIP-3α, IL-8 and IL-6. Since administration of the compositions of the invention were shown to increase the expression of immune-stimulatory (e.g. pro-inflammatory) molecules, compositions of the invention may be useful in the treatment of diseases characterised by a decrease in expression of pro-inflammatory molecules, such as pro-inflammatory cytokines. In one embodiment, the compositions of the invention are for use in treating or preventing diseases characterised by a decrease in the expression and/or activity of pro-inflammatory molecules, in particular diseases characterised by a decrease in the expression and/or activity of pro-inflammatory cytokines. In a particular embodiment, the compositions of the invention are for use in treating or preventing diseases characterised by a decrease in the expression and/or activity of IL-23, TNF-α, IL-1β, MIP-3α and/or IL-6. In a particular embodiment, the compositions of the invention are for use in treating or preventing diseases characterised by a decrease in the expression and/or activity of IL-8. In a particular embodiment, the compositions of the invention are for use in treating or preventing diseases characterised by a decrease in the expression and/or activity of CD11b. In one embodiment, the compositions of the invention are for use in treating or preventing diseases by increasing the expression and/or activity of IL-23, TNF-α, IL-1β, MIP-3α and/or IL-6. In one embodiment, the compositions of the invention are for use in treating or preventing diseases by increasing the expression and/or activity of IL-8. In one embodiment, the compositions of the invention are for use in treating or preventing diseases by increasing the expression and/or activity of CD11b. In one embodiment, compositions of the invention are for use in promoting the immune response by increasing the expression and/or activity of IL-23, TNF-α, IL-1β, MIP-3α and/or IL-6. In one embodiment, compositions of the invention are for use in promoting the immune response by increasing the expression and/or activity of IL-8. In one embodiment, compositions of the invention are for use in promoting the immune response by increasing the expression and/or activity of CD11b.

The Examples also show that administration of the compositions of the invention can lead to an increase in expression of IL-1β in PBMCs. IL-1β is a pro-inflammatory cytokine [21]. The production and secretion of IL-1β is regulated by the inflammasome, a protein complex which is associated with activation of the inflammatory response [22]. Since administration of the compositions of the invention were shown to increase the expression of IL-1β, compositions of the invention may be useful in the treatment of diseases characterised by a decrease in expression of IL-1β. In a particular embodiment, the compositions of the invention are for use in treating or preventing diseases characterised by a decrease in the expression and/or activity of IL-1β. In one embodiment, the compositions of the invention are for use in treating or preventing diseases by increasing the expression and/or activity of IL-1β. In one embodiment, the compositions of the invention are for use in promoting the immune response by increasing the expression and/or activity of IL-1β. In certain embodiments, a bacterial strain of the species *Megasphaera massiliensis* is for use in the treatment of diseases characterised by a decrease in expression and/or activity of IL-1β. In one embodiment, a bacterial strain of the species *Megasphaera massiliensis* is for use in treating or preventing diseases by increasing the expression and/or activity of IL-1β. In one embodiment, a bacterial strain of the species *Megasphaera massiliensis* is for use in promoting the immune response by increasing the expression and/or activity of IL-1β.

The Examples also show that administration of the compositions of the invention can lead to an increase in expression of IL-23. IL-23 has been linked to inflammation [23, 24]. The proposed functions of IL-23 in the immune response include promoting the proliferation of CD4+ memory T cells and promoting the secretion of IFN-γ by dendritic cells (DCs) [25]. Since administration of the compositions of the invention were shown to increase the expression of IL-23, compositions of the invention may be useful in the treatment of diseases characterised by a decrease in expression of IL-23. In a particular embodiment, the compositions of the invention are for use in treating or preventing diseases characterised by a decrease in the expression and/or activity of IL-23. In one embodiment, the compositions of the invention are for use in treating or preventing diseases by increasing the expression and/or activity of IL-23. In one embodiment, compositions of the invention are for use in promoting the immune response by increasing the expression and/or activity of IL-23. In certain embodiments, a bacterial strain of the species *Megasphaera massiliensis* is for use in the treatment of diseases characterised by a decrease in expression and/or activity of IL-23. In one embodiment, a bacterial strain of the species *Megasphaera massiliensis* is for use in treating or preventing diseases by increasing the expression and/or activity of IL-23. In one embodiment, a bacterial strain of the species *Megasphaera massiliensis* is for use in promoting the immune response by increasing the expression and/or activity of IL-23.

The Examples also show that administration of the compositions of the invention can lead to an increase in expression of Macrophage Inflammatory Protein-3 (MIP3-α), or CCL20 in PBMCs. MIP3-α is an inflammatory chemokine which binds to the CCR6 receptor, and functions as a chemoattractant for DCs and memory T-cells. MIP3-α is associated with triggering the adaptive immune response by recruiting immature DCs to the site of inflammation [26]. Dysregulated expression of MIP3-α has been associated with diseases such as inflammatory bowel disease [27]. Since administration of the compositions of the invention were shown to increase the expression of MIP3-α, compositions of the invention may be useful in the treatment of diseases characterised by a decrease in expression of MIP3-α. In a particular embodiment, the compositions of the invention are for use in treating or preventing diseases characterised by a decrease in the expression and/or activity of MIP3-α. In one embodiment, the compositions of the invention are for use in treating or preventing diseases by increasing the expression and/or activity of MIP3-α. In one embodiment, compositions of the invention are for use in promoting the immune response by increasing the expression and/or activity of MIP3-α. In certain embodiments, a bacterial strain of the species *Megasphaera massiliensis* is for use in the treatment of diseases characterised by a decrease in expression of and/or activity of MIP3-α. In one embodiment, a bacterial strain of the species *Megasphaera massiliensis* is for use in treating or preventing diseases by increasing the expression and/or activity of MIP3-α. In one embodiment, a bacterial strain of the species *Megasphaera massiliensis* is for use in promoting the immune response by increasing the expression and/or activity of MIP3-α.

The Examples show that administration of the compositions of the invention can lead to an increase in expression of Tumour Necrosis Factor alpha (TNF-α). TNF-α is a pro-inflammatory cytokine which is known to be involved in various signalling pathways to promote cell death. TNF-α initiates apoptosis by binding to its cognate receptor, TNFR-1, which leads to a cascade of cleavage events in the apoptotic pathway [28]. TNF-α can also trigger necrosis via a RIP kinase-dependent mechanism [29]. Since administration of the compositions of the invention show an increase in TNF-α expression, compositions of the invention may be useful in the treatment of diseases, in particular for use in treating or preventing diseases characterised by a decrease in expression of by TNF-α. In one embodiment, the compositions of the invention are for use in treating diseases characterised by decreased TNF-α expression. In a particular embodiment, the compositions of the invention are for use in treating or preventing diseases characterised by a decrease in the expression and/or activity of TNF-α. In one embodiment, the compositions of the invention may be useful for treating or preventing diseases by increasing the expression and/or activity of TNF-α. In one embodiment, compositions of the invention are for use in promoting the immune response by increasing the expression and/or activity of TNF-α. In certain embodiments, a bacterial strain of the species *Megasphaera massiliensis* is for use in the treatment of diseases characterised by a decrease in expression of and/or activity of TNF-α. In one embodiment, a bacterial strain of the species *Megasphaera massiliensis* is for use in treating or preventing diseases by increasing the expression and/or activity of TNF-α. In one embodiment, a bacterial strain of the species *Megasphaera massiliensis* is for use in promoting the immune response by increasing the expression and/or activity of TNF-α.

The Examples also show that administration of the compositions of the invention can lead to an increase in expression of IL-6 in PBMCs. IL-6 a pro-inflammatory cytokine that is produced during inflammation, and promotes the differentiation of immature CD4+ T cells and the differentiation of CD8+ T cells into cytotoxic T cells [30]. Since administration of the compositions of the invention were shown to increase the expression of IL-6, compositions of the invention may be useful in the treatment of diseases characterised by a decrease in expression of IL-6. In a particular embodiment, the compositions of the invention are for use in treating or preventing diseases characterised by a decrease in the expression and/or activity of IL-6. In one embodiment, the compositions of the invention are for use in treating or preventing diseases by increasing the expression and/or activity of IL-6. In one embodiment, compositions of the invention are for use in promoting the immune response by increasing the expression and/or activity of IL-6. In certain embodiments, a bacterial strain of the species *Megasphaera massiliensis* is for use in the treatment of diseases characterised by a decrease in expression of and/or activity of IL-6. In one embodiment, a bacterial strain of the species *Megasphaera massiliensis* is for use in treating or preventing diseases by increasing the expression and/or activity of IL-6. In one embodiment, a bacterial strain of the species *Megasphaera massiliensis* is for use in promoting the immune response by increasing the expression and/or activity of IL-6.

Bettelli et al. [31] reported that IL-6 inhibits the production of Tregs. Since the Examples show that compositions of the invention increase the expression of IL-6, compositions of the invention may selectively decrease the number or percentage of Tregs by increasing the expression of IL-6. In one embodiment, compositions of the invention are for use in immunostimulation by increasing the expression of IL-6. In another embodiment, compositions of the invention are for use in immunostimulation by decreasing the number or percentage of Tregs. In one embodiment, a bacterial strain of the species *Megasphaera massiliensis* is for use in immunostimulation by increasing the expression of IL-6. In another embodiment, a bacterial strain of the species *Megasphaera massiliensis* is for use in immunostimulation by decreasing the number or percentage of Tregs.

The Examples also show that administration of the compositions of the invention can lead to an increase in expression of IL-8 (see Example 8). IL-8 is a pro-inflammatory cytokine secreted predominantly by macrophages with immune-stimulatory effects. It induces chemotaxis in target cells, primarily neutrophils but also other granulocytes, causing them to migrate toward the site of infection. IL-8 also stimulates phagocytosis. Since administration of the compositions of the invention were shown to increase the expression of IL-8, compositions of the invention may be useful in the treatment of diseases characterised by a decrease in expression of IL-8. In a particular embodiment, the compositions of the invention are for use in treating or preventing diseases characterised by a decrease in the expression and/or activity of IL-8. In one embodiment, the compositions of the invention are for use in treating or preventing diseases by increasing the expression and/or activity of IL-8. In one embodiment, compositions of the invention are for use in promoting the immune response by increasing the expression and/or activity of IL-8. In certain embodiments, a bacterial strain of the species *Megasphaera massiliensis* is for use in the treatment of diseases characterised by a decrease in expression of IL-8 and/or activity of IL-8. In one embodiment, a bacterial strain of the species *Megasphaera massiliensis* is for use in treating or preventing diseases by increasing the expression and/or activity of IL-8. In one embodiment, a bacterial strain of the species *Megasphaera massiliensis* is for use in promoting the immune response by increasing the expression and/or activity of IL-8.

The Examples also show that administration of the compositions of the invention can lead to an increase in expression of CD11b (see Example 12). CD11b is a pro-inflammatory cytokine with immune-stimulatory effects. CD11b is expressed on the surface of many leukocytes involved in the innate immune system and mediates inflammation by regulating leukocyte adhesion and migration. CD11b has been implicated in several immune processes, for example phagocytosis, cell-mediated cytotoxicity, chemotaxis and cellular activation. Since administration of the compositions of the invention were shown to increase the expression of CD11b, compositions of the invention may be useful in the treatment of diseases characterised by a decrease in expression of CD11b. In a particular embodiment, the compositions of the invention are for use in treating or preventing diseases characterised by a decrease in the expression and/or activity of CD11b. In one embodiment, the compositions of the invention are for use in treating or preventing diseases by increasing the expression and/or activity of CD11b. In one embodiment, compositions of the invention are for use in promoting the immune response by increasing the expression and/or activity of CD11b. In certain embodiments, a bacterial strain of the species *Megasphaera massiliensis* is for use in the treatment of diseases characterised by a decrease in expression of CD11b and/or activity of CD11b. In one embodiment, a bacterial strain of the species *Megasphaera massiliensis* is for use in treating or preventing diseases by increasing the expression and/or activity of CD11b. In one embodiment, a bacterial strain of the species *Megasphaera massiliensis* is for use in promoting the immune response by increasing the expression and/or activity of CD11b.

The Examples show that compositions of the invention can induce NF-κB-Ap1 promoter activation (see FIG. 61). NF-κB is involved in the activation of the immune response in particular by stimulating the expression of mediators of inflammation and cytokines involved in the immune response, for example IL-6. As outlined above, an increase in the expression of IL-6 helps to stimulate the immune system and thus the activation of the NF-κB pathway has immunostimulatory activity. Accordingly, in certain embodiments, the compositions of the invention activate NF-κB signalling and thus stimulate the immune system. In certain embodiments, the compositions of the invention stimulate expression of mediators of inflammation and immunostimulatory cytokines by increasing the activation of the NF-κB promoter.

Cancer

In preferred embodiments, the compositions of the invention are for use in treating or preventing cancer. In a particular embodiment, compositions of the invention are for use in treating or preventing brain cancer, in particular neuroblastoma. In a particular embodiment, compositions of the invention are for use in treating or preventing melanoma, in particular metastatic melanoma. In certain embodiments, the compositions of the invention are for use in treating or preventing brain cancer. In certain embodiments, the compositions of the invention are for use in treating or preventing neuroblastoma. In certain embodiments, the compositions of the invention are for use in treating or preventing melanoma. In certain embodiments, the compositions of the invention are for use in treating or preventing metastatic melanoma. In a most preferred embodiment, the composition of the invention comprises a bacterial strain of the species *Megasphaera massihensis* and is for use in treating or preventing brain cancer, in particular neuroblastoma. In a further most preferred embodiment, the composition of the invention comprises a bacterial strain of the species *Megasphaera massihensis* and is for use in treating or preventing melanoma, in particular metastatic melanoma.

The Examples (Example 1) demonstrate that administration of the compositions of the invention can lead to an increase in Class III beta tubulin (133 Tubulin) expression in undifferentiated neuroblastoma cells. β3 tubulin is widely known as a neuronal marker [32]. The Examples also demonstrate that administration of the compositions of the invention can lead to an increase in Microtubule-associated protein 2 (MAP2) expression in undifferentiated neuroblastoma cells. MAP2 is predominantly expressed in neurons and functions to stabilise microtubules, to promote the development of dendrites and for neurite outgrowth [33]. MAP2 is known as a marker of differentiated neurons.

Agents which cause cell differentiation have been associated with cancer therapeutics, since administration of cell-differentiating agents has been correlated with the inhibition of tumour growth [34]. Therefore, the compositions of the invention may be useful in treating cancer. In a particular embodiment, compositions of the invention are for use in treating cancers by inducing cell differentiation, in particular neuronal differentiation. In one embodiment, compositions of the invention are for use in treating brain cancer by inducing neuronal differentiation, in particular the treatment of neuroblastoma.

Furthermore, MAP2 has been found to be highly expressed in primary cutaneous melanomas, but has reduced expression in metastatic melanomas [35]. It has been proposed that increased expression of microtubule-stabilizing proteins or treatment with microtubule stabilizing proteins such as MAP2 may interfere the dynamic instability of microtubules which is required during cell division. Therefore, upregulation of MAP2 is thought to hamper cell division and delay tumour growth in cancer [35]. Therefore, compositions of the invention may be useful for treating cancer, in particular metastatic cancers. In one embodiment, the compositions of the invention are for use in a method of treating cancer. In certain embodiments, the compositions of the invention are for use in treating or preventing cancers mediated by decreased MAP2 expression. In certain embodiments, the compositions of the invention are for use in treating or preventing cancers characterised by decreased or absent MAP2 expression. In certain embodiments, the compositions of the invention are for use in increasing MAP2 expression in the treatment of cancer. In a preferred embodiment, the compositions of the invention are for use in treating or preventing melanoma. In a particular embodiment, the compositions of the invention are for use in treating or preventing metastatic melanoma.

In certain embodiments, the therapeutic combinations of the invention are for use in treating or preventing melanoma. According to some embodiments, the therapeutic combinations of the invention have an effect on melanocytes and may be effective for treating melanoma. In certain embodiments, the therapeutic combinations of the invention are for use in reducing tumour size, reducing tumour growth, or reducing angiogenesis in the treatment of melanoma.

In particular, the Examples show that administration of the compositions of the invention can lead to an increase in MAP2 expression in undifferentiated neuroblastoma cells. Since MAP2 is widely known as a marker of differentiated neurons and its expression has been shown to have implications in cancer, the compositions of the invention may be particularly useful for treating brain cancer, such as neuroblastoma. In one embodiment, the compositions of the invention are for use in a method of treating brain cancer. In a preferred embodiment, the compositions of the invention are for use in a method of treating neuroblastoma.

Furthermore, the Examples also show that administration of the compositions of the invention can lead to a significant decrease in Dopamine Receptor D2 (DRD2) expression (see Example 2 and FIG. 3). DRD2 is a G-protein coupled receptor (GPCR) and it is part of the dopamine receptor family. DRD2 is involved in signalling pathways which promote cell survival, and is therefore associated with cancer. The overexpression or upregulation of DRD2 has been implicated in several types of cancer, as malignant cells show an increased expression of DRD2 when compared to normal cells [36]. It has been shown that inhibiting DRD2 through DRD2-specific antagonists has anti-tumour effects. DRD2 antagonists have been shown to have anti-tumour efficacy in many cancers, including breast cancer [37] [38], glioblastoma [39] [40] [41], neuroblastoma [42], hepatocellular carcinoma [43], lung cancer, prostate cancer [44], cervical cancer [45], ovarian cancer [46], lymphoma [47] and gastric cancer [48]. Therefore, compositions that decrease the expression level of DRD2 may be useful for the treatment of cancer. Since administration of the compositions of the invention were shown to decrease DRD2 expression, compositions of the invention may be useful in the treatment of cancer, in particular for use in treating or preventing cancers characterised by increased DRD2 expression. In one embodiment, the compositions of the invention may be useful for treating or preventing cancers characterised by increased expression and/or activity of DRD2. In certain embodiments, the compositions of the invention are for use in decreasing DRD2 expression and/or activity in the treatment of cancer. In one embodiment, the compositions of the invention may be useful for treating cancer, in particular breast cancer, ovarian cancer, cervical cancer, brain cancer, in particular glioblastoma and neuroblastoma, carcinoma, in particular hepatocellular carcinoma, lung cancer, prostate cancer lymphoma and/or gastric cancer. In one embodiment, the compositions of the invention may be useful for treating or preventing cancer by decreasing the level and/or activity of DRD2.

Prabhu et al. reported that ONC201, an antagonist of DRD2, has shown efficacy in shrinking tumours in glioblastoma models. DRD2 expression is upregulated in glioblastoma tumours, and therefore DRD2 is an attractive target for cancer therapeutics [49]. In certain embodiments, the compositions of the invention are for use in treating or preventing glioblastoma.

The Examples also show that administration of the compositions of the invention can lead to an increase in Caspase 3 (Casp3) expression in SH-SY5Y cells. Caspases are part of the cysteine protease family and are known to promote apoptosis. Casp3 is known as an "executioner caspase", which plays an important role in the cleavage cascade of cellular proteins in the apoptotic pathway. Downregulation of Casp3 expression has previously been shown in cancers from breast, ovarian and cervical tumour tissues, and it is thought that decreased expression of Casp3 promotes cell survival in cancerous tissue [50]. Therefore, compositions that increase the expression level of executioner caspases, in particular Casp3, may be useful for the treatment of cancer. Since administration of the compositions of the invention were shown to increase Casp3 expression, compositions of the invention may be useful in the treatment of cancer, in particular for use in treating or preventing cancers mediated by Casp3 expression. In certain embodiments, the compositions of the invention are for use in treating or preventing cancers characterised by decreased or absent Casp3 expression. In one embodiment, the compositions of the invention may be useful for treating cancers characterised by decreased or absent executioner caspase expression. In a particular embodiment, the compositions of the invention may be useful for treating or preventing cancers characterised by decreased or absent expression of Casp3. In certain embodiments, the compositions of the invention are for use in increasing Casp3 expression in the treatment of cancer. In one embodiment, the compositions of the invention may be useful for treating cancer, in particular breast cancer, ovarian cancer and/or cervical cancer. In one embodiment, the compositions of the invention may be useful for treating cancer by increasing the level and/or activity of Casp3.

Furthermore, caspases have been reported to be involved in processes other than apoptosis, such as cell differentiation [51]. The Examples (Example 1 and Example 3) demonstrate that administration of the compositions of the invention can lead to an increase in the expression of neuronal markers 133 Tubulin and MAP2, and also increase the expression of Casp3 in undifferentiated neuroblastoma cells. Since compositions of the invention can lead to an increase in expression of neuronal markers and proteins known to play a role in cell differentiation, compositions of the invention may be useful in the differentiation of neurons from undifferentiated cells.

The Examples also show that administration of the compositions of the invention can lead to a decrease in cell viability in undifferentiated neuroblastoma cells (FIG. 5). In particular, the Examples show that administration of MRx0029 at a concentration of 5% or 10% causes a significant, dose-dependent decrease in cell viability (FIG. 5).

It is known that a decrease in cell viability, or increased cell death of cancerous cells is a target for cancer treatment [52]. Therefore, compositions that decrease cell viability in cancer cell lines, such as neuroblastoma cell lines, may be useful for the treatment of cancer. In one embodiment, the compositions of the invention are for use in the treatment of cancer by decreasing cell viability. In another embodiment, compositions of the invention are for use in the treatment of cancer by increasing cell death.

Furthermore, since the Examples show that compositions of the invention both increase Casp3 expression and decrease cell viability (FIG. 4 and FIG. 5), it is proposed that the compositions of the invention decrease cell viability by upregulating apoptosis. In one embodiment, compositions of the invention are for use in upregulating apoptosis. In another embodiment, compositions of the invention are for use in the treatment of cancer by increasing cell death, in particular by increasing apoptosis. In one embodiment, compositions of the invention are for use in treating cancers by decreasing cell viability. In one embodiment, compositions of the invention are for use in treating cancers by decreasing cell viability. In one embodiment, compositions of the invention are for use in treating cancers by upregulating apoptosis. In a particular embodiment, compositions of the invention are for use in treating cancers by upregulating apoptosis. In a particular embodiment, compositions of the invention are for use in treating cancers characterised by decreased or absent Casp3 expression by upregulating apoptosis. In certain embodiments, the compositions of the invention are for use in increasing apoptosis in the treatment of cancer. In certain embodiments, the compositions of the invention are for use in decreasing cell viability in the treatment of cancer.

The Examples show that compositions of the invention increase both Casp3 and MAP2 expression. Therefore, Casp3 upregulation and MAP2 upregulation may be related.

Histone acetylation and deacetylation are important epigenetic regulators of gene expression. Epigenetic regulation is a powerful tool for regulating all aspects of cell function. Histone deacetylases (HDAC) repress gene expression by removing acetyl groups from an ε-N-acetyl lysine amino acid on a histone, allowing the histones to wrap the DNA more tightly and resulting in transcriptional suppression through nucleosomal inaccessibility. HDAC has 18 isoforms which are organised into four classes: Class I, II, III and IV. Alterations in HDAC levels have been observed in many disease types including for example cancers, infectious diseases, inflammatory diseases and neurodegenerative diseases [53,54,55].

HDAC inhibitors (HDACi) are an emerging class of promising anti-cancer drugs that have been shown to cause growth arrest, differentiation, apoptosis, reduction of angiogenesis and modulation of the immune response in a variety of cancer cell lines [56,57,58,59]. Although the precise mechanism by which the clinical activity of these agents is mediated remains unclear, a wide range of HDACi are currently being investigated as potential anticancer agents. Furthermore, due to the demonstrable anticancer activity in both in vitro and in vivo studies, many HDACi have progressed rapidly through clinical development, either as monotherapies or in combination with other anticancer agents [60]. Among them, vorinostat (Zolinza™), romidepsin (Istodax™), and belinostat (Beleodag™) have received approval from the US FDA for the treatment of lymphoma. Lymphoma and other blood cancers (also called haematologic cancers or haematologic malignancies) are particularly sensitive to HDACi. The gut microbiota, with its immense diversity and metabolic capacity, represents a huge metabolic reservoir for production of a vast variety of molecules with potential effects on HDAC activity. Few studies have assessed the HDAC inhibitory activity of microbially-derived metabolites other than butyrate, which has been shown to inhibit HDAC and is associated with improvement of motor function in Huntington's disease [61].

The Examples show that compositions of the invention inhibit HDAC activity, in particular Class I HDAC, for example HDAC2 (Examples 9 and 10). Accordingly, in certain embodiments, the compositions of the invention modulate HDAC activity. In certain embodiments, the compositions of the invention reduce HDAC activity. In certain embodiments, the compositions of the invention inhibit HDAC. In certain embodiments, the compositions of the invention are HDACi. In preferred embodiments, the compositions of the invention reduce Class I HDAC activity. In certain embodiments, the compositions of the invention reduce Class II HDAC activity. In certain embodiments, the compositions of the invention reduce Class III HDAC activity. In certain embodiments, the compositions of the invention reduce Class IV HDAC activity. In certain embodiments, the compositions of the invention reduce HDAC1 activity. In preferred embodiments, the compositions of the invention reduce HDAC2 activity. In certain embodiments, the compositions of the invention reduce HDAC3 activity. In certain embodiments, the compositions of the invention reduce HDAC activity through production of valeric acid. In certain embodiments, the compositions of the invention reduce HDAC activity through production of sodium butyrate. In preferred embodiments, the compositions of the invention are for use in treating or preventing cancer by reducing HDAC activity. In preferred embodiments, the compositions of the invention are for use in treating or preventing HDAC associated cancers. In certain embodiments, the compositions of the invention are for use in treating or preventing metastatic melanoma, breast cancer, ovarian cancer, cervical cancer, neuroblastoma, glioblastoma, carcinoma, lung cancer, chronic lymphocyte leukemia, prostate cancer, lymphoma, colorectal cancer, haematological malignancies and/or gastric cancer by reducing HDAC activity. In preferred embodiments, the compositions of the invention are for use in treating or preventing haematological malignancies by reducing HDAC activity.

In certain embodiments, the HDAC inhibitory activity of the compositions of the invention results in growth arrest. In certain embodiments, the HDAC inhibitory activity of the compositions of the invention results in cell-cycle arrest. In certain embodiments, the HDAC inhibitory activity of the compositions of the invention results in cell differentiation. In certain embodiments, the HDAC inhibitory activity of the compositions of the invention results in apoptosis. In certain embodiments, the HDAC inhibitory activity of the compositions of the invention results in reduction of angiogenesis. In certain embodiments, the HDAC inhibitory activity of the compositions of the invention results in modulation of the immune response. In certain embodiments, the compositions of the invention are for use in reducing HDAC activity as a monotherapy. In certain embodiments, the compositions of the invention are for use in reducing HDAC activity as a combination therapy. In certain embodiments, the compositions of the invention are for use in combination with another anticancer agent. In certain embodiments, the compositions of the invention are for use in combination with more than one other anticancer agent. In certain embodiments, the compositions of the invention are for use in combination with a chemotherapeutic agent. In certain embodiments, the compositions of the invention are for use in combination with a proteasome inhibitor. In further aspects, the compositions of the invention are epigenetic regulators. In certain embodiments, the compositions of the invention are for use in treating or preventing diseases characterised by epigenetic aberrations.

In certain embodiments, a bacterial strain of the species *Megasphaera massiliensis* modulates HDAC activity. In certain embodiments, a bacterial strain of the species *Megasphaera massiliensis* reduces HDAC activity. In certain embodiments, a bacterial strain of the species *Megasphaera massiliensis* inhibits HDAC. In certain embodiments, a bacterial strain of the species *Megasphaera massiliensis* is a HDACi. In preferred embodiments, a bacterial strain of the species *Megasphaera massiliensis* reduces Class I HDAC activity. In certain embodiments, a bacterial strain of the species *Megasphaera massiliensis* reduces Class II HDAC activity. In certain embodiments, a bacterial strain of the species *Megasphaera massiliensis* reduces Class III HDAC activity. In certain embodiments, a bacterial strain of the species *Megasphaera massiliensis* reduces Class IV HDAC activity. In certain embodiments, a bacterial strain of the species *Megasphaera massiliensis* reduces HDAC1 activity. In preferred embodiments, a bacterial strain of the species *Megasphaera massiliensis* reduces HDAC2 activity. In certain embodiments, a bacterial strain of the species *Megasphaera massiliensis* reduces HDAC3 activity. In certain embodiments, a bacterial strain of the species *Megasphaera massiliensis* reduces HDAC activity through production of valeric acid. In certain embodiments, a bacterial strain of the species *Megasphaera massiliensis* reduces HDAC activity through production of sodium butyrate. In preferred embodiments, a bacterial strain of the species *Megasphaera massiliensis* is for use in treating or preventing cancer by reducing HDAC activity. In preferred embodiments, a bacterial strain of the species *Megasphaera massiliensis* is for use in treating or preventing HDAC associated cancers. In certain embodiments, a bacterial strain of the species *Megasphaera massiliensis* is for use in treating or preventing metastatic melanoma, breast cancer, ovarian cancer, cervical cancer, neuroblastoma, glioblastoma, carcinoma, lung cancer, chronic lymphocyte leukemia, prostate cancer, lymphoma, colorectal cancer, haematological malignancies and/or gastric cancer by reducing HDAC activity. In preferred embodiments, a bacterial strain of the species *Megasphaera massiliensis* is for use in treating or preventing haematological malignancies by reducing HDAC activity.

In certain embodiments, the HDAC inhibitory activity of the bacterial strain of the species *Megasphaera massiliensis* results in growth arrest. In certain embodiments, the HDAC inhibitory activity of the bacterial strain of the species *Megasphaera massiliensis* results in cell-cycle arrest. In certain embodiments, the HDAC inhibitory activity of the bacterial strain of the species *Megasphaera massiliensis* results in cell differentiation. In certain embodiments, the HDAC inhibitory activity of the bacterial strain of the species *Megasphaera massiliensis* results in apoptosis. In certain embodiments, a bacterial strain of the species *Megasphaera massiliensis* results in reduction of angiogenesis. In certain embodiments, the HDAC inhibitory activity of a bacterial strain of the species *Megasphaera massiliensis* results in modulation of the immune response. In certain embodiments, a bacterial strain of the species *Megasphaera massiliensis* is for use in reducing HDAC activity as a monotherapy. In certain embodiments, a bacterial strain of the species *Megasphaera massiliensis* is for use in reducing HDAC activity as a combination therapy. In certain embodiments, a bacterial strain of the species *Megasphaera massiliensis* is for use in combination with another anticancer agent. In certain embodiments, a bacterial strain of the species *Megasphaera massiliensis* is for use in combination with more than one other anticancer agent. In certain embodiments, a bacterial strain of the species *Megasphaera massiliensis* is for use in combination with a chemotherapeutic agent. In certain embodiments, a bacterial strain of the species *Megasphaera massiliensis* is for use in combination with a proteasome inhibitor. In further aspects, a bacterial strain of the species *Megasphaera massiliensis* is an epigenetic regulator. In certain embodiments, a bacterial strain of the species *Megasphaera massiliensis* is for use in treating or preventing diseases characterised by epigenetic aberrations.

Compositions of the invention are able to regulate epithelial permeability by modifying intracellular signal transduction involved in the expression and localization of proteins involved in gut barrier function. In particular, compositions of the invention enhance Occludin, Villin, Tight Junction Protein 1 (TJP1) and Tight Junction Protein 2 (TJP2) mRNA expression. Compositions of the invention therefore function to increase gut barrier function and reduce gut permeability (Example 11). In certain embodiments, the compositions of the invention are for use in increasing gut barrier function. In certain embodiments, the compositions of the invention are for use in reducing gut permeability. In certain embodiments, the compositions of the invention are for use in treating or preventing reduction of gut barrier function. In certain embodiments, the compositions of the invention are for use in treating or preventing increased gut permeability. In certain embodiments, the compositions of the invention are for use in treating or preventing diseases or conditions that are characterised by reduction of gut barrier function. In certain embodiments, the compositions of the invention are for use in treating or preventing diseases or conditions that are characterised by increased gut permeability. In certain embodiments, the compositions of the invention are for use in treating or preventing reduction of gut barrier function resulting from radiotherapy or chemotherapy. In certain embodiments, the compositions of the invention are for use in treating or preventing increased gut permeability resulting from radiotherapy or chemotherapy. In certain embodiments, the compositions of the invention are for use in treating or preventing cachexia by increasing gut barrier function. In certain embodiments, the compositions of the invention are for use in treating or preventing cachexia by reducing gut permeability. In certain embodiments the cachexia is cancer cachexia.

In certain embodiments, a bacterial strain of the species *Megasphaera massiliensis* is for use in increasing gut barrier function. In certain embodiments, a bacterial strain of the species *Megasphaera massiliensis* is for use in reducing gut permeability. In certain embodiments, a bacterial strain of the species *Megasphaera massiliensis* is for use in treating or preventing reduction of gut barrier function. In certain embodiments, a bacterial strain of the species *Megasphaera massiliensis* is for use in treating or preventing increased gut permeability. In certain embodiments, a bacterial strain of the species *Megasphaera massiliensis* is for use in treating or preventing diseases or conditions that are characterised by reduction of gut barrier function. In certain embodiments, a bacterial strain of the species *Megasphaera massiliensis* is for use in treating or preventing diseases or conditions that are characterised by increased gut permeability. In certain embodiments, a bacterial strain of the species *Megasphaera massiliensis* is for use in treating or preventing reduction of gut barrier function resulting from radiotherapy or chemotherapy. In certain embodiments, a bacterial strain of the species *Megasphaera massiliensis* is for use in treating or preventing increased gut permeability resulting from radiotherapy or chemotherapy. In certain embodiments, a bacterial strain of the species *Megasphaera massiliensis* is for use in treating or preventing cachexia by increasing gut barrier function. In certain embodiments a bacterial strain of the species *Megasphaera massiliensis* is for use in treating or preventing cachexia by reducing gut permeability. In certain embodiments the cachexia is cancer cachexia.

In preferred embodiments, the compositions are for treating cancer in a patient undergoing radiotherapy or chemotherapy. In such embodiments, the composition may be administered prior to, during, or after radiotherapy or chemotherapy. Patients undergoing radiotherapy or chemotherapy should not be administered any agent which induces a leaky gut, but *Megasphaera massiliensis* promotes gut-barrier function [62], so the compositions of the invention are particularly suitable for treating patients undergoing radiotherapy or chemotherapy. Activation of TLR-5 has been shown to ameliorate radiation-induced epithelial damage in vivo [63]. The compositions of the invention also activate the immune system. In some embodiments, the compositions of the invention are for use in treating radiotherapy-induced damage. In certain embodiments, a bacterial strain of the species *Megasphaera massiliensis* is for use in treating radiotherapy-induced damage.

In some embodiments, compositions of the invention can lead to a reduction in tumour growth.

In certain embodiments, treatment with the compositions of the invention results in a reduction in tumour size or a reduction in tumour growth. In certain embodiments, the compositions of the invention are for use in reducing tumour size or reducing tumour growth. The compositions of the invention may be effective for reducing tumour size or growth. In certain embodiments, the compositions of the invention are for use in patients with solid tumours. In certain embodiments, the compositions of the invention are for use in reducing or preventing angiogenesis in the treatment of cancer. The compositions of the invention may have an effect on the immune or inflammatory systems, which have central roles in angiogenesis. The compositions of the invention may have anti-metastatic activity. A bacterial strain of the species *Megasphaera massiliensis* is may have anti-metastatic activity. In certain embodiments, the compositions of the invention are for use in preventing metastasis. In certain embodiments, a bacterial strain of the species *Megasphaera massiliensis* is for use in preventing metastasis.

The Examples show that administration of the compositions of the invention can lead to a decrease in the percentage of Tregs in PBMCs (FIG. 6C). Tregs have been implicated in cancer, and infiltration of Tregs in tumour tissue has been linked to poor prognosis [64]. Since administration of the compositions of the invention were shown to selectively reduce the population of Tregs (FIG. 6C), compositions of the invention may be useful in the treatment of cancer. In one embodiment, the compositions of the invention are for use in treating or preventing cancers characterised by an increase in the percentage of Tregs in a cell population. In one embodiment, the compositions of the invention may be useful for treating or preventing cancers characterised by an increase in the percentage of CD4+CD25+CD127− cells in a cell population. In one embodiment, the compositions of the invention are for use in treating or preventing cancers by decreasing the number or percentage of Tregs, in particular in cancerous tissue. In one embodiment, compositions of the invention are for use in treating cancer by the selective reduction of Tregs.

It has been proposed that selectively reducing the number of Tregs and activating effector T cells, such as CD8+ T cells, will be an effective cancer therapy [64]. The Examples also show that administration of the compositions of the invention can lead to an increase in the ratio of CD8 cells to Treg cells. Since administration of the compositions of the invention were shown to increase the ratio of both CD8/Treg cells and activated CD8/Treg cells (FIG. 6G and FIG. 6H), compositions of the invention may be useful in the treatment of cancer. In one embodiment, the compositions of the invention are for use in treating or preventing cancers characterised by a decrease in the ratio of CD8/Treg and/or activated CD8/Treg cells. In one embodiment, the compositions of the invention are for use in treating or preventing cancers characterised by a decrease in the ratio of CD8/Treg cells. In one embodiment, the compositions of the invention are for use in treating or preventing cancers characterised by a decrease in the ratio of activated CD8/Treg cells. In one embodiment, the compositions of the invention are for use in treating or preventing cancer by decreasing the percentage of Tregs in cell populations, thereby increasing the ratio of CD8/Treg cells. In another embodiment, the compositions of the invention are for use in treating or preventing cancer by decreasing the percentage of Tregs in cell populations, thereby increasing the ratio of activated CD8/Treg cells. In one embodiment, compositions of the invention are for use in treating cancer by increasing the ratio of CD8/Treg cells.

In one embodiment, compositions of the invention are for use in treating cancer by increasing the ratio of activated CD8/Treg cells.

The Examples also show that administration of the compositions of the invention can lead to an increase in expression of IL-1β. In in Colitis-associated cancer, decreased expression of IL-1β at tumour sites has been linked to symptoms such as increased disease outcome and morbidity [65]. Since administration of the compositions of the invention were shown to increase the expression of IL-1β, compositions of the invention may be useful in the treatment of cancer. In one embodiment, the compositions of the invention are for use in treating or preventing cancers characterised by decreased or absent expression of IL-1β. In one embodiment, the compositions of the invention are for use in treating or preventing cancer by increasing the expression of IL-1β.

The Examples show that administration of the compositions of the invention can lead to an increase in expression of Tumour Necrosis Factor alpha (TNF-α). TNF-α is a pro-inflammatory cytokine which is known to be involved in various signalling pathways to promote cell death. TNF-α initiates apoptosis by binding to its cognate receptor, TNFR-1, which leads to a cascade of cleavage events in the apoptotic pathway. TNF-α can also trigger necrosis via a RIP kinase-dependent mechanism. Since many types of cancers have defective apoptotic and necrotic pathways, and TNF-α is known to a mediate these cell death pathways, TNF-α is a potential target for cancer therapy. Since administration of the compositions of the invention were shown to increase TNF-α expression, compositions of the invention may be useful in the treatment of cancer, in particular for use in treating or preventing cancers mediated by TNF-α expression. In one embodiment, the compositions of the invention may be useful for treating cancers mediated by TNF-α expression, in particular cancers with decreased expression and/or activity of TNF-α. In one embodiment, the compositions of the invention may be useful for treating cancer. In one embodiment, the compositions of the invention may be useful for treating cancer by increasing the level and/or activity of TNF-α.

In preferred embodiments, the compositions of the invention are for use in treating or preventing breast cancer. In certain embodiments, the compositions of the invention are for use in reducing tumour size, reducing tumour growth, or reducing angiogenesis in the treatment of breast cancer. In preferred embodiments, a bacterial strain of the species *Megasphaera massiliensis* is for use in treating or preventing breast cancer. In certain embodiments, a bacterial strain of the species *Megasphaera massiliensis* is for use in reducing tumour size, reducing tumour growth, or reducing angiogenesis in the treatment of breast cancer. In preferred embodiments the cancer is mammary carcinoma. In preferred embodiments the cancer is stage IV breast cancer.

In certain embodiments, the compositions of the invention are for use in treating or preventing lung cancer. In certain embodiments, the compositions of the invention are for use in reducing tumour size, reducing tumour growth, or reducing angiogenesis in the treatment of lung cancer. In certain embodiments, a bacterial strain of the species *Megasphaera massiliensis* is for use in treating or preventing lung cancer. In certain embodiments, a bacterial strain of the species *Megasphaera massiliensis* is for use in reducing tumour size, reducing tumour growth, or reducing angiogenesis in the treatment of lung cancer. In preferred embodiments the cancer is lung carcinoma.

In certain embodiments, the compositions of the invention are for use in treating or preventing liver cancer. In certain embodiments, the compositions of the invention are for use in reducing tumour size, reducing tumour growth, or reducing angiogenesis in the treatment of liver cancer. In certain embodiments, a bacterial strain of the species *Megasphaera massiliensis* is for use in treating or preventing liver cancer. In certain embodiments, a bacterial strain of the species *Megasphaera massiliensis* is for use in reducing tumour size, reducing tumour growth, or reducing angiogenesis in the treatment of liver cancer. In preferred embodiments the cancer is hepatoma (hepatocellular carcinoma).

In preferred embodiments, the compositions of the invention are for use in treating or preventing melanoma. In certain embodiments, the compositions of the invention are for use in reducing tumour size, reducing tumour growth, or reducing angiogenesis in the treatment of melanoma. In preferred embodiments, a bacterial strain of the species *Megasphaera massiliensis* is for use in treating or preventing melanoma. In certain embodiments, a bacterial strain of the species *Megasphaera massiliensis* is for use in reducing tumour size, reducing tumour growth, or reducing angiogenesis in the treatment of melanoma. In preferred embodiments the melanoma is metastatic melanoma.

In preferred embodiments, the compositions of the invention are for use in treating or preventing ovarian cancer. In certain embodiments, the compositions of the invention are for use in reducing tumour size, reducing tumour growth, or reducing angiogenesis in the treatment of ovarian cancer. In preferred embodiments, a bacterial strain of the species *Megasphaera massiliensis* is for use in treating or preventing ovarian cancer. In certain embodiments, a bacterial strain of the species *Megasphaera massiliensis* is for use in reducing tumour size, reducing tumour growth, or reducing angiogenesis in the treatment of ovarian cancer.

In preferred embodiments, the compositions of the invention are for use in treating or preventing cervical cancer. In certain embodiments, the compositions of the invention are for use in reducing tumour size, reducing tumour growth, or reducing angiogenesis in the treatment of cervical cancer. In preferred embodiments, a bacterial strain of the species *Megasphaera massiliensis* is for use in treating or preventing cervical cancer. In certain embodiments, a bacterial strain of the species *Megasphaera massiliensis* is for use in reducing tumour size, reducing tumour growth, or reducing angiogenesis in the treatment of cervical cancer.

In preferred embodiments, the compositions of the invention are for use in treating or preventing neuroblastoma. In certain embodiments, the compositions of the invention are for use in reducing tumour size, reducing tumour growth, or reducing angiogenesis in the treatment of neuroblastoma. In preferred embodiments, a bacterial strain of the species *Megasphaera massiliensis* is for use in treating or preventing neuroblastoma. In certain embodiments, a bacterial strain of the species *Megasphaera massiliensis* is for use in reducing tumour size, reducing tumour growth, or reducing angiogenesis in the treatment of neuroblastoma.

In preferred embodiments, the compositions of the invention are for use in treating or preventing glioblastoma. In certain embodiments, the compositions of the invention are for use in reducing tumour size, reducing tumour growth, or reducing angiogenesis in the treatment of glioblastoma. In preferred embodiments, a bacterial strain of the species *Megasphaera massiliensis* is for use in treating or preventing glioblastoma. In certain embodiments, a bacterial strain of the species *Megasphaera massiliensis* is for use in reducing tumour size, reducing tumour growth, or reducing angiogenesis in the treatment of glioblastoma.

In preferred embodiments, the compositions of the invention are for use in treating or preventing prostate cancer. In certain embodiments, the compositions of the invention are for use in reducing tumour size, reducing tumour growth, or reducing angiogenesis in the treatment of prostate cancer. In preferred embodiments, a bacterial strain of the species *Megasphaera massiliensis* is for use in treating or preventing prostate cancer. In certain embodiments, a bacterial strain of the species *Megasphaera massiliensis* is for use in reducing tumour size, reducing tumour growth, or reducing angiogenesis in the treatment of prostate cancer.

In preferred embodiments, the compositions of the invention are for use in treating or preventing haematological malignancies. In certain embodiments, the compositions of the invention are for use in reducing tumour size, reducing tumour growth, or reducing angiogenesis in the treatment of haematological malignancies. In preferred embodiments, a bacterial strain of the species *Megasphaera massiliensis* is for use in treating or preventing haematological malignancies. In certain embodiments, a bacterial strain of the species *Megasphaera massiliensis* is for use in reducing tumour size, reducing tumour growth, or reducing angiogenesis in the treatment of haematological malignancies. In certain embodiments the haematological malignancy is acute leukemia. In certain embodiments the haematological malignancy is chronic leukemia. In certain embodiments the haematological malignancy is acute myelogenous leukemia. In certain embodiments the haematological malignancy is chronic myelogenous leukemia. In certain embodiments the haematological malignancy is acute lymphocytic leukemia. In certain embodiments the haematological malignancy is chronic lymphocytic leukemia. In certain embodiments the haematological malignancy is lymphoma. In certain embodiments the haematological malignancy is multiple myeloma. In certain embodiments the haematological malignancy is a myelodysplastic syndrome.

In preferred embodiments, the compositions of the invention are for use in treating or preventing chronic lymphocyte leukemia. In certain embodiments, the compositions of the invention are for use in reducing tumour size, reducing tumour growth, or reducing angiogenesis in the treatment of chronic lymphocyte leukemia. In preferred embodiments, a bacterial strain of the species *Megasphaera massiliensis* is for use in treating or preventing chronic lymphocyte leukemia. In certain embodiments, a bacterial strain of the species *Megasphaera massiliensis* is for use in reducing tumour size, reducing tumour growth, or reducing angiogenesis in the treatment of chronic lymphocyte leukemia.

In preferred embodiments, the compositions of the invention are for use in treating or preventing lymphoma. In certain embodiments, the compositions of the invention are for use in reducing tumour size, reducing tumour growth, or reducing angiogenesis in the treatment of lymphoma. In preferred embodiments, a bacterial strain of the species *Megasphaera massiliensis* is for use in treating or preventing lymphoma. In certain embodiments, a bacterial strain of the species *Megasphaera massiliensis* is for use in reducing tumour size, reducing tumour growth, or reducing angiogenesis in the treatment of lymphoma. In certain embodiments the lymphoma is Hodgkin's lymphoma. In certain embodiments the lymphoma is Non-Hodgkin's lymphoma.

In preferred embodiments, the compositions of the invention are for use in treating or preventing gastric cancer. In certain embodiments, the compositions of the invention are for use in reducing tumour size, reducing tumour growth, or reducing angiogenesis in the treatment of gastric cancer. In preferred embodiments, a bacterial strain of the species *Megasphaera massiliensis* is for use in treating or preventing gastric cancer. In certain embodiments, a bacterial strain of the species *Megasphaera massiliensis* is for use in reducing tumour size, reducing tumour growth, or reducing angiogenesis in the treatment of gastric cancer.

In certain embodiments, the compositions of the invention are for use in treating or preventing colon cancer. In certain embodiments, the compositions of the invention are for use in treating or preventing colorectal cancer. The compositions of the invention may have an effect on colon cancer cells and may be effective for treating colon cancer. The compositions of the invention may have an effect on colon cancer cells and may be effective for treating colorectal cancer. In certain embodiments, the compositions of the invention are for use in reducing tumour size, reducing tumour growth, or reducing angiogenesis in the treatment of colon cancer. In certain embodiments, the compositions of the invention are for use in reducing tumour size, reducing tumour growth, or reducing angiogenesis in the treatment of colorectal cancer. In certain embodiments, a bacterial strain of the species *Megasphaera massiliensis* is for use in treating or preventing colon cancer. In certain embodiments, a bacterial strain of the species *Megasphaera massiliensis* is for use in treating or preventing colorectal cancer. In certain embodiments, a bacterial strain of the species *Megasphaera massiliensis* is for use in reducing tumour size, reducing tumour growth, or reducing angiogenesis in the treatment of colon cancer. In certain embodiments, a bacterial strain of the species *Megasphaera massiliensis* is for use in reducing tumour size, reducing tumour growth, or reducing angiogenesis in the treatment of colorectal cancer. In preferred embodiments the cancer is colorectal adenocarcinoma.

In certain embodiments, the therapeutic combinations of the invention are for use in treating or preventing kidney cancer (also referred to herein as renal cancer). In certain embodiments, the therapeutic combinations of the invention are for use in reducing tumour size, reducing tumour growth, or reducing angiogenesis in the treatment of renal cancer. In certain embodiments, a bacterial strain of the species *Megasphaera massiliensis* is for use in treating or preventing kidney cancer (also referred to herein as renal cancer). In certain embodiments, a bacterial strain of the species *Megasphaera massiliensis* is for use in reducing tumour size, reducing tumour growth, or reducing angiogenesis in the treatment of renal cancer. The Examples demonstrate that the therapeutic combinations of the invention have an effect on renal cancer cells and may be effective for treating renal cancer. In preferred embodiments the cancer is renal cell carcinoma or transitional cell carcinoma. In some embodiments, the cancer is of the intestine. In some embodiments, the cancer is of a part of the body which is not the intestine. In some embodiments, the cancer is not cancer of the intestine. In some embodiments, the cancer is not colorectal cancer. In some embodiments, the cancer is not cancer of the small intestine. In some embodiments, the treating or preventing occurs at a site other than at the intestine. In some embodiments, the treating or preventing occurs at the intestine and also at a site other than at the intestine.

In certain embodiments, the compositions of the invention are for use in treating or preventing carcinoma. The compositions of the invention may be effective for treating numerous types of carcinoma. In certain embodiments, the compositions of the invention are for use in treating or preventing non-immunogenic cancer. In certain embodiments, a bacterial strain of the species *Megasphaera massiliensis* is for use in treating or preventing carcinoma. A bacterial strain of the species *Megasphaera massiliensis* may be effective for treating numerous types of carcinoma. In certain embodiments, a bacterial strain of the species *Megasphaera massiliensis* is for use in treating or preventing non-immunogenic cancer. The Examples demonstrate that the compositions of the invention may be effective for treating non-immunogenic cancers.

The therapeutic effects of the compositions of the invention on cancer may be mediated by a pro-inflammatory mechanism. The expression of a number of pro-inflammatory cytokines may be increased following administration of MRx0029. Inflammation can have a cancer-suppressive effect [66] and pro-inflammatory cytokines such as TNF-α are being investigated as cancer therapies [67]. The up-regulation of genes such as TNF-α shown in the Examples may indicate that the compositions of the invention may be useful for treating cancer via a similar mechanism. The up-regulation of a CXCR3 ligand such as CXCL9 may indicate that the compositions of the invention elicit an IFNγ-type response. IFNγ is a potent macrophage-activating factor that can stimulate tumoricidal activity [68], and CXCL9, for example, also has anti-cancer effects [69-71]. The Examples demonstrate that the expression of a number of pro-inflammatory cytokines may be increased following administration of MRx0029. Therefore, in certain embodiments, the compositions of the invention are for use in promoting inflammation in the treatment of cancer. In preferred embodiments, the compositions of the invention are for use in promoting Th1 inflammation in the treatment of cancer. Th1 cells produce IFNγ and have potent anti-cancer effects [66]. In certain embodiments, the compositions of the invention are for use in treating an early-stage cancer, such as a cancer that has not metastasized, or a stage 0 or stage 1 cancer. Promoting inflammation may be more effective against early-stage cancers [66]. In certain embodiments, the compositions of the invention are for enhancing the effect of a second anti-cancer agent. In certain embodiments, the compositions of the invention are for use in promoting inflammation to enhance the effect of a second anti-cancer agent. In certain embodiments, the treatment or prevention of cancer comprises increasing the level of expression of one or more cytokines. In certain embodiments, the treatment or prevention of cancer comprises increasing the level of expression of one or more pro-inflammatory cytokines. For example, in certain embodiments, the treatment or prevention of cancer comprises increasing the level of expression of one or more of IL-1β, IL-6, MIP-3α, CXCL9, IL-23, MCP-1, GMCSF and TNF-α. In certain embodiments, the treatment or prevention of cancer comprises increasing the level of expression of one or more of IL-1β and MIP-3a. Increases in levels of expression of any of IL-1β, IL-6 and TNF-α are known to be indicative of efficacy in treatment of cancer.

When a bacterial strain as described herein is used in combination with lipopolysaccharide (LPS), there may be a synergistic increase in IL-1β. LPS is known to elicit a pro-inflammatory effect. Thus, in certain embodiments, the treatment or prevention comprises using a bacterial strain as described herein in combination with an agent that upregulates IL-1β. In certain embodiments, the treatment or prevention comprises using a bacterial strain as described herein in combination with LPS. Accordingly, a composition of the invention may additionally comprise an agent that upregulates IL-1β. Accordingly, a composition of the invention may additionally comprise LPS.

In certain embodiments, the compositions of the invention are for use in treating a patient that has previously received chemotherapy. In certain embodiments, the compositions of the invention are for use in treating a patient that has not tolerated a chemotherapy treatment. The compositions of the invention may be particularly suitable for such patients.

In certain embodiments, the compositions of the invention are for preventing relapse. The compositions of the invention may be suitable for long-term administration. In certain embodiments, the compositions of the invention are for use in preventing progression of cancer.

In certain embodiments, the compositions of the invention are for use in treating non-small-cell lung carcinoma. In certain embodiments, the compositions of the invention are for use in treating small-cell lung carcinoma. In certain embodiments, the compositions of the invention are for use in treating squamous-cell carcinoma. In certain embodiments, the compositions of the invention are for use in treating adenocarcinoma. In certain embodiments, the compositions of the invention are for use in treating glandular tumors, carcinoid tumors, or undifferentiated carcinomas.

In certain embodiments, the compositions of the invention are for use in treating hepatoblastoma, cholangiocarcinoma, cholangiocellular cystadenocarcinoma or liver cancer resulting from a viral infection.

In certain embodiments, the compositions of the invention are for use in treating invasive ductal carcinoma, ductal carcinoma in situ or invasive lobular carcinoma.

In further embodiments, the compositions of the invention are for use in treating or preventing acute lymphoblastic leukemia (ALL), acute myeloid leukemia, adrenocortical carcinoma, basal-cell carcinoma, bile duct cancer, bladder cancer, bone tumor, osteosarcoma/malignant fibrous histiocytoma, brainstem glioma, brain tumor, cerebellar astrocytoma, cerebral astrocytoma/malignant glioma, ependymoma, medulloblastoma, supratentorial primitive neuroectodermal tumors, breast cancer, bronchial adenomas/carcinoids, Burkitt's lymphoma, carcinoid tumor, cervical cancer, chronic lymphocytic leukemia, chronic myelogenous leukemia, chronic myeloproliferative disorders, colon cancer, cutaneous T-cell lymphoma, endometrial cancer, ependymoma, esophageal cancer, Ewing's sarcoma, intraocular melanoma, retinoblastoma, gallbladder cancer, gastric cancer, gastrointestinal carcinoid tumor, gastrointestinal stromal tumor (GIST), germ cell tumor, glioma, childhood visual pathway and hypothalamic, Hodgkin lymphoma, melanoma, islet cell carcinoma, Kaposi sarcoma, renal cell cancer, laryngeal cancer, leukaemias, lymphomas, mesothelioma, neuroblastoma, non-Hodgkin lymphoma, oropharyngeal cancer, osteosarcoma, ovarian cancer, pancreatic cancer, parathyroid cancer, pharyngeal cancer, pituitary adenoma, plasma cell neoplasia, prostate cancer, renal cell carcinoma, retinoblastoma, sarcoma, testicular cancer, thyroid cancer, or uterine cancer. In further embodiments, the compositions of the invention are for use in treating or preventing haematologic malignancies, multiple myeloma, or myelodysplastic syndromes.

The compositions of the invention may be particularly effective when used in combination with further therapeutic agents. The immune-modulatory effects of the compositions of the invention may be effective when combined with more direct anti-cancer agents. Therefore, in certain embodiments, the invention provides a composition comprising the bacterial strain of the species *Megasphaera massiliensis* and an anticancer agent. In certain embodiments, the composition of the invention comprising the bacterial strain of the species *Megasphaera massiliensis* is for use in stimulating a cancer to enhance its susceptibility to treatment with a second anti-cancer agent. In certain embodiments, the composition of the invention comprising the bacterial strain of the species *Megasphaera massiliensis* is for use in treating a cancer, such as a brain cancer, by enhancing its susceptibility to treatment with a second anti-cancer agent. The second antic-cancer agent may be administered concurrently, or may be administered after the composition comprising the bacterial strain of the species *Megasphaera massiliensis*, such as at least a day, a week, or a month after.

In preferred embodiments the anticancer agent is an immune checkpoint inhibitor, a targeted antibody immunotherapy, a CAR-T cell therapy, an oncolytic virus, or a cytostatic drug. In preferred embodiments, the composition comprises an anti-cancer agent selected from the group consisting of: Yervoy (ipilimumab, BMS); Keytruda (pembrolizumab, Merck); Opdivo (nivolumab, BMS); MEDI4736 (AZ/MedImmune); MPDL3280A (Roche/Genentech); Tremelimumab (AZ/MedImmune); CT-011 (pidilizumab, CureTech); BMS-986015 (lirilumab, BMS); MEDI0680 (AZ/MedImmune); MSB-0010718C (Merck); PF-05082566 (Pfizer); MEDI6469 (AZ/MedImmune); BMS-986016 (BMS); BMS-663513 (urelumab, BMS); IMP321 (Prima Biomed); LAG525 (Novartis); ARGX-110 (arGEN-X); PF-05082466 (Pfizer); CDX-1127 (varlilumab; CellDex Therapeutics); TRX-518 (GITR Inc.); MK-4166 (Merck); JTX-2011 (Jounce Therapeutics); ARGX-115 (arGEN-X); NLG-9189 (indoximod, NewLink Genetics); INCB024360 (Incyte); IPH2201 (Innate Immotherapeutics/AZ); NLG-919 (NewLink Genetics); anti-VISTA (JnJ); Epacadostat (INCB24360, Incyte); F001287 (Flexus/BMS); CP 870893 (University of Pennsylvania); MGA271 (Macrogenix); Emactuzumab (Roche/Genentech); Galunisertib (Eli Lilly); Ulocuplumab (BMS); BKT140/BL8040 (Biokine Therapeutics); Bavituximab (Peregrine Pharmaceuticals); CC 90002 (Celgene); 852A (Pfizer); VTX-2337 (VentiRx Pharmaceuticals); IMO-2055 (Hybridon, Idera Pharmaceuticals); LY2157299 (Eli Lilly); EW-7197 (Ewha Women's University, Korea); Vemurafenib (Plexxikon); Dabrafenib (Genentech/GSK); BMS-777607 (BMS); BLZ945 (Memorial Sloan-Kettering Cancer Centre); Unituxin (dinutuximab, United Therapeutics Corporation); Blincyto (blinatumomab, Amgen); Cyramza (ramucirumab, Eli Lilly); Gazyva (obinutuzumab, Roche/Biogen); Kadcyla (ado-trastuzumab emtansine, Roche/Genentech); Perjeta (pertuzumab, Roche/Genentech); Adcetris (brentuximab vedotin, Takeda/Millennium); Arzerra (ofatumumab, GSK); Vectibix (panitumumab, Amgen); Avastin (bevacizumab, Roche/Genentech); Erbitux (cetuximab, BMS/Merck); Bexxar (tositumomab-I131, GSK); Zevalin (ibritumomab tiuxetan, Biogen); Campath (alemtuzumab, Bayer); Mylotarg (gemtuzumab ozogamicin, Pfizer); Herceptin (trastuzumab, Roche/Genentech); Rituxan (rituximab, Genentech/Biogen); volociximab (Abbvie); Enavatuzumab (Abbvie); ABT-414 (Abbvie); Elotuzumab (Abbvie/BMS);

ALX-0141 (Ablynx); Ozaralizumab (Ablynx); Actimab-C (Actinium); Actimab-P (Actinium); Milatuzumab-dox (Actinium); Emab-SN-38 (Actinium); Naptumonmab estafenatox (Active Biotech); AFM13 (Affimed); AFM11 (Affimed); AGS-16C3F (Agensys); AGS-16M8F (Agensys); AGS-22ME (Agensys); AGS-15ME (Agensys); GS-67E (Agensys); ALXN6000 (samalizumab, Alexion); ALT-836 (Altor Bioscience); ALT-801 (Altor Bioscience); ALT-803 (Altor Bioscience); AMG780 (Amgen); AMG 228 (Amgen); AMG820 (Amgen); AMG172 (Amgen); AMG595 (Amgen); AMG110 (Amgen); AMG232 (adecatumumab, Amgen); AMG211 (Amgen/MedImmune); BAY20-10112 (Amgen/Bayer); Rilotumumab (Amgen); Denosumab (Amgen); AMP-514 (Amgen); MEDI575 (AZ/MedImmune); MEDI3617 (AZ/MedImmune); MEDI6383 (AZ/MedImmune); MEDI551 (AZ/MedImmune); Moxetumomab pasudotox (AZ/MedImmune); MEDI565 (AZ/MedImmune); MEDI0639 (AZ/MedImmune); MEDI0680 (AZ/MedImmune); MEDI562 (AZ/MedImmune); AV-380 (AVEO); AV203 (AVEO); AV299 (AVEO); BAY79-4620 (Bayer); Anetumab ravtansine (Bayer); vanticumab (Bayer); BAY94-9343 (Bayer); Sibrotuzumab (Boehringer Ingleheim); BI-836845 (Boehringer Ingleheim); B-701 (BioClin); BIIB015 (Biogen); Obinutuzumab (Biogen/Genentech); BI-505 (Bioinvent); BI-1206 (Bioinvent); TB-403 (Bioinvent); BT-062 (Biotest) BIL-010t (Biosceptre); MDX-1203 (BMS); MDX-1204 (BMS); Necitumumab (BMS); CAN-4 (Cantargia AB); CDX-011 (Celldex); CDX1401 (Celldex); CDX301 (Celldex); U3-1565 (Daiichi Sankyo); patritumab (Daiichi Sankyo); tigatuzumab (Daiichi Sankyo); nimotuzumab (Daiichi Sankyo); DS-8895 (Daiichi Sankyo); DS-8873 (Daiichi Sankyo); DS-5573 (Daiichi Sankyo); MORab-004 (Eisai); MORab-009 (Eisai); MORab-003 (Eisai); MORab-066 (Eisai); LY3012207 (Eli Lilly); LY2875358 (Eli Lilly); LY2812176 (Eli Lilly); LY3012217(Eli Lilly); LY2495655 (Eli Lilly); LY3012212 (Eli Lilly); LY3012211 (Eli Lilly); LY3009806 (Eli Lilly); cixutumumab (Eli Lilly); Flanvotumab (Eli Lilly); IMC-TR1 (Eli Lilly); Ramucirumab (Eli Lilly); Tabalumab (Eli Lilly); Zanolimumab (Emergent Biosolution); FG-3019 (FibroGen); FPA008 (Five Prime Therapeutics); FP-1039 (Five Prime Therapeutics); FPA144 (Five Prime Therapeutics); catumaxomab (Fresenius Biotech); IMAB362 (Ganymed); IMAB027 (Ganymed); HuMax-CD74 (Genmab); HuMax-TFADC (Genmab); GS-5745 (Gilead); GS-6624 (Gilead); OMP-21M18 (demcizumab, GSK); mapatumumab (GSK); IMGN289 (ImmunoGen); IMGN901 (ImmunoGen); IMGN853 (ImmunoGen); IMGN529 (ImmunoGen); IMMU-130 (Immunomedics); milatuzumab-dox (Immunomedics); IMMU-115 (Immunomedics); IMMU-132 (Immunomedics); IMMU-106 (Immunomedics); IMMU-102 (Immunomedics); Epratuzumab (Immunomedics); Clivatuzumab (Immunomedics); IPH41 (Innate Immunotherapeutics); Daratumumab (Janssen/Genmab); CNTO-95 (Intetumumab, Janssen); CNTO-328 (siltuximab, Janssen); KB004 (KaloBios); mogamulizumab (Kyowa Hakko Kirrin); KW-2871 (ecromeximab, Life Science); Sonepcizumab (Lpath); Margetuximab (Macrogenics); Enoblituzumab (Macrogenics); MGD006 (Macrogenics); MGF007 (Macrogenics); MK-0646 (dalotuzumab, Merck); MK-3475 (Merck); Sym004 (Symphogen/Merck Serono); DI17E6 (Merck Serono); MOR208 (Morphosys); MOR202 (Morphosys); Xmab5574 (Morphosys); BPC-1C (ensituximab, Precision Biologics); TAS266 (Novartis); LFA102 (Novartis); BHQ880 (Novartis/Morphosys); QGE031 (Novartis); HCD122 (lucatumumab, Novartis); LJM716 (Novartis); AT355 (Novartis); OMP-21M18 (Demcizumab, OncoMed); OMP52M51 (Oncomed/GSK); OMP-59R5 (Oncomed/GSK); vanticumab (Oncomed/Bayer); CMC-544 (inotuzumab ozogamicin, Pfizer); PF-03446962 (Pfizer); PF-04856884 (Pfizer); PSMA-ADC (Progenics); REGN1400 (Regeneron); REGN910 (nesvacumab, Regeneron/Sanofi); REGN421 (enoticumab, Regeneron/Sanofi); RG7221, RG7356, RG7155, RG7444, RG7116, RG7458, RG7598, RG7599, RG7600, RG7636, RG7450, RG7593, RG7596, DCDS3410A, RG7414 (parsatuzumab), RG7160 (imgatuzumab), RG7159 (obinutuzumab), RG7686, RG3638 (onartuzumab), RG7597 (Roche/Genentech); SAR307746 (Sanofi); SAR566658 (Sanofi); SAR650984 (Sanofi); SAR153192 (Sanofi); SAR3419 (Sanofi); SAR256212 (Sanofi), SGN-LIV1A (lintuzumab, Seattle Genetics); SGN-CD33A (Seattle Genetics); SGN-75 (vorsetuzumab mafodotin, Seattle Genetics); SGN-19A (Seattle Genetics) SGN-CD70A (Seattle Genetics); SEA-CD40 (Seattle Genetics); ibritumomab tiuxetan (Spectrum); MLN0264 (Takeda); ganitumab (Takeda/Amgen); CEP-37250 (Teva); TB-403 (Thrombogenic); VB4-845 (Viventia); Xmab2512 (Xencor); Xmab5574 (Xencor); nimotuzumab (YM Biosciences); Carlumab (Janssen); NY-ESO TCR (Adaptimmune); MAGE-A-10 TCR (Adaptimmune); CTL019 (Novartis); JCAR015 (Juno Therapeutics); KTE-C19 CAR (Kite Pharma); UCART19 (Cellectis); BPX-401 (Bellicum Pharmaceuticals); BPX-601 (Bellicum Pharmaceuticals); ATTCK20 (Unum Therapeutics); CAR-NKG2D (Celyad); Onyx-015 (Onyx Pharmaceuticals); H101 (Shanghai Sunwaybio); DNX-2401 (DNAtrix); VCN-01 (VCN Biosciences); Colo-Ad1 (PsiOxus Therapeutics); ProstAtak (Advantagene); Oncos-102 (Oncos Therapeutics); CG0070 (Cold Genesys); Pexa-vac (JX-594, Jennerex Biotherapeutics); GL-ONC1 (Genelux); T-VEC (Amgen); G207 (Medigene); HF10 (Takara Bio); SEPREHVIR (HSV1716, Virttu Biologics); OrienX010 (OrienGene Biotechnology); Reolysin (Oncolytics Biotech); SVV-001 (Neotropix); Cacatak (CVA21, Viralytics); Alimta (Eli Lilly), cisplatin, oxaliplatin, irinotecan, folinic acid, methotrexate, cyclophosphamide, 5-fluorouracil, Zykadia (Novartis), Tafinlar (GSK), Xalkori (Pfizer), Iressa (AZ), Gilotrif (Boehringer Ingelheim), Tarceva (Astellas Pharma), Halaven (Eisai Pharma), Veliparib (Abbvie), AZD9291 (AZ), Alectinib (Chugai), LDK378 (Novartis), Genetespib (Synta Pharma), Tergenpumatucel-L (NewLink Genetics), GV1001 (Kael-GemVax), Tivantinib (ArQule); Cytoxan (BMS); Oncovin (Eli Lilly); Adriamycin (Pfizer); Gemzar (Eli Lilly); Xeloda (Roche); Ixempra (BMS); Abraxane (Celgene); Trelstar (Debiopharm); Taxotere (Sanofi); Nexavar (Bayer); IMMU-132 (Immunomedics); E7449 (Eisai); Thermodox (Celsion); Cometriq (Exellxis); Lonsurf (Taiho Pharmaceuticals); Camptosar (Pfizer); UFT (Taiho Pharmaceuticals); and TS-1 (Taiho Pharmaceuticals).

In some embodiments, the bacterial strain of *Megasphaera massiliensis* deposited under accession number NCIMB 42761 is the only therapeutically active agent in a composition of the invention.

The inventors have identified that bacterial strains from the genus *Megasphaera* may be particularly effective for treating or preventing cancer comprising oncogenic extracellular signal-related kinase (ERK) signalling. Extracellular signal-related kinase (ERK) is a downstream effector in the mitogen-activated protein (MAP) kinase pathway, a highly conserved signal transduction pathway found in all eukaryotes [72]. The MAP-kinase pathway regulates processes such as cell proliferation, differentiation, survival and apoptosis, and aberrant activation of the pathway is closely linked to cancer pathogenesis. As described in the examples, administration of compositions comprising *Megasphaera* strains can inhibit ERK signalling in cancer cell lines; that is, reduce cellular levels of phosphorylated ERK relative to total ERK protein. The inventors have also identified that treatment with *Megasphaera* strains can reduce the clonogenic survival of cancer cell lines comprising oncogenic ERK signalling, in particular in melanoma and colorectal cancer cell lines. The inventors have also identified that treatment with *Megasphaera* strains can induce gene expression of microtubule-associated protein 2 (MAP2), indicating particular utility in treating metastatic cancers.

Therefore, in certain embodiments, the invention provides a composition comprising a bacterial strain of the genus *Megasphaera*, for use in a method of treating or preventing cancer, wherein the cancer comprises oncogenic ERK signalling.

As used herein "oncogenic ERK signalling" refers to the cancer comprising dysregulated cellular signalling, such as stimulus-independent signalling, via the MAP kinase pathway, the result of which is overactive signalling by ERK (either the ERK1 or ERK2 isoform, or both), which drives increased cancer cell proliferation and/or survival. ERK1 is active (i.e. signalling) when phosphorylated at positions Thr202 and Tyr204. ERK 2 is active (i.e. signalling) when phosphorylated at positions Thr173 and Tyr185. Accordingly, "oncogenic ERK signalling" can result from the presence of oncogenic mutations in (gain of function mutations) or overexpression of positive regulators of the MAP kinase pathway, or oncogenic mutations in (loss of function mutations) or downregulated expression of negative regulators of the MAP kinase pathway.

Cancer comprising oncogenic ERK signalling may alternatively be defined as cancer "exhibiting" or "characterised by" oncogenic ERK signalling. Cancer comprising oncogenic ERK signalling may alternatively be defined as cancer wherein the proliferation and/or survival of malignant cells is "stimulated", "induced" or "upregulated" by ERK signalling. Cancer comprising oncogenic ERK may alternatively be defined as cancer comprising, exhibiting or characterised by "stimulus-independent" ERK signalling.

"Oncogenic mutation" encompasses any amino acid variation in a protein, relative to the wild-type protein, which promotes cancer cell proliferation and/or survival, including, but not limited to, substitutions (including single amino acid substitutions), insertions and/or deletions. As noted above, oncogenic mutations may be loss of function or gain of function mutations, depending on the protein and its function within the MAP-kinase pathway. "Overexpression" or "downregulated expression" refer respectively to increased or decreased expression of a protein in a cancerous cell relative to a non-cancerous cell.

Accordingly, cancers comprising oncogenic ERK signalling include those comprising an oncogenic mutation in, or overexpression of, BRAF, NRAS, ARAF, CRAF, EGFR, GRB2, SOS, HRAS, KRAS4A, KRAS4B, MEK1, MEK2, ERK1 or ERK2; such as BRAF, ARAF, CRAF, EGFR, GRB2, SOS, HRAS, MEK1, MEK2, ERK1 or ERK2. These proteins are positive regulators of the MAP kinase pathway (i.e. oncoproteins) [72]. For example, the cancer may comprise an oncogenic mutation in BRAF, NRAS, ARAF, CRAF, EGFR, GRB2, SOS, HRAS, MEK1, MEK2, ERK1 or ERK2.

Cancers comprising oncogenic ERK signalling also include those which comprise (either alternatively, or in addition to, the above oncogenic mutations/overexpression) an oncogenic mutation in, or downregulated expression of, RSK, DUSP1, DUSP5, DUSP6 or SPRY. These proteins are negative regulators of the MAP kinase pathway (i.e. tumour suppressor proteins) [72].

Any cancer comprising oncogenic ERK signalling can be treated or prevented using compositions of the invention, such as solid tumours or haematological malignancies. Such cancers include, but are not limited to, colorectal cancer, melanoma, acute lymphoblastic leukaemia (ALL), acute myeloid leukaemia, adrenocortical carcinoma, basal-cell carcinoma, bile duct cancer, bladder cancer, bone tumour, osteosarcoma/malignant fibrous histiocytoma, brainstem glioma, brain tumour, cerebellar astrocytoma, cerebral astrocytoma/malignant glioma, ependymoma, medulloblastoma, supratentorial primitive neuroectodermal tumours, breast cancer, bronchial adenomas/carcinoids, Burkitt's lymphoma, carcinoid tumour, cervical cancer, chronic lymphocytic leukaemia, chronic myelogenous leukaemia, chronic myeloproliferative disorders, cutaneous T-cell lymphoma, endometrial cancer, ependymoma, esophageal cancer, Ewing's sarcoma, intraocular melanoma, retinoblastoma, gallbladder cancer, gastric cancer, gastrointestinal carcinoid tumour, gastrointestinal stromal tumour (GIST), germ cell tumour, glioma, childhood visual pathway and hypothalamic, Hodgkin lymphoma, islet cell carcinoma, Kaposi sarcoma, renal cell cancer, laryngeal cancer, leukaemias, lymphomas, mesothelioma, neuroblastoma, non-Hodgkin lymphoma, oropharyngeal cancer, osteosarcoma, ovarian cancer, pancreatic cancer, parathyroid cancer, pharyngeal cancer, pituitary adenoma, plasma cell neoplasia, prostate cancer, renal cell carcinoma, retinoblastoma, sarcoma, testicular cancer, thyroid cancer, or uterine cancer.

Any cancer comprising oncogenic ERK signalling may be treated or prevented by a composition comprising a bacterial strain of the genus *Megasphaera*, and preferably colorectal cancer, melanoma, prostate cancer, lung adenocarcinoma such as non-small cell lung adenocarcinoma, pancreatic cancer, bladder cancer, leukaemia such as hairy cell leukaemia or acute myeloid leukaemia, glioma, pilocytic astrocytoma, ovarian cancer, papillary or follicular thyroid cancer, seminoma, liver cancer, myelodysplastic syndrome, kidney cancer or Hodgkin's disease.

In preferred embodiments, the invention provides a composition comprising a bacterial strain of the genus *Megasphaera*, for use in a method of treating or preventing cancer comprising an oncogenic mutation in BRAF, optionally wherein the cancer further comprises overexpression of BRAF. The inventors have identified that treatment with *Megasphaera* strains can inhibit the clonogenic survival, inhibit ERK signalling and upregulate MAP2 gene expression in cancer cell lines comprising oncogenic BRAF mutations, in particular the oncogenic BRAF V600E mutation in colorectal cancer and melanoma cell lines. Therefore, in preferred embodiments, the invention also provides a composition comprising a bacterial strain of the genus *Megasphaera*, for use in a method of treating or preventing cancer comprising an oncogenic mutation at position 600 of BRAF, preferably BRAF V600E. In especially preferred embodiments, the cancer is colorectal cancer or melanoma.

In addition to, or instead of, an oncogenic mutation at position 600 of BRAF (such as V600E), the cancer may comprise an oncogenic mutation selected from BRAF K601E, G469A, G469V, L597R, K601N, G464V, N581S, L597Q, A598V, G464R, G466A or G469E; optionally wherein the cancer is colorectal cancer. In another embodiment, in addition to, or instead of, the V600E mutation, the cancer may comprise an oncogenic mutation selected from BRAF V600K, V600R or V600D; optionally wherein the cancer is melanoma.

In a further aspect, the invention also provides a composition comprising a bacterial strain of the species *Megasphaera massiliensis*, for use in a method of treating colorectal cancer, such as metastatic colorectal cancer. As shown in the examples, the inventors have found that *Megasphaera massiliensis* strains can inhibit clonogenic survival and ERK signalling in colorectal cancer cell lines.

In a further aspect, the invention also provides a composition comprising a bacterial strain of the species *Megasphaera massiliensis*, for use in a method of treating melanoma, such as metastatic melanoma. As shown in the examples, the inventors have found that *Megasphaera massiliensis* strains can inhibit clonogenic survival and ERK signalling in melanoma cell lines. Furthermore, the ability of *Megasphaera massiliensis* strains to induce MAP2 gene expression in melanoma cell lines indicates particular efficacy against metastatic melanoma.

In preferred embodiments, a BRAF inhibitor is administered simultaneously, separately or sequentially, relative to administration of the composition comprising a bacterial strain of the genus *Megasphaera*. Preferably, the BRAF inhibitor is a selective inhibitor of BRAF$^{V600E}$, preferably selected from Vemurafenib, Dabrafinib or Encorafenib. More preferably, the BRAF inhibitor is Vemurafenib.

In a further aspect, the invention, the invention also provides a composition comprising a bacterial strain of the genus *Megasphaera* and a BRAF inhibitor, preferably those defined above, for simultaneous, separate or sequential use in the treatment or prevention of cancer.

In other preferred embodiments, a cytidine analogue is administered simultaneously, separately or sequentially, relative to administration of the composition comprising a bacterial strain of the genus *Megasphaera*. Preferably, the cytidine analogue is selected from Azacytidine-c, Decitabine, or Zebularine. More preferably, the cytidine analogue is Azacytidine-c.

In a further aspect, the invention also provides a composition comprising a bacterial strain of the genus *Megasphaera* and a cytidine analogue, preferably those defined above, for simultaneous, separate or sequential use in the treatment or prevention of cancer.

In other preferred embodiments, a tubulin polymerisation inhibitor or tubulin depolymerisation inhibitor is administered simultaneously, separately or sequentially, relative to administration of the composition comprising a bacterial strain of the genus *Megasphaera*. Preferably, the tubulin polymerisation inhibitor or tubulin depolymerisation inhibitor is selected from Paclitaxel, Abraxane, Docetaxel, Epothilone, (+)-Discodermolide, Colchicine, Combretastatin, 2-Methoxyestradiol, E7010, Vincristine, Vinblastine, Vinorelbine or Vinflunine; more preferably Paclitaxel.

In a further aspect, the invention also provides a composition comprising a bacterial strain of the genus *Megasphaera* and a tubulin polymerisation inhibitor or tubulin depolymerisation inhibitor, preferably those defined above, for simultaneous, separate or sequential use in the treatment or prevention of cancer. In a further aspect, the invention also provides a composition comprising a bacterial strain of the genus *Megasphaera*, for use in cancer therapy by increasing the susceptibility of the cancer to a tubulin polymerisation or depolymerisation inhibitor, preferably those defined above.

In further such embodiments, the invention provides:
1. A composition comprising a bacterial strain of the genus *Megasphaera*, for use in a method of treating or preventing cancer, in particular, wherein the cancer comprises oncogenic ERK signalling.
2. A composition for use according to embodiment 1, wherein the cancer comprises an oncogenic mutation in, or overexpression of, BRAF, NRAS, ARAF, CRAF, EGFR, GRB2, SOS, HRAS, KRAS4A, KRAS4B, MEK1, MEK2, ERK1 or ERK2.
3. A composition for use according to any preceding embodiment, wherein the cancer comprises an oncogenic mutation in, or downregulated expression of, RSK, DUSP1, DUSP5, DUSP6 or SPRY.
4. A composition for use according to embodiment 2, wherein the cancer comprises an oncogenic mutation in, or overexpression of, BRAF, ARAF, CRAF, EGFR, GRB2, SOS, HRAS, MEK1, MEK2, ERK1 or ERK2.
5. A composition for use according to embodiment 2, wherein the cancer comprises an oncogenic mutation in BRAF, NRAS, ARAF, CRAF, EGFR, GRB2, SOS, HRAS, MEK1, MEK2, ERK1 or ERK2.
6. The composition for use according to any preceding embodiment, wherein the cancer comprises an oncogenic mutation in BRAF or NRAS, optionally wherein the cancer further comprises overexpression of BRAF or NRAS.
7. The composition for use according to embodiment 6, wherein the cancer comprises an oncogenic mutation in BRAF, optionally wherein the cancer further comprises overexpression of BRAF.
8. The composition for use according to embodiment 7, wherein the cancer comprises an oncogenic mutation at position 600 of BRAF.
9. The composition for use according to any of embodiments 6-8, wherein the cancer comprises an oncogenic mutation selected from BRAF V600E, K601E, G469A, G469V, L597R, K601N, G464V, N581S, L597Q, A598V, G464R, G466A or G469E; optionally wherein the cancer is colorectal cancer.
10. The composition for use according to any of embodiments 6-8, wherein the cancer comprises an oncogenic mutation selected from BRAF V600E, V600K, V600R or V600D; optionally wherein the cancer is melanoma.
11. The composition for use according to any of embodiments 6-10, wherein the cancer comprises the oncogenic mutation BRAF V600E.
12. The composition for use according to any of embodiments 6-11, wherein the cancer comprises the oncogenic mutation NRAS Q61R, optionally wherein the cancer is melanoma.
13. The composition for use according to any preceding embodiment, wherein the cancer is selected from colorectal cancer, melanoma, prostate cancer, lung adenocarcinoma such as non-small cell lung adenocarcinoma, pancreatic cancer, bladder cancer, leukaemia such as hairy cell leukaemia or acute myeloid leukaemia, glioma, pilocytic astrocytoma, ovarian cancer, papillary or follicular thyroid cancer, seminoma, liver cancer, myelodysplastic syndrome, kidney cancer or Hodgkin's disease.
14. The composition for use according to any preceding embodiment, wherein the cancer is colorectal cancer.
15. The composition for use according to any of embodiments 1-13, wherein the cancer is melanoma.
16. The composition for use according to any preceding embodiment, wherein the bacterial strain is of the species *Megasphaera massihensis*.

17. The composition for use according to any preceding embodiment, in a method of inhibiting ERK1 and/or ERK2 signalling in the treatment or prevention of the cancer.
18. The composition for use according to any preceding embodiment, in a method of inhibiting ERK1 and/or ERK2 phosphorylation in the treatment or prevention of the cancer.
19. The composition for use according to any preceding embodiment, in a method of inducing MAP2 gene expression in the treatment or prevention of the cancer.
20. The composition for use according to any preceding embodiment, in a method of reducing tumour size, tumour growth, preventing or inhibiting metastasis, or preventing angiogenesis in the treatment or prevention of the cancer.
21. The composition for use according to any preceding embodiment, in a method of inhibiting metastasis in the treatment of the cancer.
22. The composition for use according to any preceding embodiment, wherein the method comprises simultaneous, separate or sequential administration of a BRAF inhibitor, relative to administration of the composition.
23. The composition for use according to embodiment 22, wherein the BRAF selectively inhibits BRAF$^{V600E}$, preferably wherein the BRAF inhibitor is selected from Vemurafenib, Dabrafinib or Encorafenib.
24. The composition for use according to embodiment 23, wherein the BRAF inhibitor is Vemurafenib.
25. The composition for use according to any preceding embodiment, wherein the method comprises simultaneous, separate or sequential administration of a cytidine analogue, relative to administration of the composition.
26. The composition for use according to embodiment 25, wherein the cytidine analogue is selected from Azacytidine-c, Decitabine, or Zebularine.
27. The composition for use according to embodiment 26, wherein the cytidine analogue is Azacytidine-c.
28. The composition for use according to any preceding embodiment, wherein the method comprises simultaneous, separate or sequential administration of a tubulin polymerisation inhibitor or tubulin depolymerisation inhibitor, relative to administration of the composition.
29. The composition for use according to embodiment 28, wherein the tubulin polymerisation inhibitor or tubulin depolymerisation inhibitor is selected from Paclitaxel, Abraxane, Docetaxel, Epothilone, (+)-Discodermolide, Colchicine, Combretastatin, 2-Methoxyestradiol, E7010, Vincristine, Vinblastine, Vinorelbine or Vinflunine.

Preferably, cancers comprising oncogenic ERK signalling which can be treated or prevented using compositions of the invention (in particular, those comprising a bacterial strain of the species *Megasphaera massiliensis*) include, but are not limited to, colorectal cancer, melanoma, prostate cancer, lung adenocarcinoma such as non-small cell lung adenocarcinoma, pancreatic cancer, bladder cancer, leukaemia such as hairy cell leukaemia or acute myeloid leukaemia, glioma, pilocytic astrocytoma, ovarian cancer, papillary or follicular thyroid cancer, seminoma, liver cancer, myelodysplastic syndrome, kidney cancer and Hodgkin's disease. Such cancers have been reported as comprising an overactive MAP-kinase pathway (i.e. oncogenic ERK signalling) [72].

In a particular embodiment, compositions of the invention are for use in treating or preventing cancer comprising an oncogenic mutation in BRAF or NRAS, optionally wherein the cancer further comprises overexpression of BRAF or NRAS. Preferably, compositions of the invention (in particular, those comprising a bacterial strain of the species *Megasphaera massiliensis*) are for use in treating or preventing cancer which comprises an oncogenic mutation in BRAF, and optional overexpression of BRAF.

Oncogenic mutations in BRAF include V600E, K601E, G469A, G469V, L597R, K601N, G464V, N581S, L597Q, A598V, G464R, G466A or G469E, which have been identified in colorectal cancers [73], and compositions of the invention compositions (in particular, those comprising a bacterial strain of the species *Megasphaera massiliensis*) may be used to treat or prevent such cancers. Further oncogenic mutations in BRAF include V600E, V600K, V600R or V600D, which have been identified in melanomas [74], and compositions of the invention compositions (in particular, those comprising a bacterial strain of the species *Megasphaera massiliensis*) may be used to treat or prevent such cancers. Amino acids in BRAF are numbered according to UniProt entry P15056 [75] (wild-type BRAF).

In an especially preferred embodiment, compositions of the invention (in particular, those comprising a bacterial strain of the species *Megasphaera massiliensis*) are for use in treating or preventing cancer which comprises the mutation BRAF V600E. The cancer cell lines SKMEL28, 451Lu and HT29 comprise this mutation in BRAF, and a strain of *Megasphaera* was found in the Examples to inhibit clonogenic survival, inhibit ERK signalling and induce MAP2 gene expression in such cell lines. The cancer may further comprise the oncogenic mutation NRAS Q61R. The cancer cell line SKMEL2 comprises this mutation in NRAS, and a strain of *Megasphaera* was found in the Examples to induce MAP2 gene expression in this cell line.

The HT29 cell line used in the Examples is a colorectal cancer cell line, and a strain of *Megasphaera* was found to inhibit clonogenic survival and inhibit ERK signalling in this cell line. Therefore, in especially preferred embodiments, compositions of the invention (in particular, those comprising a bacterial strain of the species *Megasphaera massiliensis*) are used to treat or prevent colorectal cancer, such as colorectal cancer which comprises the mutation BRAF V600E.

The SKMEL2 and SKMEL28 and 451Lu cell lines used in the Examples are melanoma cell lines, and a strain of *Megasphaera* was found to inhibit clonogenic survival, inhibit ERK signalling and induce MAP2 gene expression in such cell lines. Therefore, in especially preferred embodiments, compositions of the invention (in particular, those comprising a bacterial strain of the species *Megasphaera massiliensis*) are used to treat or prevent melanoma, such as melanoma which comprises the mutation BRAF V600E.

In another aspect, the composition of the invention comprises a bacterial strain of the species *Megasphaera massiliensis*, for use in a method of treating colorectal cancer. In another aspect, the composition of the invention comprises a bacterial strain of the species *Megasphaera massiliensis*, for use in a method of treating melanoma.

In any of the aspects and embodiments detailed above, the composition of the invention (in particular, a composition comprising a bacterial strain of the species *Megasphaera massiliensis*) is preferably for use in treating a metastatic cancer. As reported in the Examples, a strain of *Megasphaera* was found to upregulated MAP2 gene expression. MAP2 has been found to be highly expressed in primary cutaneous melanomas, but has reduced expression in metastatic melanomas [76]. It has been proposed that increased expression of microtubule-stabilizing proteins or treatment with microtubule stabilizing proteins such as MAP2 may interfere with the dynamic instability of microtubules which is required during cell division. Therefore, upregulation of MAP2 is thought to hamper cell division and delay tumour growth in cancer [76], indicating that compositions of the invention may have particular use in treating metastatic cancers.

As demonstrated in the Examples, compositions of the invention comprising a *Megasphaera* strain have the effects of inducing MAP2 gene expression and inhibiting ERK signalling in melanoma and colorectal cancer cell lines. Therefore, compositions of the invention are useful in methods of inhibiting ERK signalling, such as ERK1 and/or ERK2 signalling, in the treatment or prevention of cancers comprising oncogenic ERK signalling, as defined above. Compositions of the invention are also useful in methods of inhibiting ERK phosphorylation, such as ERK1 and/or ERK2 phosphorylation, in the treatment or prevention of such cancers. Compositions of the invention are also useful in methods of inducing MAP2 gene expression in the treatment or prevention of such cancers. MAP2 gene expression has been associated with increased cancer sensitivity to microtubule-targeting compounds such as Paclitaxel [77]. Therefore, compositions of the invention may be used to increase the susceptibility of such cancers to a tubulin polymerisation or depolymerisation inhibitor, in particular Paclitaxel. Compositions of the invention are also useful in methods of reducing tumour size, reducing tumour growth, preventing or inhibiting metastasis, or preventing angiogenesis in the treatment or prevention of cancers comprising oncogenic ERK signalling. Due to the effects on MAP2 gene expression demonstrated in the Examples, compositions of the invention are preferably for use in methods of inhibiting metastasis in the treatment of such cancers.

In a further aspect, a composition comprising a bacterial strain of the genus *Megasphaera* is for use in a method of inhibiting ERK1 and/or ERK2 signalling in the treatment or prevention of cancer. In a further aspect, a composition comprising a bacterial strain of the genus *Megasphaera* is for use in a method of inhibiting ERK1 and/or ERK2 phosphorylation in the treatment or prevention of cancer. In a further aspect, a composition comprising a bacterial strain of the genus *Megasphaera* is for use in a method of inducing MAP2 gene expression in the treatment or prevention of cancer. In said further aspects, preferably the cancers are characterised as detailed above ("Cancers and characteristics thereof").

In certain embodiments, the composition of the invention is for use in treating small bowel cancer, such as small bowel adenocarcinoma. The methotrexate-treated HT29 cell line used in the examples has a phenotype resembling epithelial cells of the small intestine and the compositions of the invention were shown to have a useful effect on such cells. In certain embodiments, the compositions of the invention are used to promote apoptosis in the treatment or prevention of cancer, in particular of small bowel cancer.

In certain embodiments, the composition of the invention is for use in a method of inducing GPR109a gene expression in the treatment or prevention of cancer.

In certain embodiments, the composition of the invention is for use in a method of increasing IL-8 levels in the treatment or prevention of cancer.

In certain embodiments, the composition of the invention is for use in treating colorectal cancer, such as colorectal adenocarcinoma. The Caco-2 cell line used in the examples is a colorectal adenocarcinoma cell line and the compositions of the invention were shown to have a useful effect on such cells.

In certain embodiments, the compositions are for use in treating or preventing metastatic melanoma, small cell lung cancer or adenosqamous lung carcinoma. The effect on NSE shown in the examples suggests that the compositions of the invention may be particular effective against these cancers.

In certain embodiments, the composition of the invention is not for use in treating cancer. In certain embodiments, the composition of the invention is for use in treating a disease or disorder that is not cancer.

Use as a Vaccine Adjuvant

The Examples show that administration of the compositions of the invention can lead to an increase in expression of Tumour Necrosis Factor alpha (TNF-α). TNF-α is known to be important for vaccine responses. For example, TNF-α has been shown to be required for an efficient vaccine response in a flu vaccination of the elderly population [78]. Since administration of the compositions of the invention were shown to increase TNF-α expression, compositions of the invention may be useful as a vaccine adjuvant. In one embodiment, the compositions of the invention are for use as a vaccine adjuvant by increasing the level and/or activity of TNF-α. In one embodiment, the compositions of the invention are for use as a vaccine adjuvant. In one embodiment, the compositions of the invention are for use as a vaccine adjuvant in influenza therapy. In certain embodiments, the compositions of the invention are for use in enhancing an immune response against an antigen. In certain embodiments, the invention provides a composition to be administered in combination with an antigen. In certain embodiments, the compositions of the invention are for administration to a patient shortly prior to or after vaccination.

The Examples also show that administration of the compositions of the invention can lead to an increase in expression of IL-6. Increased IL-6 expression has been associated with vaccine responses for many diseases. For example, IL-6 was produced by CD14+CD16-inflammatory monocytes after adults were administered an influenza vaccine [79], and higher levels of IL-6 were associated with achieving a vaccine response to an influenza vaccine [80]. Furthermore, IL-6 was produced after injection of the AS03 adjuvant system [81] and downregulation of IL-6 in mice was shown to reduce the helper T cell response after administration of a tuberculosis vaccine [82]. Since administration of the compositions of the invention were shown to increase IL-6 expression, compositions of the invention may be useful as a vaccine adjuvant. In one embodiment, the compositions of the invention are for use as a vaccine adjuvant by increasing the level and/or activity of IL-6. In one embodiment, the compositions of the invention are for use as a vaccine adjuvant. In one embodiment, the compositions of the invention are for use as a vaccine adjuvant in tuberculosis therapy.

Furthermore, IL-6 and TNF-α expression have been shown to be correlated with the efficacy of a therapeutic HIV vaccine [Huang et al] a tuberculosis vaccine and a *chlamydia* vaccine [83]. Su et al. [84] showed that co-inoculation of IL-6 or TNF-α with the FMDV DNA vaccine resulted in increased IFN-γ expression by CD4+ and CD8+ T cells, higher expression of IL-4 in CD4+ T cells and a higher antigen-specific cytotoxic response. Since administration of the compositions of the invention were shown to increase IL-6 and TNF-α expression, compositions of the invention may be useful as a vaccine adjuvant. In one embodiment, the compositions of the invention may be useful as a vaccine adjuvant by increasing the level and/or activity of TNF-α. In one embodiment, the compositions of the invention may be useful as a vaccine adjuvant by increasing the level and/or activity of IL-6. In a particular embodiment, the compositions of the invention may be useful as a vaccine adjuvant by increasing the level and/or activity of TNF-α and IL-6. In one embodiment, the compositions of the invention are for use as a vaccine adjuvant in HIV therapy. In one embodiment, the compositions of the invention are for use as a vaccine adjuvant in *chlamydia* therapy.

The Examples show that administration of the compositions of the invention can lead to an increase in expression of MIP-3α. MIP-3α has been shown to increase the response to a HIV vaccine [85]. Since administration of the compositions of the invention were shown to increase MIP-3α expression, compositions of the invention may be useful as a vaccine adjuvant.

The Examples also show that administration of the compositions of the invention can lead to an increase in expression of IL-1β. Li et al. [86] showed that the adjuvant aluminium hydroxide activated the secretion of IL-1β, and suggested that IL-β itself can act as an adjuvant. Since administration of the compositions of the invention were shown to increase IL-1βexpression, compositions of the invention may be useful as a vaccine adjuvant. The Examples show that administration of the compositions of the invention can increase the ratio of CD8+ T cells to Tregs. Adjuvants have been shown to stimulate CD8+ T cells [87] and since administration of the compositions of the invention were shown to increase the ratio of CD8+ T cells to Tregs, compositions of the invention may be useful as a vaccine adjuvant. In one embodiment, compositions of the invention are for use as a vaccine adjuvant. In one embodiment, the compositions of the invention are for use as a vaccine adjuvant by increasing the ratio of CD8+ T cells to Tregs.

The Examples also show that administration of the compositions of the invention can lead to an increase in expression of IL-8. Increased Il-8 expression has been associated with vaccine responses for many diseases. For example, higher levels of IL-8 were associated with achieving a vaccine response to an avian influenza vaccine [88]. Furthermore, IL-8 serves as a molecular adjuvant in a DNA vaccination model [89]. Therefore, IL-8 may be used as an immunostimulant to enhance the immune efficiency of, for example, an avian influenza vaccine. Since administration of the compositions of the invention were shown to increase IL-8 expression, compositions of the invention may be useful as a vaccine adjuvant. In one embodiment, the compositions of the invention are for use as a vaccine adjuvant by increasing the level and/or activity of IL-8. In one embodiment, the compositions of the invention are for use as a vaccine adjuvant. In one embodiment, the compositions of the invention are for use as a vaccine adjuvant in influenza therapy. In some embodiments, when used as a vaccine adjuvant, the compositions of the invention will be administered on their own to provide an adjuvant effect for an antigen that has been separately administered to the patient. In certain embodiments, the composition of the invention is administered orally, whilst the antigen is injected parenterally.

The compositions of the invention may be used for enhancing an immune response to any useful antigen. Exemplary antigens for use with the invention include: viral antigens, such as viral surface proteins; bacterial antigens, such as protein and/or saccharide antigens; fungal antigens; parasite antigens; and tumor antigens. The invention is particularly useful for vaccines against influenza virus, HIV, hookworm, hepatitis B virus, herpes simplex virus, rabies, respiratory syncytial virus, cytomegalovirus, *Staphylococcus aureus*, *chlamydia*, SARS coronavirus, varicella zoster virus, *Streptococcus pneumoniae*, *Neisseria meningitidis*, *Mycobacterium tuberculosis*, *Bacillus anthracis*, Epstein Barr virus, human papillomavirus, etc. Further antigens for use with the invention include glycoprotein and lipoglycan antigens, archaea antigens, melanoma antigen E (MAGE), Carcinoembryonic antigen (CEA), MUC-1, HER2, sialyl-Tn (STn), human telomerase reverse transcriptase (hTERT), Wilms tumour gene (WT1), CA-125, prostate-specific antigen (PSA), Epstein-Barr virus antigens, neoantigens, oncoproteins, amyloid-beta, Tau, PCSK9 and habit forming substances, for example nicotine, alcohol or opiates.

Preferred antigens for use with the invention include pathogen antigens and tumour antigens. An antigen will elicit an immune response specific for the antigen that will be effective for protecting against infection with the pathogen or attacking the tumour. Antigens may be, for example, peptides or polysaccharides.

The invention also provides the use of: (i) an aqueous preparation of an antigen; and (ii) a composition comprising a bacterial strain of the genus *Megasphaera*, preferably the species *Megasphaera massiliensis*, in the manufacture of a medicament for raising an immune response in a patient.

The immune response raised by these methods and uses will generally include an antibody response, preferably a protective antibody response.

In some embodiments, a bacterial strain of the genus *Megasphaera* is engineered to present an antigen. Presenting an antigen on the bacterial strain of the invention may maximise the immunostimulatory activities and further enhance the protective immune response generated against the antigen. In addition, manufacturing and delivering therapeutics comprising an antigen and a bacteria of the invention may be more efficient and effective this way than when each of the antigen and the composition comprising the bacterial strain are manufactured and administered separately. Therefore, in some embodiments, the invention provides a composition comprising a bacterial strain of the genus *Megasphaera* that presents an antigen, for example on its cell surface. In some embodiments, the composition comprising the bacterial strain that presents an antigen is for use as a vaccine antigen. In some embodiments, the antigen is derived from HIV, hookworm, hepatitis B virus, herpes simplex virus, rabies, respiratory syncytial virus, cytomegalovirus, *Staphylococcus aureus*, *chlamydia*, SARS coronavirus, varicella zoster virus, *Streptococcus pneumoniae*, *Neisseria meningitidis*, *Mycobacterium tuberculosis*, *Bacillus anthracis*, Epstein Barr virus or human papillomavirus. In some embodiments, the antigen is a glycoprotein antigen, lipoglycan antigen, archaea antigen, melanoma antigen E (MAGE), Carcinoembryonic antigen (CEA), MUC-1, HER2, sialyl-Tn (STn), human telomerase reverse transcriptase (hTERT), Wilms tumour gene (WT1), CA-125, prostate-specific antigen (PSA), Epstein-Barr virus antigens, neoantigens, oncoproteins, amyloid-beta, Tau, PCSK9 or a habit forming substance, such as, alcohol, opiates and the like.

In some embodiments, the bacteria of the invention expresses one or more antigens. Generally the antigen will be expressed recombinantly and will be heterologous to the bacteria of the invention. Therefore, the invention provides a bacterial strain of the genus *Megasphaera* that expresses a heterologous antigen. The antigen may be part of a fusion polypeptide expressed with one or more polypeptides homologous to the bacteria. In some embodiments, the bacteria expresses the antigen as a non-fusion polypeptide. In some embodiments, the invention provides a composition comprising a cell of a bacterial strain of the genus *Megasphaera*, wherein the cell expresses a heterologous antigen.

In some embodiments, the composition is for use as a vaccine. In some embodiments, the invention provides a cell of a bacterial strain of the genus *Megasphaera*, wherein the cell expresses a heterologous antigen. In some embodiments, the cell is for use as a vaccine.

Exemplary antigens for use with the invention include: viral antigens, such as viral surface proteins; bacterial antigens, such as protein and/or saccharide antigens; fungal antigens; parasite antigens; and tumor antigens. Further antigens for expressing in a bacterial strain of the genus *Megasphaera* include glycoprotein and lipoglycan antigens, archaea antigens, melanoma antigen E (MAGE), Carcinoembryonic antigen (CEA), MUC-1, HER2, sialyl-Tn (STn), human telomerase reverse transcriptase (hTERT), Wilms tumour gene (WT1), CA-125, prostate-specific antigen (PSA), Epstein-Barr virus antigens, neoantigens, oncoproteins, amyloid-beta, Tau, PCSK9 and habit forming substances, for example nicotine, alcohol, opiates, or the like.

The invention may also be useful for enhancing the response to vaccines against non-communicable diseases such as Alzheimer's Disease and other neurodegenerative disorders, in which case the antigen for use with the invention may be amyloid-beta or Tau. Other such antigens for non-communicable diseases include PCSK9 (for the treatment of elevated cholesterol).

The invention may also be useful for enhancing the response to vaccines against habit forming substances, for example nicotine, alcohol or opiates.

Cell Therapies
Chimeric Antigen Receptor T Cell (CAR-T) Therapy

The Examples also show that administration of the compositions of the invention can lead to an increase in expression of IL-6. Increased Il-6 expression has been correlated with response to CD19 CAR-T therapy of chronic lymphocyte leukaemia. An increase in serum IL-6 was associated with CAR-T cell expansion, whereas inhibition of IL-6 was associated with inhibition of CAR-T cell proliferation [90]. Since administration of the compositions of the invention were shown to increase IL-6 expression, compositions of the invention may be useful in cell therapy, in particular CAR-T cell therapy. In one embodiment, the compositions of the invention are for use in cell therapy. In one embodiment, the compositions of the invention are for use in CAR-T cell therapy. In one embodiment, compositions of the invention are for use in the treatment of chronic lymphocyte leukaemia.

Surprisingly, the Examples also show that administration of the compositions of the invention selectively reduced the percentage of Tregs in a population of PBMCs (FIG. 6C). Selective depletion of Tregs has been shown to enhance the efficacy of cytotoxic lymphocytes [91]. CAR-T cells are a subset of cytotoxic lymphocytes, and therefore it is thought that selective depletion of Tregs is effective in CAR-T cell therapy. Since administration of the compositions of the invention were shown to deplete Tregs, compositions of the invention may be useful in cell therapy, in particular CAR-T cell therapy.

Therefore, the compositions of the invention may be useful in cell therapy, in particular in enhancing the response to a cell therapy.

Mesynchymal Stem Cell (MSC) Therapy

Mesynchymal stem cell (MSC) therapy has been reported to have immunostimulatory properties. When MSCs are treated with LPS, they upregulate pro-inflammatory cytokines IL-6 and IL-8 which causes increased B cell proliferation [92]. Therefore, since compositions of the invention were shown to increase the expression of IL-6, they may be useful in combination with MSC cell therapy.

Stem Cell Transplantation Therapy

It has been reported that, instead of using undifferentiated stem cells in stem cell transplantation therapy, it may be beneficial to differentiate stem cells to some extent prior to transplantation. For example, Heng et al. [93] reported that cardiomyogenic differentiation of stem cells may be beneficial by having a higher engraftment efficiency, enhanced regeneration of myocytes and increased restoration of heart function. Since administration of the compositions of the invention initiated neuronal differentiation in undifferentiated neuroblastoma cells, compositions of the invention may be useful for stem cell differentiation in stem cell transplantation therapy.

Immunosenescence

The Examples also show that administration of the compositions of the invention can selectively deplete Tregs and increase B cell numbers (FIG. 6C and FIG. 6F). Fulop et al. [94] identified that an increase in Treg cell number and a decrease in B cell number are associated with aging in the adaptive immune system. Therefore, compositions of the invention may be used to prevent or delay immunosenescence. In one embodiment, compositions of the invention are for use in preventing immunosenescence. In another embodiment, compositions of the invention are for use in delaying immunosenescence characterised by an increase in Treg cell number. In another embodiment, compositions of the invention are for use in delaying immunosenescence characterised by a decrease in B cell number. In another embodiment, compositions of the invention are for use in delaying immunosenescence characterised by an increase in Treg cell number and a decrease in B cell number. In one embodiment, compositions of the invention are for use in delaying immunosenescence by decreasing Treg cell number. In one embodiment, compositions of the invention are for use in delaying immunosenescence by increasing B cell number. In another embodiment, compositions of the invention are for use in delaying immunosenescence by decreasing Treg cell number and increasing B cell number. In one embodiment, compositions of the invention are for use in treating diseases caused by immunosenescence. In one embodiment, compositions of the invention are for use in treating aging-related diseases by delaying and/or preventing immunosenescence.

Furthermore, it has been proposed that vaccine adjuvants may overcome immunosenescence [95]. Since the compositions of the invention are suitable for use as a vaccine adjuvant, compositions of the invention may be useful for preventing or delaying immunosenescence. In another embodiment, compositions of the invention are for use in delaying and/or preventing immunosenescence as a vaccine adjuvant. In another embodiment, compositions of the invention are for use as a vaccine adjuvant, wherein the compositions delay and/or prevent immunosenescence.

Diseases that are associated with immunosenescence include cardiovascular disease, neurodegenerative diseases, such as Alzheimer's disease and Parkinson's disease, cancer, diabetes mellitus type 2 [96] and autoimmune disorders [97]. In one embodiment, compositions of the invention are for use in treating cardiovascular disease. In one embodiment, compositions of the invention are for use in treating cardiovascular disease by delaying and/or preventing immunosenescence. In one embodiment, compositions of the invention are for use in treating neurodegenerative diseases. In one embodiment, compositions of the invention are for use in treating neurodegenerative diseases in particular Alzheimer's disease and Parkinson's disease by delaying and/or preventing immunosenescence. In one embodiment, compositions of the invention are for use in treating cancer by delaying and/or preventing immunosenescence. In one embodiment, compositions of the invention are for use in treating diabetes mellitus type 2. In one embodiment, compositions of the invention are for use in treating diabetes mellitus type 2 by delaying and/or preventing immunosenescence. In one embodiment, compositions of the invention are for use in treating autoimmune disorders. In one embodiment, compositions of the invention are for use in treating autoimmune disorders by delaying and/or preventing immunosenescence.

Modes of Administration

Preferably, the compositions of the invention are to be administered to the gastrointestinal tract in order to enable delivery to and/or partial or total colonisation of the intestine with the bacterial strain of the invention. Generally, the compositions of the invention are administered orally, but they may be administered rectally, intranasally, or via buccal or sublingual routes.

In certain embodiments, the compositions of the invention may be administered as a foam, as a spray or a gel.

In certain embodiments, the compositions of the invention may be administered as a suppository, such as a rectal suppository, for example in the form of a theobroma oil (cocoa butter), synthetic hard fat (e.g. suppocire, witepsol), glycero-gelatin, polyethylene glycol, or soap glycerin composition.

In certain embodiments, the composition of the invention is administered to the gastrointestinal tract via a tube, such as a nasogastric tube, orogastric tube, gastric tube, jejunostomy tube (J tube), percutaneous endoscopic gastrostomy (PEG), or a port, such as a chest wall port that provides access to the stomach, jejunum and other suitable access ports.

The compositions of the invention may be administered once, or they may be administered sequentially as part of a treatment regimen. In certain embodiments, the compositions of the invention are to be administered daily.

In certain embodiments of the invention, treatment according to the invention is accompanied by assessment of the patient's gut microbiota. Treatment may be repeated if delivery of and/or partial or total colonisation with the strain of the invention is not achieved such that efficacy is not observed, or treatment may be ceased if delivery and/or partial or total colonisation is successful and efficacy is observed.

In certain embodiments, the composition of the invention may be administered to a pregnant animal, for example a mammal such as a human in order to reduce the likelihood of cancer developing in her child in utero and/or after it is born.

The compositions of the invention may be administered to a patient that has been diagnosed with a disease or condition mediated reduced immune activity, or that has been identified as being at risk of a disease or condition mediated by reduced immune activity. The compositions may also be administered as a prophylactic measure to prevent the development of diseases or conditions mediated by reduced immune activity in a healthy patient.

The compositions of the invention may be administered to a patient that has been diagnosed with cancer, or that has been identified as being at risk of a cancer. For example, the patient may have reduced or absent colonisation by *Megasphaera*, and in particular *Megasphaera massihensis*.

The compositions of the invention may be administered as a food product, such as a nutritional supplement.

Generally, the compositions of the invention are for the treatment of humans, although they may be used to treat animals including monogastric mammals such as poultry, pigs, cats, dogs, horses or rabbits. The compositions of the invention may be useful for enhancing the growth and performance of animals. If administered to animals, oral gavage may be used.

Compositions

Generally, the composition of the invention comprises bacteria. In preferred embodiments of the invention, the composition is formulated in freeze-dried form. For example, the composition of the invention may comprise granules or gelatin capsules, for example hard gelatin capsules, comprising a bacterial strain of the invention.

Preferably, the composition of the invention comprises lyophilised bacteria. Lyophilisation of bacteria is a well-established procedure and relevant guidance is available in, for example, references [98,100].

Alternatively, the composition of the invention may comprise a live, active bacterial culture.

In preferred embodiments, the composition of the invention is encapsulated to enable delivery of the bacterial strain to the intestine. Encapsulation protects the composition from degradation until delivery at the target location through, for example, rupturing with chemical or physical stimuli such as pressure, enzymatic activity, or physical disintegration, which may be triggered by changes in pH. Any appropriate encapsulation method may be used. Exemplary encapsulation techniques include entrapment within a porous matrix, attachment or adsorption on solid carrier surfaces, self-aggregation by flocculation or with cross-linking agents, and mechanical containment behind a microporous membrane or a microcapsule. Guidance on encapsulation that may be useful for preparing compositions of the invention is available in, for example, references [101] and [102].

The composition may be administered orally and may be in the form of a tablet, capsule or powder. Encapsulated products are preferred because *Megasphaera* are anaerobes. Other ingredients (such as vitamin C, for example), may be included as oxygen scavengers and prebiotic substrates to improve the delivery and/or partial or total colonisation and survival in vivo. Alternatively, the probiotic composition of the invention may be administered orally as a food or nutritional product, such as milk or whey based fermented dairy product, or as a pharmaceutical product.

The composition may be formulated as a probiotic.

A composition of the invention includes a therapeutically effective amount of a bacterial strain of the invention. A therapeutically effective amount of a bacterial strain is sufficient to exert a beneficial effect upon a patient. A therapeutically effective amount of a bacterial strain may be sufficient to result in delivery to and/or partial or total colonisation of the patient's intestine.

A suitable daily dose of the bacteria, for example for an adult human, may be from about $1 \times 10^3$ to about $1 \times 10^{11}$ colony forming units (CFU); for example, from about $1 \times 10^7$ to about $1 \times 10^{10}$ CFU; in another example from about $1 \times 10^6$ to about $1 \times 10^{10}$ CFU; in another example from about $1 \times 10^7$ to about $1 \times 10^{11}$ CFU; in another example from about $1 \times 10^8$ to about $1 \times 10^{10}$ CFU; in another example from about $1 \times 10^8$ to about $1 \times 10^{11}$ CFU.

In certain embodiments, the dose of the bacteria is at least $10^9$ cells per day, such as at least $10^{10}$, at least $10^{11}$, or at least $10^{12}$ cells per day.

In certain embodiments, the composition contains the bacterial strain in an amount of from about $1\times10^6$ to about $1\times10^{11}$ CFU/g, respect to the weight of the composition; for example, from about $1\times10^8$ to about $1\times10^{10}$ CFU/g. The dose may be, for example, 1 g, 3 g, 5 g, and 10 g.

In certain embodiments, the invention provides the above pharmaceutical composition, wherein the amount of the bacterial strain is from about $1\times10^3$ to about $1\times10^{11}$ colony forming units per gram with respect to a weight of the composition.

In certain embodiments, the invention provides the above pharmaceutical composition, wherein the composition is administered at a dose of between 500 mg and 1000 mg, between 600 mg and 900 mg, between 700 mg and 800 mg, between 500 mg and 750 mg or between 750 mg and 1000 mg. In certain embodiments, the invention provides the above pharmaceutical composition, wherein the lyophilised bacteria in the pharmaceutical composition is administered at a dose of between 500 mg and 1000 mg, between 600 mg and 900 mg, between 700 mg and 800 mg, between 500 mg and 750 mg or between 750 mg and 1000 mg.

Typically, a probiotic, such as the composition of the invention, is optionally combined with at least one suitable prebiotic compound. A prebiotic compound is usually a non-digestible carbohydrate such as an oligo- or polysaccharide, or a sugar alcohol, which is not degraded or absorbed in the upper digestive tract. Known prebiotics include commercial products such as inulin and transgalacto-oligosaccharides.

In certain embodiments, the probiotic composition of the present invention includes a prebiotic compound in an amount of from about 1 to about 30% by weight, respect to the total weight composition, (e.g. from 5 to 20% by weight). Carbohydrates may be selected from the group consisting of: fructo-oligosaccharides (or FOS), short-chain fructo-oligosaccharides, inulin, isomalt-oligosaccharides, pectins, xylo-oligosaccharides (or XOS), chitosan-oligosaccharides (or COS), beta-glucans, arable gum modified and resistant starches, polydextrose, D-tagatose, acacia fibers, carob, oats, and citrus fibers. In one aspect, the prebiotics are the short-chain fructo-oligosaccharides (for simplicity shown herein below as FOSs-c.c); said FOSs-c.c. are not digestible carbohydrates, generally obtained by the conversion of the beet sugar and including a saccharose molecule to which three glucose molecules are bonded.

The compositions of the invention may comprise pharmaceutically acceptable excipients or carriers. Examples of such suitable excipients may be found in the reference [103]. Acceptable carriers or diluents for therapeutic use are well known in the pharmaceutical art and are described, for example, in reference [104]. Examples of suitable carriers include lactose, starch, glucose, methyl cellulose, magnesium stearate, mannitol, sorbitol and the like. Examples of suitable diluents include ethanol, glycerol and water. The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s). Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol. Examples of suitable lubricants include sodium oleate, sodium stearate, magnesium stearate, sodium benzoate, sodium acetate, sodium chloride and the like. Preservatives, stabilizers, dyes and even flavouring agents may be provided in the pharmaceutical composition. Examples of preservatives include sodium benzoate, sorbic acid and esters of p-hydroxybenzoic acid. Antioxidants and suspending agents may be also used.

The compositions of the invention may be formulated as a food product. For example, a food product may provide nutritional benefit in addition to the therapeutic effect of the invention, such as in a nutritional supplement. Similarly, a food product may be formulated to enhance the taste of the composition of the invention or to make the composition more attractive to consume by being more similar to a common food item, rather than to a pharmaceutical composition. In certain embodiments, the composition of the invention is formulated as a milk-based product. The term "milk-based product" means any liquid or semi-solid milk- or whey-based product having a varying fat content. The milk-based product can be, e.g., cow's milk, goat's milk, sheep's milk, skimmed milk, whole milk, milk recombined from powdered milk and whey without any processing, or a processed product, such as yoghurt, curdled milk, curd, sour milk, sour whole milk, butter milk and other sour milk products. Another important group includes milk beverages, such as whey beverages, fermented milks, condensed milks, infant or baby milks; flavoured milks, ice cream; milk-containing food such as sweets.

In certain embodiments, the compositions of the invention contain a single bacterial strain or species and do not contain any other bacterial strains or species. Such compositions may comprise only de minimis or biologically irrelevant amounts of other bacterial strains or species. Such compositions may be a culture that is substantially free from other species of organism.

The compositions for use in accordance with the invention may or may not require marketing approval.

In some cases, the lyophilised bacterial strain is reconstituted prior to administration. In some cases, the reconstitution is by use of a diluent described herein.

The compositions of the invention can comprise pharmaceutically acceptable excipients, diluents or carriers.

In certain embodiments, the invention provides a pharmaceutical composition comprising: a bacterial strain of the invention; and a pharmaceutically acceptable excipient, carrier or diluent; wherein the bacterial strain is in an amount sufficient to treat a disorder when administered to a subject in need thereof; and wherein the disorder is cancer, such as neuroblastoma, brain cancer, melanoma, prostate cancer, colorectal cancer, breast cancer, lung cancer, liver cancer or gastric cancer. In a further embodiment the cancer is ovarian cancer, cervical cancer, glioblastoma, carcinoma, chronic lymphocyte leukemia, lymphoma or haematological malignancies.

In certain embodiments, the invention provides pharmaceutical composition comprising: a bacterial strain of the invention; and a pharmaceutically acceptable excipient, carrier or diluent; wherein the bacterial strain is in an amount sufficient to treat or prevent a disease or condition mediated by MAP2. In preferred embodiments, said disease or condition is cancer, such as neuroblastoma, brain cancer, melanoma, prostate cancer, colorectal cancer, breast cancer, lung cancer, liver cancer or gastric cancer. In a further embodiment the cancer is ovarian cancer, cervical cancer, glioblastoma, carcinoma, chronic lymphocyte leukemia, lymphoma or haematological malignancies.

In certain embodiments, the invention provides pharmaceutical composition comprising: a bacterial strain of the invention; and a pharmaceutically acceptable excipient, carrier or diluent; wherein the bacterial strain is in an amount sufficient to treat or prevent a disease or condition mediated by B3 Tubulin. In preferred embodiments, said disease or condition is cancer, such as neuroblastoma, brain cancer, melanoma, prostate cancer, colorectal cancer, breast cancer, lung cancer, liver cancer or gastric cancer. In a further embodiment the cancer is ovarian cancer, cervical cancer, glioblastoma, carcinoma, chronic lymphocyte leukemia, lymphoma or haematological malignancies.

In certain embodiments, the invention provides pharmaceutical composition comprising: a bacterial strain of the invention; and a pharmaceutically acceptable excipient, carrier or diluent; wherein the bacterial strain is in an amount sufficient to treat or prevent a disease or condition mediated by DRD2. In preferred embodiments, said disease or condition is cancer, such as neuroblastoma, brain cancer, melanoma, prostate cancer, colorectal cancer, breast cancer, lung cancer, liver cancer or gastric cancer. In a further embodiment the cancer is ovarian cancer, cervical cancer, glioblastoma, carcinoma, chronic lymphocyte leukemia, lymphoma or haematological malignancies.

In certain embodiments, the invention provides pharmaceutical composition comprising: a bacterial strain of the invention; and a pharmaceutically acceptable excipient, carrier or diluent; wherein the bacterial strain is in an amount sufficient to treat or prevent a disease or condition mediated by HDAC. In preferred embodiments, said disease or condition is cancer, such as neuroblastoma, brain cancer, melanoma, prostate cancer, colorectal cancer, breast cancer, lung cancer, liver cancer or gastric cancer, ovarian cancer, cervical cancer, glioblastoma, carcinoma, chronic lymphocyte leukemia, lymphoma or haematological malignancies.

In certain embodiments, the invention provides pharmaceutical composition comprising: a bacterial strain of the invention; and a pharmaceutically acceptable excipient, carrier or diluent; wherein the bacterial strain is in an amount sufficient to treat or prevent a disease or condition mediated by pro-inflammatory cytokines, such as IL-1β, TNF-α, MIP-3α, IL-23 or IL-6. In a preferred embodiment, the invention provides pharmaceutical composition comprising: a bacterial strain of the invention; and a pharmaceutically acceptable excipient, carrier or diluent; wherein the bacterial strain is in an amount sufficient to treat or prevent a disease or condition mediated by TNF-α. In a preferred embodiment, the invention provides pharmaceutical composition comprising: a bacterial strain of the invention; and a pharmaceutically acceptable excipient, carrier or diluent; wherein the bacterial strain is in an amount sufficient to treat or prevent a disease or condition mediated by IL-8. In a preferred embodiment, the invention provides pharmaceutical composition comprising: a bacterial strain of the invention; and a pharmaceutically acceptable excipient, carrier or diluent; wherein the bacterial strain is in an amount sufficient to treat or prevent a disease or condition mediated by CD11b. In preferred embodiments, said disease or condition is cancer, such as neuroblastoma, brain cancer, melanoma, prostate cancer, colorectal cancer, breast cancer, lung cancer, liver cancer or gastric cancer. In a further embodiment said cancer is ovarian cancer, cervical cancer, glioblastoma, carcinoma, chronic lymphocyte leukemia, lymphoma or haematological malignancies.

In certain embodiments, the invention provides pharmaceutical composition comprising: a bacterial strain of the invention; and a pharmaceutically acceptable excipient, carrier or diluent; wherein the bacterial strain is in an amount sufficient to treat or prevent a disease or condition mediated by Casp3. In preferred embodiments, said disease or condition is cancer, such as neuroblastoma, brain cancer, melanoma, prostate cancer, colorectal cancer, breast cancer, lung cancer, liver cancer or gastric cancer.

In a further embodiment said cancer is ovarian cancer, cervical cancer, glioblastoma, carcinoma, chronic lymphocyte leukemia, lymphoma or haematological malignancies.

In certain embodiments, the invention provides the above pharmaceutical composition, wherein the amount of the bacterial strain is from about $1 \times 10^3$ to about $1 \times 10^{11}$ colony forming units per gram with respect to a weight of the composition.

In certain embodiments, the invention provides the above pharmaceutical composition, wherein the composition is administered at a dose of 1 g, 3 g, 5 g or 10 g.

In certain embodiments, the invention provides the above pharmaceutical composition, wherein the composition is administered by a method selected from the group consisting of oral, rectal, subcutaneous, nasal, buccal, and sublingual.

In certain embodiments, the invention provides the above pharmaceutical composition, comprising a carrier selected from the group consisting of lactose, starch, glucose, methyl cellulose, magnesium stearate, mannitol and sorbitol.

In certain embodiments, the invention provides the above pharmaceutical composition, comprising a diluent selected from the group consisting of ethanol, glycerol and water.

In certain embodiments, the invention provides the above pharmaceutical composition, comprising an excipient selected from the group consisting of starch, gelatin, glucose, anhydrous lactose, free-flow lactose, beta-lactose, corn sweetener, acacia, tragacanth, sodium alginate, carboxymethyl cellulose, polyethylene glycol, sodium oleate, sodium stearate, magnesium stearate, sodium benzoate, sodium acetate and sodium chloride.

In certain embodiments, the invention provides the above pharmaceutical composition, further comprising at least one of a preservative, an antioxidant and a stabilizer.

In certain embodiments, the invention provides the above pharmaceutical composition, comprising a preservative selected from the group consisting of sodium benzoate, sorbic acid and esters of p-hydroxybenzoic acid.

In certain embodiments, the invention provides the above pharmaceutical composition, wherein said bacterial strain is lyophilised.

In certain embodiments, the invention provides the above pharmaceutical composition, wherein when the composition is stored in a sealed container at about 4.0 or about 25.0 and the container is placed in an atmosphere having 50% relative humidity, at least 80% of the bacterial strain as measured in colony forming units, remains after a period of at least about: 1 month, 3 months, 6 months, 1 year, 1.5 years, 2 years, 2.5 years or 3 years.

Culturing Methods

The bacterial strains for use in the present invention can be cultured using standard microbiology techniques as detailed in, for example, references [105,107].

The solid or liquid medium used for culture may be YCFA agar or YCFA medium. YCFA medium may include (per 100 ml, approximate values): Casitone (1.0 g), yeast extract (0.25 g), NaHCO$_3$ (0.4 g), cysteine (0.1 g), K$_2$HPO$_4$ (0.045 g), KH$_2$PO$_4$ (0.045 g), NaCl (0.09 g), (NH$_4$)$_2$SO$_4$ (0.09 g), MgSO$_4$·7H$_2$O (0.009 g), CaCl$_2$) (0.009 g), resazurin (0.1 mg), hemin (1 mg), biotin (1 µg), cobalamin (1 µg), p-aminobenzoic acid (3 µg), folic acid (5 µg), and pyridoxamine (15 µg).

Bacterial Strains for Use in Vaccine Compositions

The inventors have identified that the bacterial strains of the invention are useful for treating or preventing diseases or conditions associated with reduce immune activity. This is likely to be a result of the effect that the bacterial strains of the invention have on the host immune system. Therefore, the compositions of the invention may also be useful for preventing diseases or conditions such as cancer, when administered as vaccine compositions. In certain such embodiments, the bacterial strains of the invention may be killed, inactivated or attenuated. In certain such embodiments, the compositions may comprise a vaccine adjuvant. In certain embodiments, the compositions are for administration via injection, such as via subcutaneous injection.

In certain embodiments, a bacterial strain of the species *Megasphaera massiliensis* reduces the levels of formic acid. Formic acid is the conjugate base of formate which has been implicated in disrupting mitochondrial electron transport and energy production by inhibiting cytochrome oxidase activity, the terminal electron acceptor of the electron transport chain. Accordingly, the reduction of formic acid, and thus formate, would reduce incidence of cell death via either cytochrome oxidase inhibition or accumulation of reactive oxygen species. Accordingly, in certain embodiments, a bacterial strain of the species *Megasphaera massiliensis* stimulates the immune system in the treatment of disease by reducing the levels of formic acid.

General

The practice of the present invention will employ, unless otherwise indicated, conventional methods of chemistry, biochemistry, molecular biology, immunology and pharmacology, within the skill of the art. Such techniques are explained fully in the literature. See, e.g., references [108] and [109,115], etc.

The term "comprising" encompasses "including" as well as "consisting" e.g. a composition "comprising" X may consist exclusively of X or may include something additional e.g. X+Y.

The term "about" in relation to a numerical value x is optional and means, for example, x±10%.

The word "substantially" does not exclude "completely" e.g. a composition which is "substantially free" from Y may be completely free from Y. Where necessary, the word "substantially" may be omitted from the definition of the invention.

References to a percentage sequence identity between two nucleotide sequences means that, when aligned, that percentage of nucleotides are the same in comparing the two sequences. This alignment and the percent homology or sequence identity can be determined using software programs known in the art, for example those described in section 7.7.18 of ref. [116]. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in ref. [117].

Unless specifically stated, a process or method comprising numerous steps may comprise additional steps at the beginning or end of the method, or may comprise additional intervening steps. Also, steps may be combined, omitted or performed in an alternative order, if appropriate.

Various embodiments of the invention are described herein. It will be appreciated that the features specified in each embodiment may be combined with other specified features, to provide further embodiments. In particular, embodiments highlighted herein as being suitable, typical or preferred may be combined with each other (except when they are mutually exclusive).

MODES FOR CARRYING OUT THE INVENTION

Example 1—MRx0029 Induces a Mature Phenotype in SH-SY5Y Cells

Introduction

The inventors sought to identify the effect of MRx0029 on the expression of neurodifferentiation markers, β3Tubulin and MAP2 in neuroblastoma cells. β3Tubulin is a marker of pre-differentiation in neurons and MAP2 is a marker of mature (differentiated) neurons.

Bacterial Strain
*Megasphaera massiliensis* MRx0029
Cell Line
SH-SY5Y Cells
Method
qPCR SH-SY5Y were plated in 10 cm petri dishes a density of $2 \times 10^6$ cells. After 24 h cells were treated in differentiation medium (growth medium containing 1% FBS without RA) with 10% bacteria supernatants or YCFA+, 10 uM RA, 200 uM hexanoic acid or 200 uM valproic acid, for 17 hrs. There after representative images were taken using phase contrast EVOS XL core microscope at 40×10.65 magnification. Cells were collected, and total RNA was isolated according to RNeasy mini kit protocol (Qiagen). cDNAs were made using the high capacity cDNA reverse transcription kit (Applied Biosystems). Gene expression was measured using qPCR. GAPDH was used as internal control. Fold change was calculated according to the $2^{(-\Delta\Delta ct)}$ method.

Immunolabelling and Cell Imaging

Cells were seeded onto 8-well chamber slides (Marienfeld Laboratory Glassware) at $5 \times 10^4$ cells/well overnight and were treated with 10% bacterial supernatant for 24 h. For differentiation, cells were treated with 10 nM RA for 5 days before treating with cell-free bacterial supernatant for 24 h.

Afterwards, the cells were fixed with 4% paraformaldehyde in PBS for 20 minutes at room temperature (RT). Fixed cells were washed with PBS, and permeabilized with 1% Triton X-100 in PBS for 10 minutes. After washing with PBS, the slides were incubated with blocking buffer (4% BSA/PBS) for 1 h at RT before adding anti-MAP2 antibody or β3-tubulin (sc-74421 and sc-80005 respectively, Santa Cruz Biotechnology Inc) diluted in 1% BSA/PBS for 12 h at 4° C. They were then washed twice with PBS, followed by incubation with Alexa Flour 488 conjugated anti-mouse (Molecular Probes Inc) and Alexa Flour 594 conjugated Phalloidin (ab176757, Abcam) for 1 h at RT. After washing 3× with PBS, the slides were staining with DAPI and mounted with Vectashield® (Vector Laboratories). Slides were viewed using a Axioskop 50 microscope (Zeiss) equipped with a 63×/1.2 W Korr objective and filter sets suitable for detection of the fluorochromes used. Manual exposure times for the digital acquisition of images immuno-labelled with MAP-2 were kept constant allowing comparison between different wells and treatments. Phalloidin (F-actin) and DAPI exposure times varied to suit the field of view. Randomised fields of view were acquired using a QImaging camera controlled by Image Pro Plus software. Images were saved as TIFF files and opened in Adobe Photoshop CC 2015.1.2. Images of the MAP-2, DAPI and Phalloidin images were then overlaid and merged. Representative images were selected to illustrate the differences in abundance and location of the proteins examined Immunoblotting SH-SY5Y cells cultured under the indicated conditions described above, treated with MRx0029 for 24 h and then lysed in RIPA buffer containing cocktail of protease inhibitors (Roche Diagnostics, UK). Protein concentration was estimated using the BCA protein assay kit (Pierce Biotechnology, Rockford, Ill.), separated by SDS-PAGE and transferred to a PVDF membrane. Membranes were then blocked with 5% non-fat dry milk or 5% BSA and incubated overnight at 4° C. with the primary antibodies (respectively MAP2 and β3-tubulin). The blots were then incubated with the appropriate horseradish peroxidase (HRP)-conjugated secondary antibody, and proteins were detected by chemiluminescence detection kit (Pierce Biotechnology, Rockford, Ill.). For both MAP2 and β3-tubulin, β-actin served as a control to monitor protein loading variability amongst samples.

Results

MRx0029 induces the expression of β3Tubulin in undifferentiated neuroblastoma SH-SY5Y cells. FIG. 1 shows that treatment with MRx0029 increases the expression of β3Tubulin in comparison to untreated SH-SY5Y cells.

MRx0029 induces the expression of MAP2 in undifferentiated neuroblastoma SH-SY5Y cells. FIGS. 2A-2C show that treatment with MRx0029 significantly increased the expression of MAP2 in comparison to untreated SH-SY5Y cells.

Discussion

The results show that MRx0029 may be an effective composition in promoting differentiation, in particular neuronal differentiation. Furthermore, the results show that MRx0029 may be an effective composition in the treatment of brain cancer, in particular neuroblastoma, and melanoma, in particular metastatic melanoma.

Example 2—MRx0029 Decreases the Expression of DRD2 in SH-SY5Y Cells

Introduction

The inventors sought to identify the effect of MRx0029 on the expression of DRD2 in neuroblastoma cells.

Bacterial Strain

*Megasphaera massiliensis* MRx0029

Cell Line

SH-SY5Y Cells

Method

The inventors measured the change in DRD2 expression in neuroblastoma cells using the same method as described in Example 1.

Results

MRx0029 decreases the expression of DRD2 in neuroblastoma SH-SY5Y cells. FIG. 3 shows that treatment with MRx0029 significantly decreased the expression of DRD2 in comparison to untreated SH-SY5Y cells.

Discussion

This shows that MRx0029 may be an effective composition in the treatment of cancer.

Example 3—MRx0029 Induces the Upregulation of Caspase 3 in SH-SY5Y Cells

Introduction

The inventors sought to identify the effect of MRx0029 on the expression of Caspase 3 (Casp3) in neuroblastoma cells.

Bacterial Strain

*Megasphaera massiliensis* MRx0029

Cell Line

SH-SY5Y Cells

Method

The inventors measured the change in Casp3 expression in neuroblastoma cells.

Results

MRx0029 induces the upregulation of Casp3 in undifferentiated neuroblastoma SH-SY5Y cells. FIG. 4 shows that treatment with MRx0029 increases the expression of Casp3 in comparison to untreated SH-SY5Y cells. In particular, FIG. 4 shows that administration of MRx0029 increased the expression of Casp3 threefold in comparison to the control.

Discussion

In undifferentiated SH-SY5Y cells, the increase in Casp3 gene expression by MRx0029 could be linked to both cell differentiation and the induction of programmed cell death, such as apoptosis.

Caspase 3 is an executioner caspase and therefore is associated with apoptosis. Dysregulated apoptosis has been implicated in cancers and therefore, the results show that MRx0029 may be an effective composition in the treatment of cancer.

It has been shown that caspases have roles in cellular differentiation. Therefore the increase in Casp3 expression after treatment with MRx0029 shows that MRx0029 may be an effective composition to increase cell differentiation.

Example 4—MTT Assay in SH-SY5Y Cells

Introduction

The inventors sought to identify the effect of MRx0029 on neuroblastoma cell viability, using the MTT assay, which is a widely used method for assessing the cell metabolic activity which reflects in the number of viable cells.

Bacterial Strains

*Megasphaera massiliensis* MRx0029

Cell Line

SH-SY5Y Cells

Method

MTT Assay

SH-SY5Y cells were plated at a seeding density of 10,000 cells/well, 24 hrs later cells were treated in 100 ul of 1% FBS growth media with different concentrations (express as percentage v/v) of cell-free bacterial supernatants from stationary phase cultures for 22 h. Thereafter 10 μl of MTT solution was added and cells were incubated in CO2 incubator for 4 h, at the end of this time 100 μl of isopropanol with 0.04 HCL was added to each well. The absorbance was measured at 560 nm wavelength and a reference wavelength of 655 nm. MTT assay kit was purchased from Merck Millipore (Cat n. CT01).

Results

MRx0029 showed dose dependent effects on neuroblastoma cell viability, wherein 10% MRx0029 reduced viability by approximately 70% in comparison to the control. Treatment with 10% of MRx0029 cell-free bacterial supernatant showed a decrease in cell viability. The results of the experiments are shown in FIG. 5.

Discussion

This shows that MRx0029 may be an effective composition in increasing cell death, and therefore MRx0029 may be an effective composition for use in the treatment of cancer.

Example 5—Basic Cell Phenotyping on PBMCs from Healthy Donors

Bacterial Strain
*Megasphaera massiliensis* MRx0029
Method
PBMCs Treatment

Frozen healthy human PBMCs were purchased from Stem Cells Technologies (Cambridge UK). Briefly cells were thaw and left to rest overnight in full growth media (RPMI 1640 with 10% FBS, 2 mM L. Glutamine, 55 µM 2-Mercapoethanol and 100 U/ml penicillin, 100 µg/ml streptomycin) in CO2 incubator at 37° C. For the experiment cells were plated at a density of 750,000 Cell/well in 48 well plates and treated in full growth media with 10% bacteria supernatants in the presence or absence of 1 ng/ml LPS. Cell culture media was added to untreated wells. Cells were left to rest for 72 h, thereafter cell free supernatants were collected and spun down for 3 minutes at 10,000 g at 4° C. Samples were stored at −80° C. for cytokine analysis.

Immunophenotyping $1.5 \times 10^6$ cells per sample were stained with viability fixable dye (Miltenyi) to discriminate between live and dead cells for 10 min at RT. Afterwards the cells were stained with the cocktail of antibodies listed below (Miltenyi) for basic immunophenotyping (CD3/CD4/CD8/CD25/CD127 and CD19) and incubated for 10 min at RT.

Experiments were carried out to measure the percentage of the following cell populations:
- CD4+CD3+ cells (markers of CD4 T-helper cells)
- CD4+CD25+ cells (markers of CD4+ activated cells)
- CD25++CD17− cells out of the CD4+ cell population (markers of Tregs cells)
- CD8+CD3+ cells (markers of cytotoxic T cells)
- CD25+CD8+ cells (markers of CD8+ activated cells)
- CD19+CD3− cells (markers of B cells).

The ratio of CD8+/Tregs and the ratio of activated CD8/Treg cells were determined.

Antibodies

| Aria | AB-Fluorochrome |
|---|---|
| V2 | CD3-VioBlue |
| APC Cy7 | CD4-APC-Vio 770 |
| PE-Cy7 | CD8-PE-Vio 770 |
| PE | CD25-PE |
| APC | CD127-APC |
| FITC | CD19-VioBright 515 |

Results

The results of the experiments are shown in FIG. 6.

The most surprising result is the effect of MRx0029 treatment on the percentage of CD25++CD17− cells, which represent Treg cells (see FIG. 6C). MRx0029 selectively reduced the percentage of Tregs in the PBMC population. MRx0029 treatment did not significantly change the percentage of CD4 T-helper cells, CD4+ activated cells, cytotoxic T cells, CD8+ activated cells or B cells.

Figure 6G:
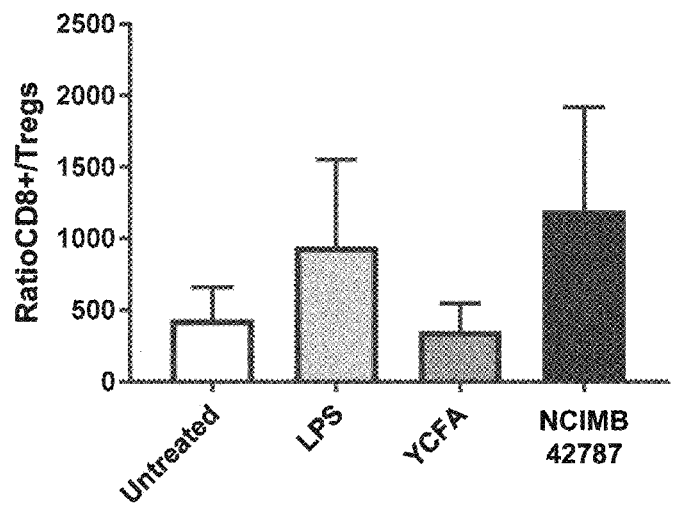
Figure 6H:
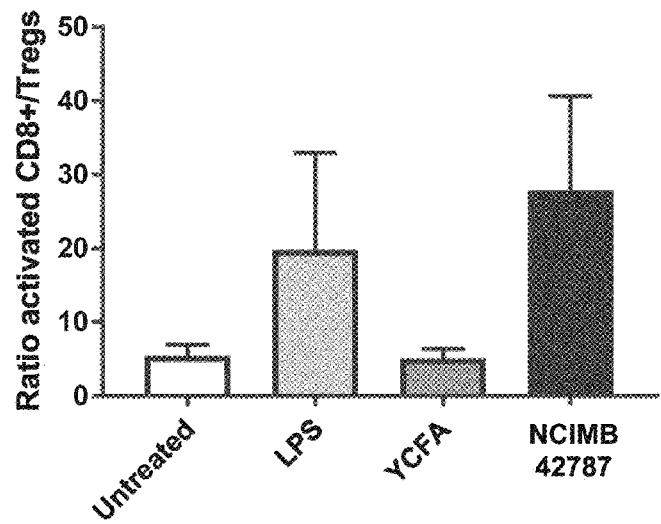
Figure 7A:
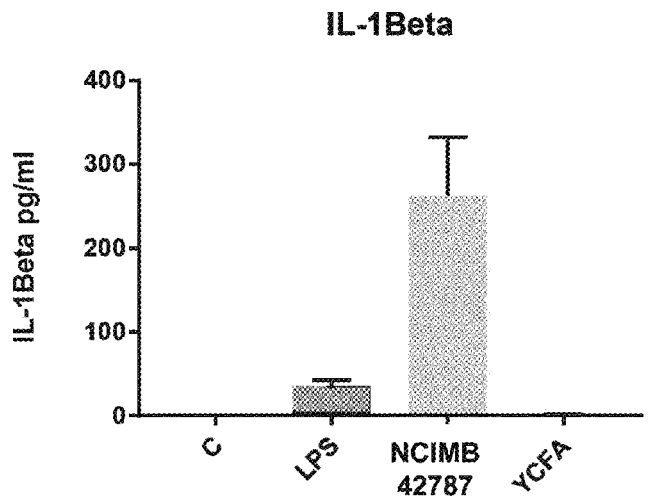
FIGS. 7A-7I: Cytokine analysis of IL-1β(FIG. 7A); TNF-α (FIG. 7B); IL-23 (FIG. 7C); IL-6 (FIG. 7D); MIP-3α (FIG. 7E); CXCL9 (FIG. 7F); MCP-1 (FIG. 7G); IL-10 (FIG. 7H); GM-CSF (FIG. 7I).
Figure 7B:
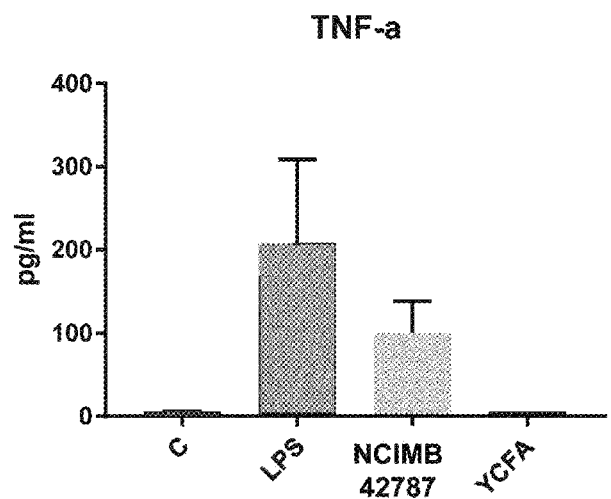
Figure 7C:
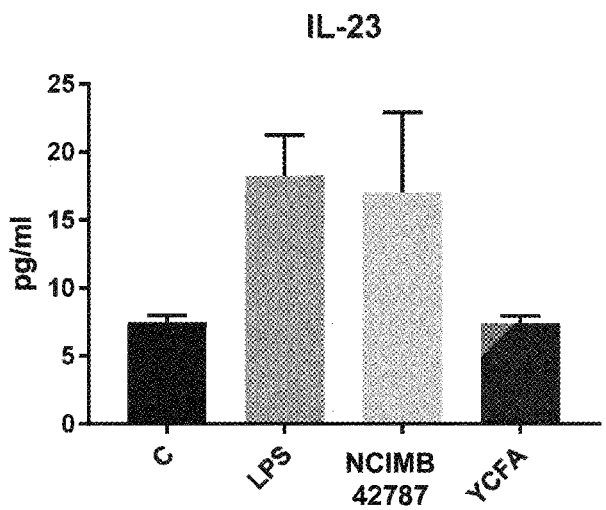
Figure 7D:
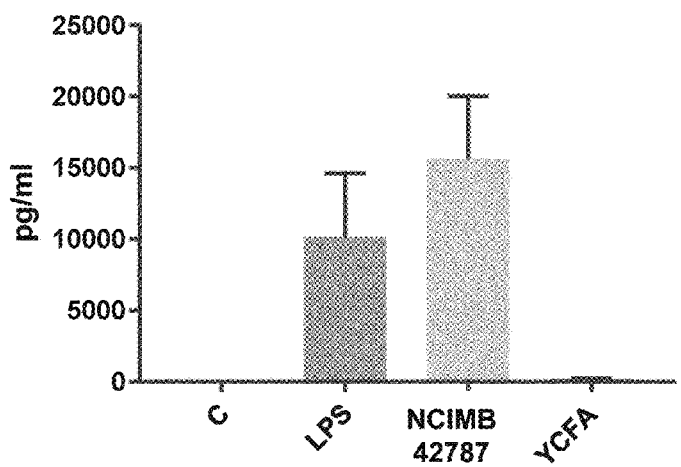
Figure 7E:
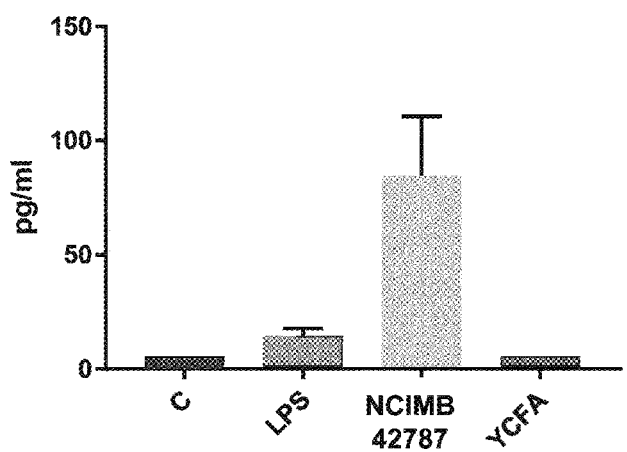
Figure 7F:
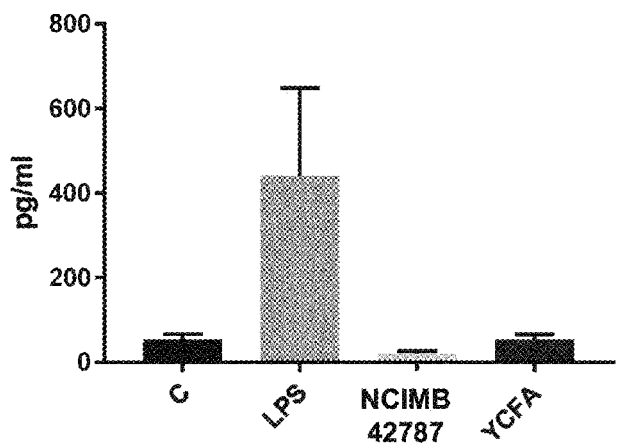
Figure 7G:
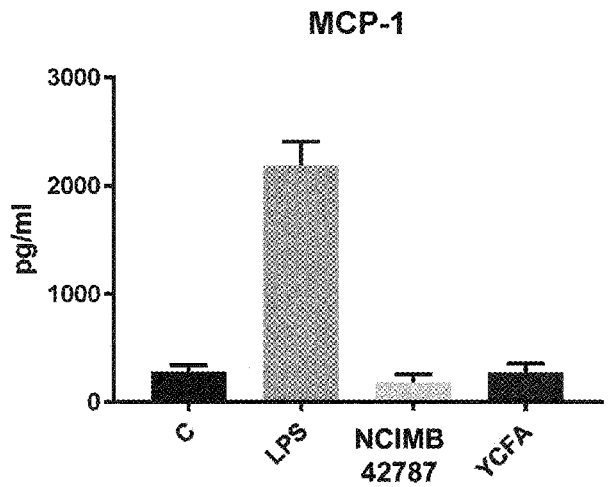
Figure 7H:
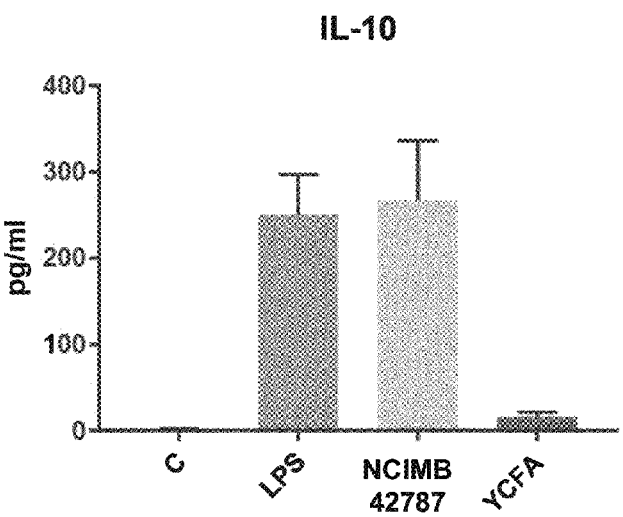
Figure 7I:
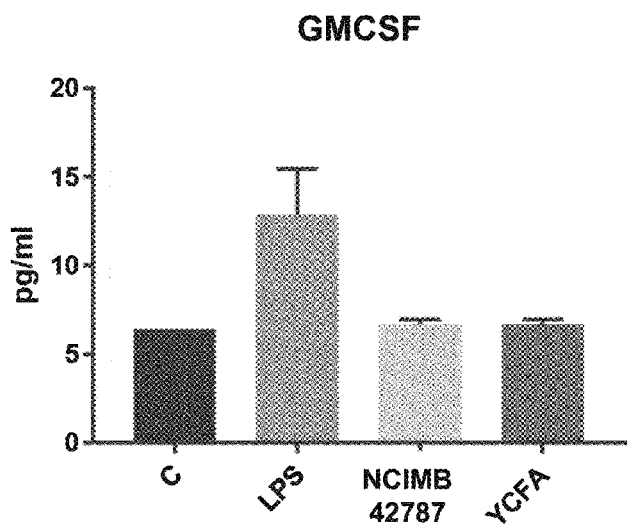

Treatment with MRx0029 increased the ratio of CD8+/Tregs and the ratio of activated CD8/Treg cells in comparison to untreated cells (see FIG. 6G and FIG. 6H).

Discussion

The observation that treatment with MRx0029 selectively decreased the percentage of Tregs, thereby increasing the ratios of CD8/Treg and activated CD8/Treg is surprising because MRx0029 produces butyrate, and butyrate production has been associated with increases in the population of Tregs.

Basic immunophenotyping profile of MRx0029 in PBMCs from healthy donors suggests that treatment with MRx0029 decreases the relative percentage of Tregs in the lymphocyte population, which reflects in an increasing ratio between CD8/Tregs cells.

This shows that MRx0029 may be an effective composition in stimulating the immune response, and decreasing immune suppression by Tregs. The results also show that MRx0029 may be an effective composition for use in the treatment of cancer.

Example 6—Cytokine Analysis of PBMCs from Healthy Donors

Introduction

The inventors sought to further analyse PBMCs post-incubation with MRx0029. The inventors analysed the expression of particular cytokines from PBMCs upon treatment with MRx0029, including pro-inflammatory cytokines TNF-α, IL-1β and IL-23.

Bacterial Strain
*Megasphaera massiliensis* MRx0029
Method
PBMCs Treatment

PBMCs were treated as described in Example 5.

Cytokine Quantification

Cytokine quantification was conducted using a Procarta-Plex multiplex immunoassay following the manufacturer's recommendations (Thermo Fischer Scientific). Briefly, 50 µl of cell-free co-culture supernatants were used for cytokine quantification using a MAGPIX® MILLIPLEX® system (Merck) with the xPONENT software (Luminex, Austin, Tex., USA). Data was analysed using the MILLIPLEX® analyst software (Merck) using a 5-parameter logistic curve and background subtraction to convert mean fluorescence intensity to pg/ml values.

Results

The results for the Cytokine analysis of MRx0029 in PBMC culture from healthy donors showed an immune-stimulatory signature for MRx0029. In particular, MRx0029 treatment increased the expression of TNF-α, IL-1β and IL-23.

The results also show that treatment with MRx0029 increased the expression of MIP-3α, IL-6 and IL-10. The expression levels of MCP-1, CXCL9, and GMCSF were similar to controls.

Discussion

This shows that MRx0029 has immunostimulatory properties, and may be an effective composition for immunostimulation. The results also show that MRx0029 may be an effective composition in the treatment of cancer.

Example 7—Flow Cytometry Analysis of Different Cell Populations

Introduction

The inventors sought to further analyse PBMCs post-incubation with MRx0029. Flow cytometry analysis was used to determine the percentages of CD4 cells (CD4+CD3+), Tregs (CD25++CD127−) CD8 cells (CD8+CD3+) and B cells (CD19+CD3−).

Figure 8A:
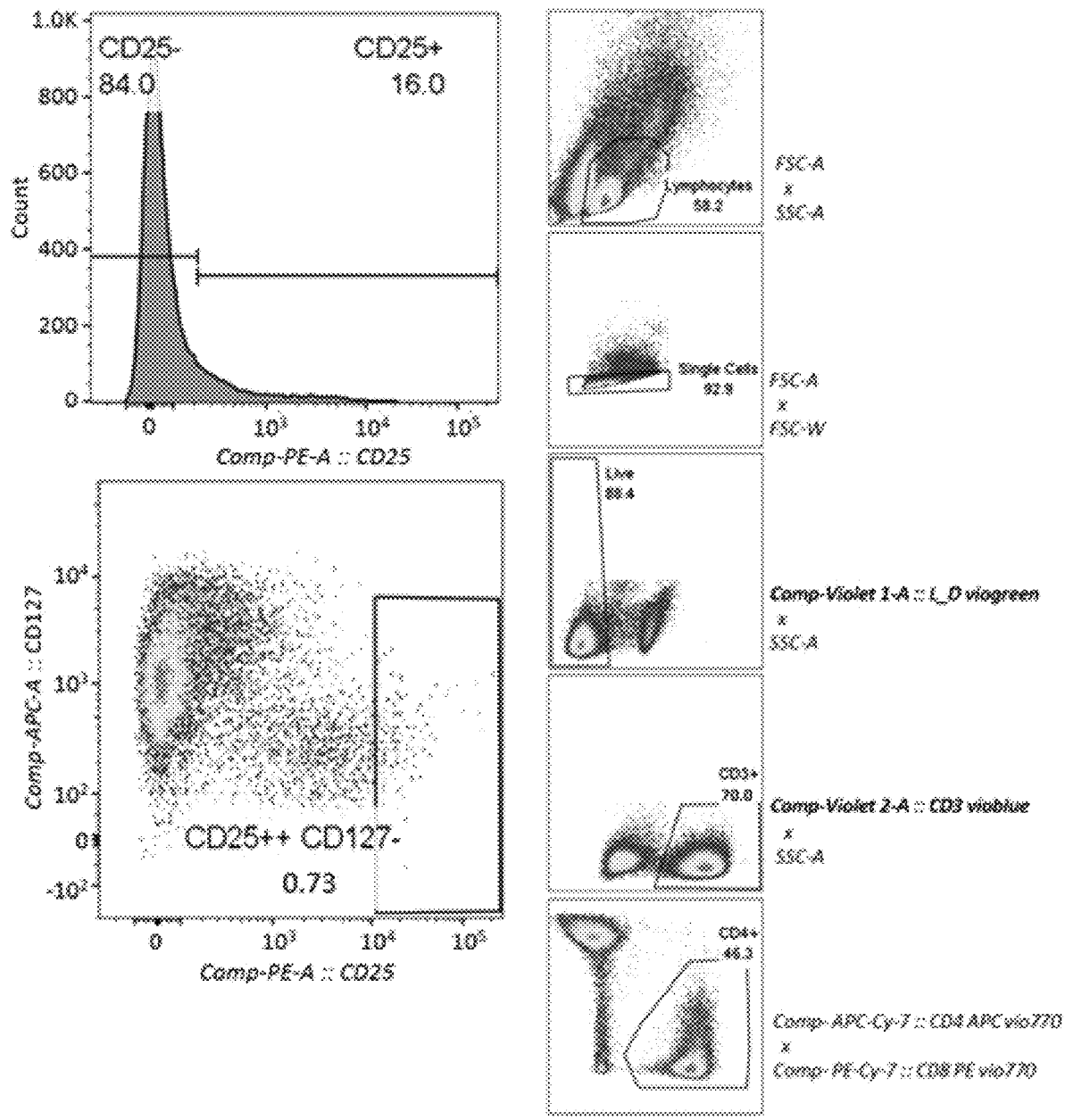
FIGS. 8A-8C: Gating strategy used to analyse the different population of immune cells (CD4, CD8 and CD19+ cells.
Figure 8B:
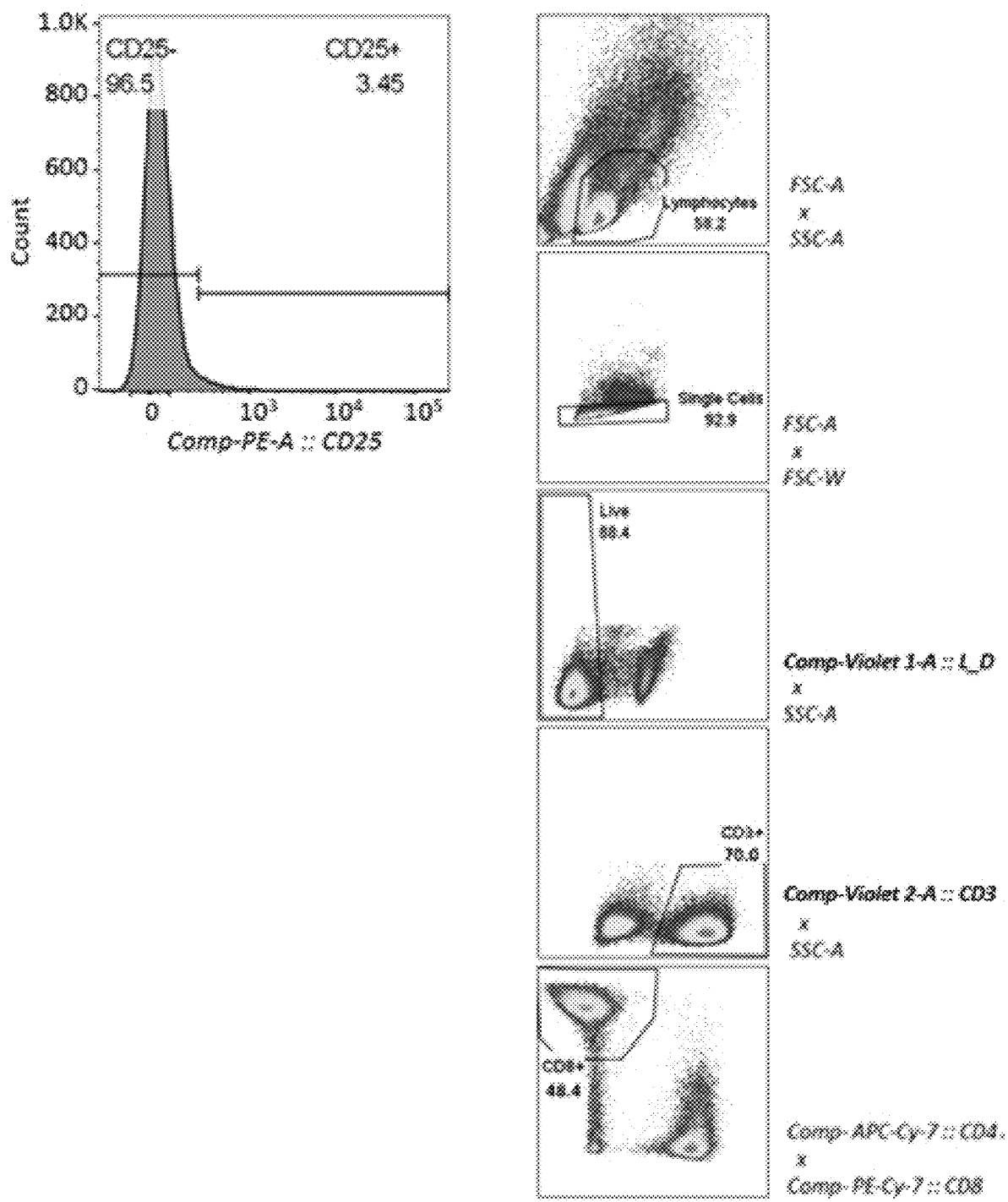
Figure 8C:
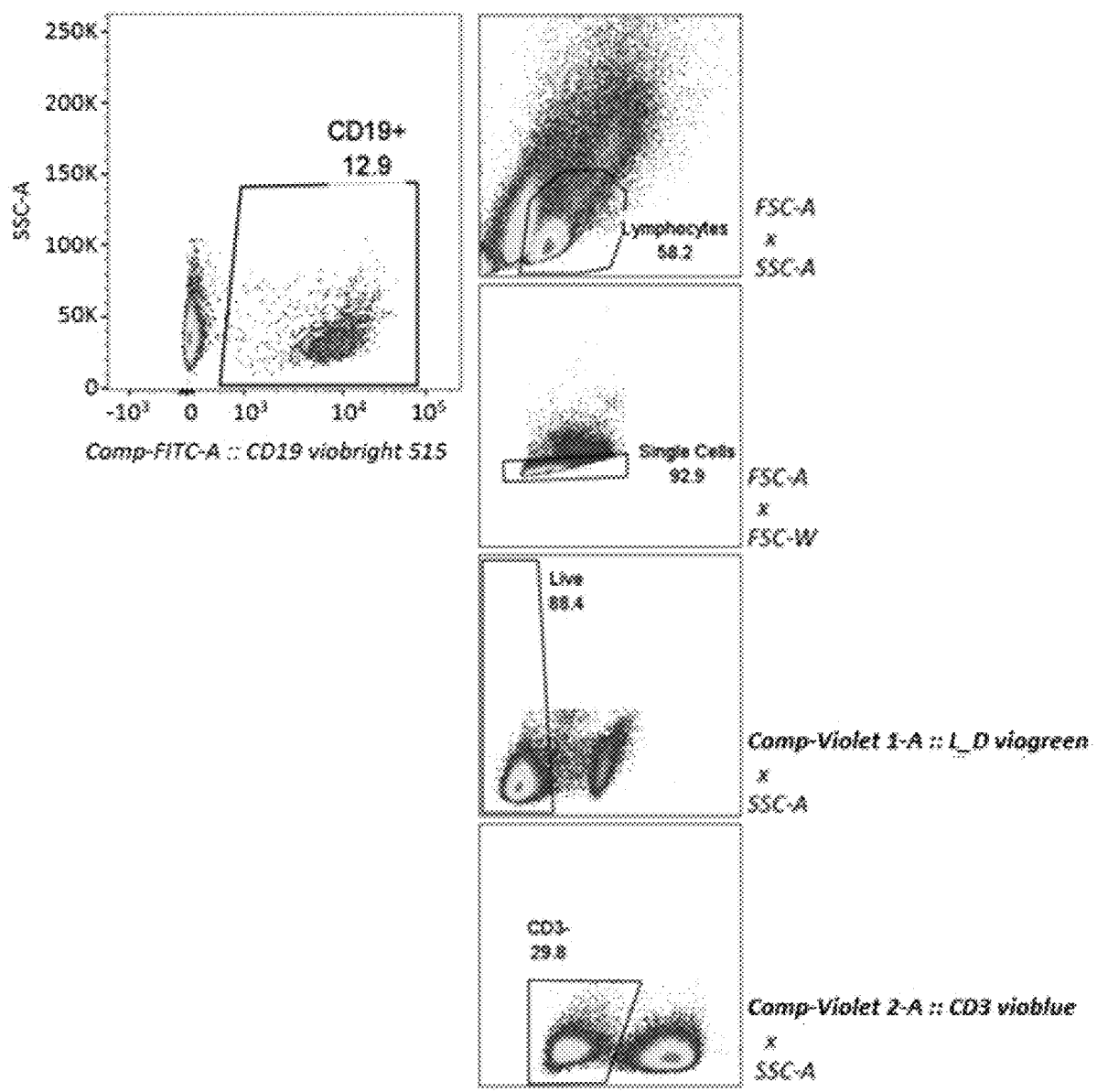

Method
PBMC Treatment
PBMCs were treated as described in Example 5.
Flow cytometry analysis of different cell populations 1.5×10$^6$ cells per sample were stained with viability fixable dye (Miltenyi) to discriminate between live and dead cells for 10 min at RT. Afterwards the cells were stained with the cocktail of antibodies listed below (Miltenyi) for basic immunophenotyping (CD3/CD4/CD8/CD25/CD127 and CD19) and incubated for 10 min at RT. Cells were then washed and resuspended in PBS and immediately analysed using a FACS Aria II equipped with Blue (488 nm), Red (633 nm) and Violet (405 nm) lasers. FMOs were included throughout all the experiments. For the analysis Flowjo version 10.4.2 software (FlowJo, LLC) was used.
Results
The results for the flow cytometry experiments are shown in FIGS. 8A-8C.
FIG. 8A shows that 0.73% of PBMCs were Tregs (CD25++CD127-).
Discussion
The results show that MRx0029 may be useful for down-regulating Tregs. Furthermore, the results show that MRx0029 may be an effective composition in stimulating the immune response, and decreasing immune suppression by Tregs. The results also show that MRx0029 may be an effective composition for use in the treatment of cancer.

Example 8—MRx0029 Increases IL-8 Secretion in MG U373 Cells

Introduction
The inventors sought to identify the effect of MRx0029 on the secretion of IL-8 in neuroblastoma cells. Human glioblastoma astrocytoma cells were treated with compositions comprising MRx0029 in combination with LPS to observe their ability to modulate the levels of IL-8. IL-8 is a pro-inflammatory cytokine secreted predominantly by macrophages with immune-stimulatory effects.
Bacterial Strain
*Megasphaera massiliensis* MRx0029
Cell Line
MG U373 is a human glioblastoma astrocytoma derived from a malignant tumour and were purchased from Sigma-Aldrich (cat n. 08061901-1VL). MG U373 human glioblastoma astrocytoma cells were grown in MEM (Sigma Aldrich, cat n. M-2279) supplemented with 10% FBS, 1% Pen Strep, 4 mM L-Glut, 1×MEM Non-essential Amino Acid solution and 1× Sodium Piruvate.
Method
Once grown the MG U373 cells were plated on 24-well plate at 100,000 cells/well. The cells were treated with LPS (1 ug/mL) alone or with 10% of bacteria supernatant from MRx0029 for 24 h. LPS is a known stimulator of proinflammatory cytokines such as IL-8. Afterwards the cell free supernatants were collected, centrifuged at 10,000 g for 3 min at 4° C. IL-8 was measured using Human IL-8 ELISA Kit from Peprotech (cat n. #900-K18) according to manufacturer instruction.
Results
The results of these experiments are shown in FIG. 9. Treatment the cells with the bacteria strains lead to an increase in IL-8 secretion independently of the presence of LPS.
Discussion
The results show that MRx0029 may be useful for increasing IL-8 secretion. Therefore, compositions of the invention may be useful in the treatment of disease, in particular diseases characterised by reduced immune activation and diseases treatable by an increased immune response.

Example 9—MRx0029 Reduces the Levels of Histone Deacetylase Activity in HT-29 Cells Introduction
The ability of compositions comprising MRx0029 to alter histone deacetylase activity was investigated. HDACi have been shown to cause growth arrest, differentiation, apoptosis, reduction of angiogenesis and modulation of the immune response in a variety of cancer cell lines.
Bacterial Strain
*Megasphaera massiliensis* MRx0029
Cell Line
The cell line HT-29 was used because histone deacetylase is present.
Method
Cell free supernatants of stationary phase bacterial cultures were isolated by centrifugation and filtering in a 0.22 uM filter. HT-29 cells were used 3 days post confluence and stepped down in 1 mL DTS 24 hours prior to commencement of the experiment. The HT-29 cells were challenged with 10% cell free supernatant diluted in DTS and was is left to incubate for 48 hours. Nuclease proteins were then extracted using the Sigma Aldrich Nuclease extraction kit and samples were snap frozen prior to HDAC activity measurement. HDAC activity was assessed fluorometrically using the Sigma Aldrich (UK) kit.
Results
The results of the experiments are shown in FIG. 10. FIG. 109 shows that MRx0029 is able reduce the levels of histone deacetylase activity.
Discussion
The results show that MRx0029 is a promising candidate for use in treating or preventing diseases characterised by epigenetic aberrations, through inhibition of HDAC activity. Cancer is a disease characterised by epigenetic aberrations. Furthermore, HDAC inhibitors (HDACi) are an emerging class of promising anti-cancer drugs that have been shown to cause growth arrest, differentiation, apoptosis, reduction of angiogenesis and modulation of the immune response in a variety of cancer cell lines. Therefore, the results shows that compositions of the invention may be effective for use in the treatment or prevention of cancer.

Example 10—Further Analysis of the Mechanism of Histone Deacetylation Inhibition Introduction
The gut microbiota, with its immense diversity and metabolic capacity, represents a huge metabolic reservoir for production of a vast variety of molecules with potential to influence HDAC activity. The inventors therefore sought to determine which metabolites are responsible for HDAC inhibition and further elucidate the mechanisms by which inhibition is achieved.
Bacterial Strain
*Megasphaera massiliensis* MRx0029
Method
Bacterial Culture and Cell-Free Supernatant Collection
Pure cultures of bacteria were grown anaerobically in YCFA+ broth until they reached their stationary growth phase. Cultures were centrifuged at 5,000×g for 5 minutes and the cell-free supernatant (CFS) was filtered using a 0.2

µM filter (Millipore, UK). 1 mL aliquots of the CFS were stored at −80° C. until use. Sodium butyrate, hexanoic and valeric acid were obtained from Sigma Aldrich (UK) and suspensions were prepared in YCFA+ broth.

SCFA and MCFA Quantification of Bacterial Supernatants

Short chain fatty acids (SCFAs) and medium chain fatty acids (MCFAs) from bacterial supernatants were analysed and quantified by MS Omics APS as follows. Samples were acidified using hydrochloride acid, and deuterium labelled internal standards where added. All samples were analyzed in a randomized order. Analysis was performed using a high polarity column (Zebron™ ZB-FFAP, GC Cap. Column 30 m×0.25 mm×0.25 µm) installed in a GC (7890B, Agilent) coupled with a quadropole detector (59977B, Agilent). The system was controlled by ChemStation (Agilent). Raw data was converted to netCDF format using Chemstation (Agilent), before the data was imported and processed in Matlab R2014b (Mathworks, Inc.) using the PARADISe software described in [118].

Specific HDAC Activity Analysis

Specific HDAC inhibition activity was analysed for HDAC1, 2, 3, 4, 5, 6, 9 using fluorogenic assay kits for each type of HDAC (BPS Bioscience, CA). Assays were conducted according to manufacturer's instructions and each sample were performed in replicates. Cell free supernatants were diluted 1 in 10 and exposed to specific HDAC proteins provided in the kit to maintain consistency between methods.

Results

Histone Deacetylase-Inhibiting Gut Commensal Microbial Metabolites are Butyrate and Valeric Acid MRx0029, whose supernatant showed strong HDAC inhibition in both HT29 whole cells and HT29 cell lysates (see FIG. 11A), produced valeric acid and hexanoic acid at mean concentrations of 5.08 mM and 1.60 mM, respectively (see FIG. 11B).

To investigate which metabolites were responsible for the strain-induced HDAC inhibition, different concentrations of hexanoic acid, valeric acid and sodium butyrate were measured for their HDAC inhibition on whole HT-29 cells and on HT-29 cell lysate. The results in FIG. 11C show significant ($P<0.05$) inhibition of HDAC activity by sodium butyrate on whole cells as well as on the cell lysate, while hexanoic acid did not show significant inhibitory activity. Valerie acid also inhibited HDAC activity on whole cells as well as on the cell lysate (* ($p<0.05$),  ($p<0.005$), * ($p<0.001$), **** ($p<0.0001$)).

Potent Total HDAC Inhibitors Investigated Target Class I HDACs.

The specific HDAC inhibition profile of the test bacteria strain was investigated. Specific HDAC inhibition assays (BPS Bioscience, CA) were carried out for Class I and Class II HDACs. The ability of the bacterial strain to inhibit HDAC enzymes was compared to butyrate, hexanoic and valeric acid.

Our results demonstrate that MRx0029 is a very potent inhibitor of Class 1 HDAC enzymes (HDAC1, 2 and 3). Inhibition of class II HDACs was not as significant (data not shown).

Discussion

The strain with HDAC inhibitory activity produced significant amounts of valeric acid and hexanoic acid as well as significant amounts of sodium butyrate (FIG. 11B). When tested as pure substances, valeric acid and sodium butyrate resulted in significant HDAC inhibition ($p<0.0001$).

Interestingly, the results for specific HDAC activity show that the tested strain is a potent inhibitor of Class I HDACs, and particularly HDAC2 (FIG. 12 and FIG. 13). Class I HDACs (HDAC1, 2, 3 and 8) reside in the nucleus and are ubiquitously expressed in several human cell types. HDACs 1-3 share more than 50% homology, but have distinct structures and cellular functions [119]. They are primarily involved in cell survival, proliferation and differentiation, and thus their inhibition may be useful is wide array of diseases [120]; [121]; [122]; [123]; [124]. Therefore, compositions of the invention may be particularly useful for treatment of diseases where Class I HDACs activity is upregulated. In particular, compositions of the invention may be particularly useful for treatment of cancers where Class I HDACs activity is upregulated. For example, compositions of the invention may be particularly useful for treatment of cancers where HDAC2 activity is upregulated.

Example 11—Modulation of Gut Barrier Function and Gut Permeability by MRx0029

Introduction

The ability of MRx0029 to cause any intestinal barrier dysfunction was investigated. HT29-mtx epithelial, mucin-producing cell monolayers [125] were used as an in vitro model to evaluate gut barrier disruption and immune stimulation following treatment with MRx0029.

Bacterial Strain

*Megasphaera massiliensis* MRx0029

Methods

RNA Extraction and qPCR Analysis

Total RNA was extracted using the RNeasy mini kit (Qiagen, Manchester, JUK) according to the manufacturer's instructions, and the RNA concentration determined by absorbance at 260/280 nm using a spectrophotometer (nano-Drop ND-1000; Thermo Scientific, Wilmington, Del.). For mRNA expression analysis, cDNA was prepared from total RNA using the High-Capacity cDNA reverse transcription kit (Applied Biosystems, UK) according to the manufacturer's instructions. The reverse transcription reactions were performed in a Thermo cycler (Biometra, Germany) at 25° C. for 10 min, 37° C. for 120 min, and 85° C. for 5 min, hold on at 4° C. Resulting cDNA was amplified in duplicates by the SYBR-Green PCR assay, and products were detected on QuantStudio 6 flex real-time PCR machine (Applied Biosystems, UK) using a standardised profile (initial denaturation of 95° C. for 10 minutes, followed by 40 cycles of 15 seconds of denaturation at 95° C. and 60 seconds of annealing/extension at 60/65° C., depending on the primers. A dissociation stage was added after the 40 cycles to generate a melting curve. Analysis was performed using the Applied Biosystems QuantStudio Real-Time PCR Software v1.2.

Results

Differentiated HT29-mtx cells exposed to phorbol 12-myristate-13-acetate (PMA) secreted a significant amount of IL-8; in contrast treatment for 24 h with MRx0029 bacterial supernatants, induced an even lower secretion of IL-8 compared than both untreated and YCFA+-treated cells (FIG. 14A).

The ability of MRx0029 to regulate epithelial permeability by modifying intracellular signal transduction involved in the expression and localization of proteins involved in the gut barrier formation was then investigated.

RNA was isolated and Quantitative RT-PCR (qRT-PCR) analysis was performed to characterize the changes in gene expression of tight junction proteins during incubation with MRx0029. The administration of MRx0029 enhanced Occludin, Villin, Tight Junction Protein 1 and 2 (respectively TJP1 and TJP2) mRNA expression after 2 h incubation (FIG. 14B).

The in vitro results were compared with data from the ex vivo parallel analysis on the gut of mice fed with MRx0029. Gene expression of TJP1 and Occludin was quantified in the colon and ileum. The ex vivo data perfectly mirror the in vitro data as MRx0029 was able to significantly up-regulate TJP1 and Occludin (p=0.073) in the colon region of the murine intestine (FIG. 14C+14D). MRx0029 was also able to decrease the permeability function in the colon of the same mice (FIG. 14F).

Discussion

The results show that MRx0029 is able to regulate epithelial permeability by modifying intracellular signal transduction involved in the expression and localization of proteins involved in gut barrier function (e.g. Occludin, Villin, TJP1 and TJP2). The results therefore show that MRx0029 functions to increase gut barrier function and reduce gut permeability. Therefore, compositions of the invention are effective for the treatment or prevention of diseases or conditions that are characterised by reduction of gut barrier function or increased gut permeability.

Example 12

Introduction

The inventors sought to analyse expression of genes for inflammatory markers in brain tissue from the hippocampus, amygdala and prefrontal cortex of mice fed with MRx0029. The inventors also explored the effects on cytokine production from the spleen in the same mice administered MRx0029.

Bacterial Strain

*Megasphaera massiliensis* MRx0029

Methods

Animals

BALBc (Envigo, UK) adult male mice were group housed under a 12 h light-dark cycle; standard rodent chow and water were available ad libitum. All experiments were performed in accordance with European guidelines following approval by University College Cork Animal Ethics Experimentation Committee. Animals were 8 weeks old at the start of the experiment.

Study Design

Animals were allowed to habituate to their holding room for one week after arrival into the animal unit. They receive oral gavage (200 µL dose) of live biotherapeutics at a dose of $1 \times 10^9$ CFU for 6 consecutive days between 15:00 and 17:00. On day 7, the animals are decapitated, and tissues are harvested for experimentation.

Tissue Collection

Animals were sacrificed in a random fashion regarding treatment and testing condition; sampling occurred between 9.00 a.m. and 2:30 p.m. Trunk blood was collected in potassium EDTA (Ethylene Diamine Tetra Acetic Acid) tubes and spun for 15 min at 4000 g. Plasma was isolated and stored at −80° C. for further analysis. The brain was quickly excised, dissected and each brain region was snap-frozen on dry ice and stored at −80° C. for further analysis. Spleen was removed, collected in 5 mL RPMI media (with L-glutamine and sodium bicarbonate, R8758 Sigma+10% FBS (F7524, Sigma)+1% Pen/Strep (P4333, Sigma)) and processed immediately after culls for ex-vivo immune stimulation. Intestinal tissue (2 3 cm segments of ileum and colon closest to the caecum were excised, and the furthest 1 cm 2 cm of tissue from the caecum were used) were mounted into the Ussing chambers for intestinal permeability assay. The caecum was removed, weighted and stored at −80° C. for SCFAs analysis.

Spleen Cytokine Assay

Spleens were collected immediately in 5 mL RPMI media following sacrifice and cultured immediately. Spleen cells were first homogenised in this RPMI media, followed by 5 mins incubation with 1 ml of RBC lysis buffer (11814389001 ROCHE, Sigma). A further 10 ml of RPMI media was added, followed by 200G centrifugation for 5 mins. The supernatant was then filtered through 40 um strainer. Cells were counted and seeded (4,000,000/mL media). After 2.5 h of adaptation, cells were stimulated with lipopolysaccharide (LPS-2 µg/ml) or concanavalin A (ConA-2.5 µg/ml) for 24 h. Following stimulation, the supernatants were harvested to assess the cytokine release using Proinflammatory Panel 1 (mouse) V-PLEX Kit (Meso Scale Discovery, Maryland, USA) for TNF-α, IL-10, IL-1β, Interferon γ, CXCL2 and IL6. The analyses were performed using MESO QuickPlex SQ 120, SECTOR Imager 2400, SECTOR Imager 6000, SECTOR S 600.

Gene Expression Analysis

Total RNA was extracted using the mirVana™ miRNA Isolation kit (Ambion/Llife technologies, Paisley, UK) and DNase treated (Turbo DNA-free, Ambion/life technologies) according to the manufacturers recommendations. RNA was quantified using NanoDrop™ spectrophotometer (Thermo Fisher Scientific Inc., Wilmington, Del., USA) according to the manufacturer's instructions. RNA quality was assessed using the Agilent Bioanalyzer (Agilent, Stockport, UK) according to the manufacturer's procedure and an RNA integrity number (RIN) was calculated. RNA with RIN value >7 was used for subsequent experiments. RNA was reverse transcribed to cDNA using the Applied Biosystems High Capacity cDNA kit (Applied Biosystems, Warrington, UK) according to manufacturer's instructions. Briefly, Multiscribe Reverse Transcriptase (50 U/µL) (1)(2)(1)(10) was added as part of RT master mix, incubated for 25° C. for 10 min, 37° C. for 2 h, 85° C. for 5 min and stored at 4° C. Quantitative PCR was carried out using probes (6 carboxy fluorescein—FAM) designed by Applied Biosystems to mouse specific targeted genes, while using β-actin as an endogenous control. Amplification reactions contained 1 µl cDNA, 5 µl of the 2×PCR Master mix (Roche), 900 nM of each primer and were brought to a total of 10 µl by the addition of RNase-free water. All reactions were performed in triplicate using 96-well plates on the LightCycler®480 System. Thermal cycling conditions were as recommended by the manufacturer (Roche) for 55 cycles. To check for amplicon contamination, each run contained no template controls in triplicate for each probe used. Cycle threshold (Ct) values were recorded. Data was normalized using β-actin and transformed using the 2-ΔΔCT method and presented as a fold change vs. control group.

Statistical Analysis

Normally distributed data are presented as mean±SEM; Non-parametric datasets are presented as median with interquartile range. Unpaired two-tailed t-test were applied to analyse parametric data and Mann-Whitney test was used for non-parametric. Spearman's rank correlation coefficient was employed for the correlation analysis in the pooled datasets. A p value <0.05 was deemed significant in all cases.

Results—Gene Expression

Expression of genes for inflammatory markers [IL-1β, IL6, CD11b, TNF-α and TLR-4] were analysed in brain tissue from the hippocampus, amygdala and prefrontal cortex. FIGS. 15-25 show the changes in gene expression after MRx0029 treatment in the hippocampal, amygdala and prefrontal cortex. Treatment with MRx0029 significantly increased the expression of TLR-4 in the amygdala (FIG. 20). Treatment with MRx0029 also increased expression of CD11b in the amygdala (FIG. 21).

Results—Effect on Cytokine Expression from Splenocytes

The ex-vivo splenocyte assay involves challenging the splenocytes (cells isolated from the spleen—a main organ involved in immune defence), with a bacterio- or viral-mimetic challenge.

Treatment with MRx0029 led to a reduction in interferon-γ, interleukin-1β and interleukin-6 following a challenge with LPS (FIGS. 26, 27 and 28, respectively).

Treatment with MRx0029 led to an increase in the levels of the chemoattractant CXCL1 (FIG. 30).

Discussion

Treatment with MRx0029 significantly increased the expression of the pro-inflammatory cytokines TLR-4 and CD11b in the amygdala. Therefore, compositions of the invention may be useful in the treatment of disease, in particular diseases characterised by reduced immune activation and diseases treatable by an increased immune response.

Example 13—Stability Testing

A composition described herein containing at least one bacterial strain described herein is stored in a sealed container at 25° C. or 4° C. and the container is placed in an atmosphere having 30%, 40%, 50%, 60%, 70%, 75%, 80%, 90% or 95% relative humidity. After 1 month, 2 months, 3 months, 6 months, 1 year, 1.5 years, 2 years, 2.5 years or 3 years, at least 50%, 60%, 70%, 80% or 90% of the bacterial strain shall remain as measured in colony forming units determined by standard protocols.

Example 14—Analysis of the Effect of M.Massiliensis on the ERK Signalling Pathway Materials and Methods
RNA Extraction and MAP2 qPCR Analysis Cells were plated in 12-well plates at density of $2 \times 10^5$ cells/well. After 24 h cells were treated with either DMSO or Vemurafenib (662005; EMD Millipore; VEMU; SKMEL28, SKMEL31, 451Lu, HT29 (1 µM) SKMEL2 (10 µM) or Azacytidine-C (A3656; Sigma Aldrich; AzaC; 5 µg/ml) or both drugs (VEMU+Aza) together, in presence of 10% bacteria supernatants or absence of it (YCFA+). Total RNA was extracted using the RNeasy mini kit (Qiagen, Manchester, UK) according to the manufacturer's instructions, and the RNA concentration was determined by spectrophotometer at 260/280 nm (NanoDrop ND-1000; Thermo Fisher Scientific, Loughborough). For mRNA expression analysis, cDNA was prepared from 2000 ng of total RNA using the High-Capacity cDNA reverse transcription kit (Thermo Fisher, Loughborough) according to the manufacturer's instructions. The reverse transcription reactions were performed in a thermocycler (Biometra, Germany) at 25° C. for 10 min, 37° C. for 120 min, and 85° C. for 5 min Resulting cDNA was amplified in duplicates by the SYBR-Green PCR assay, and products were detected on QuantStudio 6 flex real-time PCR machine (Applied Biosystems, UK) using a standardised profile (initial denaturation of 95° C. for 10 minutes, followed by 40 cycles of 10 seconds of denaturation at 95° C. and 30 seconds of annealing/extension at 65° C.). A dissociation stage was added after the 40 cycles to generate a melting curve. Analysis was performed using the Applied Biosystems QuantStudio Real-Time PCR Software v1.2. The primer sequences for GAPDH, and MAP2 are shown below.

Western Blot Analysis

Following 24 h treatment with the appropriate drugs either in presence of 10% bacterial supernatant or absence (YCFA+), protein extracts were obtained by lysing cells in RIPA buffer (R0278; Sigma Aldrich) supplemented with protease inhibitors (cOmplete Protease Inhibitor Cocktail Tablets; Roche, Switzerland) and 1 mM/L sodium orthovanadate, 0.5 mM/L PMSF. Protein quantification was done by the BCA protein assay. Equal amounts of total protein (20 µg/lane) were then separated by SDS-PAGE on 4-15% gradient gel (BioRad) and transferred to polyvinylidene difluoride (PVDF) membranes (Thermo Fisher Scientific, Loughborough). After blocking with 5% BSA or nonfat dry milk in TBST (10 mM Tris, pH 7.5, 150 mM NaCl, 0.5% Tween 20) for 60 min, membranes were probed with primary antibodies against phospho-ERK (9101S, 1:1000, Cell Signalling; New England Biolabs (UK)) or total ERK (4696S, 1:1000, Cell signalling; New England Biolabs (UK)).

Proteins of interest were detected with the appropriate HRP-conjugated secondary antibody (1:10,000, Thermo Fisher Scientific, Loughborough), developed with the ECL Western blotting Super Signal PicoPlus substrate (34577; Thermo Fisher Scientific, Loughborough), and visualised in Chemidoc XRS Imager (BioRad).

Anchorage-Independent Growth (Soft Agar Growth Assay) in 96-Well Plates

A mixture of 25 µL prewarmed (37° C.) 2x appropriate growth medium (EMEM for melanoma cell lines; DMEM high glucose for HT29) containing 20% FBS, 4 mM L-Glu, 2xNEAA, 0.6% sodium bicarbonate, 200 U/mL penicillin/streptomycin (Invitrogen), and 25 µL prewarmed (47° C.) 1.2% Noble Agar (A5431; Sigma Aldrich) were plated onto each well of a 96-well microplate to serve as a prelayer for the assay. Ten microliters of cell suspensions containing $0\text{-}2 \times 10^3$ cells were mixed with 25 µL 2x growth media and 35 µL 0.8% Noble Agar in a 96-well round-bottom polypropylene microplate and transferred to the 96-well microplate containing the solidified prelayers. The cells were allowed to grow for 2 days and then fed with media containing drugs in presence of 10% bacterial supernatants or YCFA+ every three days. They left to grow in the humidified 37° C. incubator with 5% CO2 for 1-2 weeks before soft agar growth was scored using the CytoSelect 96 well cell transformation assay (CBA-130; Cell Biolabs) according to the manufacturer's protocol. Cell growth was measured using a Tecan Infinite F200 Pro Series Multi-Well Plate Reader (Tecan Biosystems), with excitation at 485 nm and emission at 530 nm.

Anchorage-Independent Growth (Soft Agar Growth Assay) in a 32-Mm Plate

A mixture of 1 mL of prewarmed (37° C.) 2x appropriate growth media (EMEM for melanoma cell lines; DMEM high glucose for HT29) and 1 mL prewarmed (47° C.) 0.8% Noble Agar per plate (0.4% final agar) were mixed with 1 mL cell suspension and seeded over a 0.6% agar/cell growth prelayer (2 mL) in a 6-well plate. The cells were allowed to grow in the humidified 37° C. incubator with 5% $CO_2$ for 21-28 days. They fed with drugs in absence (YCFA+) or presence of 10% bacterial supernatant every three days. Colonies were photographed using Evos XL Core microscope (Thermo Fisher Scientific, Loughborough).

Clonogenic Assay

Cells were trypsinized and 200 cells/well were seeded in 12-well plates. After 48 h cells were treated with the appropriate drugs in absence (YCFA+) or presence of 10% bacterial supernatant and were re-fed every three days. On day 21 after seeding, cells were fixed in ice-cold methanol and stained with Crystal Violet blue. Colonies (0.50 cells) were counted and survival fraction was calculated as number of colonies divided by the number of plated cells (plating efficiency) of treated divided by the plating efficiency of control.

Example 14A—SKMEL2 Melanoma Cell Line

The effects of the following treatments were assessed on the SKMEL2 melanoma cell line (WT BRAF; N61R oncogenic mutation in Nras): (1) MRX0029; (2) Vemurafenib (VEMU) in YCFA+ medium; (3) VEMU and MRX029; (4) Azacytidine-C (Aza-c) in YCFA+ medium; (5) Aza-c and MRX029; (6) VEMU, Aza-c and MRX0029.

Figure 31:
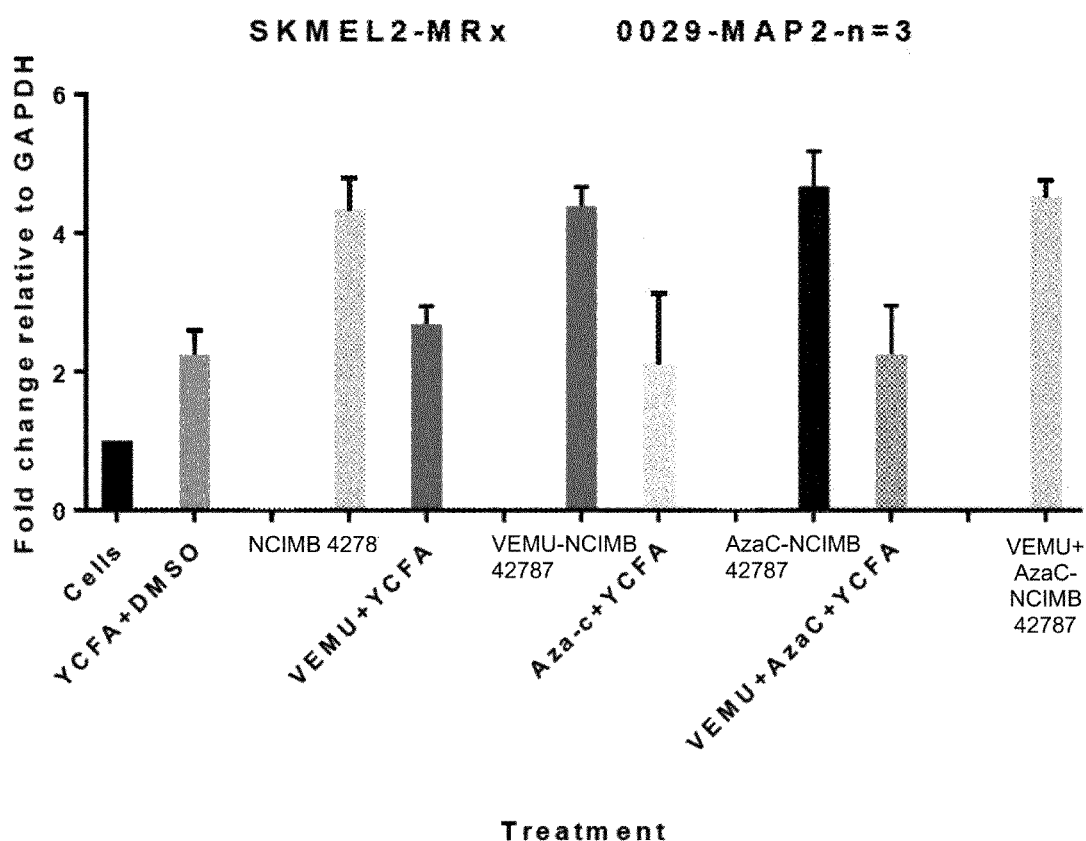
FIG. 31: Gene expression of MAP2 in the SKMEL2 cell line following various treatments, relative to GAPDH. "YCFA"=YCFA+
Figure 32:
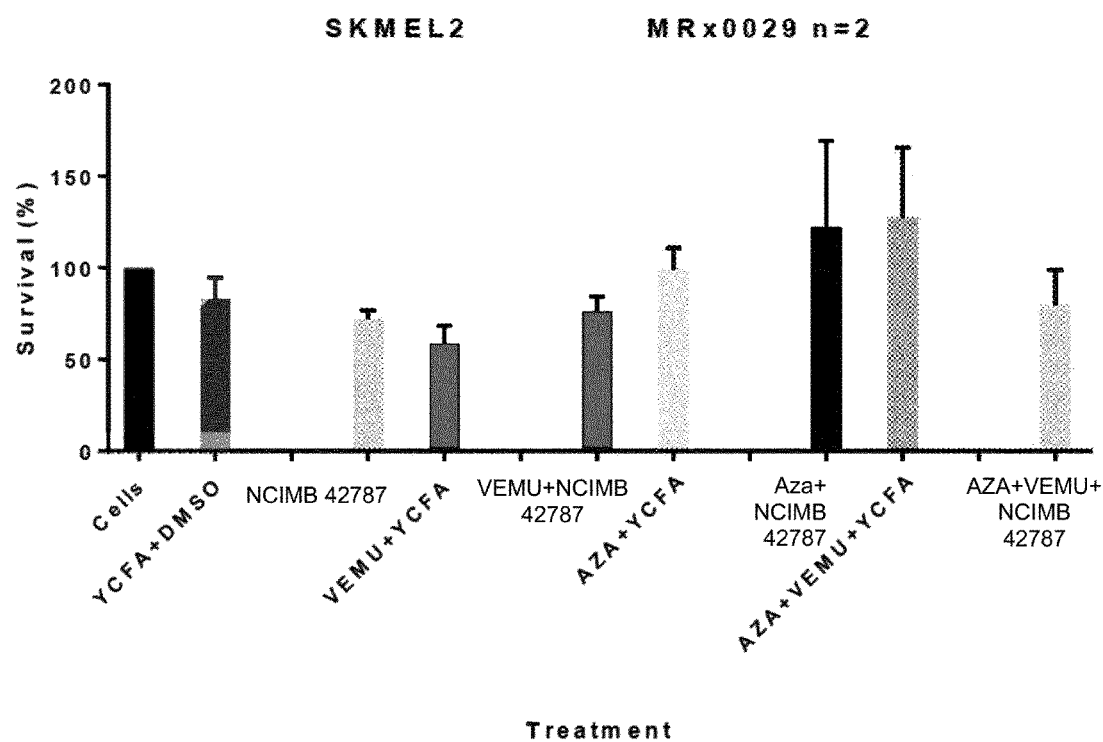
FIG. 32: Clonogenic survival of the SKMEL2 cell line following various treatments. "YCFA"=YCFA+
Figure 33:
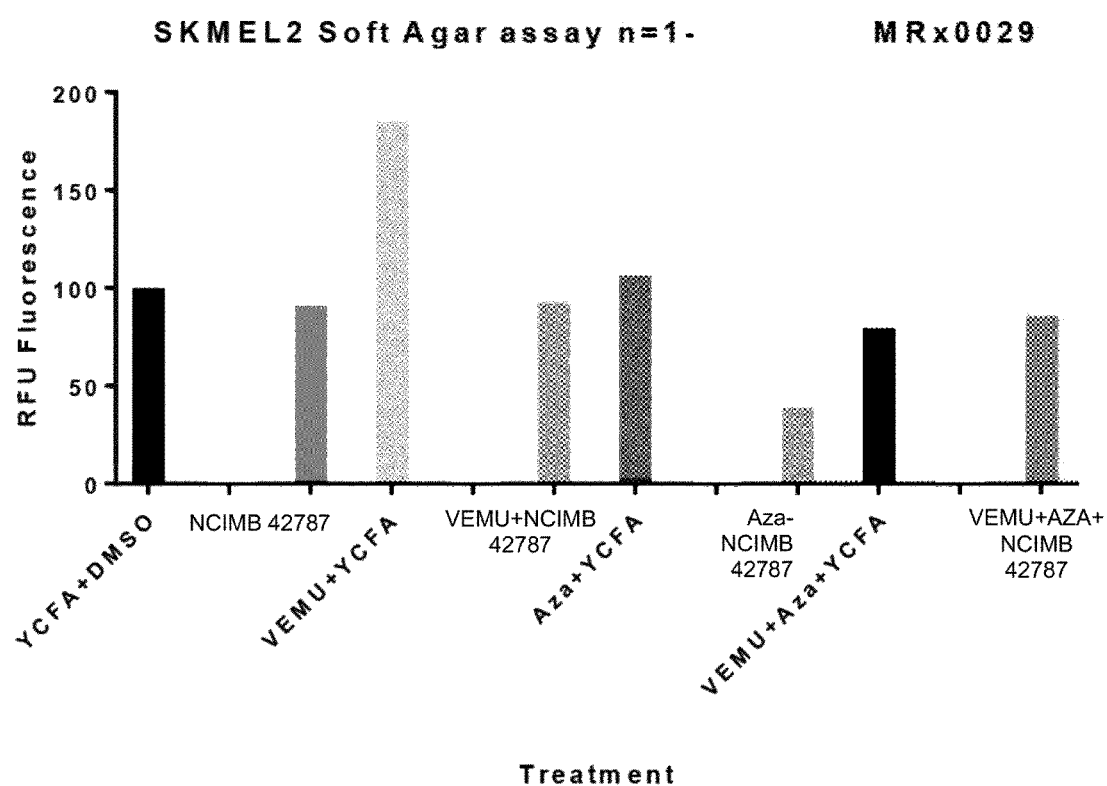
FIG. 33: Soft agar growth of the SKMEL2 cell line following various treatments. "YCFA"=YCFA+
Figure 34:
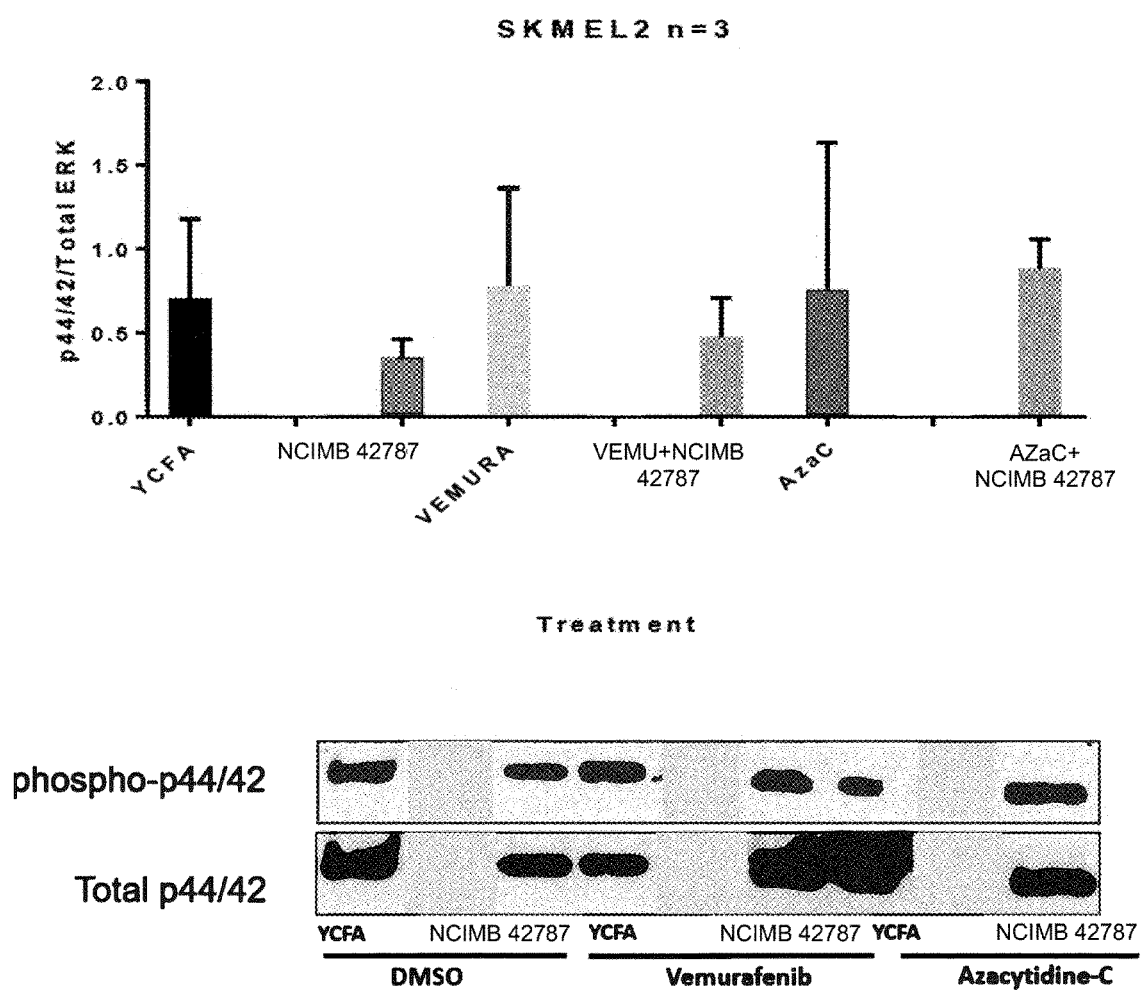
FIG. 34: ERK signalling (phosphorylated ERK1 and 2 (p44 and p42)/total ERK) in the SKMEL2 cell line following various treatments. "YCFA"=YCFA+

MAP2 gene expression in the SKMEL2 cell line was assessed using the protocol in Materials and Methods, and the results are shown in FIG. 31. All treatments with MRX029 (alone or in combination with VEMU and/or Aza-c) increased MAP2 gene expression relative to both negative controls (cell line only, and YCFA+). Clonogenic survival of the SKMEL2 cell line was assessed using the protocol in Materials and Methods, and the results are shown in FIG. 32. Soft agar growth of the SKMEL2 cell line was assessed using the protocol in Materials and Methods, and the results are shown in FIG. 33. VEMU+Aza-c improved soft agar growth inhibition by MRX029. ERK signalling in the SKMEL2 cell line was assessed using the protocol in Materials and Methods, and the results are shown in FIG. 34 (VEMU, Aza-c and MRX029 was not assessed).

These results indicate that MRX0029 alone or in combination with Vemurafenib and/or Azacytidine-C may have the effects of inducing MAP2 gene expression in a melanoma cell line (SKMEL2). Furthermore, Vemurafenib+Azacytidine-C enhanced soft agar growth inhibition by MRX0029. On this basis, compositions of the invention are expected to be useful in the treatment or prevention of various cancers, in particular metastatic cancers, in particular metastatic melanoma.

Example 14B—SKMEL28 Melanoma Cell Line

The effects of the following treatments were assessed on the SKMEL28 melanoma cell line (V600E oncogenic mutation in BRAF): (1) MRx0029; (2) Vemurafenib (VEMU) in YCFA+ medium; (3) VEMU and MRx0029; (4) Azacytidine-C (Aza-c) in YCFA+ medium; (5) Aza-c and MRX0029; (6) VEMU, Aza-c and MRx0029.

Figure 35:
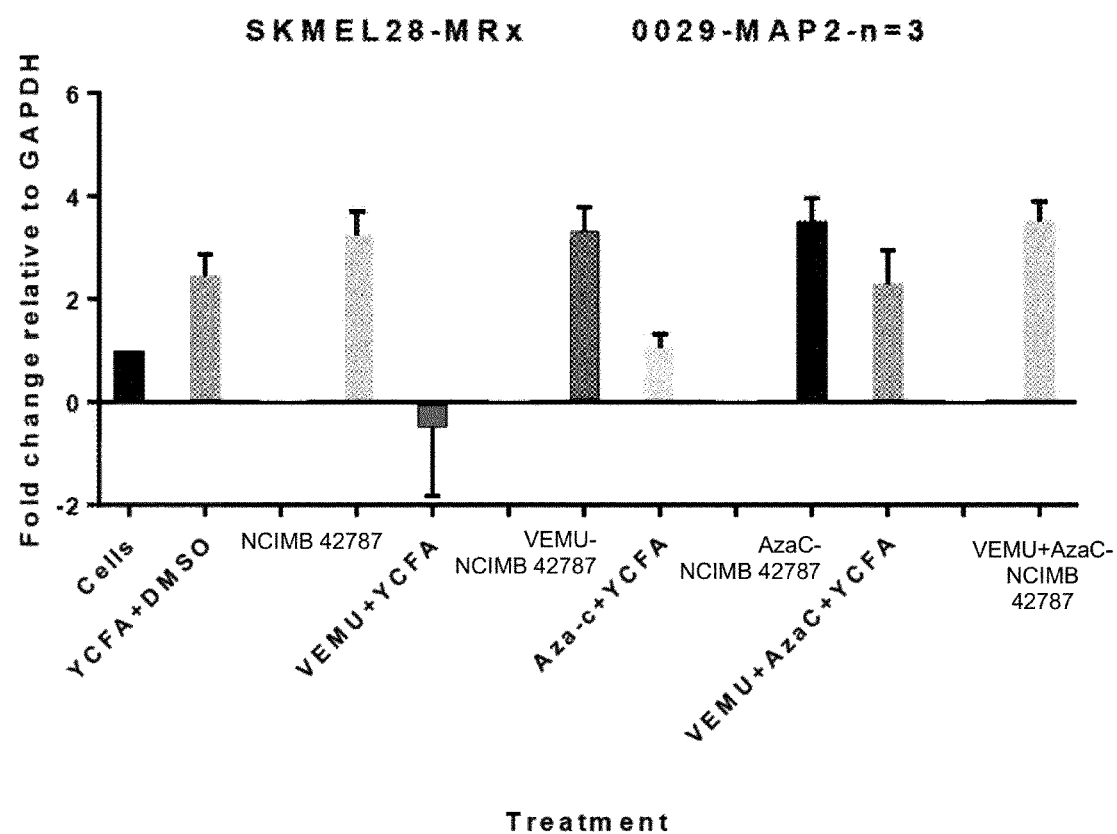
FIG. 35: Gene expression of MAP2 in the SKMEL28 cell line following various treatments, relative to GAPDH. "YCFA"=YCFA+
Figure 36:
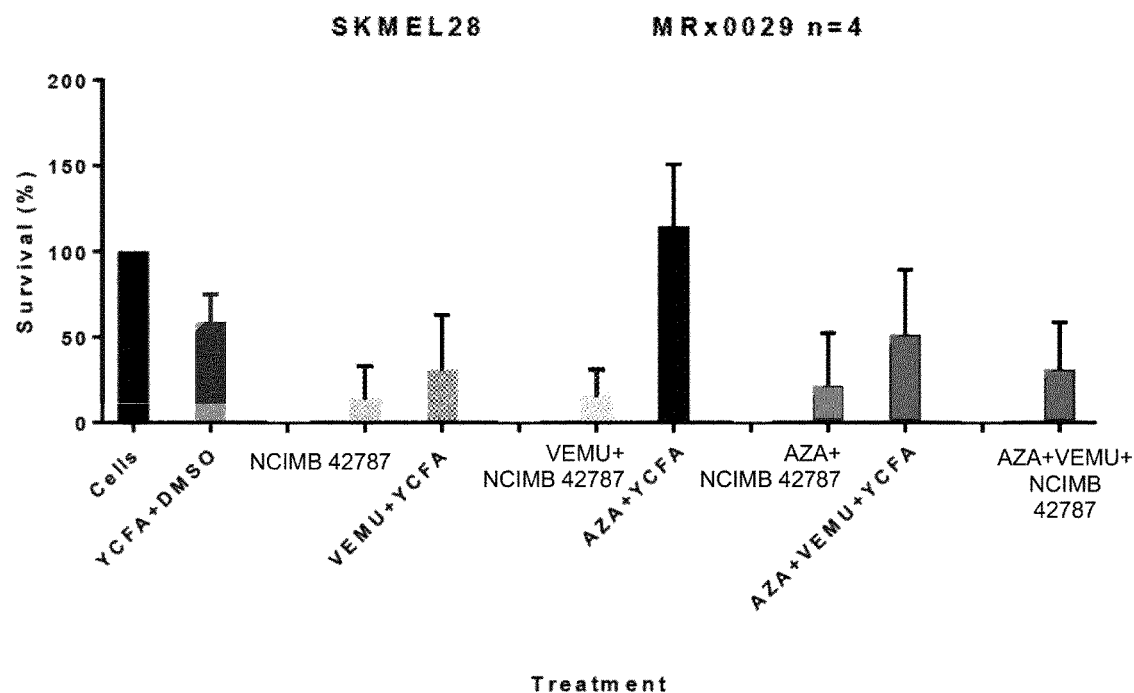
FIG. 36: Clonogenic survival of the SKMEL28 cell line following various treatments. "YCFA"=YCFA+
Figure 37:
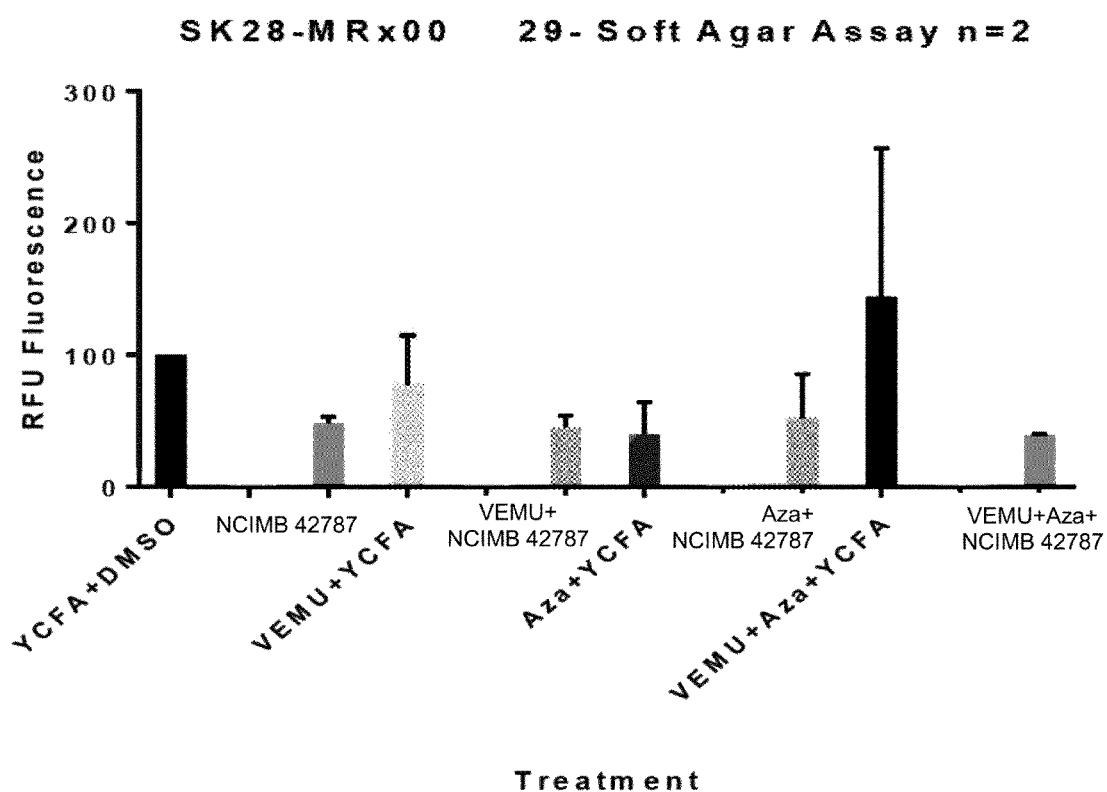
FIG. 37: Soft agar growth of the SKMEL28 cell line following various treatments. "YCFA"=YCFA+
Figure 38:
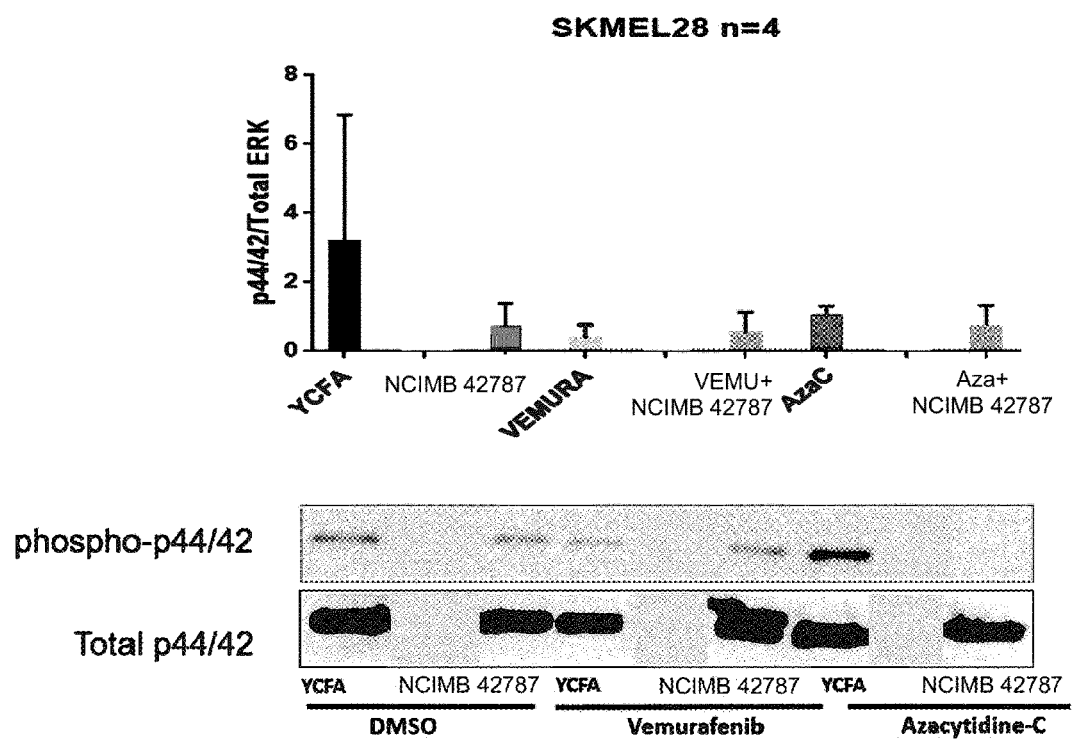
FIG. 38: ERK signalling (phosphorylated ERK1 and 2 (p44 and p42)/total ERK) in the SKMEL28 cell line following various treatments. "YCFA"=YCFA+

MAP2 gene expression in the SKMEL28 cell line was assessed using the protocol in Materials and Methods, and the results are shown in FIG. 35. Clonogenic survival of the SKMEL28 cell line was assessed using the protocol in Materials and Methods, and the results are shown in FIG. 36. MRx0029 in combination with VEMU and/or Aza-c decreased clonogenic survival relative to both negative controls (YCFA+ and cell line only). Soft agar growth of the SKMEL28 cell line was assessed using the protocol in Materials and Methods, and the results are shown in FIG. 37. ERK signalling in the SKMEL28 cell line was assessed using the protocol in Materials and Methods, and the results are shown in FIG. 38 (VEMU, Aza-c and MRx0029 was not assessed). All treatments with MRx0029 (alone or in combination with VEMU or Aza-c) reduced ERK signalling relative to the negative control (YFCA+).

These results indicate that MRx0029 alone or in combination with Vemurafenib and/or Azacytidine-C may have the effects of inhibiting ERK signalling and decreasing clonogenic survival of a melanoma cell line comprising the BRAF V600E mutation (SKMEL28). On this basis, compositions of the invention are expected to be useful in the treatment or prevention of cancers, in particular those comprising oncogenic ERK signalling, especially melanomas. In particular, compositions of the invention are expected to be useful in the treatment or prevention of such cancers comprising an oncogenic mutation in BRAF, in particular at position 600, and especially the mutation BRAF V600E.

Example 14C—SKMEL31 Melanoma Cell Line

The effects of the following treatments were assessed on the SKMEL31 melanoma cell line (heterozygous for BRAF V600E): (1) MRx0029; (2) Vemurafenib (VEMU) in YCFA+ medium; (3) VEMU and MRx0029; (4) Azacytidine-C (Aza-c) in YCFA+ medium; (5) Aza-c and MRx0029; (6) VEMU, Aza-c and MRx0029.

Figure 39:
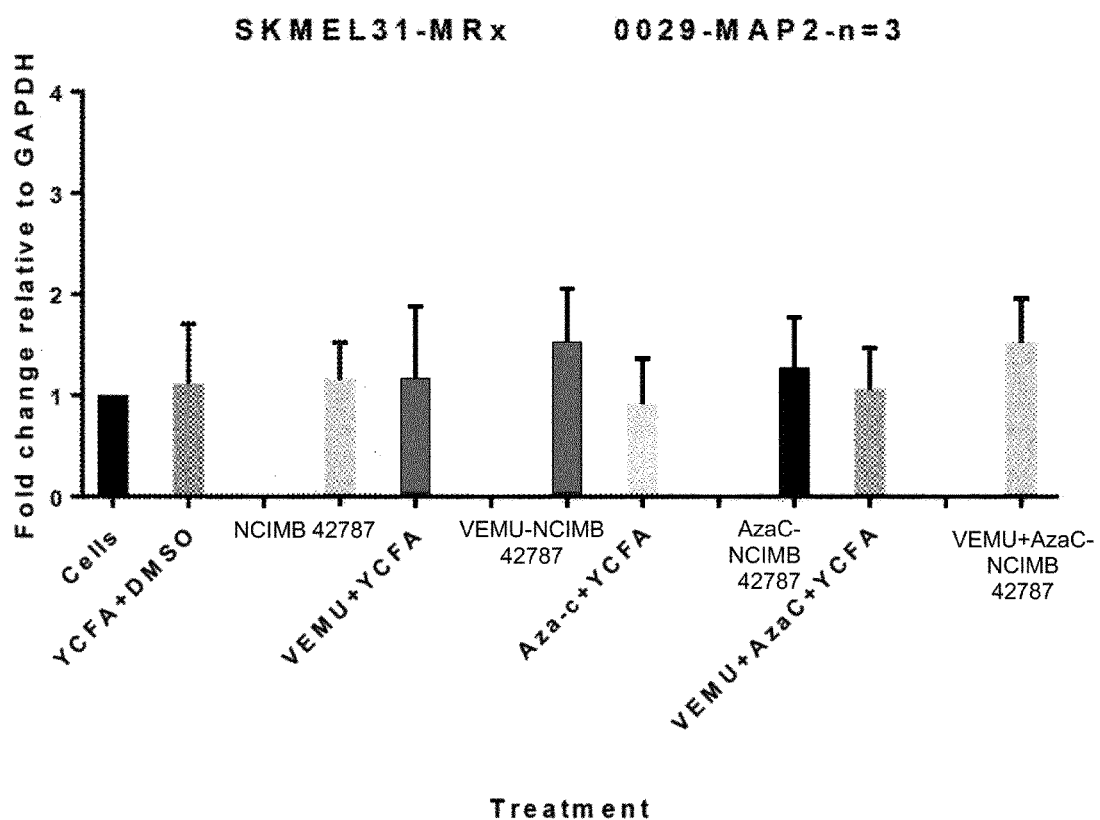
FIG. 39: Gene expression of MAP2 in the SKMEL31 cell line following various treatments, relative to GAPDH. "YCFA"=YCFA+
Figure 40:
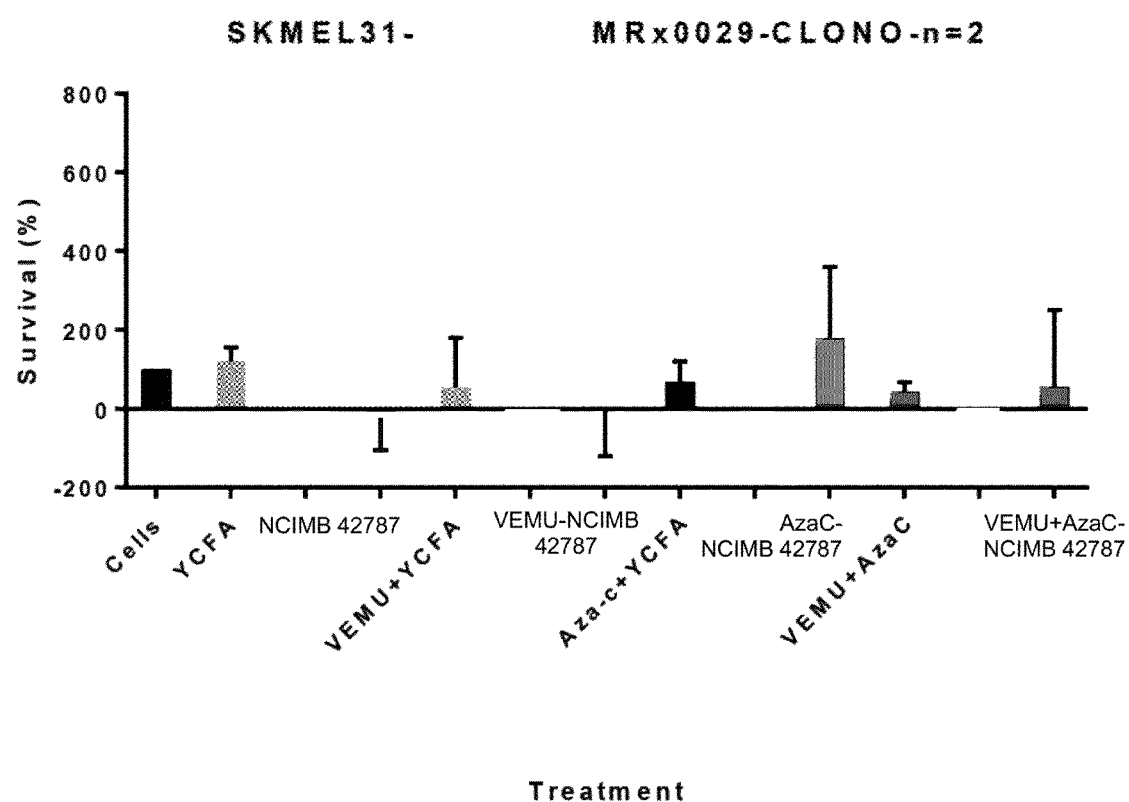
FIG. 40: Clonogenic survival of the SKMEL31 cell line following various treatments. "YCFA"=YCFA+
Figure 41:
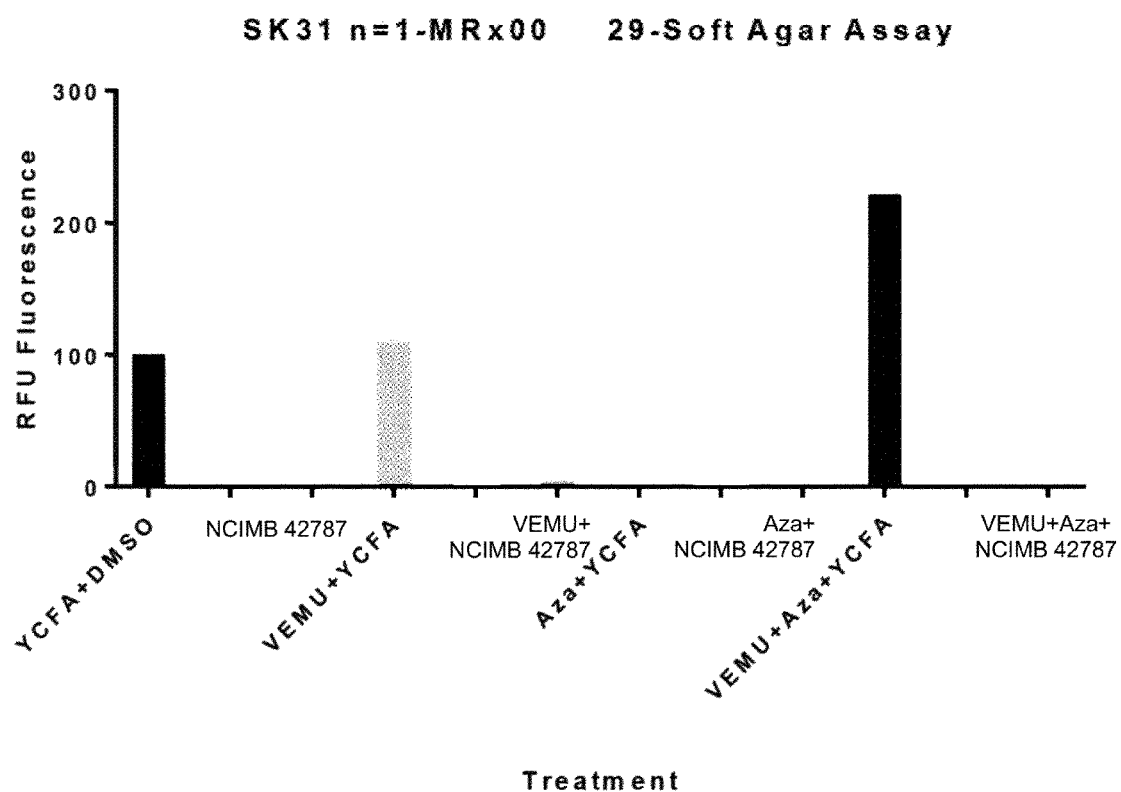
FIG. 41: Soft agar growth of the SKMEL31 cell line following various treatments. "YCFA"=YCFA+
Figure 42:
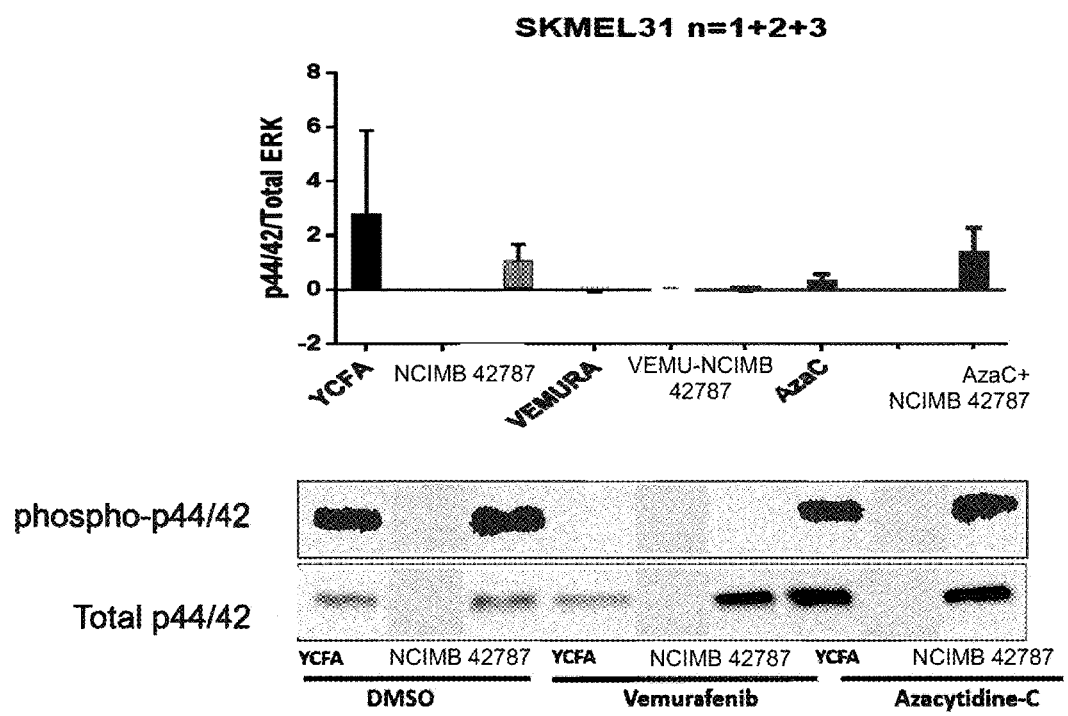
FIG. 42: ERK signalling (phosphorylated ERK1 and 2 (p44 and p42)/total ERK) in the SKMEL31 cell line following various treatments. "YCFA"=YCFA+

MAP2 gene expression in the SKMEL31 cell line was assessed using the protocol in Materials and Methods, and the results are shown in FIG. 39. Clonogenic survival of the SKMEL31 cell line was assessed using the protocol in Materials and Methods, and the results are shown in FIG. 40. Soft agar growth of the SKMEL31 cell line was assessed using the protocol in Materials and Methods, and the results are shown in FIG. 41. VEMU, Aza-c and VEMU+Aza-c improved soft agar growth and clonogenic survival inhibition by MRx0029. ERK signalling in the SKMEL31 cell line was assessed using the protocol in Materials and Methods, and the results are shown in FIG. 42 (VEMU, Aza-c and MRx0029 in combination was not assessed). All treatments with MRx0029 (alone or in combination with VEMU or Aza-c) reduced ERK signalling relative to the negative control (YFCA+).

Example 14D—451Lu Melanoma Cell Line

The effects of the following treatments were assessed on the 451Lu melanoma cell line (V600E oncogenic mutation in BRAF): (1) MRx0029; (2) Vemurafenib (VEMU) in YCFA+ medium; (3) VEMU and MRx0029; (4) Azacytidine-C (Aza-c) in YCFA+ medium; (5) Aza-c and MRx0029; (6) VEMU, Aza-c and MRx0029.

Figure 43:
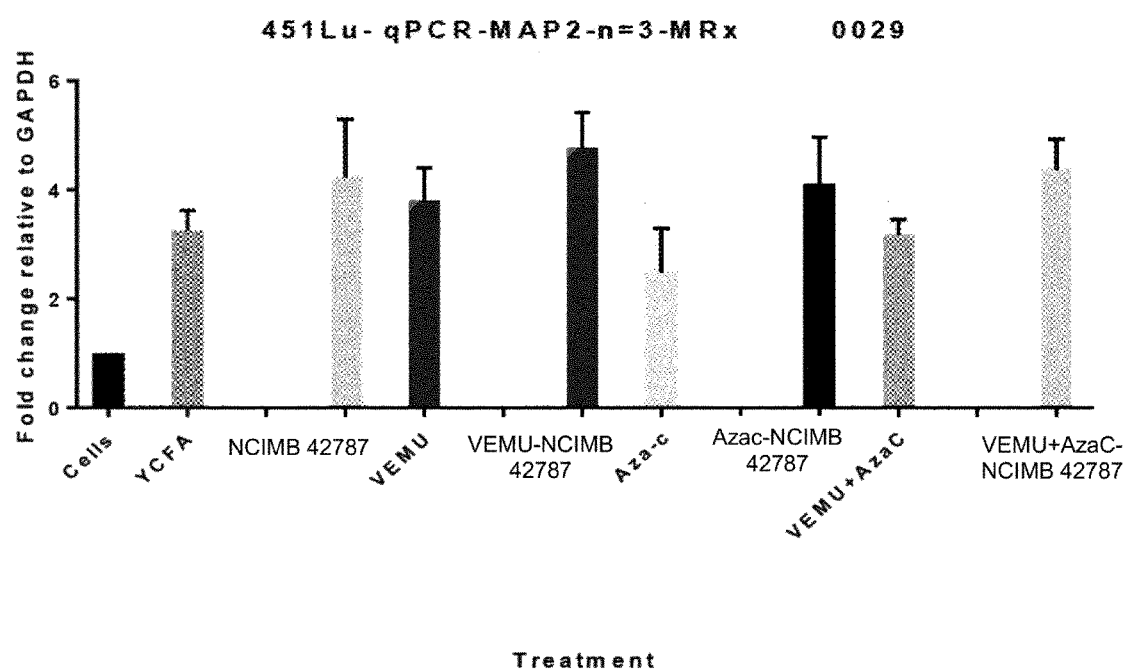
FIG. 43: Gene expression of MAP2 in the 451Lu cell line following various treatments, relative to GAPDH. "YCFA"=YCFA+
Figure 44:
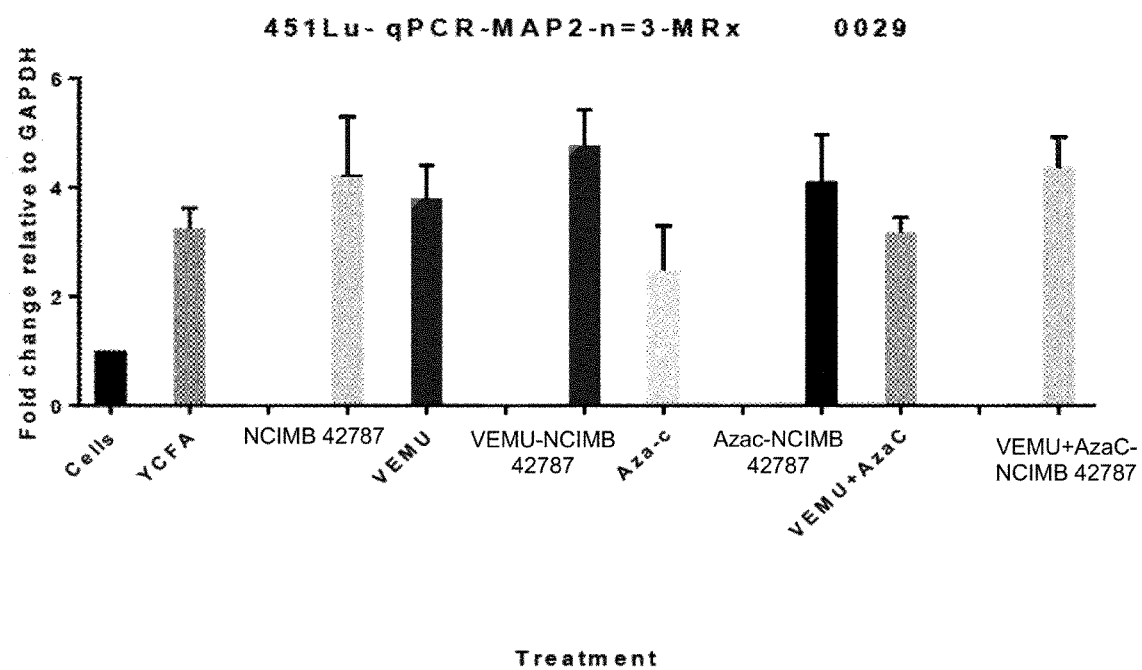
FIG. 44: Clonogenic survival of the 451Lu cell line following various treatments. "YCFA"=YCFA+
Figure 45:
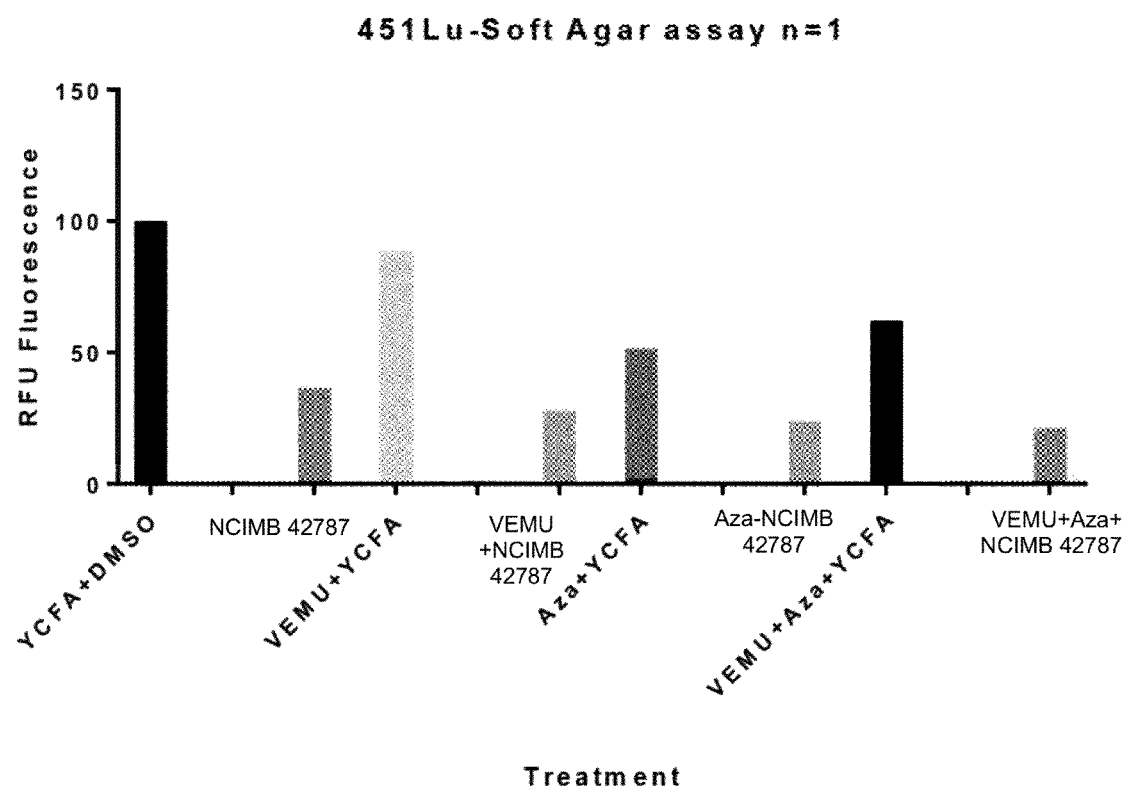
FIG. 45: Soft agar growth of the 451Lu cell line following various treatments. "YCFA"=YCFA+
Figure 46:
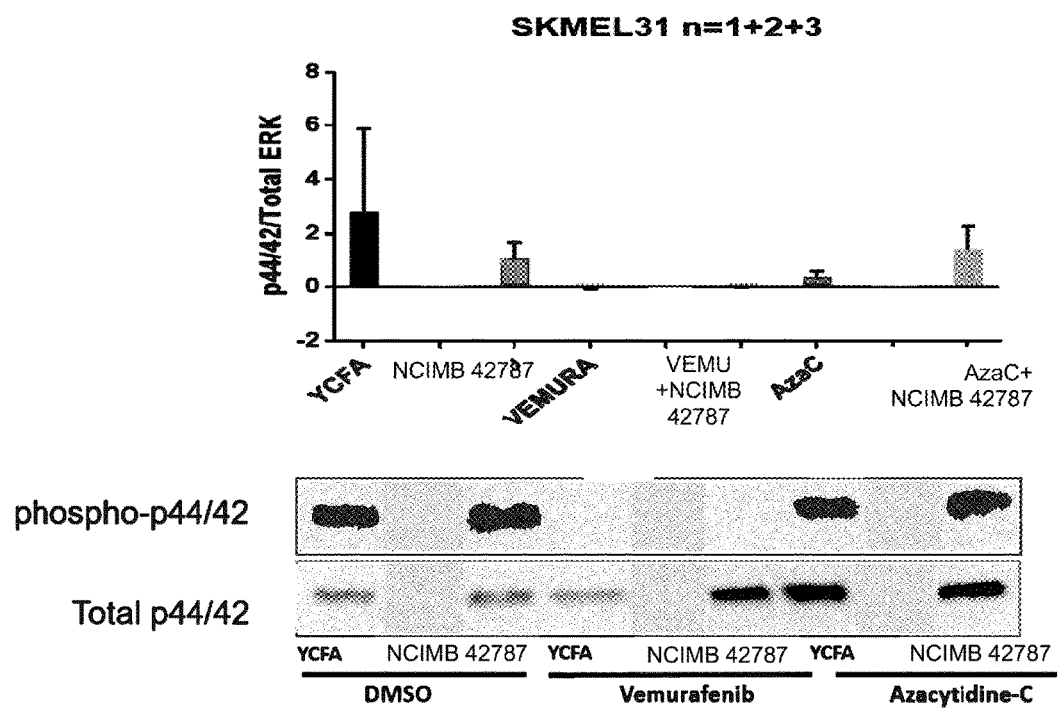
FIG. 46: ERK signalling (phosphorylated ERK1 and 2 (p44 and p42)/total ERK) in the 451Lu cell line following various treatments. "YCFA"=YCFA+

MAP2 gene expression in the 451Lu cell line was assessed using the protocol in Materials and Methods, and the results are shown in FIG. 43. All treatments with MRx0029 (alone or in combination with VEMU and/or Aza-c) increased MAP2 gene expression relative to the cell line only negative control. Clonogenic survival of the 451Lu cell line was assessed using the protocol in Materials and Methods, and the results are shown in FIG. 44. All treatments with MRx0029 (alone or in combination with VEMU and/or Aza-c) decreased clonogenic survival relative to both negative controls (cell line only, and YCFA+ +DMSO). Soft agar growth of the 451Lu cell line was assessed using the protocol in Materials and Methods, and the results are shown in FIG. 45. Azacytidine C enhanced soft agar growth inhibition by MRx0029. ERK signalling in the 451Lu cell line was assessed using the protocol in Materials and Methods, and the results are shown in FIG. 46 (VEMU, Aza-c and MRx0029 in combination was not assessed). MRx0029 in combination with VEMU or Aza-c reduced ERK signalling relative to the negative control (YFCA+ +DMSO).

These results indicate that MRx0029 alone or in combination with Vemurafenib and/or Azacytidine-C has the effects of inducing MAP2 gene expression, and decreasing clonogenic survival and growth of a melanoma cell line carrying a BRAF V600E oncogenic mutation (451Lu). On this basis, compositions of the invention are expected to be useful in the treatment or prevention of cancers, in particular those comprising oncogenic ERK signalling, especially melanomas such as metastatic melanomas. In particular, compositions of the invention are expected to be useful in the treatment or prevention of such cancers comprising an oncogenic mutation in BRAF, in particular at position 600, and especially the mutation BRAF V600E.

Example 14E—HT29 Colorectal Cancer Cell Line

The effects of the following treatments were assessed on the HT29 colorectal cancer cell line (V600E oncogenic mutation in BRAF): (1) MRx0029; (2) Vemurafenib (VEMU) in YFCA+ medium; (3) VEMU and MRx0029; (4) Azacytidine-C (Aza-c) in YCFA+ medium; (5) Aza-c and MRx0029; (6) VEMU, Aza-c and MRx0029.

Figure 47:
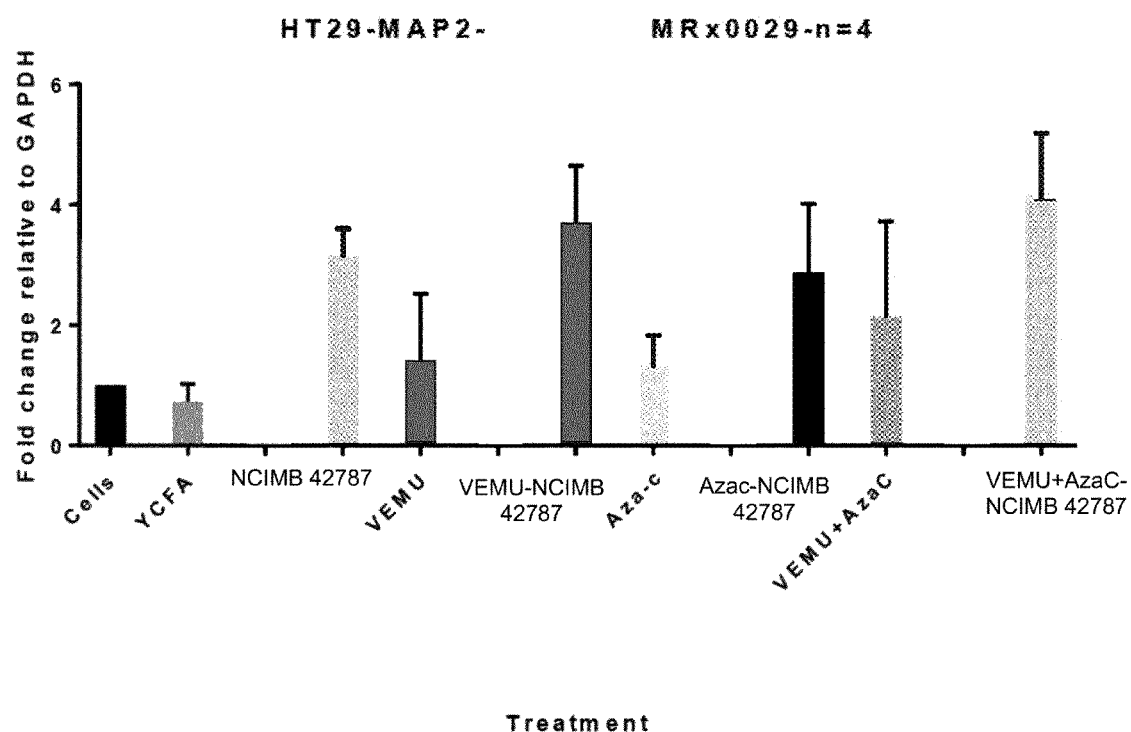
FIG. 47: Gene expression of MAP2 in the HT-29 cell line following various treatments, relative to GAPDH. "YCFA"=YCFA+
Figure 48:
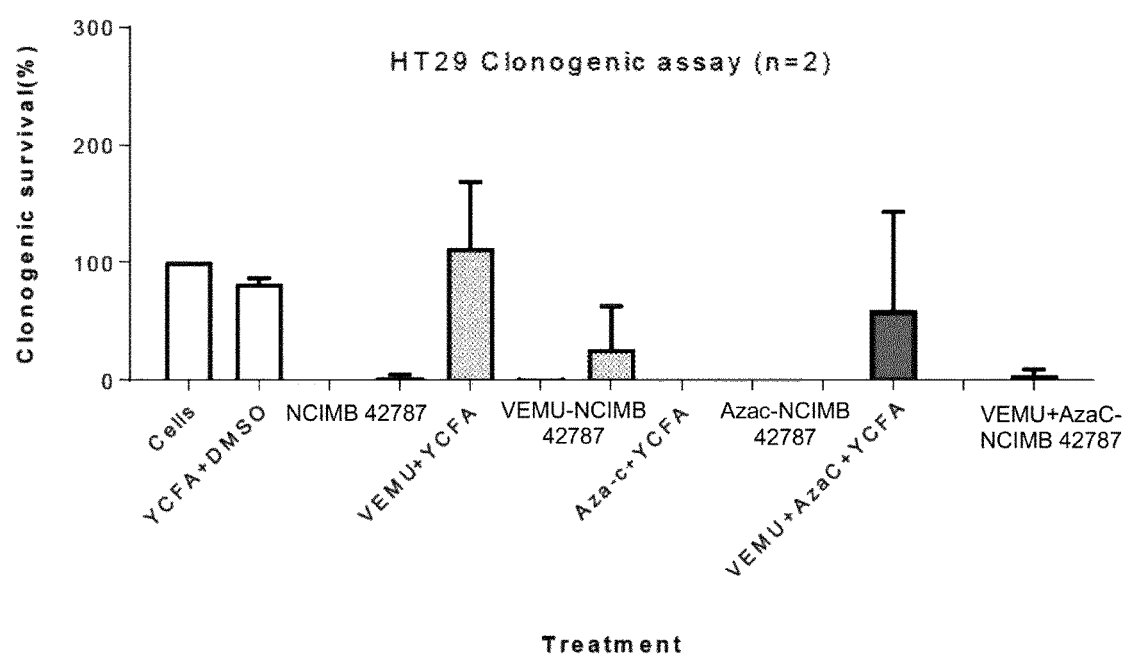
FIG. 48: Clonogenic survival of the HT-29 cell line following various treatments. "YCFA"=YCFA+
Figure 49A:
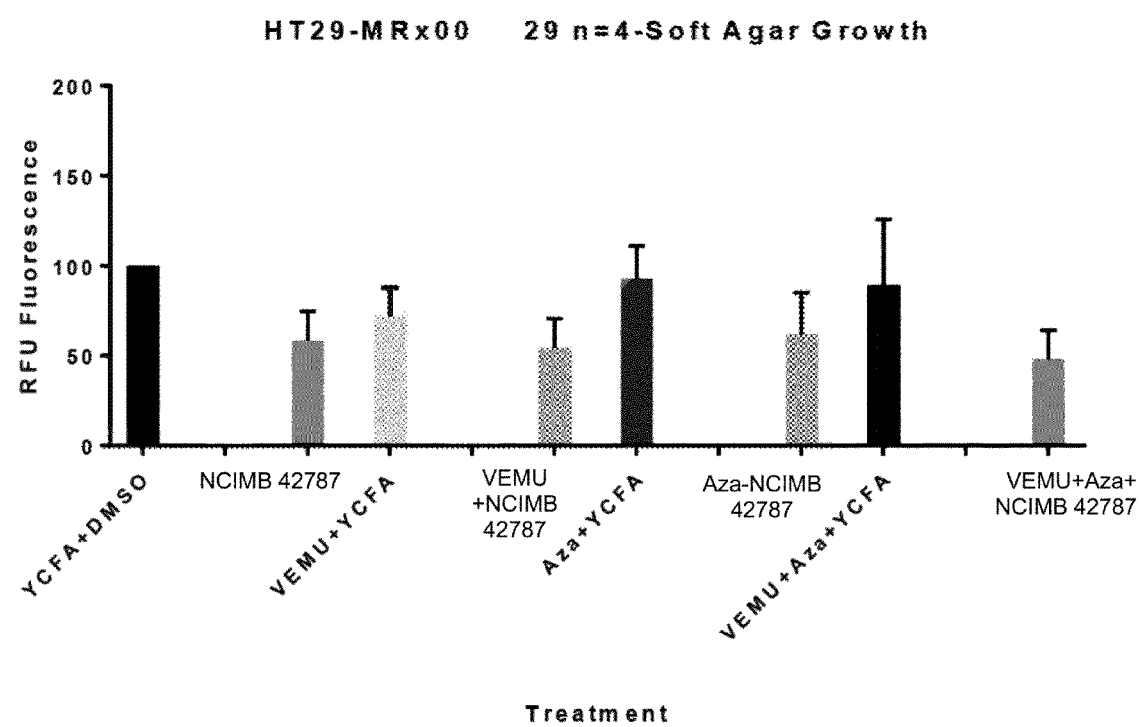
FIG. 49A: Soft agar growth of the HT-29 cell line following various treatments. "YCFA"=YCFA+
Figure 49B:
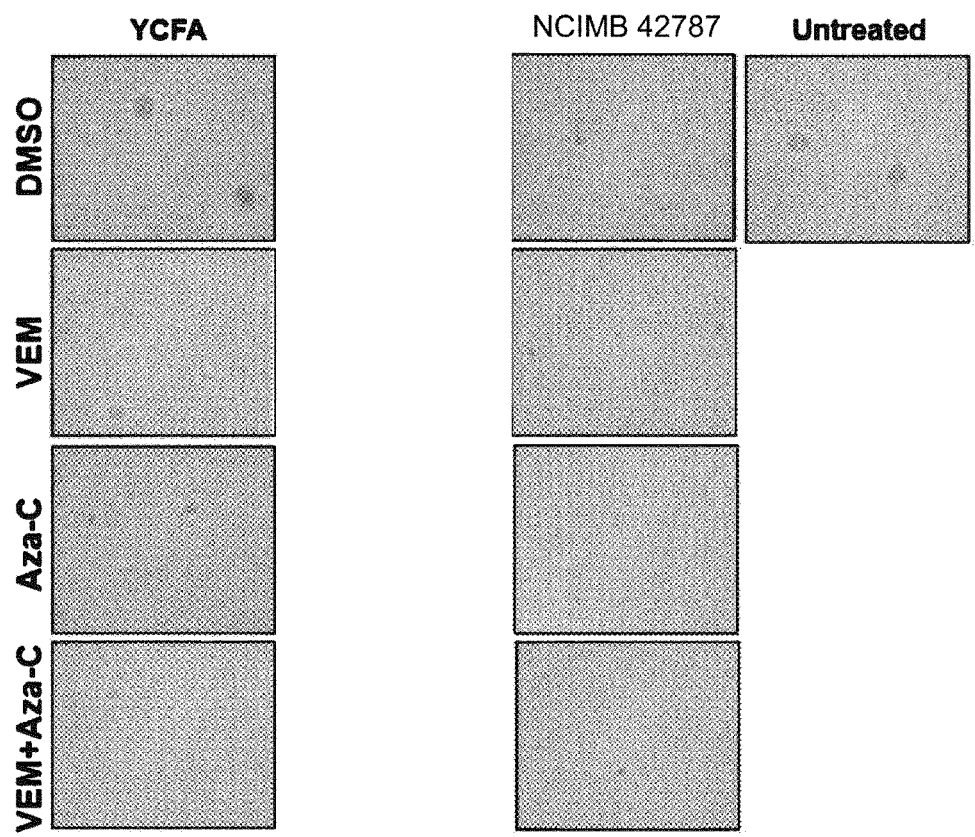
FIG. 49B: Soft agar growth of the HT-29 cell line following various treatments (photograph of agar plates). "YCFA"=YCFA+
Figure 50:
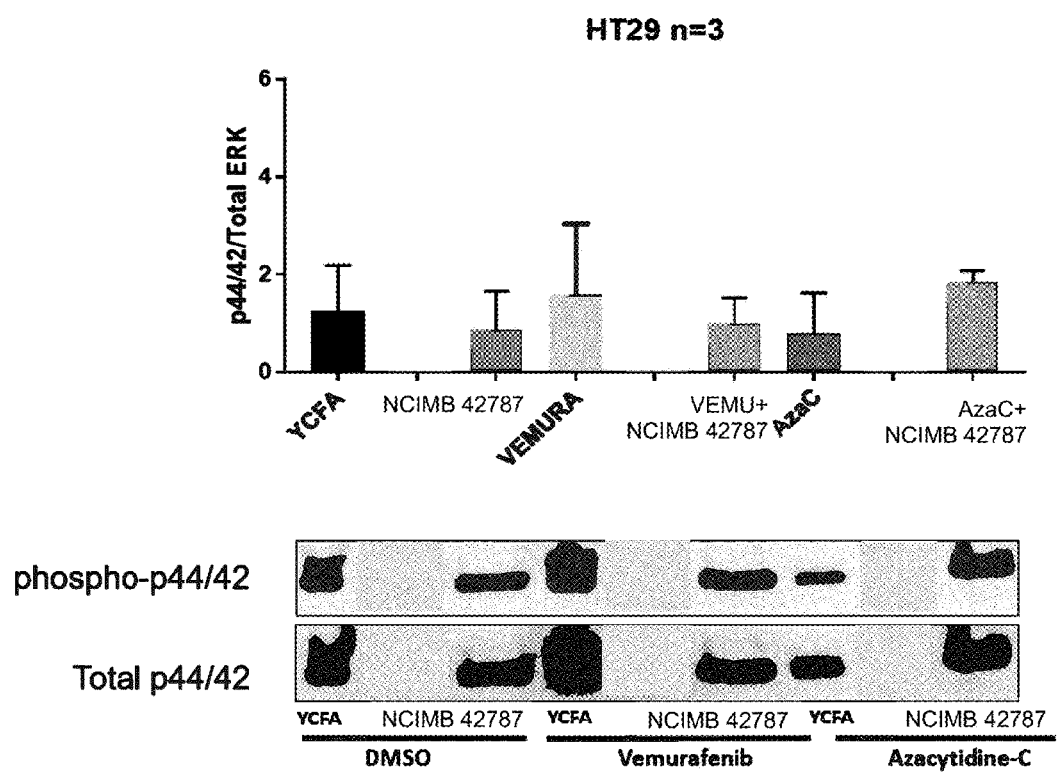
FIG. 50: ERK signalling (phosphorylated ERK1 and 2 (p44 and p42)/total ERK) in the HT29 cell line following various treatments. "YCFA"=YCFA+
Figure 51:
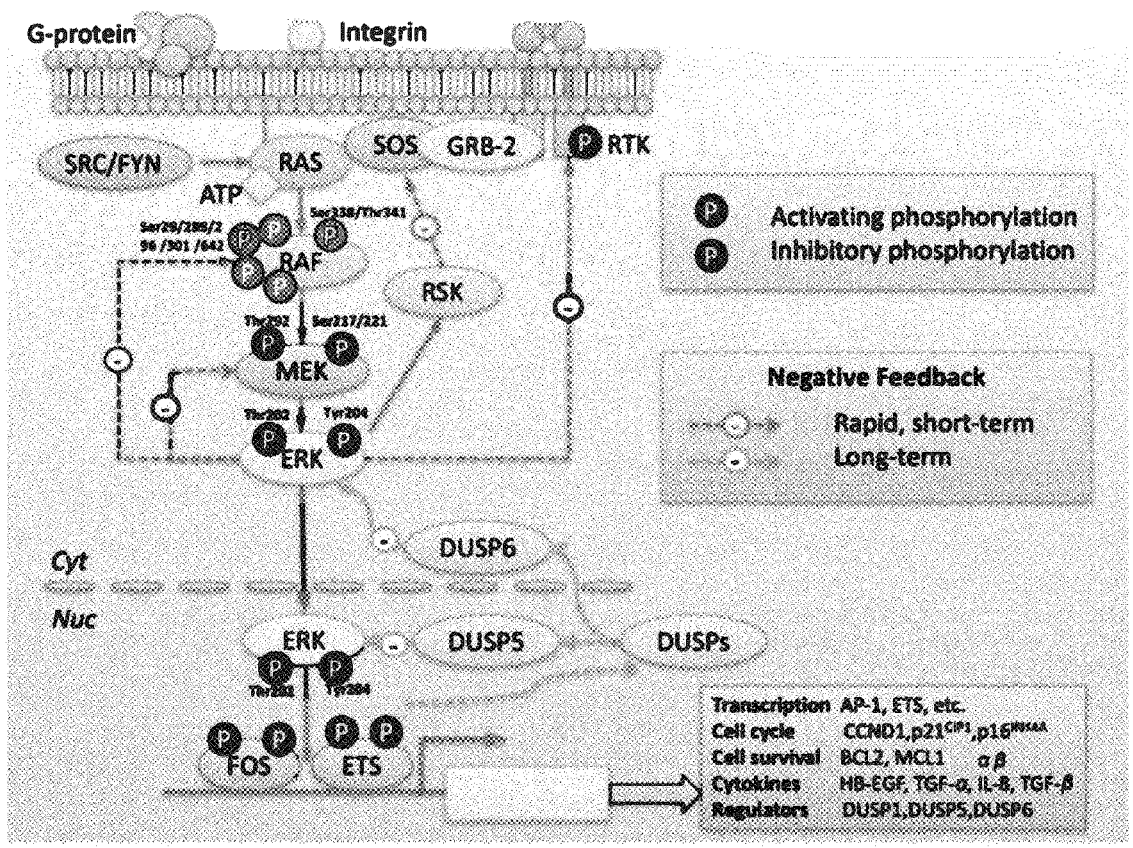
FIG. 51: Overview of the MAP-kinase pathway (from [72]).

MAP2 gene expression in the HT29 cell line was assessed using the protocol in Materials and Methods, and the results are shown in FIG. 47. MRx0029 in combination with VEMU and/or Aza-c increased MAP2 gene expression relative to both negative controls (cell line only and YCFA+). Clonogenic survival of the HT29 cell line was assessed using the protocol in Materials and Methods, and the results are shown in FIG. 48. All treatments with MRx0029 (alone or in combination with VEMU and/or Aza-c) decreased clonogenic survival relative to both negative controls (cell line only, and YCFA+ +DMSO). Aza-c improved the effects of MRx0029 in inhibiting clonogenic survival. Soft agar growth of the HT29 cell line was assessed using the protocol in Materials and Methods, and the results are shown in FIGS. 49a and b. ERK signalling in the HT29 cell line was assessed using the protocol in Materials and Methods, and the results are shown in FIG. 50 (VEMU, Aza-c and MRx0029 in combination was not assessed). MRx0029 alone ERK signalling relative to the negative control (YFCA+ +DMSO).

These results indicate that MRx0029 alone or in combination with Vemurafenib and/or Azacytidine-C has the effects of inducing MAP2 gene expression, decreasing clonogenic survival and inhibiting ERK signalling in a cell line carrying the V600E oncogenic mutation (HT29). On this basis, compositions of the invention are expected to be useful in the treatment or prevention of cancers, in particular those comprising oncogenic ERK signalling, especially colorectal cancers such as metastatic colorectal cancer. In particular, compositions of the invention are expected to be useful in the treatment or prevention of such cancers comprising an oncogenic mutation in BRAF, in particular at position 600, and especially the mutation BRAF V600E.

Example 15—GPR109a RNA Expression in Differentiated Caco-2 Cells

GPR109a is a G-protein coupled receptor expressed in the lumen-facing apical membrane of colonic and intestinal epithelial cells. GPR109a expression silencing is found in colon cancers cell lines, and the induction of its expression has been reported to induce tumour cell apoptosis in the presence of bacterial fermentation products such as butyrate [126].

HT29mtx cells seeded on 12 well plates and differentiated for 10 days; then they were serum-starved for 12 hours and subsequently exposed to 10% supernatant derived from stationary phase bacteria for 24 h. Cells were collected, and total RNA was isolated according to the RNeasy mini kit protocol (Qiagen). cDNA was made using the high capacity cDNA reverse transcription kit (Applied Biosystems). Gene expression was measured by qPCR. βactin was used as internal control. Fold change was calculated according to the $2^{(-\Delta\Delta ct)}$ method [127]. The sequences of the forward and reverse primers used are provided as SEQ ID NO: 6 and 7, respectively.

Figure 52A:
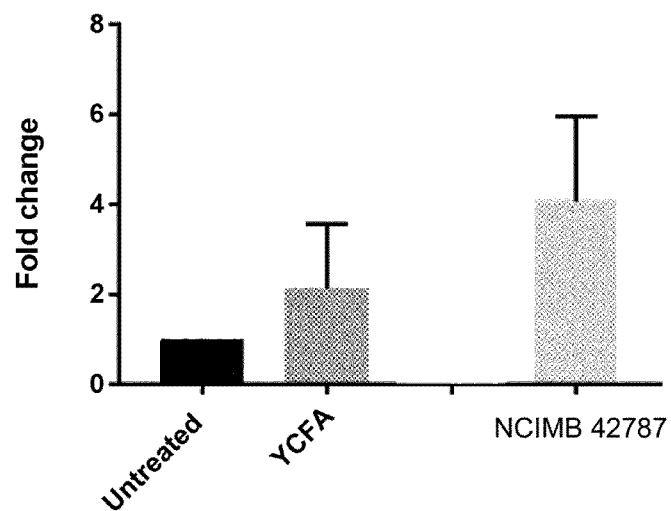
FIGS. 52A and 52B: GPR109a RNA expression in differentiated Caco-2 cells (FIG. 52A) without, and (FIG. 52B) with phorbolmyristate treatment in addition to MRx0029. "YCFA"=YCFA+
Figure 52B:
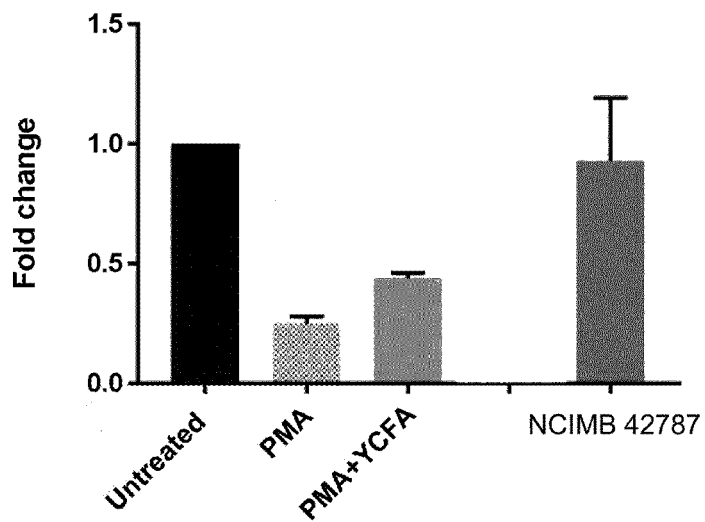

Differentiated Caco-2 form polarised apical/mucosal and basolateral/serosal membranes that are impermeable and are structurally and functionally similar to epithelial cells of the small intestine. Treatment of Caco-2 cells with MRx0029 elicited increased expression of GPR109a (FIG. 52A). Also, Caco-2 treated with phorbol-12-myristate-13-acetate (PMA) supernatant exhibited greater expression of GPR109a RNA, than treatment with PMA alone (or PMA in YCFA+ medium)—see FIG. 52B. Therefore, these data suggest that compositions of the invention may be useful in the treatment of cancers, especially metastatic cancers, in particular metastatic colorectal cancer or small bowel cancer such as small bowel adenocarcinoma, and in particular those comprising oncogenic ERK signalling. These data also suggest that compositions of the invention may effect such treatment through the mechanism of inducing apoptosis, as a result of GPR109a expression.

Example 16—Effect of MRx0029 on IL-8 Secretion by the HT29 Cell Line

Differentiated HT29 cells form polarized apical/mucosal and basolateral/serosal membranes that are impermeable and are structurally and functionally similar to epithelial cells of the small intestine.

HT29 cells were plated in 12 well plates at a density of 200,000 cells/well. Cells were being differentiated for 10 days (media change every 2 days). The day of the experiment cells were placed in the anaerobic hood and washed with anaerobic equilibrated HANKs solution. Then 900 ul of growth media (without FBS and antibiotics) was added to the cells. Bacteria cells were resuspended in of growth media (without FBS and antibiotics) and were then added at 10^7 CFU in total in 100 ul. Cells were co-incubated with bacteria for 2 hr in an anaerobic hood. Afterwards cells were washed in growth media without FBS but containing antibiotics. Cells were left to rest in 1 ml of THP1 condition media for 24 h. After 24 h incubation the supernatant was collected and spun down at 10,000 g for 3 min and 4° C. Samples were frozen at −80° C. until further use.

THP1 condition media: THp1 were seeded on T25 flask at density of 4×10^6/flask. Cells were treated in RPMI media (contain 2 mM L-glutamine without FBS) with 1 ug/ml LPS or LPS+5 mM ATP (ATP added 3 hours after LPS). Cells were left to rest for 24 hr. Thereafter Condition Media (CM) was collected by spinning down the cells at 250 g for 5 min and RT. Different CMs were used to treat HT29 Cells. A small aliquot was frozen at 80° C. for ELISA.

Supernatants from the different samples were collected and cytokine analysis performed according to manufacturer's instruction using a human IL-8 ELISA kit from Peprotech. GraphPad Prism7 was used to plot and analyse the data.

Figure 53A:
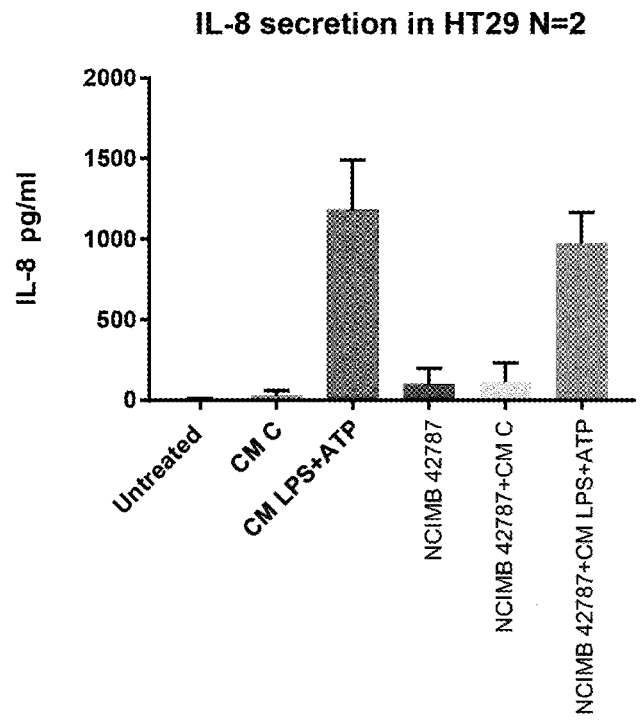
FIGS. 53A and 53B: Induction of IL-8 secretion from HT29 cells by (FIG. 53A) MRx0029 with conditioned media and (FIG. 53B) MRx0029 alone.
Figure 53B:
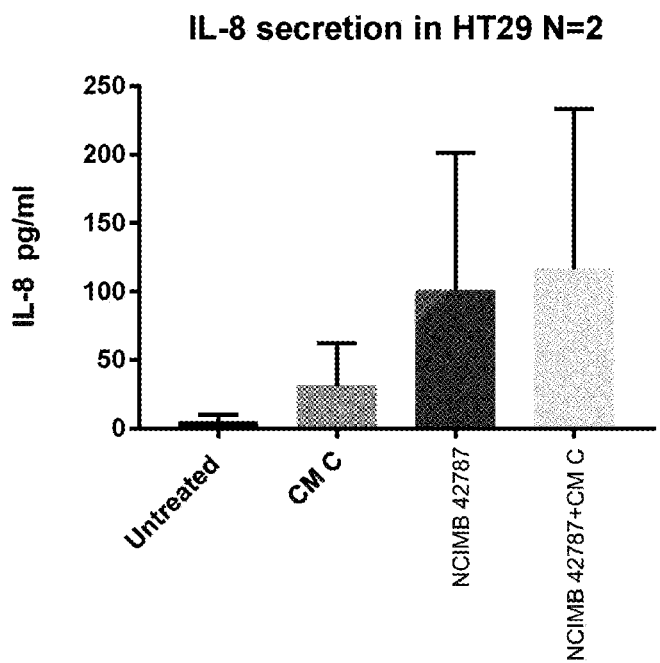

MRx0029 increased IL-8 secretion, which is a potent immunostimulatory cytokine (FIGS. 53A and 53B). These data demonstrate the immunostimulatory activity of MRx0029.

As noted above, secretion of IL-8 increases B cell proliferation. B cells have been implicated in modulating the immune response to tumours. Indeed, the secretion of anti-tumour antibodies by B cells is a potent mechanisms of tumour control. It is well known that the production of tumour specific antibodies can trigger natural killer cells to bind to the constant domain of antibodies, resulting in tumor cell lysis through antibody-dependent cell-mediated cytotoxicity (ADCC). Therefore, the compositions of the invention may effect the treatment of cancer through the appropriate modulation of the B cell response ensuring increased anti-tumour immune responses.

Based on the fact that the mechanism of pathology of the majority of cancers involves evasion of surveillance by the host immune system, any mechanism involved in the stimulation of the immune response would have a therapeutically beneficial impact. Therefore, the compositions of the invention are expected to be useful in the treatment or prevention of various cancers.

Example 17—Metabolite Analysis

Introduction

The gut microbiota, with its immense diversity and metabolic capacity, represents a huge metabolic reservoir for production of a vast variety of molecules. The inventors sought to determine what short chain fatty acids and medium chain fatty acids are produced and consumed by the *M.massiliensis* strain NCIMB 42787 and other *M.massiliensis* strain identified herein as Ref 1, Ref 2 and Ref 3.

Material and Methods

Bacterial Culture and Cell-Free Supernatant Collection

Pure cultures of bacteria were grown anaerobically in YCFA+ broth until they reached their stationary growth phase. Cultures were centrifuged at 5,000×g for 5 minutes and the cell-free supernatant (CFS) was filtered using a 0.2 µM filter (Millipore, UK). 1 mL aliquots of the CFS were stored at −80° C. until use. Sodium butyrate, hexanoic and valeric acid were obtained from Sigma Aldrich (UK) and suspensions were prepared in YCFA+ broth.

SCFA and MCFA Quantification of Bacterial Supernatants

Short chain fatty acids (SCFAs) and medium chain fatty acids (MCFAs) from bacterial supernatants were analysed and quantified by MS Omics APS as follows. Samples were acidified using hydrochloride acid, and deuterium labelled internal standards where added. All samples were analysed in a randomized order. Analysis was performed using a high polarity column (Zebron™ ZB-FFAP, GC Cap. Column 30 m×0.25 mm×0.25 µm) installed in a GC (7890B, Agilent) coupled with a quadropole detector (59977B, Agilent). The system was controlled by ChemStation (Agilent). Raw data was converted to netCDF format using Chemstation (Agilent), before the data was imported and processed in Matlab R2014b (Mathworks, Inc.) using the PARADISe software described in [128].

Results

Figure 54:
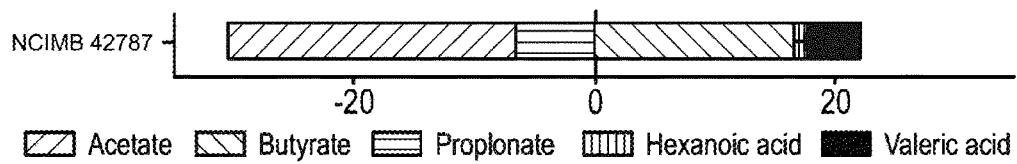
FIG. 54: Metabolite analysis for *Megasphaera massiliensis* strain NCIMB 42787.
Figure 55:
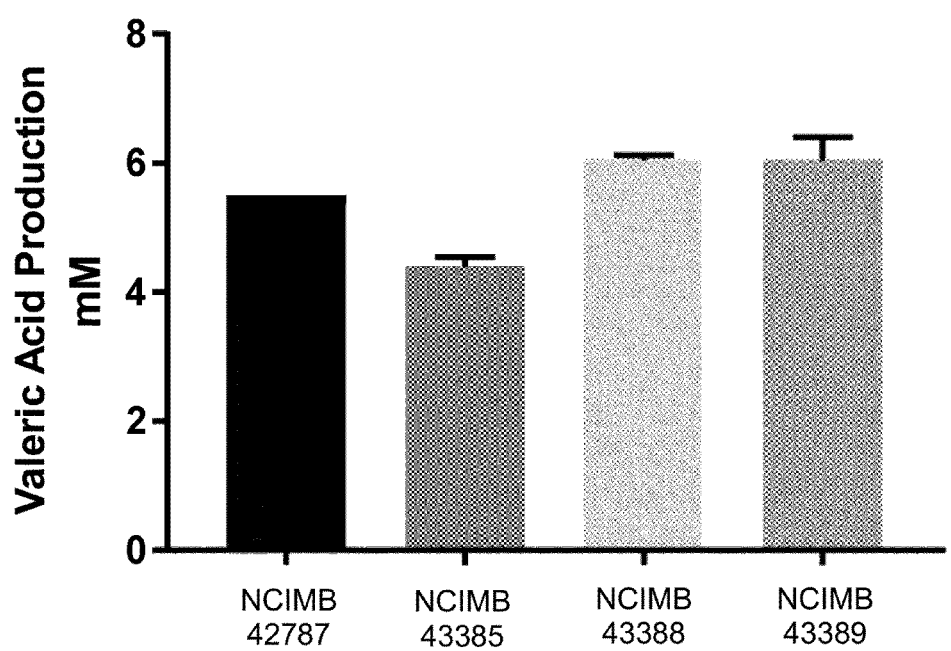
FIG. 55: Valeric acid production in the supernatant for MRx0029 and reference *Megasphaera massiliensis* strains.
Figure 56:
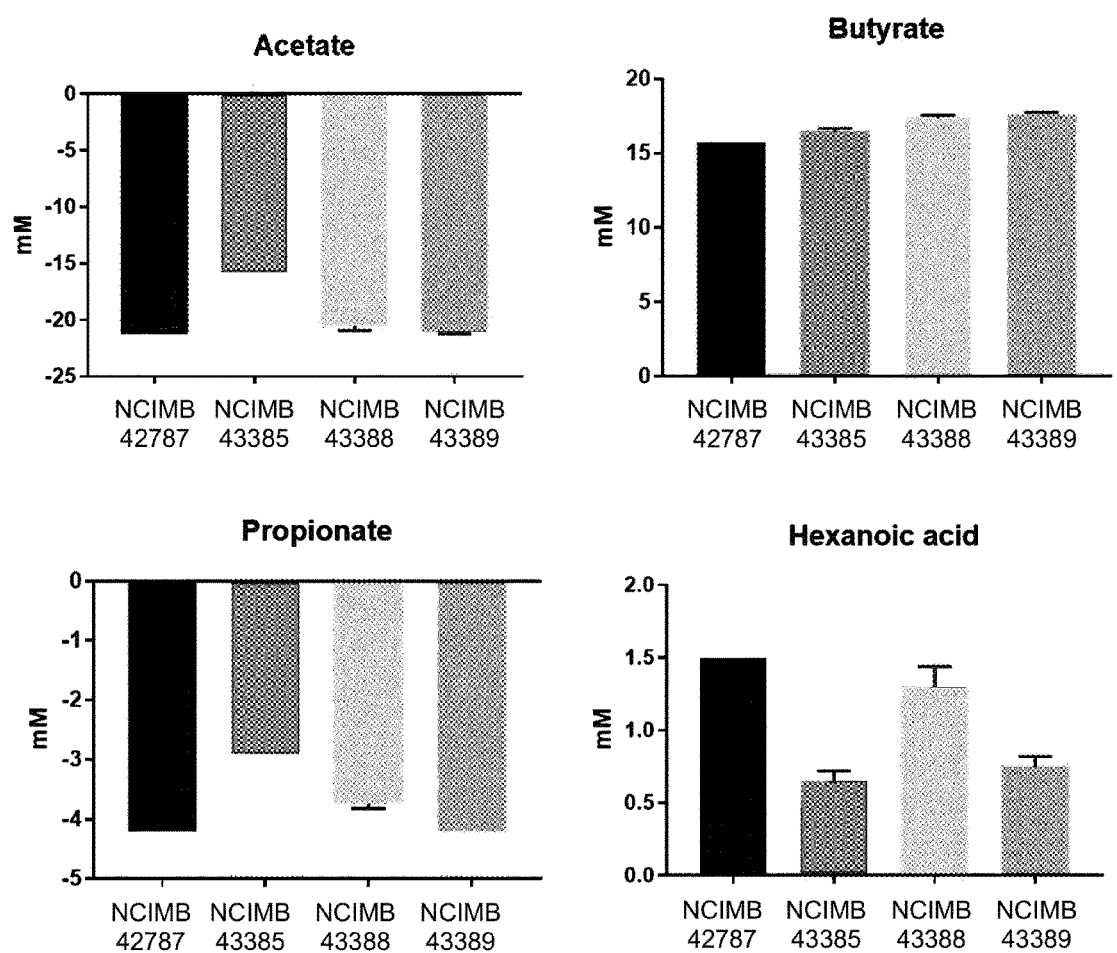
FIG. 56: organic acid production and consumption by MRx0029 and reference *Megasphaera massiliensis* strains.

As shown in FIGS. 54-56, strain 42787 produces valeric acid, butyrate and hexanoic acid and consumes propionate and acetate. The inventors also found other strains of the species *M.massiliensis* that produce comparable levels of valeric acid, hexanoic acid and butyrate and that consume similar amounts of acetate and propionate.

Example 18—Suppression of Enolase 2

Figure 57:
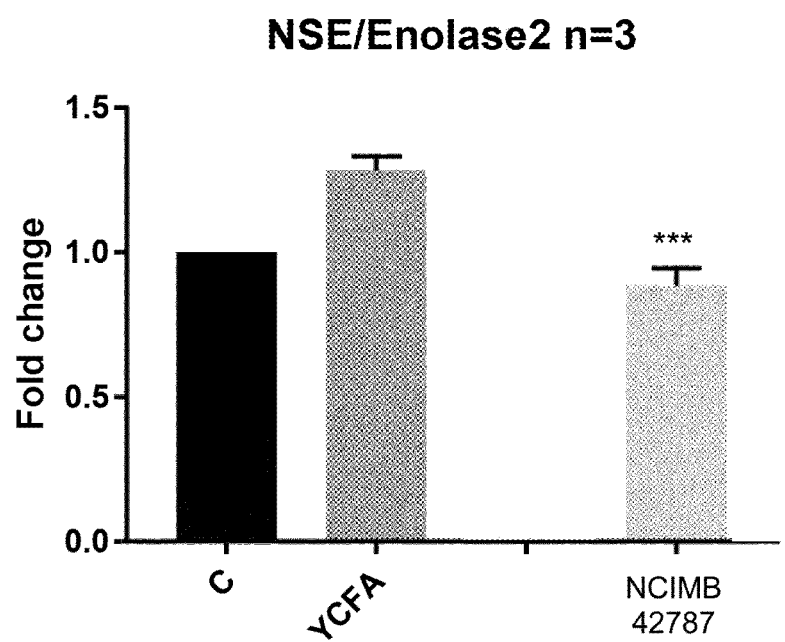
FIG. 57: Suppression of NSE/Enolase 2 by MRX029. "YCFA"=YCFA+.

FIG. 57 demonstrates that MRx0029 has a statistically-significant effect suppressing neuron specific enolase (NSE)/enolase 2. NSE is thought to support increased tumour cell metabolic demands, protect tumour cells from stressful conditions and promote their invasion and migration [129]. It is also implicated in progression of metastatic melanoma [130], survival and progression in small cell lung cancer [131], and prognosis of adenosqamous lung carcinoma [132]. Therefore, the compositions of the invention are expected to be effective for treating and preventing cancer, in particular, metastatic melanoma, small cell lung cancer and adenosqamous lung carcinoma.

Example 19—Metabolite Analysis

Further to the data provided in Example 17, FIG. 58 demonstrates what other short chain fatty acids are produced and consumed by the *M.massiliensis* strain NCIMB 42787 and other strains deposited under accession numbers NCIMB 43385, NCIMB 43388 and NCIMB 43389.

*M. massiliensis* strain NCIMB 42787 reduces formic acid while increasing levels of 2-methyl-propanoic and 3-methyl-butanoic acid (FIG. 58). Therefore, strain NCIMB 42787 produces 2-methyl-propanoic and 3-methyl-butanoic acid and consumes formic acid. The inventors also found that other of the deposited strains produce comparable levels of 2-methyl-propanoic and 3-methyl-butanoic acid and consume similar amounts of formic acid.

Example 20—Upregulation of IL-6

Introduction

Bacterial strains were investigated for their ability to trigger an increase in IL-6 secretion by the astrocytoma cell line U373.

Materials and Methods

Human glioblastoma astrocytoma cell line (U373), were maintained in 25 ml MEME 4.5 g/L D-glucose supplemented with 10% heat-inactivated FBS, 4 mM L-Glutamine, 100 U/ml penicillin, 100 µg/ml streptomycin and 5 µg/ml plasmocin, 1% Non-Essential Amino Acids, 1% Sodium Pyruvate (referred to as full growth media).

Cells were plated in 24-well plates at a density of 100,000 cells/well in 1 ml of full growth media and left to rest at 37° C./5% CO2 for 72 h. On the day of the treatment, the media was removed from each well, cells were rinsed with 0.5 ml wash media (serum free MEME), 0.9 ml stimulation media (MEME media containing 2% FBS). After 1 h pre-incubation, cells were removed from CO2 incubator and treated with 100 µl bacteria supernatant. YCFA+ media was used as control. Cells were then incubated for a further 24 h at 37° C./5% CO2, after which cell-free supernatants were collected and spun down at 10,000 g at 4° C. for 3 min Samples were aliquoted in 1.5 ml microtubes and stored in −80° C. for hIL-6 ELISA.

Results and Conclusions

Figure 59:
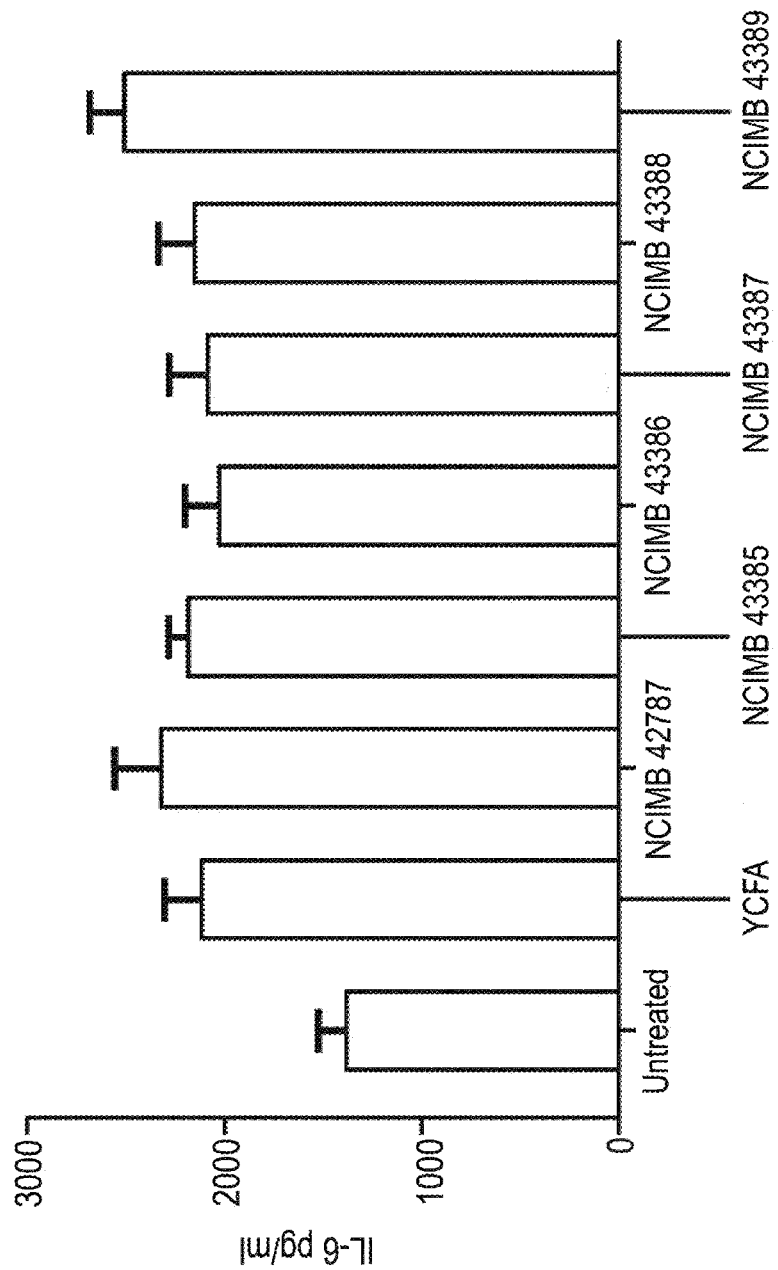
FIG. 59: Upregulation of IL-6 secretion in U373 cells by NCIMB 42787 and other deposited strains (n=3).

FIG. 59 demonstrates that *M.massiliensis* strain NCIMB 42787 upregulates IL-6 secretion in U373 cells compared to untreated and YCFA+ controls. Other deposited strains, in particular NCIMB 43389, also increased secretion of IL-6. The additional deposited strains are NCIMB 43385, NCIMB 43388, NCIMB 43386 and NCIMB 43387.

Secretion of IL-6 increases B cell proliferation. As outlined above, increased B cell proliferation can act as a potent mechanism for improving the immune response against a cancer (e.g. via the production of antibodies and triggering ADCC).

Indeed, the immunostimulatory activity is demonstrated, not only by the deposited strain, but also by the related deposited strains. Therefore, the compositions of the invention comprising strains of the *Megasphaera* genus, or biotypes thereof, are expected to be useful in the treatment or prevention of various cancers.

Example 21—Suppression of Enolase 2

Materials and Methods

Neuroblastoma cell line SH-SY5Y, were grown in 50% MEM and 50% Nutrient Mixture F-12 Ham media supplemented with 2 mM L-Glutamine, 10% heat-inactivated FBS, 100 U/ml penicillin and 100 µg/ml streptomycin. SH-SY5Y were plated in 6 well plates at a density of $0.5 \times 10^6$ cells. After 24 h, cells were treated in differentiation medium (growth medium containing 1% FBS) with 10% bacterial supernatants or YCFA+ for 17 h. Cells were collected, and total RNA was isolated according to the RNeasy mini kit protocol (Qiagen). cDNA was made using the High Capacity cDNA reverse transcription kit (Applied Biosystems). Gene expression was measured by qPCR. GAPDH was used as internal control. Fold change was calculated according to the $2^{(-\Delta\Delta ct)}$ method. Primer sets used are listed as SEQ ID NOs: 2, 3, 13 and 14.

Results

Figure 60:
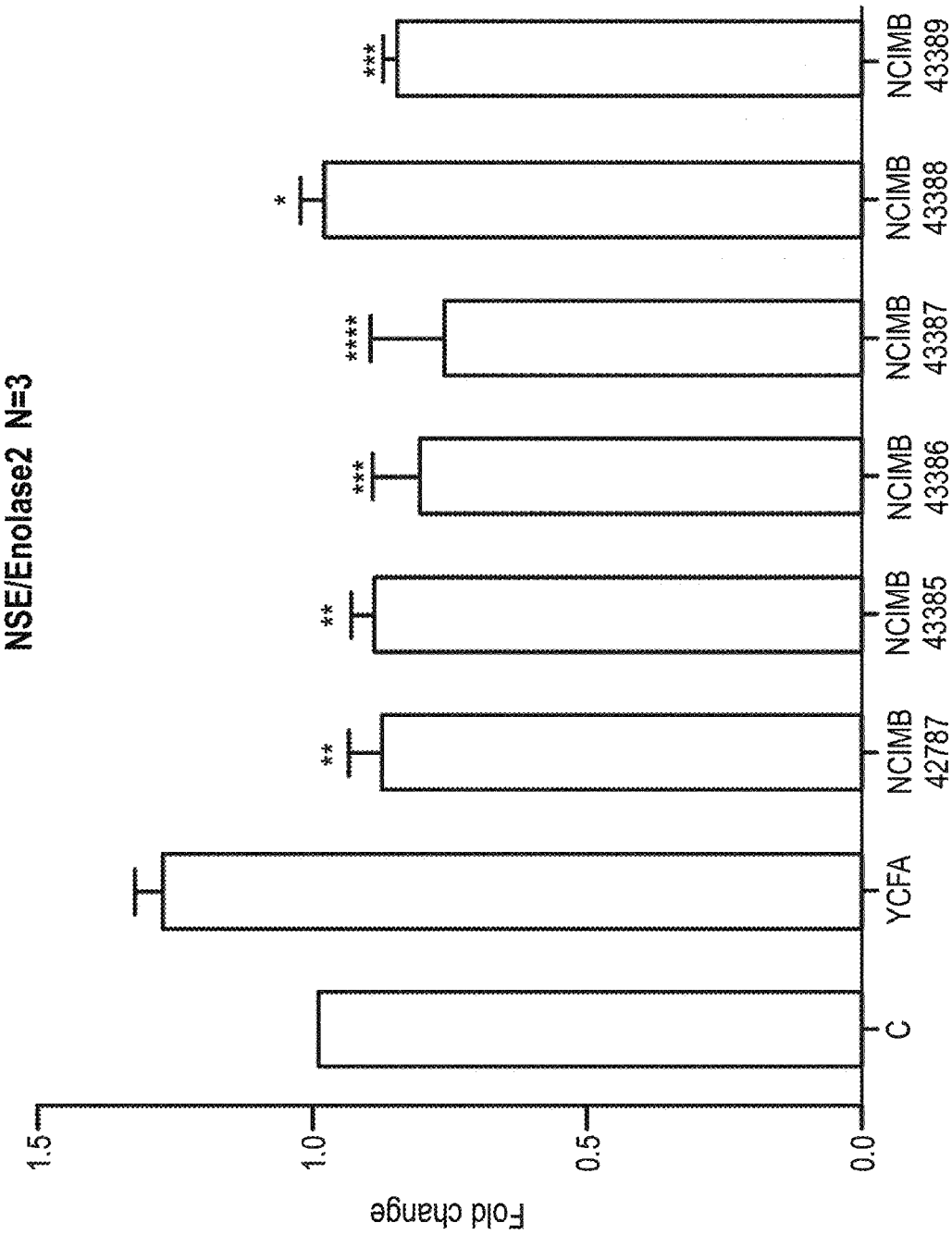
FIG. 60: Suppression of Enolase 2 by NCIMB 42787, NCIMB 43385, NCIMB 43388, NCIMB 43389, NCIMB 43386 and NCIMB 43387.

FIG. 60 demonstrates *M. massiliensis* strain NCIMB 42787 has a statistically-significant effect of suppressing neuron specific enolase (NSE)/enolase 2. In addition, the inventors also found deposited reference strains trigger a statistically-significant reduction of Enolase 2 compared to the YCFA+ culture control. In particular, strains deposited under accession numbers NCIMB 43385, NCIMB 43388, NCIMB 43389, NCIMB 43386 and NCIMB 43387 caused a significant suppression of enolase 2.

Conclusion

Accordingly, in line with the comments in Example 18 above, the compositions of the invention, in certain embodiments comprising the exemplary reference strains, are expected to be effective for treating and preventing cancer, in particular, metastatic melanoma, small cell lung cancer and adenosqamous lung carcinoma.

Example 22—Upregulation of MAP2

Materials and Methods

Neuroblastoma cell line SH-SY5Y, were grown in 50% MEM and 50% Nutrient Mixture F-12 Ham media supplemented with 2 mM L-Glutamine, 10% heat-inactivated FBS, 100 U/ml penicillin and 100 µg/ml streptomycin. SH-SY5Y were plated in 6 well plates at a density of $0.5 \times 10^6$ cells. After 24 h, cells were treated in differentiation medium (growth medium containing 1% FBS) with 10% bacterial supernatants or YCFA+ for 17 h. Cells were collected, and total RNA was isolated according to the RNeasy mini kit protocol (Qiagen). cDNA was made using the High Capacity cDNA reverse transcription kit (Applied Biosystems). Gene expression was measured by qPCR. GAPDH was used as internal control. Fold change was calculated according to the $2^{(-\Delta\Delta ct)}$ method. Primer sets used are listed as SEQ ID NOs: 2, 3, 4 and 5.

Results

Figure 61A:
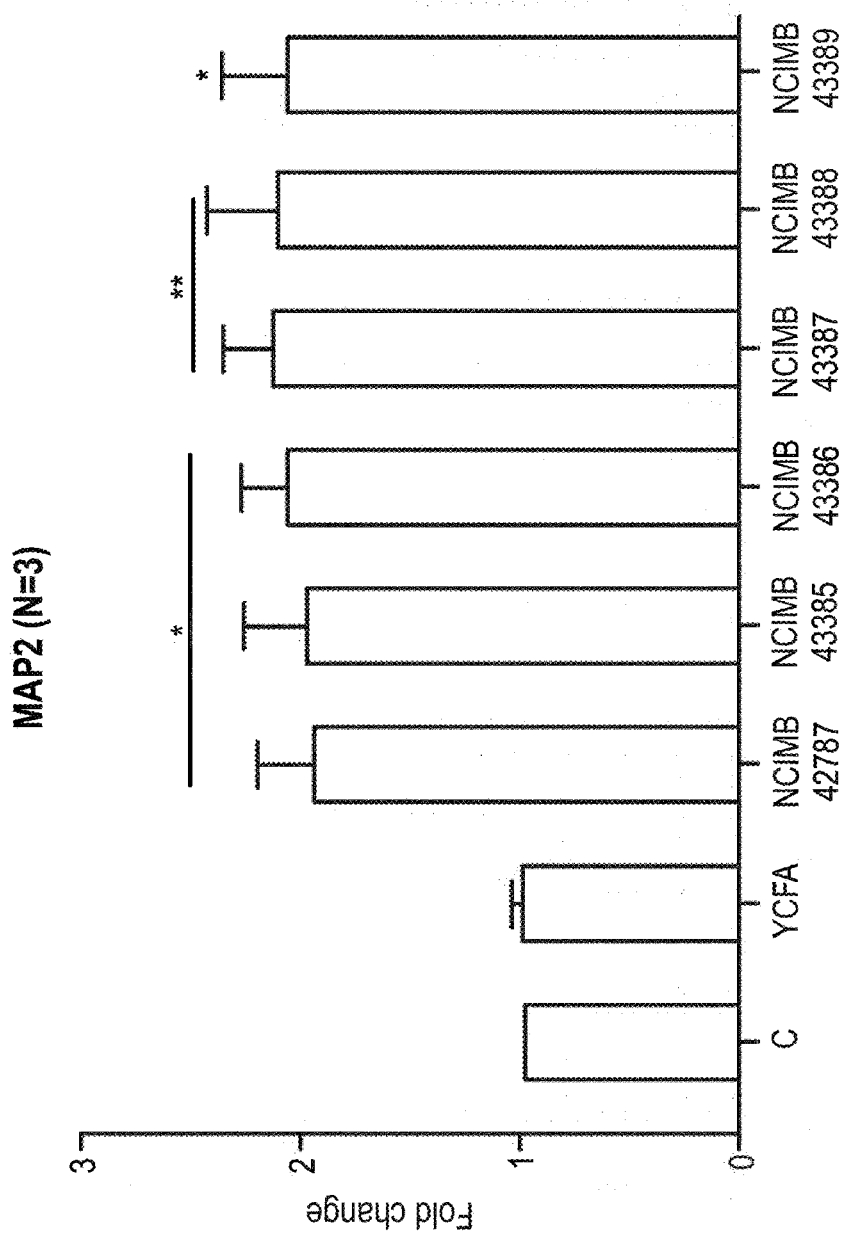
FIG. 61A: NCIMB 42787 and other deposited increase MAP2 expression.

FIG. 61A displays that *M. massiliensis* strain NCIMB 42787 and other deposited strains trigger a statistically-significant increase of MAP2 expression compared to the controls (i.e. negative control and media control). In particular, strains deposited under accession numbers NCIMB 43385, NCIMB 43388, NCIMB 43389, NCIMB 43386 and NCIMB 43387 caused a significant increase in MAP2 expression. On this basis, compositions of the invention are expected to be useful in the treatment or prevention of various cancers, in particular metastatic cancers, in particular metastatic melanoma.

Example 23—Modulation of Cytokine Secretion in HMC3 Cells Exposed to TNFα Upon Treatment with *M. massiliensis* Strain NCIMB 42787

Introduction

HMC3 cells were treated with TNFα, and secretion of IL-8 was measured upon treatment with cell-free supernatants from stationary phase culture of NCIMB 42787.

Materials and Methods

Human microglia HMC3 cells were grown in glutamine-supplemented EMEM media containing 15% heat inactivated FBS and 100 U/ml penicillin and 100 µg/ml streptomycin. HMC3 cells were plated in 24 well plates at a density of 50,000 cells/well. Cells were left in CO2 incubator to rest for 48 h. The cells were then washed in blank EMEM and pre-treated in 2% FBS growth media with 10 ng/ml TNF-α for 1 h. Thereafter 10% cell-free bacterial supernatants for NCIMB 42787 stationary growth cultures (isolated as described above) were added to TNF-α-treated and untreated wells and incubated in CO2 incubator at 37° C. for 24 h. Cell-free supernatants were collected and centrifugated at 10,000×g for 3 min and 4° C. Samples were aliquoted in 1.5 ml microtubes and stored in −80° C. for hIL-8 ELISA.

Secretion of IL-8 was analysed using hIL-8 Standard ELISA Kits, according to the manufacturer's protocol in the cell-free supernatants from HMC3 cells treated as described above. Samples were measured at 405 nm with correction wavelength set at 655 nm on a microplate reader (iMark, Bio-Rad). Raw data were plotted and analysed using Graph-Pad Prism 7 software.

Statistical Analysis

Normally distributed data are presented as mean±SEM; One-way Anova (Sidak's multiple comparison test) was used to analyse the data presented in this paper. A p value <0.05 was deemed significant in all cases.

Results

Figure 61B:
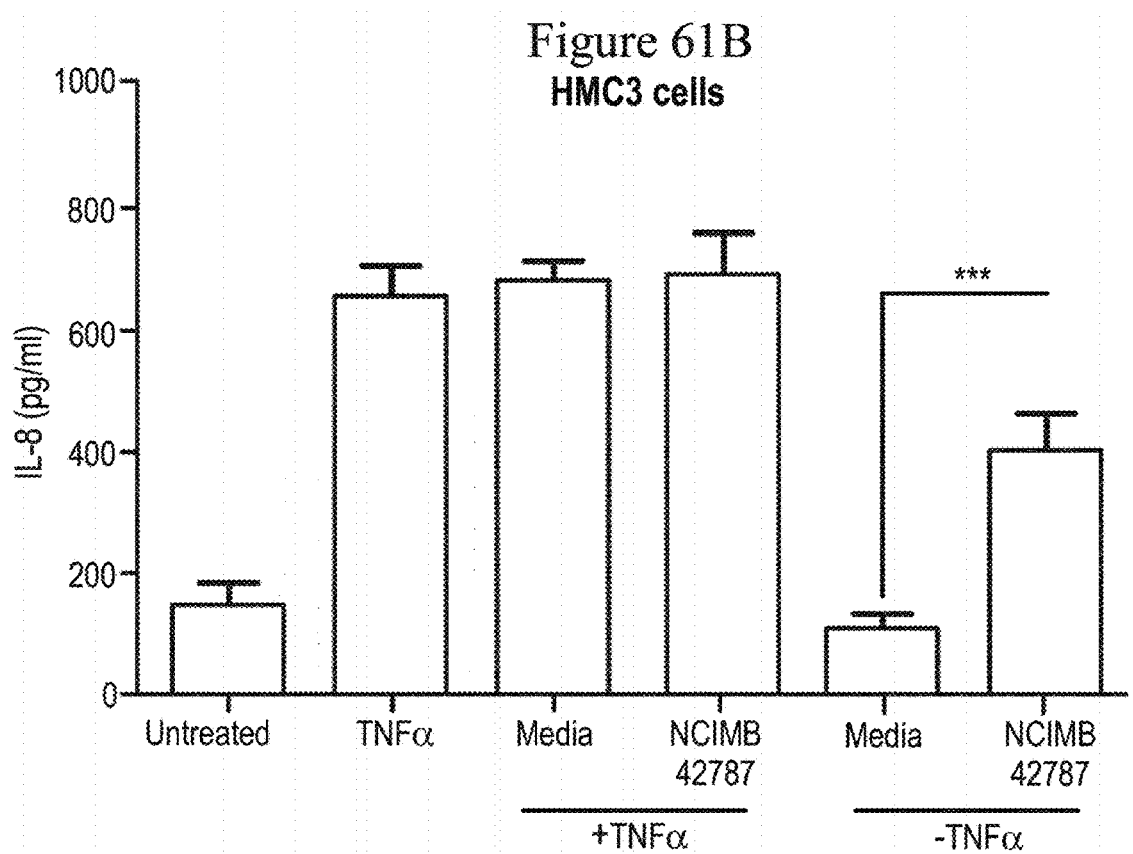
FIGS. 61B and 61C: Modulation of cytokine levels and NFκB-AP1 promoter by NCIMB 42787.

NCIMB 42787 induces IL-8 secretion in the absence of stimulation (FIG. 61B). As outlined above, IL-8 is involved in the activation of the immune system, in particular by stimulation of B cell proliferation.

Example 24—NF-κB Promoter Activation in HEK-TLR4 Cells by *M. Massiliensis* NCIMB 42787

Introduction

To verify whether treatment with NCIMB 42787 would induce NF-κB-Ap1 promoter activity induced by engagement of TLR4, HEK-TLR4 cells were treated with cell-free bacterial supernatants for NCIMB 42787 alone or in combination with LPS.

Materials and Methods

HEK293-Blue reporter cells stably expressing human TLR4 (HEK-TLR4), were cultured according to the manufacturer's instructions. Briefly, HEK-TLR4 cells were maintained in DMEM 4.5 g/L D-glucose supplemented with 10% (v/v) heat-inactivated FBS, 4 mM L-Glutamine, 100 U/ml penicillin, 100 µg/ml streptomycin, 100 µg/ml normocin, 1×HEK-Blue selection media.

Briefly, cells were washed with PBS, dissociated in PBS and collected in growth media. Cells were plated in 96-well plates at a density of 25,000 cells/well. To evaluate the effect of bacteria strains on LPS inducing NF-κB promoter activation, cells were treated with 10 ng/ml LPS in presence or absence of 10% supernatants (isolated as described above) and incubated in a CO2 incubator. Treatments proceeded for 22 h at 37° C. and 5% CO, after which the detection of Secreted Embryonic Alkaline Phosphatase (SEAP) activity from cell culture supernatant was performed using QUANTI-blue solution according to manufacturer's instructions. Briefly, 20 µl of cell-free supernatant was collected and analysed for the presence of SEAP by mixing with 200 µl of sterile-filtered QUANTI-Blue detection media. After 2 h incubation at 37° C., optical density was measured at 655 nm on a microplate reader (iMark microplate, Bio-Rad).

Statistical Analysis

Normally distributed data are presented as mean±SEM; One-way Anova (Sidak's multiple comparison test) was used to analyse the data presented in this paper. A p value <0.05 was deemed significant in all cases.

Results

Figure 61C:
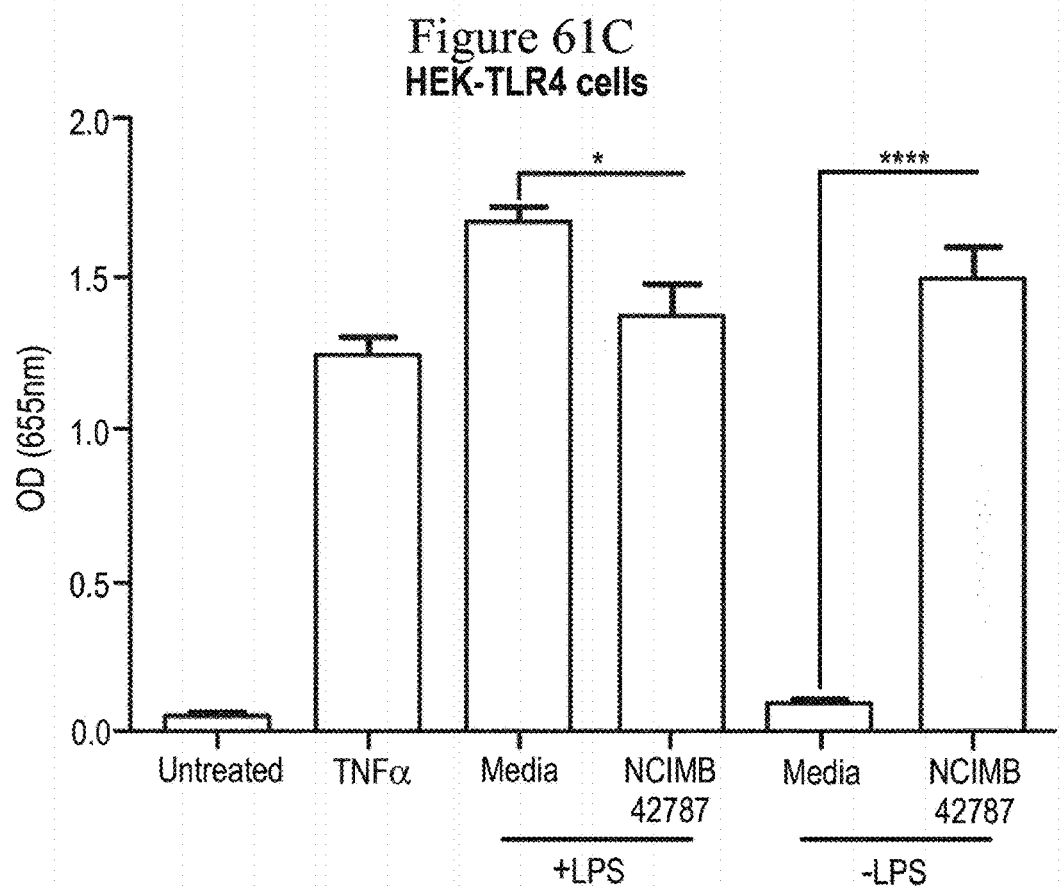

NCIMB 42787 induced NF-κB-Ap1 promoter activation on its own (FIG. 61C).

NF-κB is involved in the activation of the immune response in particular by stimulating the expression of mediators of inflammation and cytokines involved in the immune response, for example IL-6. As outlined above, an increase in the expression of IL-6 helps to stimulate the immune system and thus the activation of the NF-κB pathway has immunostimulatory activity. Accordingly, in certain embodiments, the compositions of the invention activate NF-κB signalling and thus stimulate the immune system.

Example 25—*M. Massiliensis* Strains Produce Butyric, Valeric and Hexanoic Acid

Materials and Methods

SCFA extraction from YCFA+, YCFA+ spiked with a standard mix of SCFAs (40 mM acetic acid and 20 mM formic acid, propionic acid, butyric acid, valeric acid and hexanoic acid) was conducted according to the method of De Baere et al.[133].

HPLC Analysis of SCFAs

HPLC detection and quantification of SCFAs was conducted according to the method of De Baere et al.[133] with slight modifications. Briefly, HPLC analysis was performed using a Waters e2695 HPLC system equipped with a Waters Photodiode Array (PDA) detector 2998 (Waters Limited, Elstree, UK). HPLC analysis of SCFAs standards, SCFAs extracted from MRx0005 and MRx0029 BCFS and MRx0005 and MRx0029 hexane, diethyl ether, ethyl acetate, acetonitrile and methanol extracts were performed using an Xselect® HSS T3 3.5 µm 4.6×150 mm LC column (Waters Limited, Elstree, UK). The LC analysis was performed using the photodiode array detector (PDA) set to analyse wavelengths of 200-800 nm. SCFA detection and quantification was performed at 210 nm. The mobile phase consisted in 25 mM sodium phosphate buffer in HPLC water (pH adjusted to 3.0 using phosphoric acid (A) and acetonitrile (B). The LC method for SCFA detection and quantification was run using the solvent system with the following gradient: t0' A=95%, B=5%; t10' A=95%, B=5%; t30' A=30%, B=70%; t31' A=0%, B=100%; t36' A=0%, B=100%; t38' A=5%, B=95%; t60' A=5%, B=95%; flow=1 ml/min.

A seven-point calibration curve was prepared for each SCFA by injecting 20 µl of a two-fold serial dilution of a SCFA (40 mM acetic acid and 20 mM formic acid, propionic acid, butyric acid, valeric acid and hexanoic acid). Quantification-extraction efficiency was calculated using the formula below:

$$[\text{SCFA in YCFA+spiked and extracted}]/[\text{SCFA in YCFA+spiked not extracted}]$$

Extraction efficiency was used to determine the concentrations of individual SCFAs in each sample. The production of specific SCFAs was calculated by subtracting the amount of corresponding SCFA present in the unspiked media control.

Targeted Metabolomics: Bacterial Metabolites and Fatty Acid Analysis

Sample analysis was carried out by MS-Omics (Copenhagen, Denmark). A mixed pooled sample (QC sample) was created by taking an aliquot from each sample. This sample was analysed with regular intervals throughout the sequence. Matrix effects were tested for quantified compounds by spiking the QC sample in a minimum of two levels.

For GC-metabolite analysis, samples were derivatized with methyl chloroformate using a slightly modified version of the protocol described by Smart et al.[134]. All samples were analysed in a randomized order. Analysis was performed using GC (7890B, Agilent) coupled with a quadrupole detector (59977B, Agilent). Raw data was converted to netCDF format using Chemstation (Agilent), before the data was imported and processed in Matlab R2014b (Mathworks, Inc.) using the PARADISe software described by Johnsen et al.[135].

For SCFA analysis, samples were acidified using hydrochloric acid, and deuterium-labelled internal standards were added. Analysis was performed using a high-polarity column (Zebron™ ZB-FFAP, GC Cap. Column 30 m×0.25 mm×0.25 µm) installed in a GC (7890B, Agilent) coupled with a quadrupole detector (59977B, Agilent). Raw data was converted to netCDF format using Chemstation (Agilent), before the data was imported and processed in Matlab R2014b (Mathworks, Inc.) using the PARADISe software described by Johnsen et al.[135].

Results

Figure 62A:
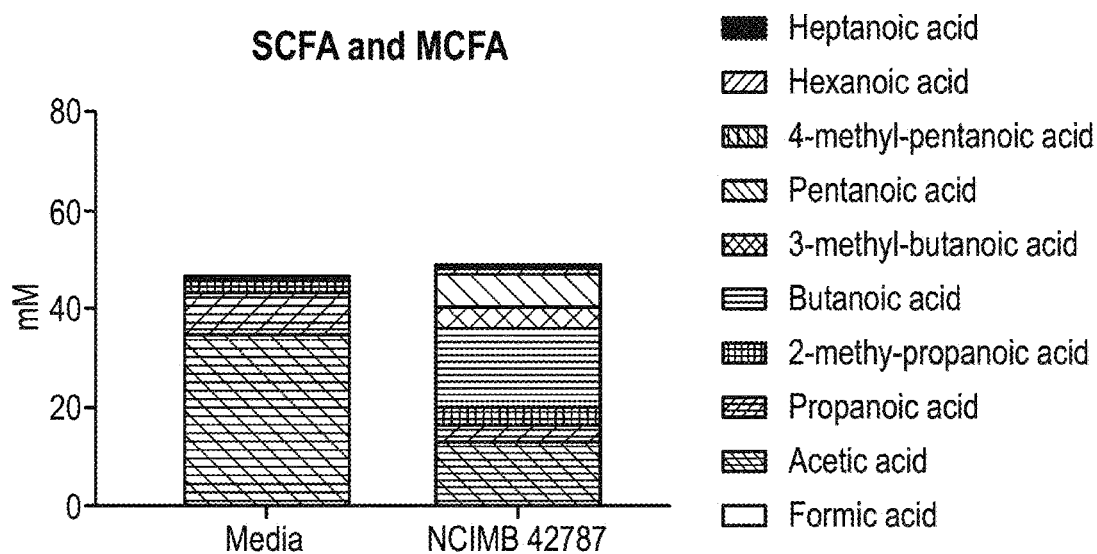
FIGS. 62A-62C: NCIMB 42787 produces butyric, valeric and hexanoic acid.
Figure 62B:
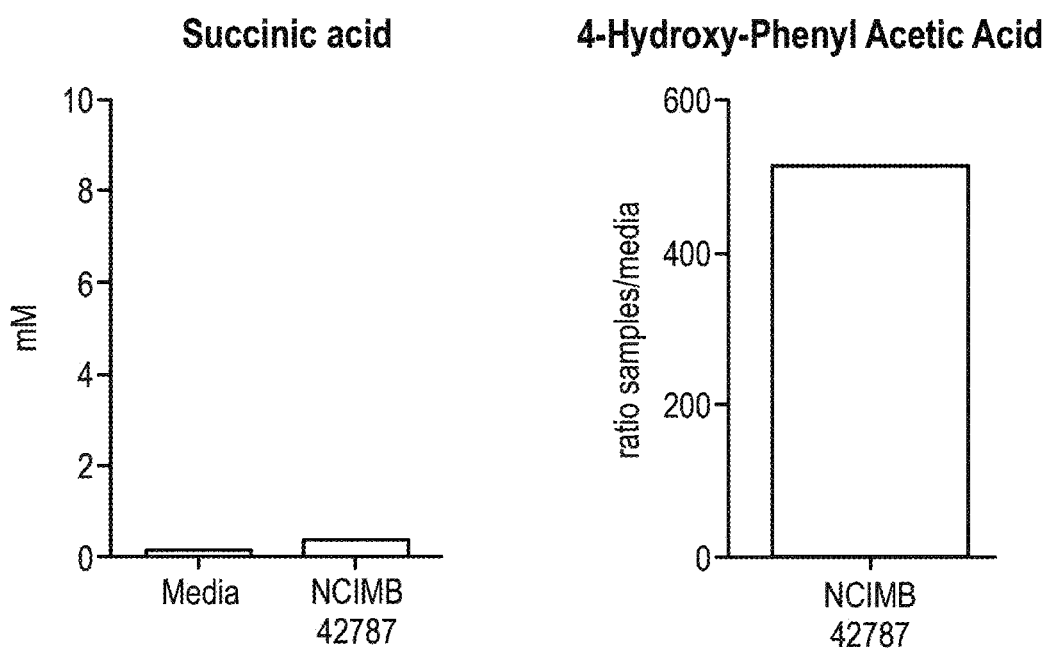
Figure 62C:
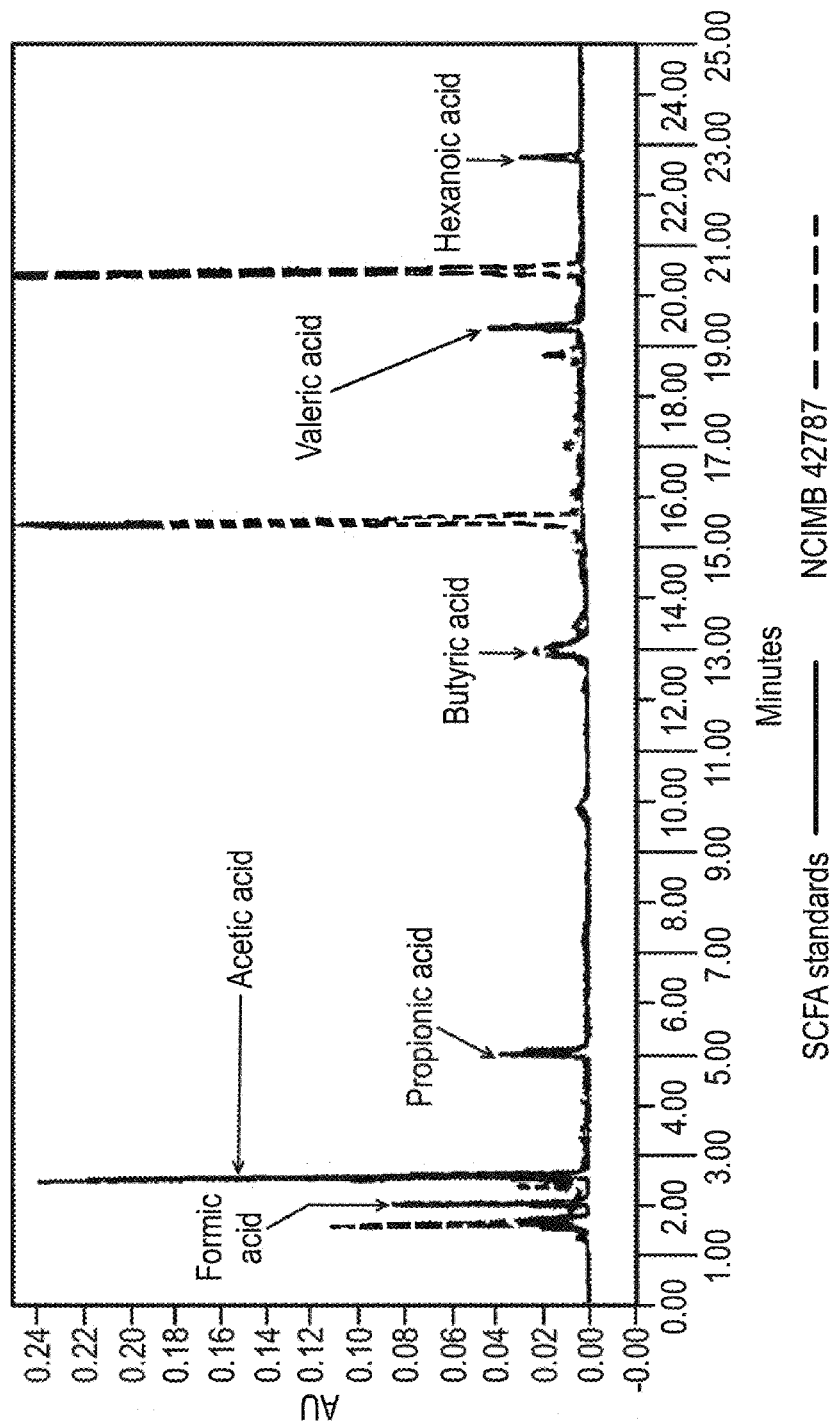

Fatty acid analysis, using targeted metabolomics, demonstrated that NCIMB 42787 produces butanoic (butyric), pentanoic (valeric) and hexanoic (caproic) acid, both in the linear and branched forms (C4-C6) (FIG. 62A). Moreover, the ratio of 4-hydroxy-phenylacetic acid:media was increased in NCIMB 42787 cell-free supernatant. HPLC analysis of cell-free supernatants was used to monitor the production of formic, acetic, propionic, butyric, valeric, and hexanoic acid (based on retention time and absorbance spectrum of relevant SCFAs) by NCIMB 42787. Representative chromatograms for SCFA standards overlaid to NCIMB 42787 cell-free supernatants extracted for SCFAs are reported in FIG. 62C. HPLC analysis confirmed the production of butyric, valeric and hexanoic acid by NCIMB 42787.

Example 26—*M. massiliensis* Methanolic Fractions Containing Butyrate and Valerate Show Immunostimulatory Activity in U373 Cells To investigate the role of SCFAs in reducing secretion of IL-8, U373 cells were treated with increasing concentrations of sodium butyrate (SB), sodium valerate (SV) and hexanoic acid (HA).

Methods

U373 cells were prepared as described above. Cells were pre-treated for 1 h with 1 μg/ml LPS indicated above and incubated at 37° C. and 5% CO2. After 1 h pre-incubation, cells were removed from CO2 incubator and treated with increasing concentration of fresh prepared Sodium Butyrate (SB), Sodium Valerate (SV) and Hexanoic Acid (HA).

Statistical Analysis

Normally distributed data are presented as mean±SEM; One-way Anova (Sidak's multiple comparison test) was used to analyse the data presented in this paper. A p value <0.05 was deemed significant in all cases.

Results and Conclusions

Figure 63:
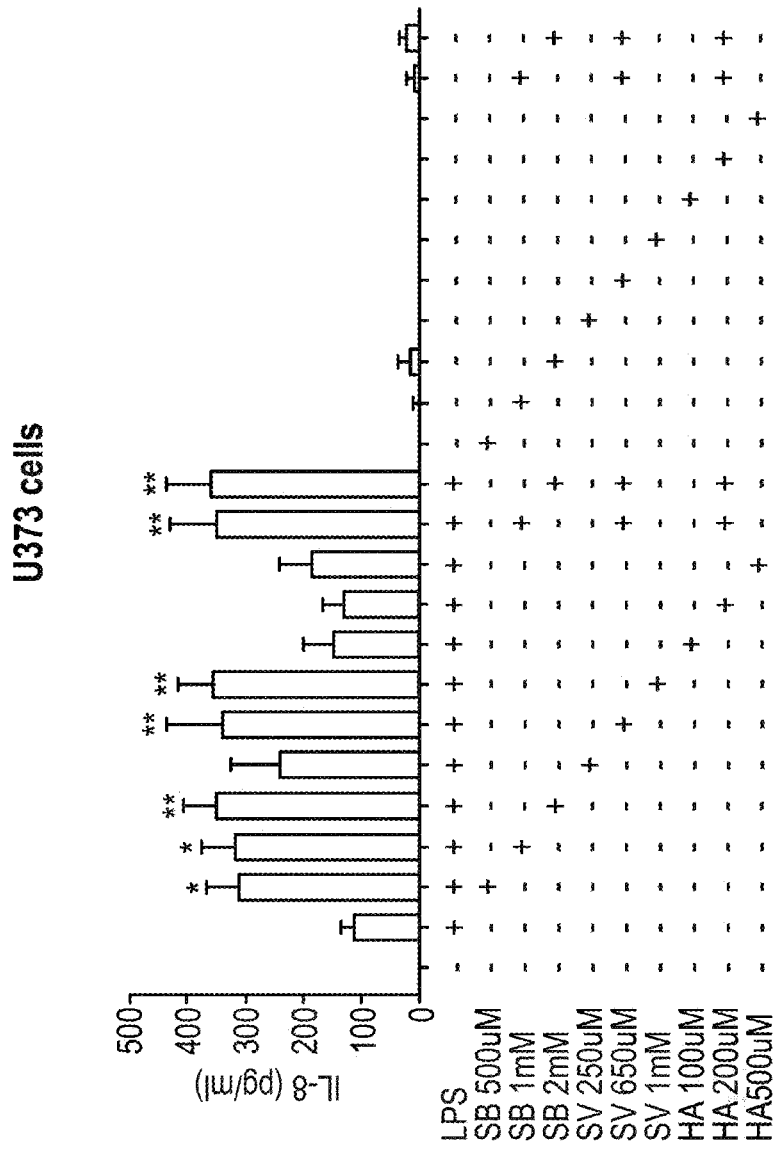
FIG. 63: Immunostimulatory activity of metabolites produced by NCIMB 42787.

The concentrations tested covered the range of concentrations measured in the cell-free supernatants for the different fatty acids and took into account the fact that only 10% of the above-mentioned supernatants was used in the cell-based assays. Both SB and SV increased LPS-induced secretion of IL-8 in the same cells (FIG. 63), suggesting that the presence of both SCFAs likely contributed to IL-8 induction when NCIMB 42787 is added to the culture. HA did not inhibit IL-8 secretion after challenge with LPS. None of the SFCAs tested induced per se secretion of IL-8 above the basal level (untreated cell control). The reconstituted mixture of the three SCFAs reproduced the biological activity of NCIMB 42787 cell-free supernatant, both in the presence and absence of LPS.

Accordingly, in certain embodiments butyric and/or valeric acid are involved in the generation of IL-8, and therefore are important for stimulating the immune system, for example via B cell proliferation. Therefore, in certain embodiments, the bacterial strains of the invention stimulate the immune system via the production of butyric and/or valeric acid.

Example 27—SCFAs Generated by NCIMB 42787 are at Least Partially Responsible for Immunostimulatory Activity Introduction In order to further confirm whether the activity of NCIMB 42787 was due at least in part to SCFAs, cell-free bacterial supernatant was fractionated with different solvents of increasing polarity. HPLC analysis of the de-proteinased crude extracts (hexane, F5; diethyl ether, F4; ethyl acetate, F3; acetonitrile, F4; methanol, F1) of this strain supernatants was conducted to analyse the biochemical complexity of the stationary phase cell-free supernatants of NCIMB 42787, as well as to sub-fractionate compounds based on polarity and solubility.

Methods

Sequential Solvent Extractions—Preparation of Crude Extracts

Three biological replicates of NCIMB 42787 strain BCFSs and YCFA+(media control) were extracted sequentially with HPLC-grade hexane (HEX), diethyl ether (DE), ethyl acetate (EtOAc), acetonitrile (ACN) and methanol (MeOH). Briefly, 20 ml of BCFS were placed in glass vials and extracted at room temperature (RT) in 20 ml of HEX on a rotary shaker (70 rpm) for 30 min A total of three extractions were performed on each BCFS and YCFA+ media control. The remaining aqueous layers were then extracted at RT in 20 ml of DE, EtOAc on a MX-RD-Pro rotary shaker (70 rpm) for 30 min a total of three times. The combined extracts of each sample were dried under reduced pressure in an R-300 rotary evaporator equipped with a V-300 vacuum pump (Büchi, Flawil, Switzerland) at a temperature not exceeding 30° C. The resulting extracts were re-solubilised in 2 ml of corresponding solvent and aliquoted in four 1.5 ml Eppendorf tubes (500 μl each corresponding to 5 ml of original sample). The remaining aqueous layers were then extracted at RT in 20 ml of DE, EtOAc on a MX-RD-Pro rotary shaker (70 rpm) for 30 min a total of three times. The combined extracts of each sample were dried under reduced pressure in a R-300 rotary evaporator equipped with a V-300 vacuum pump (Büchi, Flawil, Switzerland) at a temperature not exceeding 30° C. The resulting extracts were re-solubilised in 2 ml of corresponding solvent and aliquoted in four 1.5 ml Eppendorf tubes (500 μl each corresponding to 5 ml of original sample).

The remaining aqueous layers were evaporated to dryness using an R-300 rotary evaporator. The resulting dry extracts were extracted for 30 min in 20 ml of ACN a total of three times. The ACN extracts were combined, evaporated to dryness using a rotary evaporator, resolubilised in 2 ml of ACN and aliquoted in four 1.5 ml Eppendorf tubes (500 μl each). The remaining dry extracts (ACN insoluble portion of the extracts) were then extracted for 30 min in 20 ml of MeOH a total of three times. The MeOH extracts were combined, evaporated to dryness using an R-300 Rotary Evaporator, resolubilised in 2 ml of MeOH and aliquoted in four 1.5 ml Eppendorf tubes (500 μl each).

Aliquots of the crude extracts were kept overnight at −20° C. inducing the precipitation of proteinaceous components. Following overnight precipitation, each aliquot was centrifuged at 10,000×g for 6 min and transferred to a new 2 ml tube. Overnight precipitation was repeated three times after which extracts were dried in a RVC 2-18 CDPlus speedvac (Christ, Osterode am Harz, Germany) and weighed. All dried aliquots of each extract were stored at −80° C. until further use.

Treatment

U373 cells were prepared as described above. Cells were pre-treated for 1 h with 1 μg/ml LPS as indicated above. Afterwards, cells were removed from CO2 incubator and treated with 100 μl of the different fractions. Fractions from media were used as controls. Cell-free supernatants were collected 24 h after treatment and analysed by ELISA for IL-8 secretion (as outlined above).

Statistical Analysis

Normally distributed data are presented as mean±SEM; One-way Anova (Sidak's multiple comparison test) was used to analyse the data presented in this paper. A p value <0.05 was deemed significant in all cases.

Results

Figure 64A:
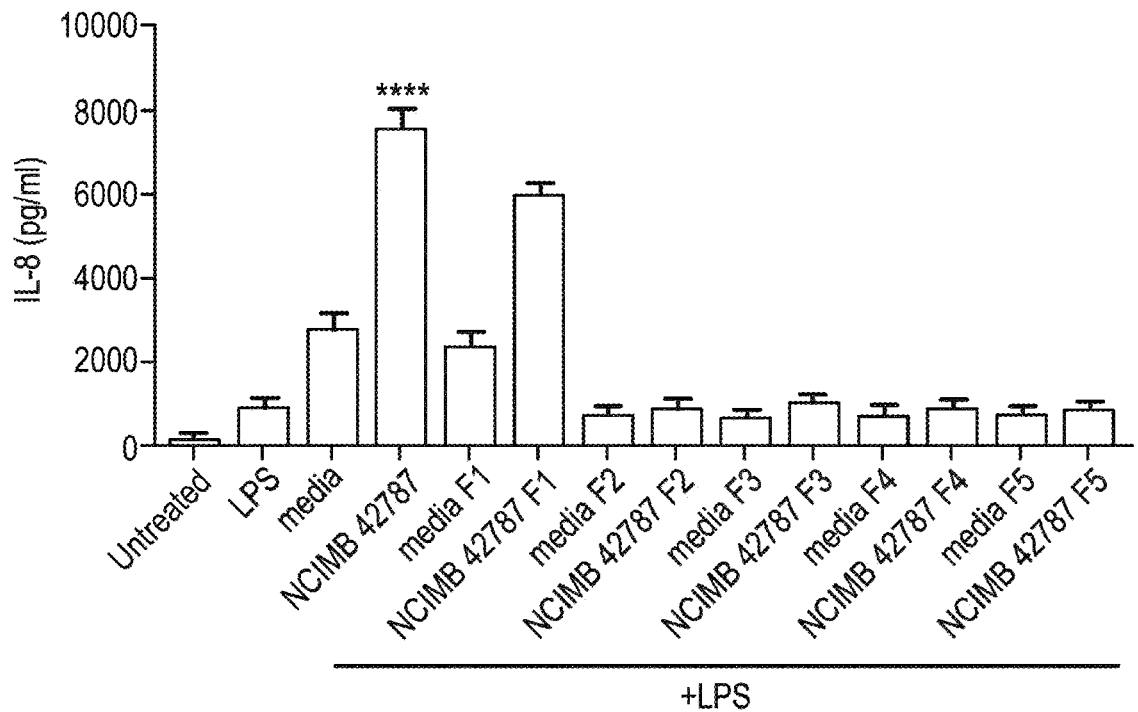
FIGS. 64A and 64B: Analysis of role of metabolites in immunostimulatory activity of NCIMB 42787.
Figure 64B:
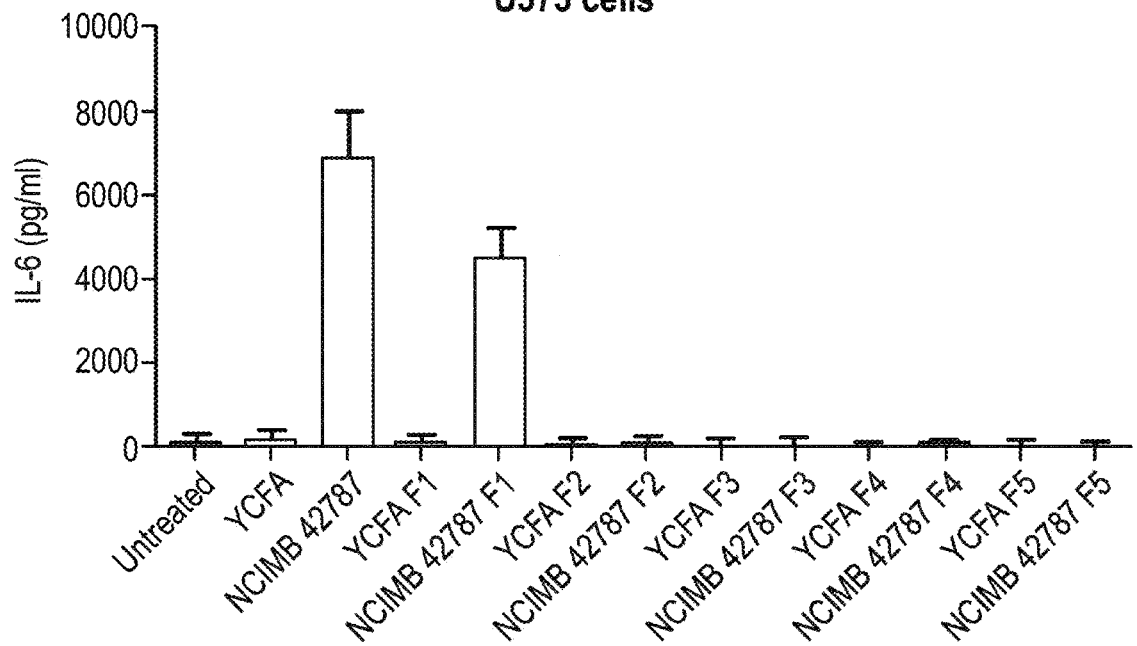

HPLC analysis confirmed the selective extraction and crude fractionation of compounds present in the de-proteinased supernatants. The unfractionated NCIMB 42787 induced IL-8 secretion in U373 cells both in the presence and absence of LPS, and the same activity was produced by the methanolic fraction F1, thus reiterating the important role of butyric and valeric acid in IL-8 production by these cell-types (FIGS. 64A and 64B).

Therefore, as outlined above, in certain embodiments, the production of butyric and/or valeric acid stimulated the immune system. Accordingly, in certain embodiments, the bacterial strains of the invention stimulate the immune system via the production of butyric and/or valeric acid.

Example 28—*Megasphaera* Reference Strain NCIMB 43387 Significantly Reduces Colonic IDO-1 mRNA Expression in BALB/c Mice FIG. 65 demonstrates that NCIMB 43387 causes a significant reduction (quantified by qPCR normalised to β-actin) in IDO-1 mRNA expression in the colon of BALB/c mice compared with the vehicle control.

IDO-1 has been implicated in promoting immunosuppression in response to inflammation or infection. Accordingly, driving a decrease in IDO-1 expression is associated with immunostimulation. Furthermore, reductions in IDO-1 reduce the proliferatory and migratory capacity of cancer cells, and improves immune surveillance against tumours. Therefore, in certain embodiments, the bacterial strains of the invention serve to reduce IDO-1 expression. In certain embodiments, immunostimulation is associated with reduction of IDO-1 expression. In addition, in certain embodiments, the compositions of the present invention prevent metastatic cancer growth. In certain embodiments, the compositions of the present invention are effective for treating and preventing cancer, in particular, metastatic melanoma, small cell lung cancer and adenosqamous lung carcinoma in light of their activity against metastasis.

Example 29—*Megasphaera* Strains Deposited Under Accession Numbers NCIMB 43385 and NCIMB 43387 Reduce Colonic Tph-1 mRNA Expression in BALB/c Mice BALB/c mice were administered live biotherapeutic and tissues were isolated for analysis of gene expression using qPCR.

FIG. 66 demonstrates the ability of the compositions of the invention to reduce expression of Tph-1 mRNA (using quantification by qPCR normalised to β-actin) compared to the vehicle control.

Decreases in Tph-1 are known to be associated with increased cancer resistance and reduced cancer cell growth. In addition, a decrease in Tph-1 activity stimulates the immune system by providing sufficient levels of the essential amino acid tryptophan for mast cells to drive antitumour immunity. Accordingly, in certain embodiments, the compositions of the invention decrease the levels of Tph-1 expression. In certain embodiments, the compositions of the invention trigger immunostimulation and treat and/or prevent the diseases disclosed herein by reducing the levels of Tph-1.

Example 30—*Megasphaera* Strain Deposited Under Accession Number NCIMB 43385 Increases IFNγ and IL-6 Production Upon ConA Stimulation of Splenocytes from BALB/c Mice Live biotherapeutic strains were screened ex vivo for efficacy of immune marker production in splenocytes isolated from BALB/c mice and stimulated with ConA.

Figure 67A:
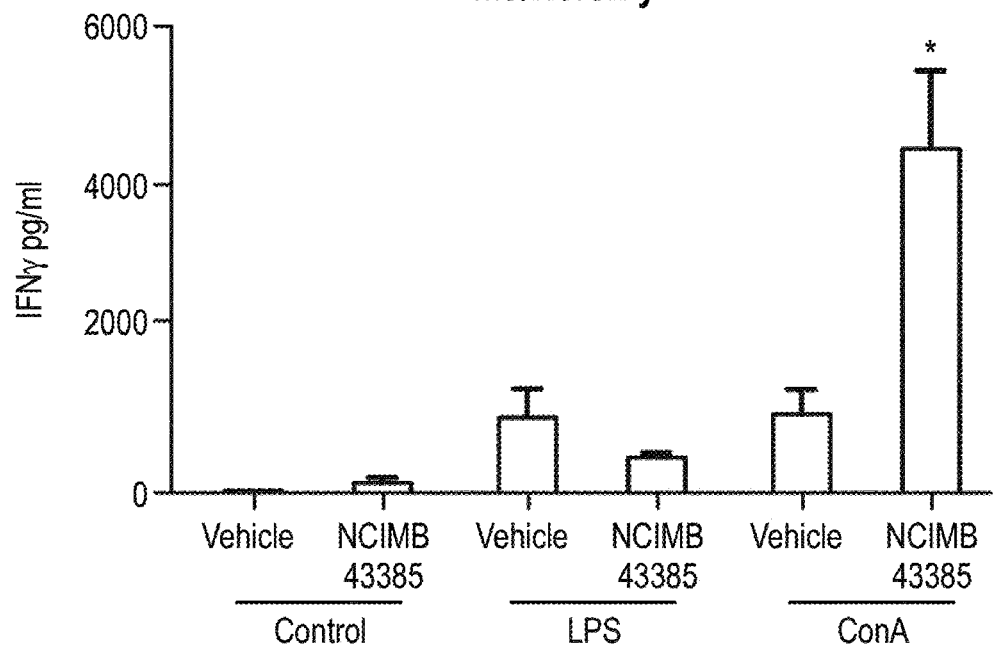
FIGS. 67A and 67B: *Megasphaera* strain NCIMB 43385 modulates IFNγ and IL-6 production upon ConA stimulation of splenocytes from BALB/c mice.
Figure 67B:
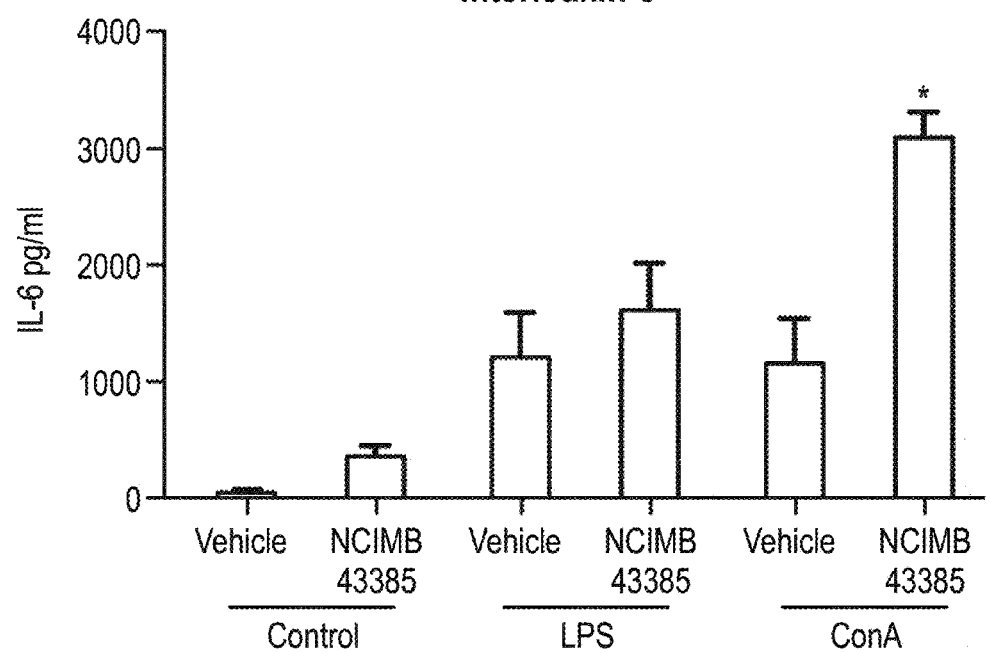

FIGS. 67A and 67B displays the ability of compositions of the invention to significantly increase production of the pro-inflammatory cytokines IFNγ and IL-6. As outlined above, both of these cytokines are involved in the stimulation of the immune response. Furthermore, IFNγ has significant tumoricidal activity.

Accordingly, as outlined above, in certain embodiments, the compositions of the invention increase the production of IFNγ and/or IL-6 and therefore drive stimulation of the immune response. Accordingly, in certain embodiments, the therapeutic benefit of the compositions of the present invention is linked to an increase in IFNγ and/or IL-6 production.

Example 30—*Megasphaera* Reference Strain Deposited Under Accession Number NCIMB 43385 Significantly Increases IL-6 and CD11b Expression BALB/c mice were administered live biotherapeutic and tissues were isolated for analysis of gene expression using qPCR.

Figure 68:
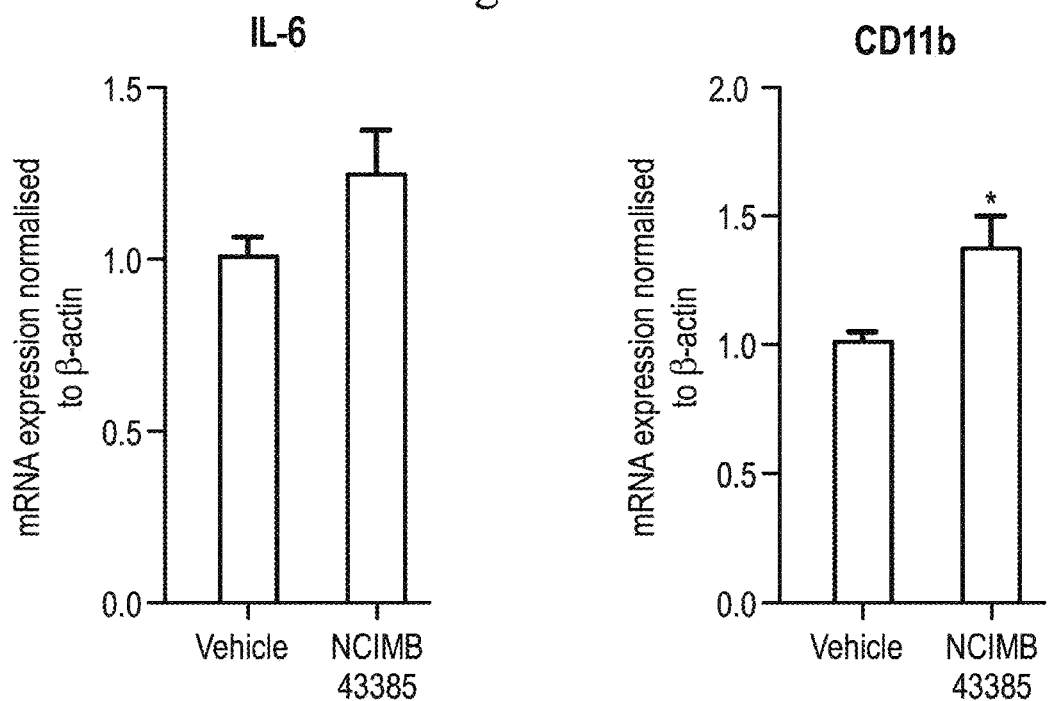
FIG. 68: *Megasphaera* strain NCIMB 43385 modulates IL-6 and CD11b expression in the brain of BALB/c mice.

FIG. 68 demonstrates the ability of NCIMB 43385 to significantly increase IL-6 and CD11b expression in the hippocampus of BALB/c mice compared to vehicle control.

Accordingly, as outlined above, the compositions of the present invention, in certain embodiments increase the expression of pro-inflammatory cytokines involved in the stimulation of the immune response, in particular IL-6 and CD11b. In certain embodiments, the compositions of the invention are therapeutically effective in light of the increase in IL-6 and CD11b expression.

Example 31—NCIMB 42787 Increases TLR4 Expression

BALB/c mice were administered live biotherapeutic and tissues were isolated for analysis of gene expression using qPCR.

Figure 69:
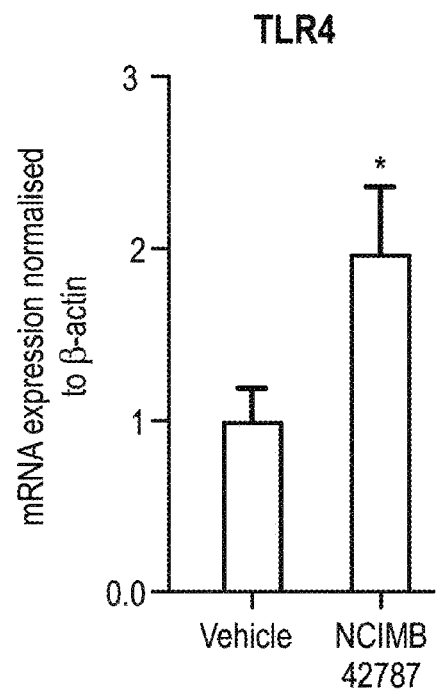
FIG. 69: NCIMB 42787 modulates TLR4 expression in the amygdala of BALB/c mice.

FIG. 69 demonstrates the ability of NCIMB 42787 to significantly increase TLR4 expression in the amygdala of BALB/c mice compared to vehicle control.

TLR4 is associated with activating the immune response. Accordingly, increasing TLR4 expression will improve immunostimulation. In certain embodiments, the compositions of the invention increase expression of TLR4. In certain embodiments, the increase in TLR4 expression increases the immune response. In certain embodiments, the compositions of the present invention increase the immune response and are therapeutically effect in treating the diseases disclosed herein via the increase in TLR4 expression.

```
Sequences
(consensus 16S rRNA sequence for Megasphaera
massihensis strain MRx0029)
                                         SEQ ID NO: 1
TGAGAAGCTTGCTTCTTATCGATTCTAGTGGCAAACGGGTGAGTAACGCG

TAAGCAACCTGCCCTTCAGATGGGGACAACAGCTGGAAACGGCTGCTAAT

ACCGAATACGTTCTTTCCGCCGCATGACGGGAAGAAGAAAGGGAGGCCTT

CGGGCTTTCGCTGGAGGAGGGGCTTGCGTCTGATTAGCTAGTTGGAGGGG

TAACGGCCCACCAAGGCGACGATCAGTAGCCGGTCTGAGAGGATGAACGG

CCACATTGGGACTGAGACACGGCCCAGACTCCTACGGGAGGCAGCAGTGG

GGAATCTTCCGCAATGGACGAAAGTCTGACGGAGCAACGCCGCGTGAACG

ATGACGGCCTTCGGGTTGTAAAGTTCTGTTATATGGGACGAACAGGACAT

CGGTTAATACCCGGTGTCTTTGACGGTACCGTAAGAGAAAGCCACGGCTA

ACTACGTGCCAGCAGCCGCGGTAATACGTAGGTGGCAAGCGTTGTCCGGA

ATTATTGGGCGTAAAGGGCGCGCAGGCGGCATCGCAAGTCGGTCTTAAAA
```

```
GTGCGGGCTTAACCCCGTGAGGGGACCGAAACTGTGAAGCTCGAGTGTC

GGAGAGGAAAGCGGAATTCCTAGTGTAGCGGTGAAATGCGTAGATATTAG

GAGGAACACCAGTGGCGAAAGCGGCTTTCTGGACGACAACTGACGCTGAG

GCGCGAAAGCCAGGGGAGCAAACGGGATTAGATACCCCGGTAGTCCTGGC

CGTAAACGATGGATACTAGGTGTAGGAGGTATCGACTCCTTCTGTGCCGG

AGTTAACGCAATAAGTATCCCGCCTGGGGAGTACGGCCGCAAGGCTGAAA

CTCAAAGGAATTGACGGGGGCCCGCACAAGCGGTGGAGTATGTGGTTTAA

TTCGACGCAACGCGAAGAACCTTACCAAGCCTTGACATTGATTGCTACGG

AAAGAGATTTCCGGTTCTTCTTCGGAAGACAAGAAAACAGGTGGTGCACG

GCTGTCGTCAGCTCGTGTCGTGAGATGTTGGGTTAAGTCCCGCAACGAGC

GCAACCCCTATCTTCTGTTGCCAGCACCTCGGGTGGGGACTCAGAAGAGA

CTGCCGCAGACAATGCGGAGGAAGGCGGGGATGACGTCAAGTCATCATGC

CCCTTATGGCTTGGGCTACACACGTACTACAATGGCTCTTAATAGAGGGA

AGCGAAGGAGCGATCCGGAGCAAACCCCAAAAACAGAGTCCCAGTTCGGA

TTGCAGGCTGCAACTCGCCTGCATGAAGCAGGAATCGCTAGTAATCGCAG

GTCAGCATACTGCGGTGAATACGTTCCCGGGCCTTGTACACACCGCCGT

CACACCACGAAAGTCATTCACACCCGAAGCCGGTGAGGCAACCGCAAG
```

Primers Used for qPCR

| Name | Forward sequence | Reverse sequence |
|---|---|---|
| GAPDH | GGTATCGTGGAAGGACTCATG (SEQ ID NO: 2) | ATGCCAGTGAGCTTCCCGTTC (SEQ ID NO: 3) |
| M4P2 | CTCAGCACCGCTAACAGAGG (SEQ ID NO: 4) | CATTGGCGCTTCTCTCCTC (SEQ ID NO: 5) |
| GPR109a | ATGTTGGCTATGAACCGCCAG (SEQ ID NO: 6) | GCTGCTGTCCGATTGGAGA (SEQ ID NO: 7) |

(consensus 16S rRNA sequence for the Megasphaera strain deposited under accession number NCIMB 43385)

SEQ ID NO: 8

```
GGCTGGTTCCTTGCGGTTGCCTCACCGGCTTCGGGTGTGAATGACTTTCG

TGGTGTGACGGGCGGTGTGTACAAGGCCCGGGAACGTATTCACCGCAGTA

TGCTGACCTGCGATTACTAGCGATTCCTGCTTCATGCAGGCGAGTTGCAG

CCTGCAATCCGAACTGGGACTCTGTTTTTGGGGTTTGCTCCGGATCGCTC

CTTCGCTTCCCTCTATTAAGAGCCATTGTAGTACGTGTGTAGCCCAAGCC

ATAAGGGGCATGATGACTTGACGTCATCCCCGCCTTCCTCCGCATTGTCT

GCGGCAGTCTCTTCTGAGTCCCCACCCTTAGTGCTGGCAACAGAAGATAG

GGGTTGCGCTCGTTGCGGGACTTAACCCAACATCTCACGACACGAGCTGA

CGACAGCCGTGCACCACCTGTTTTCTTGTCTTCCGAAGAAGAACCGGAAA

TCTCTTTCCGTAGCAATCAATGTCAAGGCTTGGTAAGGTTCTTCGCGTTG

CGTCGAATTAAACCACATACTCCACCGCTTGTGCGGGCCCCCGTCAATTC

CTTTGAGTTTCAGCCTTGCGGCCGTACTCCCCAGGCGGGATACTTATTGC

GTTAACTCCGGCACAGAAGGAGTCGATACCTCCTACACCTAGTATCCATC

GTTTACGGCCAGGACTACCGGGGTATCTAATCCCGTTTGCTCCCCTGGCT

TTCGCGCCTCAGCGTCAGTTGTCGTCCAGAAAGCCGCTTTCGCCACTGGT

GTTCCTCCTAATATCTACGCATTTCACCGCTACACTAGGAATTCCGCTTT

CCTCTCCGACACTCGAGCTTCACAGTTTCGGTCCCCTCACGGGGTTAAGC

CCCGCACTTTTAAGACCGACTTGCGATGCCGCCTGCGCGCCCTTTACGCC

CAATAATTCCGGACAACGCTTGCCACCTACGTATTACCGCGGCTGCTGGC

ACGTAGTTAGCCGTGGCTTTCTCTTACGGTACCGTCAAAGACACCGGGTA

TTAACCGATGTCCTGTTCGTCCCATATAACAGAACTTTACAACCCGAAGG

CCGTCATCGTTCACGCGGCGTTGCTCCGTCAGACTTTCGTCCATTGCGGA
```

(consensus 16S rRNA sequence for the Megasphaera massilhensis strain deposited under accession number NCIMB 43388)

SEQ ID NO: 9

```
GGCTGGTTCCTTGCGGTTGCCTCACCGGCTTCGGGTGTGAATGACTTTCG

TGGTGTGACGGGCGGTGTGTACAAGGCCCGGGAACGTATTCACCGCAGTA

TGCTGACCTGCGATTACTAGCGATTCCTGCTTCATGCAGGCGAGTTGCAG

CCTGCAATCCGAACTGGGACTCTGTTTTTGGGGTTTGCTCCGGATCGCTC

CTTCGCTTCCCTCTATTAAGAGCCATTGTAGTACGTGTGTAGCCCAAGCC

ATAAGGGGCATGATGACTTGACGTCATCCCCGCCTTCCTCCGCATTGTCT

GCGGCAGTCTCTTCTGAGTCCCCACCCGAGGTGCTGGCAACAGAAGATAG

GGGTTGCGCTCGTTGCGGGACTTAACCCAACATCTCACGACACGAGCTGA

CGACAGCCGTGCACCACCTGTTTTCTTGTCTTCCGAAGAAGAACCGGAAA

TCTCTTTCCGTAGCAATCAATGTCAAGGCTTGGTAAGGTTCTTCGCGTTG

CGTCGAATTAAACCACATACTCCACCGCTTGTGCGGGCCCCCGTCAATTC

CTTTGAGTTTCAGCCTTGCGGCCGTACTCCCCAGGCGGGATACTTATTGC

GTTAACTCCGGCACAGAAGGAGTCGATACCTCCTACACCTAGTATCCATC

GTTTACGGCCAGGACTACCGGGGTATCTAATCCCGTTTGCTCCCCTGGCT

TTCGCGCCTCAGCGTCAGTTGTCGTCCAGAAAGCCGCTTTCGCCACTGGT

GTTCCTCCTAATATCTACGCATTTCACCGCTACACTAGGAATTCCGCTTT

CCTCTCCGACACTCGAGCTTCACAGTTTCGGTCCCCTCACGGGGTTAAGC

CCCGCACTTTTAAGACCGACTTGCGATGCCGCCTGCGCGCCCTTTACGCC

CAATAATTCCGGACAACGCTTGCCACCTACGTATTACCGCGGCTGCTGGC

ACGTAGTTAGCCGTGGCTTTCTCTTACGGTACCGTCAGGGATAACGGGTA

TTGACCGCTATCCTGTTCGTCCCATATAACAGAACTTTACAACCCGAAGG

CCGTCATCGTTCACGCGGCGTTGCTCCGTCAGACTTTCGTCCATTGCGGA

AGATTCCCCACTGCTGCCTCCCGTAGGAGTCTGGGCCGTGTCTCAGTCCC

AATGTGGCCGTTCATCCTCTCAGACCGGCTACTGATCGTCGCCTTGGTGG

GCCGTTACCCCTCCAACTAGCTAATCAGACGCAAGCCCCTCCTCCAGCGA

AAGCCCGAAGGCCTCCCTTTCTTCATCCCGTCATGCGGCGGAAAGAACGT

ATTCGGTATTAGCAGCCGTTTCCAGCTGTTGTCCCCATCTGAAGGGCAGG

TTGCTTACGCGTTACTCACCCGTTTGCCACTCGAATTGATAAGAAGCAAG

CTTCTCATC
```

AGATTCCCCACTGCTGCCTCCCGTAGGAGTCTGGGCCGTGTCTCAGTCCC
AATGTGGCCGTTCATCCTCTCAGACCGGCTACTGATCGTCGCCTTGGTGG
GCCGTTACCCCTCCAACTAGCTAATCAGACGCAAGCCCCTCCTCCAGCGA
AAGCCCGAAGGCCTCCCTTTCTTCTTCCCGTCATGCGGCGGAAAGAACGT
ATTCGGTATTAGCAGCCGTTTCCAGCTGTTGTCCCCATCTGAAGGGCAGG
TTGCTTACGCGTTACTCACCCGTTTGCCACTAGAATCGATAAGAAGCAAG
CTTCTCATGTCTTCT (consensus 16S rRNA sequence for the Megasphaera
massilhensis strain deposited under accession
number NCIMB 43389)
SEQ ID NO: 10
CGACGGCTGGTTCCTTGCGGTTGCCTCACCGGCTTCGGGTGTGAATGACT
TTCGTGGTGTGACGGGCGGTGTGTACAAGGCCCGGGAACGTATTCACCGC
AGTATGCTGACCTGCGATTACTAGCGATTCCTGCTTCATGCAGGCGAGTT
GCAGCCTGCAATCCGAACTGGGACTCTGTTTTTGGGGTTTGCTCCGGATC
GCTCCTTCGCTTCCCTCTATTAAGAGCCATTGTAGTACGTGTGTAGCCCA
AGCCATAAGGGGCATGATGACTTGACGTCATCCCCGCCTTCCTCCGCATT
GTCTGCGGCAGTCTCTTCTGAGTCCCCACCCGAGGTGCTGGCAACAGAAG
ATAGGGGTTGCGCTCGTTGCGGGACTTAACCCAACATCTCACGACACGAG
CTGACGACAGCCGTGCACCACCTGTTTTCTTGTCTTCCGAAGAAGAACCG
GAAATCTCTTTCCGTAGCAATCAATGTCAAGGCTTGGTAAGGTTCTTCGC
GTTGCGTCGAATTAAACCACATACTCCACCGCTTGTGCGGGCCCCCGTCA
ATTCCTTTGAGTTTCAGCCTTGCGGCCGTACTCCCCAGGCGGGATACTTA
TTGCGTTAACTCCGGCACAGAAGGAGTCGATACCTCCTACACCTAGTATC
CATCGTTTACGGCCAGGACTACCGGGGTATCTAATCCCGTTTGCTCCCCT
GGCTTTCGCGCCTCAGCGTCAGTTGTCGTCCAGAAAGCCGCTTTCGCCAC
TGGTGTTCCTCCTAATATCTACGCATTTCACCGCTACACTAGGAATTCCG
CTTTCCTCTCCGACACTCGAGCTTCACAGTTTCGGTCCCCTCACGGGGTT
AAGCCCCGCACTTTTAAGACCGACTTGCGATGCCGCCTGCGCGCCCTTTA
CGCCCAATAATTCCGGACAACGCTTGCCACCTACGTATTACCGCGGCTGC
TGGCACGTAGTTAGCCGTGGCTTTCTCTTACGGTACCGTCAAAGACACCG
GGTATTAACCGATGCCCTGTTCGTCCCATATAACAGAACTTTACAACCCG
AAGGCCGTCATCGTTCACGCGGCGTTGCTCCGTCAGACTTTCGTCCATTG
CGGAAGATTCCCCACTGCTGCCTCCCGTAGGAGTCTGGGCCGTGTCTCAG
TCCCAATGTGGCCGTTCATCCTCTCAGACCGGCTACTGATCGTCGCCTTG
GTGGGCCGTTACCCCTCCAACTAGCTAATCAGACGCAAGCCCCTCCTCCA
GCGAAAGCCCGAAGGCCTCCCTTTCTTCTTCCCGTCATGCGGCGGAAAGA
ACGTATTCGGTATTAGCAGCCGTTTCCAGCTGTTGTCCCCATCTGAAGGG
CAGGTTGCTTACGCGTTACTCACCCGTTTGCCACTAGAATCGATAAGAAG
CAAGCTTCTCATGTCTTCTCGTTCGACTTGCAT (consensus 16S rRNA sequence for the Me gasphaera
strain deposited under accession number NCIMB
43386)
SEQ ID NO: 11
CGACGGCTGGTTCCTTGCGGTTGCCTCACCGGCTTCGGGTGTGAATGACT
TTCGTGGTGTGACGGGCGGTGTGTACAAGGCCCGGGAACGTATTCACCGC
AGTATGCTGACCTGCGATTACTAGCGATTCCTGCTTCATGCAGGCGAGTT
GCAGCCTGCAATCCGAACTGGGACTCTGTTTTTGGGGTTTGCTCCGGATC
GCTCCTTCGCTTCCCTCTATTAAGAGCCATTGTAGTACGTGTGTAGCCCA
AGCCATAAGGGGCATGATGACTTGACGTCATCCCCGCCTTCCTCCGCATT
GTCTGCGGCAGTCTCTTCTGAGTCCCCACCCTTAGTGCTGGCAACAGAAG
ATAGGGGTTGCGCTCGTTGCGGGACTTAACCCAACATCTCACGACACGAG
CTGACGACAGCCGTGCACCACCTGTTTTCTTGTCTTCCGAAGAAGAACCG
GAAATCTCTTTCCGTAGCAATCAATGTCAAGGCTTGGTAAGGTTCTTCGC
GTTGCGTCGAATTAAACCACATACTCCACCGCTTGTGCGGGCCCCCGTCA
ATTCCTTTGAGTTTCAGCCTTGCGGCCGTACTCCCCAGGCGGGATACTTA
TTGCGTTAACTCCGGCACAGAAGGAGTCGATACCTCCTACACCTAGTATC
CATCGTTTACGGCCAGGACTACCGGGGTATCTAATCCCGTTTGCTCCCCT
GGCTTTCGCGCCTCAGCGTCAGTTGTCGTCCAGAAAGCCGCTTTCGCCAC
TGGTGTTCCTCCTAATATCTACGCATTTCACCGCTACACTAGGAATTCCG
CTTTCCTCTCCGACACTCGAGCTTCACAGTTTCGGTCCCCTCACGGGGTT
AAGCCCCGCACTTTTAAGACCGACTTGCGATGCCGCCTGCGCGCCCTTTA
CGCCCAATAATTCCGGACAACGCTTGCCACCTACGTATTACCGCGGCTGC
TGGCACGTAGTTAGCCGTGGCTTTCTCTTACGGTACCGTCAGGGATAACG
GGTATTGACCGCTATCCTGTTCGTCCCATATAACAGAACTTTACAACCCG
AAGGCCGTCATCGTTCACGCGGCGTTGCTCCGTCAGACTTTCGTCCATTG
CGGAAGATTCCCCACTGCTGCCTCCCGTAGGAGTCTGGGCCGTGTCTCAG
TCCCAATGTGGCCGTTCATCCTCTCAGACCGGCTACTGATCGTCGCCTTG
GTGGGCCGTTACCCCTCCAACTAGCTAATCAGACGCAAGCCCCTCCTCCA
GCGAAAGCCCGAAGGCCTCCCTTTCTTCATCCCGTCATGCGGCGGAAAGA
ACGTATTCGGTATTAGCAGCCGTTTCCAGCTGTTGTCCCCATCTGAAGGG
CAGGTTGCTTACGCGTTACTCACCCGTTTGCCACTCGAATTGATAAGAAG
CAAGCTTCTCATCTCTTCGTTCGACTGCA (consensus 16S rRNA sequence for the Me gasphaera
strain deposited under accession number NCIMB
43387)
SEQ ID NO: 12
TCGAACGGCTGGTTCCTTGCGGTTGCCTCACCGGCTTCGGGTGTGAATGA
CTTTCGTGGTGTGACGGGCGGTGTGTACAAGGCCCGGGAACGTATTCACC
GCAGTATGCTGACCTGCGATTACTAGCGATTCCTGCTTCATGCAGGCGAG
TTGCAGCCTGCAATCCGAACTGGGACTCTGTTTTTGGGGTTTGCTCCGGA
TCGCTCCTTCGCTTCCCTCTATTAAGAGCCATTGTAGTACGTGTGTAGCC
CAAGCCATAAGGGGCATGATGACTTGACGTCATCCCCGCCTTCCTCCGCA
TTGTCTGCGGCAGTCTCTTCTGAGTCCCCACCCTTAGTGCTGGCAACAGA -continued

```
AGATAGGGGTTGCGCTCGTTGCGGGACTTAACCCAACATCTCACGACACG

AGCTGACGACAGCCGTGCACCACCTGTTTTCTTGTCTTCCGAAGAAGAAC

CGGAAATCTCTTTCCGTAGCAATCAATGTCAAGGCTTGGTAAGGTTCTTC

GCGTTGCGTCGAATTAAACCACATACTCCACCGCTTGTGCGGGCCCCGT

CAATTCCTTTGAGTTTCAGCCTTGCGGCCGTACTCCCCAGGCGGGATACT

TATTGCGTTAACTCCGGCACAGAAGGAGTCGATACCTCCTACACCTAGTA

TCCATCGTTTACGGCCAGGACTACCGGGGTATCTAATCCCGTTTGCTCCC

CTGGCTTTCGCGCCTCAGCGTCAGTTGTCGTCCAGAAAGCCGCTTTCGCC

ACTGGTGTTCCTCCTAATATCTACGCATTTCACCGCTACACTAGGAATTC

CGCTTTCCTCTCCGACACTCGAGCTTCACAGTTTCGGTCCCCTCACGGGG

TTAAGCCCCGCACTTTTAAGACCGACTTGCGATGCCGCCTGCGCGCCCTT

TACGCCCAATAATTCCGGACAACGCTTGCCACCTACGTATTACCGCGGCT

GCTGGCACGTAGTTAGCCGTGGCTTTCTCTTACGGTACCGTCAGGGATAA

CGGGTATTGACCGCTATCCTGTTCGTCCCATATAACAGAACTTTACAACC

CGAAGGCCGTCATCGTTCACGCGGCGTTGCTCCGTCAGACTTTCGTCCAT

TGCGGAAGATTCCCCACTGCTGCCTCCCGTAGGAGTCTGGGCCGTGTCTC

AGTCCCAATGTGGCCGTTCATCCTCTCAGACCGGCTACTGATCGTCGCCT

TGGTGGGCCGTTACCCCTCCAACTAGCTAATCAGACGCAAGCCCTCCTC

CAGCGAAAGCCCGAAGGCCTCCCTTTCTTCATCCCGTCATGCGGCGGAAA

GAACGTATTCGGTATTAGCAGCCGTTTCCAGCTGTTGTCCCCATCTGAAG

GGCAGGTTGCTTACGCGTTACTCACCCGTTTGCCACTCGAATTGATAAGA

AGCAAGCTTCTCATCTCTTCTCGTTCGACTTGCA
```

Primers Used for qPCR of Enolase

| Name | Forward sequence | Reverse sequence |
|---|---|---|
| NSE | CCCTGTATCGTAAGAACGGT (SEQ ID NO: 13) | GCCACCATTGATCACGTTGA (SEQ ID NO: 14) |

```
(biotype identifying repetitive sequence)
                                    SEQ ID NO: 15
GTGGTGGTGG TGGT
```

REFERENCES

[1] Spor et al. (2011) *Nat Rev Microbiol.* 9(4):279-90.
[2] Eckburg et al. (2005) *Science.* 10; 308(5728):1635-8.
[3] Macpherson et al. (2001) *Microbes Infect.* 3(12):1021-35
[4] Macpherson et al. (2002) *Cell Mol Life Sci.* 59(12):2088-96.
[5] Mazmanian et al. (2005) *Cell* 15; 122(1):107-18.
[6] Frank et al. (2007) *PNAS* 104(34):13780-5.
[7] Scanlan et al. (2006) *J Clin Microbiol.* 44(11):3980-8.
[8] Kang et al. (2010) *Inflamm Bowel Dis.* 16(12):2034-42.
[9] Machiels et al. (2013) *Gut.* 63(8):1275-83.
[10] WO 2013/050792
[11] WO 03/046580
[12] WO 2013/008039
[13] WO 2014/167338
[14] Goldin and Gorbach (2008) *Clin Infect Dis.* 46 Suppl 2:S96-100.
[15] Azad et al. (2013) *BMJ.* 347:f6471.
[16] Padmanabhan et al. (2013) *Standards in Genomic Sciences* 8:525-538
[17] Masco et al. (2003) *Systematic and Applied Microbiology,* 26:557-563.
[18] Srůtková et al. (2011) *J. Microbiol. Methods,* 87(1):10-6.
[19] Kondělková et al. (2010) *Acta Medica (Hradec Kralove).*; 53(2):73-7.
[20] Zhang et al. (2016) *BMC Gastroenterol.*; 16: 84.
[21] Ren and Tones (2009) *Brain Res Rev.*; 60(1):57-64
[22] Martinon et al. (2002) *Mol Cell.*; 10(2):417-26.
[23] Murphy et al. (2003) *J Exp Med.* 2003; 198(12): 1951-1957.
[24] Chan et al. (2006) *J Exp Med.*; 203(12): 2577-2587.
[25] *The Immune Response Basic and Clinical Principles,* 1st Edition (2006)
[26] Hoover et al. (2002)*J Biol Chem.* 277(40):37647-54.
[27] Kaser et al. (2004) *J Clin Immunol.*; 24(1):74-85.
[28] Gaur and Aggarwal (2003). *Biochem Pharmacol.*; 66(8):1403-8.
[29] Wang and Lin (2008) *Acta* Pharmacol Sin.; 29(11): 1275-1288.
[30] Tanaka et al. (2014) *Cold Spring Harb Perspect Biol.*; 6(10): a016295.
[31] Bettelli et al. (2006) *Nature* 441:235-238
[32] Menezes and Luskin (1994) *Journal of Neuroscience,* 14 (9) 5399-5416;
[33] Bhat et al. (2006) *Nucleic Acids Res.*; 34(13):3819-32.
[34] Andreeff et al. (2003), *Holland-Frei Cancer Medicine.* 6th edition.
[35] Soltani M H et al, (2005) *Am J Pathol*; 166:1841-50
[36] Jandaghi et al. (2016) *Gastroenterology*; 151 (6): 1218-1231.
[37] Pornour et al. (2015) *Recent Pat Anticancer Drug Discov.*; 10(2):214-23.
[38] Sachlos et al. (2012) *Cell.*; 149(6):1284-97
[39] Li et al. (2014), *Oncotarget.*; 5(4):882-93.
[40] Visnyei et al. (2011) *Mol Cancer Ther.*; 10(10):1818-28.
[41] Cheng et al. (2015) *Cell Death Dis.*; 6:e1753
[42] Shin et al. (2012) *Biol Pharm Bull.*; 35(7):1069-75.
[43] Chen et al. (2011) *PLoS One.*; 6(11):e27186
[44] Arvigo et al. (2010) *J Endocrinol.*; 207(3):309-17.
[45] Mao et al. (2015) *J Obstet Gynaecol Res.*; 41(8):1240-5
[46] Park et al. (2014) *Oncotarget.*; 5(13):4929-34.
[47] Spengler et al. (2011) *Anticancer Res.*; 31(12):4201-5.
[48] Mu et al. (2014) *Oncol Rep.*; 31 (5):2107-14.
[49] Prabhu et al. (2017) *Neuro-Oncology,* 19(6) vi60
[50] Devarajan et al. (2002) *Oncogene.* 12; 21(57):8843-51.
[51] Bell and Megeney (2017) *Cell Death Differ.*; 24(8): 1359-1368.
[52] Gerl and Vaux (2005) *Carcinogenesis.* 2005 February; 26(2):263-70.
[53] Barnes et al. (2005) *Eur Respir J.* 25:552-563.
[54] Gray S G, Dangond F. (2006) *Epigenetics.* 1:67-75.
[55] Grabiec et al. (2008) *Arthritis Res Ther.* 10:226.
[56] Saito et al. (1999) *Proc Natl Acad Sci USA.* 96:4592-4597.
[57] Butler et al. (2000) *Cancer Res.* 60:5165-5170.
[58] Mwakwari et al. (2010) *Curr Top Med Chem.* 10 (14): 1423-40.
[59] Monneret C. (2007) *Anti-Cancer Drugs.* 18 (4): 363-70.
[60] Chun, (2015) *Arch Pharm Res.* 38(6):933-49.

[61] Abel and Zukin (2008) *Curr Opin Pharmacol,* 2008. 8(1): 57-64.
[62] PCT/EP2018/065858
[63] Toshkov et al. (2017) *Radiat Res.* 187(5):570-580
[64] Tanaka and Sakaguchi (2017) *Cell Res.;* 27(1):109-118.
[65] Allen et al. (2010) *J Exp Med.;* 207(5):1045-56.
[66] Haabeth et al. (2012) *Oncolmmunology* 1(1): 1146-1152.
[67] Lejeune et al. (2006) *Cancer Immun.* 6:6
[68] Pace et al. (1983) *PNAS.* 80:8782-6.
[69] Sgadari et al. (1996) *PNAS.* 93:13791-6.
[70] Arenberg et al. (1996) *J. Exp. Med.* 184:981-92.
[71] Sgadari et al. (1997) *Blood.* 89:2635-43.
[72] Liu et al., (2018) Acta Pharmaceutica Sinica B; 8, 4; 552-562
[73] Jones et al. (2017). J Clin Oncol. 2017 Aug. 10; 35(23): 2624-2630
[74] Ascierto et al. (2012) Journal of Translational Medicine. 10, 85
[75] https://www.uniprot.org/uniprot/P15056
[76] Soltani M H et al, (2005) *Am J Pathol;* 166:1841-50
[77] Xie (2016); *Med Res Rev;* 36, 2: 300-312
[78] Bloch et al. (2016) *Eur Cytokine Netw.;* 27(3):63-67
[79] Mohanty et al. (2015) *J Infect Dis,* 211(7) 1174-1184.
[80] Fernandez-Ruiz et al., (2015) *Vaccine* 2015 33(51)
[81] Morel et al., (2011) *Vaccine,* 29(13) 2461-2473.
[82] Leal et al., (2001) *Immunol* 103(3) 375-381
[83] Knudsen et al. (2016), *Sci Reps,* 6 (19570).
[84] Su et al., (2008) *Vaccine* 26(40), 5111-22
[85] Song, Mol Ther 2007
[86] Li et al, (2007) *J Immunol,* 178(8), 5271-5276
[87] Coffman et al., (2012) *Immunity* 33(4) 492-503
[88] Ruan et al. (2014) *Acta Virol.* 58(4):356-8
[89] Wang et al. (2016) *Oncotarget.* 20; 7(51)
[90] Fraietta, Nat Med 2018
[91] Zhou, Blood 2010
[92] Glenn and Whartenby (2014) *World J Stem Cells.;* 6(5): 526-539.
[93] Heng et al. (2004) *Cardiovasc Res.* 2004 Apr. 1; 62(1):34-42.
[94] Fulop et al
[95] Bektas et al. (2017) *J Leukoc Biol.;* 102(4):977-988.
[96] Fulop et al (2016) *Rev Invest Clin.;* 68(2):84-91.
[97] Fulop et al. (2018) *Front Immunol.;* 8:1960.
[98] Miyamoto-Shinohara et al. (2008) *J. Gen. Appl. Microbiol.,* 54, 9-24.
[99] Cryopreservation and Freeze-Drying Protocols, ed. by Day and McLellan, Humana Press.
[100] Leslie et al. (1995) *Appl. Environ. Microbiol.* 61, 3592-3597.
[101] Mitropoulou et al. (2013) *J Nutr Metab.* (2013) 716861.
[102] Kailasapathy et al. (2002) *Curr Issues Intest Microbiol.* 3(2):39-48.
[103] Handbook of Pharmaceutical Excipients, 2nd Edition, (1994), Edited by A Wade and P J Weller
[104] Remington's Pharmaceutical Sciences, Mack Publishing Co. (A. R. Gennaro edit. 1985)
[105] *Handbook of Microbiological Media, Fourth Edition* (2010) Ronald Atlas, CRC Press.
[106] *Maintaining Cultures for Biotechnology and Industry* (1996) Jennie C. Hunter-Cevera, Academic Press
[107] Strobel (2009) *Methods Mol Biol.* 581:247-61.
[108] Gennaro (2000) *Remington: The Science* and Practice of Pharmacy. 20th edition, ISBN: 0683306472.
[109] *Molecular Biology Techniques: An Intensive Laboratory Course,* (Ream et al., eds., 1998, Academic Press).
[110] *Methods In Enzymology* (S. Colowick and N. Kaplan, eds., Academic Press, Inc.)
[111] *Handbook of Experimental Immunology,* Vols. I-IV (D. M. Weir and C. C. Blackwell, eds, 1986, Blackwell Scientific Publications)
[112] Sambrook et al. (2001) *Molecular Cloning: A Laboratory Manual,* 3rd edition (Cold Spring Harbor Laboratory Press).
[113] *Handbook of Surface and Colloidal Chemistry* (Birdi, K. S. ed., CRC Press, 1997)
[114] Ausubel et al. (eds) (2002) *Short protocols in molecular biology,* 5th edition (Current Protocols).
[115] *PCR (Introduction to Biotechniques Series),* 2nd ed. (Newton & Graham eds., 1997, Springer Verlag)
[116] *Current Protocols in Molecular Biology* (F. M. Ausubel et al., eds., 1987) Supplement 30
[117] Smith & Waterman (1981) *Adv. Appl. Math.* 2: 482-489
[118] Johnsen et al (2017) *Journal of Chromatography A.* 1503: 57-64
[119] West and Johnstone (2014) *J Clin Invest.* 124, 30-39
[120] Glauben et al. (2006) *J Immunol,* 176: 5015-5022
[121] Angiolilli et al. (2017) *Ann Rheum Dis,* 76: 277-285
[122] Gonneaud et al. (2014) *J Inflamm,* 11:43
[123] Alenghat et al. (2013) *Nature,* 504: 153-157
[124] Felice et al. (2015) *Ailment Pharmacol Ther,* 41: 26-38
[125] Gagnon et al (2013) *J Microbiological Methods.* 94: 274-279
[126] Thangaraju et al. (2009). *Cancer Res.* 67, 9: 2826-2832
[127] Livak & Schmittgen (2001). *Methods.* 25, 4:402-8
[128] Johnsen et al (2017) *Journal of Chromatography A.* 1503: 57-64
[129] Vizin and Kos (2015) *Radiol Oncol.* 49(3): 217-226
[130] Selvan et al. (2008) *AACR Annual Meeting* Apr. 12-16, 2008
[131] Bonner et al. (2000) *Clinical Cancer Research* 6:597-601
[132] Zhi et al. (2016) *Oncotarget.* 7(40):64798-64809
[133] De Baere et al. (2013) *J Pharm Biomed Anal,* 80: 107-115
[134] Smart et al. (2010) *Nat Protoc,* 5(10), 1709-1729
[135] Johnsen et al. (2017) *J Chromatogr A,* 1503, 57-64

The invention claimed is:

1. A method of treating cancer in a subject in need thereof, comprising administering to said subject a pharmaceutical composition that comprises a therapeutically effective amount of a bacteria strain of the species *Megasphaera massiliensis,*
   wherein said bacteria strain comprises a 16S rRNA gene that has at least 98.5% sequence identity to the polynucleotide sequence of SEQ ID NO: 1, as determined by a Smith-Waterman homology search algorithm using an affine gap search with a gap open penalty of 12 and a gap extension penalty of 2, and
   wherein said administering is effective to slow cancer progression or induce cancer cell death, thereby treating cancer in said subject;

wherein said cancer is associated with oncogenic Extracellular Signal-Related Kinase (ERK) signaling, Histone Deacetylase (HDAC) activity, overexpression or upregulation of Dopamine Receptor D2 (DRD2), or reduced Mitogen-Activated Protein 2 (MAP2) expression.

2. The method of claim 1, wherein said cancer is solid tumor cancer.

3. The method of claim 1, wherein said cancer is metastatic melanoma, breast cancer, ovarian cancer, cervical cancer, neuroblastoma, glioblastoma, carcinoma, lung cancer, chronic lymphocyte leukemia, prostate cancer, lymphoma, gastric cancer, colorectal cancer or haematological malignancies.

4. The method of claim 1, further comprising administering to said subject a second anti-cancer agent or an anti-cancer therapy.

5. The method of claim 4, wherein said second anti-cancer agent is a chemotherapeutic agent, a proteasome inhibitor, an epigenetic regulator, or a combination thereof.

6. The method of claim 4, wherein said anti-cancer therapy is chimeric antigen receptor T cell (CAR-T) therapy, mesenchymal stem cell (MSC) therapy, stem cell transplantation therapy, or a combination thereof.

7. The method of claim 1, wherein said bacterial strain is dried.

8. The method of claim 1, wherein said therapeutically effective amount of said bacteria strain comprises from about $1\times10^3$ to about $1\times10^{11}$ colony forming units (CFU)/g of said bacteria strain with respect to the total weight of said pharmaceutical composition.

9. The method of claim 1, wherein said administering comprises oral, rectal, nasal, buccal, sublingual, or subcutaneous administration.

10. The method of claim 1, wherein said bacteria strain is capable of at least partially colonizing an intestine of said subject.

11. The method of claim 1, wherein said pharmaceutical composition is formulated for delivery to an intestine of said subject.

12. The method of claim 1, wherein said subject is a human.

13. The method of claim 1, wherein said bacteria strain comprises a 16S rRNA gene sequence that is the polynucleotide sequence of SEQ ID NO: 1, SEQ ID NO: 8, SEQ ID NO: 9, SEQ ID NO: 10, SEQ ID NO: 11, or SEQ ID NO: 12.

14. The method of claim 1, wherein said bacterial strain is the strain deposited under accession number NCIMB 42787, NCIMB 43385, NCIMB 43386, NCIMB 43387, NCIMB 43388, or NCIMB 43389.

* * * * *